US008012931B2

(12) United States Patent
Cujec et al.

(10) Patent No.: US 8,012,931 B2
(45) Date of Patent: Sep. 6, 2011

(54) MODIFIED FGF-21 POLYPEPTIDES AND THEIR USES

(75) Inventors: Thomas P. Cujec, San Diego, CA (US); Roberto Mariani, San Diego, CA (US); Anna-Maria A. Hays Putnam, San Diego, CA (US); William M. Keefe, West Hollywood, CA (US); Nick Knudsen, San Diego, CA (US); Lillian Ho, San Diego, CA (US); Jason Pinkstaff, Encinitas, CA (US); Vadim Kraynov, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 12/051,830

(22) Filed: Mar. 19, 2008

(65) Prior Publication Data
US 2008/0255045 A1 Oct. 16, 2008

Related U.S. Application Data

(60) Provisional application No. 60/921,297, filed on Mar. 30, 2007, provisional application No. 60/988,060, filed on Nov. 14, 2007.

(51) Int. Cl.
*A61K 38/18* (2006.01)
*C12P 21/00* (2006.01)
*C07K 14/50* (2006.01)
*C12N 1/16* (2006.01)
*C07H 21/00* (2006.01)

(52) U.S. Cl. .... 514/9.1; 435/69.1; 435/70.1; 435/255.2; 530/350; 530/399; 536/23.1

(58) Field of Classification Search .................. None
See application file for complete search history.

(56) References Cited

U.S. PATENT DOCUMENTS

| | | |
|---|---|---|
| 2,968,158 A | 1/1961 | Ruschig et al. |
| 3,097,242 A | 7/1963 | Hoehn et al. |
| 3,454,635 A | 7/1969 | Weber et al. |
| 3,501,495 A | 3/1970 | Beregi et al. |
| 3,654,357 A | 4/1972 | Bretschneider et al. |
| 3,668,215 A | 6/1972 | Plumpe et al. |
| 3,669,966 A | 6/1972 | Ambrogi et al. |
| 3,708,486 A | 1/1973 | Kutter et al. |
| 3,773,919 A | 11/1973 | Boswell et al. |
| 4,287,200 A | 9/1981 | Kawamatsu et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,572,912 A | 2/1986 | Yoshioka et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,687,777 A | 8/1987 | Meguro et al. |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,873,080 A | 10/1989 | Brickl et al. |
| 4,873,255 A | 10/1989 | Yoshioka et al. |
| 4,876,197 A | 10/1989 | Burke et al. |
| 4,880,734 A | 11/1989 | Burke et al. |
| 4,897,405 A | 1/1990 | Alessi et al. |
| 4,902,502 A | 2/1990 | Nitecki et al. |
| 4,904,584 A | 2/1990 | Shaw |
| 4,929,555 A | 5/1990 | Cregg et al. |
| 5,002,953 A | 3/1991 | Hindley |
| 5,021,234 A | 6/1991 | Ehrenfeld |
| 5,061,717 A | 10/1991 | Clark et al. |
| 5,089,398 A | 2/1992 | Rosenberg et al. |
| 5,120,754 A | 6/1992 | Clark et al. |
| 5,122,614 A | 6/1992 | Zalipsky |
| 5,132,317 A | 7/1992 | Cantello et al. |
| 5,162,601 A | 11/1992 | Slightom |
| 5,218,092 A | 6/1993 | Sasaki et al. |
| 5,219,564 A | 6/1993 | Zalipsky et al. |
| 5,223,522 A | 6/1993 | Clark et al. |
| 5,229,490 A | 7/1993 | Tam |

(Continued)

FOREIGN PATENT DOCUMENTS
DE      3218121 A1    11/1983
(Continued)

OTHER PUBLICATIONS

Abuchowski, A. et al. "Cancer therapy with chemically modified enzymes. I. Antitumor properties of polyethylene glycol-asparaginase conjugates," Cancer Biochem Biophys. Jun. 1984;7(2):175-86. Altschul, SF et al. "Gapped Blast and PSI-Blast: a new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.
Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2000;9(2):237-44.
Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.

(Continued)

Primary Examiner — Elly-Gerald Stoica
(74) Attorney, Agent, or Firm — John W. Wallen, III; Kristin S. Eaton

(57) ABSTRACT

Modified FGF-21 polypeptides and uses thereof are provided.

52 Claims, 40 Drawing Sheets

U.S. PATENT DOCUMENTS

| | | | |
|---|---|---|---|
| 5,231,178 A | 7/1993 | Holtz et al. | |
| 5,252,714 A | 10/1993 | Harris et al. | |
| 5,258,185 A | 11/1993 | Bauer et al. | |
| 5,281,698 A | 1/1994 | Nitecki | |
| 5,290,686 A | 3/1994 | Kendal et al. | |
| 5,324,639 A | 6/1994 | Brierley et al. | |
| 5,324,844 A | 6/1994 | Zalipsky | |
| 5,382,657 A | 1/1995 | Karasiewicz et al. | |
| 5,446,090 A | 8/1995 | Harris | |
| 5,468,478 A | 11/1995 | Saifer et al. | |
| 5,473,034 A | 12/1995 | Yasui et al. | |
| 5,476,653 A | 12/1995 | Pitt et al. | |
| 5,516,657 A | 5/1996 | Murphy et al. | |
| 5,516,673 A | 5/1996 | Margel et al. | |
| 5,532,142 A | 7/1996 | Johnston et al. | |
| 5,559,213 A | 9/1996 | Hakimi et al. | |
| 5,571,709 A | 11/1996 | Devauchelle et al. | |
| 5,580,723 A | 12/1996 | Wells et al. | |
| 5,583,023 A | 12/1996 | Cerutti et al. | |
| 5,602,034 A | 2/1997 | Tekamp-Olson | |
| 5,605,827 A | 2/1997 | Jackwood et al. | |
| 5,612,460 A | 3/1997 | Zalipsky | |
| 5,629,203 A | 5/1997 | Shuster | |
| 5,629,384 A | 5/1997 | Veronese et al. | |
| 5,643,575 A | 7/1997 | Martinez et al. | |
| 5,650,234 A | 7/1997 | Dolence et al. | |
| 5,672,662 A | 9/1997 | Harris et al. | |
| 5,674,706 A | 10/1997 | Shuster | |
| RE35,749 E | 3/1998 | Rosenberg et al. | |
| 5,736,625 A | 4/1998 | Callstrom et al. | |
| 5,739,208 A | 4/1998 | Harris | |
| 5,747,646 A | 5/1998 | Hakimi et al. | |
| 5,750,373 A | 5/1998 | Garrard et al. | |
| 5,753,220 A | 5/1998 | Suzuki et al. | |
| 5,762,939 A | 6/1998 | Smith et al. | |
| 5,766,883 A | 6/1998 | Ballance et al. | |
| 5,766,885 A | 6/1998 | Carrington et al. | |
| 5,808,096 A | 9/1998 | Zalipsky | |
| 5,824,778 A | 10/1998 | Ishikawa et al. | |
| 5,824,784 A | 10/1998 | Kinstler et al. | |
| 5,834,250 A | 11/1998 | Wells et al. | |
| 5,834,594 A | 11/1998 | Hakimi et al. | |
| 5,843,733 A | 12/1998 | Estes | |
| 5,849,860 A | 12/1998 | Hakimi et al. | |
| 5,858,368 A | 1/1999 | Smith et al. | |
| 5,859,037 A | 1/1999 | Whitcomb | |
| 5,861,279 A | 1/1999 | Zhang et al. | |
| 5,871,986 A | 2/1999 | Boyce | |
| 5,874,454 A | 2/1999 | Antonucci et al. | |
| 5,876,969 A | 3/1999 | Fleer et al. | |
| 5,880,270 A * | 3/1999 | Berninger et al. | 530/391.9 |
| 5,891,676 A | 4/1999 | Estes | |
| 5,900,461 A | 5/1999 | Harris | |
| 5,932,462 A | 8/1999 | Harris et al. | |
| 5,939,285 A | 8/1999 | Devauchelle et al. | |
| 5,965,393 A | 10/1999 | Hasnain et al. | |
| 5,980,948 A | 11/1999 | Goedemoed et al. | |
| 5,989,868 A | 11/1999 | Harrison et al. | |
| 5,990,237 A | 11/1999 | Bentley et al. | |
| 6,001,800 A | 12/1999 | Mehta et al. | |
| 6,004,573 A | 12/1999 | Rathi et al. | |
| 6,013,433 A | 1/2000 | Pellett et al. | |
| 6,013,478 A | 1/2000 | Wells et al. | |
| 6,017,731 A | 1/2000 | Tekamp-Olson et al. | |
| 6,083,723 A | 7/2000 | Tekamp-Olson | |
| 6,096,304 A | 8/2000 | McCutchen | |
| 6,126,944 A | 10/2000 | Pellett et al. | |
| 6,129,912 A | 10/2000 | Hortin et al. | |
| 6,168,932 B1 | 1/2001 | Uckun et al. | |
| 6,183,985 B1 | 2/2001 | Shuster | |
| 6,183,987 B1 | 2/2001 | Van De Wiel et al. | |
| 6,184,344 B1 | 2/2001 | Kent et al. | |
| 6,201,072 B1 | 3/2001 | Rathi et al. | |
| 6,214,966 B1 | 4/2001 | Harris | |
| 6,225,060 B1 | 5/2001 | Clark et al. | |
| 6,235,710 B1 | 5/2001 | Mehta et al. | |
| 6,245,528 B1 | 6/2001 | Chao | |
| 6,261,805 B1 | 7/2001 | Wood | |
| RE37,343 E | 8/2001 | Tekamp-Olson | |
| 6,281,211 B1 | 8/2001 | Cai et al. | |
| 6,306,821 B1 | 10/2001 | Mikos et al. | |
| 6,312,923 B1 | 11/2001 | Tekamp-Olson | |
| 6,337,191 B1 | 1/2002 | Swartz et al. | |
| 6,338,846 B1 | 1/2002 | Kang et al. | |
| 6,342,216 B1 | 1/2002 | Fidler et al. | |
| 6,361,969 B1 | 3/2002 | Galeotti | |
| 6,368,825 B1 | 4/2002 | Chao | |
| 6,420,339 B1 | 7/2002 | Gegg et al. | |
| 6,423,685 B1 | 7/2002 | Drummond et al. | |
| 6,428,954 B1 | 8/2002 | Wells et al. | |
| 6,436,386 B1 | 8/2002 | Roberts et al. | |
| 6,451,346 B1 | 9/2002 | Shah et al. | |
| 6,451,561 B1 | 9/2002 | Wells et al. | |
| 6,461,603 B2 | 10/2002 | Bentley et al. | |
| 6,515,100 B2 | 2/2003 | Harris | |
| 6,521,427 B1 | 2/2003 | Evans | |
| 6,552,167 B1 | 4/2003 | Rose | |
| 6,586,207 B2 | 7/2003 | Tirrell et al. | |
| 6,602,498 B2 | 8/2003 | Shen | |
| 6,608,183 B1 | 8/2003 | Cox | |
| 6,610,281 B2 | 8/2003 | Harris | |
| 6,646,110 B2 | 11/2003 | Nissen et al. | |
| 6,716,626 B1 | 4/2004 | Itoh et al. | |
| 6,927,042 B2 | 8/2005 | Schultz et al. | |
| 7,045,337 B2 * | 5/2006 | Schultz et al. | 435/252.3 |
| 7,083,970 B2 | 8/2006 | Schultz et al. | |
| 7,259,248 B2 | 8/2007 | Itoh et al. | |
| 7,408,047 B1 * | 8/2008 | Thomason et al. | 536/23.1 |
| 7,576,190 B2 * | 8/2009 | Glaesner et al. | 530/399 |
| 7,582,607 B2 * | 9/2009 | Frye et al. | 514/1.1 |
| 7,622,445 B2 * | 11/2009 | Frye et al. | 514/1.1 |
| 7,655,627 B2 * | 2/2010 | Frye et al. | 514/1.1 |
| 2001/0012628 A1 | 8/2001 | Agarwal et al. | |
| 2001/0021763 A1 | 9/2001 | Harris | |
| 2001/0044526 A1 | 11/2001 | Shen | |
| 2001/0056171 A1 | 12/2001 | Kozlowski | |
| 2002/0002250 A1 | 1/2002 | Bentley et al. | |
| 2002/0037949 A1 | 3/2002 | Harris et al. | |
| 2002/0040076 A1 | 4/2002 | Harris et al. | |
| 2002/0042097 A1 | 4/2002 | Tirrell et al. | |
| 2002/0052009 A1 | 5/2002 | Hornauer et al. | |
| 2002/0052430 A1 | 5/2002 | Harris et al. | |
| 2002/0055169 A1 | 5/2002 | Tekamp-Olson | |
| 2002/0072573 A1 | 6/2002 | Bentley et al. | |
| 2002/0081660 A1 | 6/2002 | Swartz et al. | |
| 2002/0082345 A1 | 6/2002 | Kozlowski et al. | |
| 2002/0086939 A1 | 7/2002 | Kozlowski | |
| 2002/0099133 A1 | 7/2002 | Kozlowski | |
| 2002/0156047 A1 | 10/2002 | Zhao | |
| 2002/0164713 A1 | 11/2002 | Itoh et al. | |
| 2003/0023023 A1 | 1/2003 | Harris et al. | |
| 2003/0082575 A1 * | 5/2003 | Schultz et al. | 435/6 |
| 2003/0105224 A1 | 6/2003 | Roberts et al. | |
| 2003/0105275 A1 | 6/2003 | Bentley et al. | |
| 2003/0108885 A1 | 6/2003 | Schultz et al. | |
| 2003/0114647 A1 | 6/2003 | Harris et al. | |
| 2003/0143596 A1 | 7/2003 | Bentley et al. | |
| 2003/0158333 A1 | 8/2003 | Roberts et al. | |
| 2003/0162949 A1 | 8/2003 | Cox | |
| 2003/0208046 A1 | 11/2003 | Hunter et al. | |
| 2003/0220447 A1 | 11/2003 | Harris | |
| 2003/0228274 A1 | 12/2003 | Rose | |
| 2003/0228593 A1 | 12/2003 | Suga et al. | |
| 2004/0001838 A1 | 1/2004 | Zhao et al. | |
| 2004/0013637 A1 | 1/2004 | Bentley et al. | |
| 2004/0115774 A1 * | 6/2004 | Kochendoerfer et al. | 435/69.5 |
| 2004/0138412 A1 | 7/2004 | Botti et al. | |
| 2004/0185494 A1 | 9/2004 | Itoh et al. | |
| 2004/0198637 A1 | 10/2004 | Schultz et al. | |
| 2004/0259780 A1 | 12/2004 | Glasebrook et al. | |
| 2005/0009049 A1 | 1/2005 | Chin et al. | |
| 2005/0037457 A1 | 2/2005 | Itoh et al. | |
| 2005/0085619 A1 | 4/2005 | Wilson et al. | |
| 2005/0170404 A1 | 8/2005 | Cho et al. | |
| 2005/0176631 A1 | 8/2005 | Heuer et al. | |
| 2005/0208522 A1 * | 9/2005 | Jing et al. | 435/6 |
| 2005/0220762 A1 | 10/2005 | Cho et al. | |

| | | | |
|---|---|---|---|
| 2006/0194256 A1 | 8/2006 | Miao et al. | |
| 2006/0217289 A1 | 9/2006 | Miao et al. | |
| 2006/0217532 A1 | 9/2006 | Miao et al. | |

FOREIGN PATENT DOCUMENTS

| | | |
|---|---|---|
| EP | 036 676 A1 | 9/1981 |
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A1 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| JP | 83-118008 A | 1/1985 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | 92/01801 A1 | 2/1992 |
| WO | 92/02628 A1 | 2/1992 |
| WO | 92/16555 A1 | 10/1992 |
| WO | 92/16619 A1 | 10/1992 |
| WO | 93/03173 A1 | 2/1993 |
| WO | 93/15189 A1 | 8/1993 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 7/1997 |
| WO | WO 97/24445 A1 | 7/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | WO 98/44921 A1 | 10/1998 |
| WO | WO 98/45285 A1 | 10/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | WO 99/22735 A1 | 5/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/67291 A1 | 12/1999 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | 01/05956 A2 | 1/2001 |
| WO | WO 01/18172 A2 | 3/2001 |
| WO | 01/27301 A2 | 4/2001 |
| WO | WO 01/25228 A1 | 4/2001 |
| WO | WO 01/36640 A2 | 5/2001 |
| WO | WO 01/38325 A1 | 5/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | WO 02/098902 A2 | 12/2002 |
| WO | WO 03/011213 A2 | 2/2003 |
| WO | WO 03/042204 A1 | 5/2003 |
| WO | WO 03/042235 A2 | 5/2003 |
| WO | WO 03/059270 A2 | 7/2003 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | WO 2004/110472 A2 | 12/2004 |
| WO | 2005/007624 A2 | 1/2005 |
| WO | 2005/007870 A2 | 1/2005 |
| WO | 2005/019415 A2 | 3/2005 |
| WO | 2005/035727 A2 | 4/2005 |
| WO | WO 2005/061712 A1 | 7/2005 |
| WO | 2005/074524 A2 | 8/2005 |
| WO | 2005/074546 A2 | 8/2005 |
| WO | 2005/074650 A2 | 8/2005 |
| WO | WO 2005/072769 A1 | 8/2005 |
| WO | WO 2005/074546 A2 | 8/2005 |
| WO | WO/2005/091944 * | 10/2005 |
| WO | WO 2005/091944 A2 | 10/2005 |
| WO | WO 2005/113606 A2 | 12/2005 |
| WO | WO 2006/028595 A2 | 3/2006 |
| WO | WO 2006/028714 A1 | 3/2006 |
| WO | WO 2006/050247 A2 | 5/2006 |
| WO | WO 2006/065582 A2 | 6/2006 |
| WO | WO 2006/069246 A2 | 6/2006 |
| WO | WO 2006/078463 A2 | 7/2006 |
| WO | WO 2007/070659 A2 | 6/2007 |
| WO | WO 2007/079130 A2 | 7/2007 |

OTHER PUBLICATIONS

Bain, JD, et al. "Biosynthetic site-specific incorporation of a non-natural amino acid into a polypeptide," J. Am Chem Soc 1989;111(20):8013-8014.

Ballance, DJ et al., "Transformation of *Aspergillus nidulans* by the orotidine-5'-phosphate decarboxylase gene of *Neurospora crassa*," Biochem Biophys Res Commun. Apr. 15, 1983;112(1):284-9.

Barany, F. et al., "Genetic disease detection and DNA amplification using cloned thermostable ligase," Proc Natl Acad Sci U S A. Jan. 1, 1991;88(1):189-93.

Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.

Bass, S et al., "Mutant Trp repressors with new DNA-binding specificities," Science (1988) 242:240-245.

Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977; 112:535-542.

Boissel, JP et al., "Erythropoietin structure-function relationships. Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortle, "Strategies and applications of in vitro mutagenesis," Science. Sep. 20, 1985;229 (4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. "Functionalization of Poly(ethylene glycol) and Monomethoxy-Poly(ethylene glycol), "Makromol. Chem. 1981;182:1379-84.

Budisa, N. et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N. et al., "Bioincorporation of telluromethionine into proteins: a promising new approach for X-ray structure analysis of proteins," J Mol Biol. Jul. 25, 1997;270(4):616-23.

Budisa, N. et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al. "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124 (31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11): 1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987; 238(4832):1401-1403.

Cornish, VW, et al., "Site-Specific Protein Modification Using a Ketone Handle," J. Am. Chem. Soc. 1996; 118 (34):8150-8151.

Cornish, VW et al., "Probing Protein Structure and Function with an Expanded Genetic Code,"Angew Chem Int Ed Engl,1995;34(6):621-33.

Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.

Cregg, JM et al., "*Pichia pastoris* as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of *Kluyveromyces fragilis*," J Bacteriol. Jun. 1984;158(3):1165-7.

Dawson, P. E. and S. B. H. Kent, "Synthesis of native proteins by chemical ligation," Annu. Rev. Biochem. 2000; 69:923-60.

De Boer, HA et al., "The tac promoter: a functional hybrid derived from the trp and lac promoters," Proc Natl Acad Sci U S A. Jan. 1983;80(1):21-5.

De Louvencourt, L et al., "Transformation of *Kluyveromyces lactis* by killer plasmid DNA," J Bacteriol. May 1983;154(2):737-42.

Van Hest, J. C. et al., "Efficient Incorporation of Unsaturated Methionine Analogues into Proteins in Vivo," J. Am. Chem. Soc2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985; 11(2):141-52.

Vlak, JM et al., "Functional studies on the p10 gene of Autographa californica nuclear polyhedrosis virus using a recombinant expressing a p10-beta-galactosidase fusion gene," J Gen Virol. Apr. 1988;69 (Pt 4):765-76.

Wang, Q., et al., "Bioconjugation by Copper(I)-Catalyzed Azide-Alkyne [3 + 2] Cycloaddition," J. Am. Chem. Soc. 2003; 125(11):3192-3193.

Wang, L. et al., "Addition of the keto functional group to the genetic code of *Escherichia coli*," Proc. Natl. Acad. Sci. (2003); 100(1):56-61.

Wang, L et al., "Expanding the genetic code of *Escherichia coli*," Science. Apr. 20, 2001;292(5516):498-500.

Zoller, MJ & Smith M, "Oligonucleotide-directed mutagenesis: a simple method using two oligonucleotide primers and a single-stranded DNA template," Methods Enzymol. 1987;154:329-50.

Mehl, RA et al. "Generation of a bacterium with a 21 amino acid genetic code," J Am Chem Soc. Jan. 29, 2003;125 (4):935-9.

Santoro, SW et al. "An efficient system for the evolution of aminoacyl-tRNA synthetase specificity," Nat Biotechnol. Oct. 2002;20(10):1044-8. Epub Sep. 16, 2002.

Caliceti, P. et FM Veronese. "Pharmacokinetic and biodistribution properties of poly(ethylene glycol)-protein conjugates," Adv Drug Deliv Rev. Sep. 26, 2003;55(10):1261-77.

Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Bioeng Nov. 20, 1999;65(4):382-8.
Kharitonekov et al., "FGF-21 as a novel metabolic regulator" J. Clin. Investigation, Jun. 1, 2005, 115(6):1627-1635.
Kharitonekov et al., "The Metabolic State of Diabetic Monkeys is Regulated by Fibroblast Growth Factor-21" Endocrinology, Feb. 1, 2007, 148(2):774-781.
Moyers et al., "Molecular determinants of FGF-21 activity synergy and cross-talk with PPARgamma signaling", J Cellular Physiology, Jan. 1, 2007, 210(1):1-6.
Nishimura et al. "Identification of a Novel FGF, FGF-21, Preferentially Express in the Liver", Biochimica et Biophysica Acta, Jan. 1, 2000, 1492(1):, 203-206.
Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996;7(1):38-44.
Gu, Z et al. "Chromatographic methods for the isolation of, and refolding of proteins from, *Escherichia coli* inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6 (6):809-15.
Lilie, H et al. "Advances in refolding of proteins produced in *E. coli*," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185 (2):129-88.
Tondelli, L. et al. "Poly(ethylene Glycol) Imidazolyl Formates as Oligomeric Drug-Binding Matrices," J. Controlled Release 1985;1(4):251-7.
Tornoe, CW et al. "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.
Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.
Tschumper, G. et al., "Sequence of a yeast DNA fragment containing a chromosomal replicator and the TRP1 gene," GENE 1980; 10(2):157-66.
Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.
Van Den Berg, JA et al., "Kluyveromyces as a host for heterologous gene expression: expression and secretion of prochymosin," Biotechnology (N Y). Feb. 1990;8(2):135-9.
Van Hest, JC and DA Tirrell, "Efficient introduction of alkene functionality into proteins in vivo," FEBS Lett. May 22, 1998;428(1-2):68-70.
Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.
Deiters, A., et al., "Adding Amino Acids with Novel Reactivity to the Genetic Code of *Saccharomyces cerevisiae*," J. Am. Chem. Soc. 2003; 125(39):11782-11783.
Delgado, C et al., "The uses and properties of PEG-linked proteins," Crit Rev Ther Drug Carrier Syst. 1992;9 (3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.
Dougherty, DA. "Unnatural amino acids as probes of protein structure and function," Curr Opin Chem Biol. Dec. 2000;4(6):645-52.
Duewel, H et al., "Incorporation of trifluoromethionine into a phage lysozyme: implications and a new marker for use in protein 19F NMR," Biochemistry. Mar. 18, 1997;36(11):3404-16.
Eghtedarzadeh MK & S Henikoff "Use of oligonucleotides to generate large deletions" Nucleic Acids Res. Jun. 25, 1986;14(12):5115.
Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Elliott, S et al., "Yeast-derived recombinant human insulin-like growth factor I: production, purification, and structural characterization," J Protein Chem. Feb. 1990;9(1):95-104.
Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.
Ellman, JA, et al. "Site-specific incorporation of novel backbone structures into proteins," Science. Jan. 10, 1992;255 (5041):197-200.
England, P. M., et al., "Backbone mutations in transmembrane domains of a ligand-gated ion channel: implications for the mechanism of gating," Cell. Jan. 8, 1999;96(1):89-98.
Eppstein et al., "Biological Activity of Liposome-Encapsulated Murine Interferon is Mediated by a Cell Membrane Receptor," Proc. Natl. Acad. Sci. U.S.A.(1985); 82: 3688-3692.
Fieschko, JC et al., "Controlled expression and purification of human immune interferon from high-cell-density fermentations of *Saccharomyces cerevisiae*," Biotech. Bioeng. (1987) 29(9):1113-21.
Forster, AC et al., "Programming peptidomimetic syntheses by translating genetic codes designed de novo," Proc Natl Acad Sci U S A. May 27, 2003;100(11):6353-7. Epub May 16, 2003.
Frankel, A et al., "Encodamers: unnatural peptide oligomers encoded in RNA," Chem Biol. Nov. 2003;10 (11):1043-50.
Fraser, MJ et al., "Expression of eucaryotic genes in insect cell cultures," In Vitro Cell. Dev. Biol. 1989; 25:225-235.
Friedman, O.M. & R. Chatterrji. "Synthesis of Derivatives of Glutamine as Model Substrates for Anti-Tumor Agents," J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988;16(14B):6987-99.
Fromm, M. et al., "Expression of Genes Transferred into Monocot and Dicot Plant Cells by Electroporation," Proc. Natl. Acad. Sci. USA (1985) 82:5824-8.
Furter, R. "Expansion of the genetic code: site-directed p-fluorophenylalanine incorporation in *Escherichia coli*," Protein Sci. Feb. 1998;7(2):419-26.
Gaertner, HF et al., "Construction of protein analogues by site-specific condensation of unprotected fragments," Bioconjug Chem. May-Jun. 1992;3(3):262-8.
Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.
Gallivan, JP et al., "Site-specific incorporation of biotinylated amino acids to identify surface-exposed residues in integral membrane proteins," Chem Biol. Oct. 1997;4(10):739-49.
Gellissen, G et al., "Heterologous protein production in yeast," Antonie Van Leeuwenhoek. Aug. 1992;62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.
Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.
Gleeson, MA et al., "Transformation of the methylotrophic yeast hansenula polymorphica," J. Gen. Microbiol. (1986) 132:3459-3465.
Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8 (18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34 (9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25 (3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Natl Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.

Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic Code," J. Am. Chem. Soc. 1999; 121(51):12194-12195.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with Autographa californica nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307 (3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide-1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. R and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Yelton, MM et al., "Transformation of *Aspergillus nidulans* by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9 (3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42 (22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10 (20):6487-500.

Zoller, MJ & M. Smith, "Oligonucleotide-directed mutagenesis of DNA fragments cloned into M13 vectors" Methods Enzymol. 1983;100:468-500.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271 (39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast Hansenula polymorpha by autonomous replication and integration vectors," Mol. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.

Sayers, JR, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase A Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif Apr. 1998;12(3):323-30.

Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N. et al., "Efficient introduction of aryl bromide functionality into proteins in vivo," FEBS Lett. Feb. 4, 2000;467 (1):37-40.

Shimatake, H et M Rosenberg, "Purified gamma regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254 (5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in *Saccharomyces cerevisiae*," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: in vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111 (21):8322-8323.

Tabor, S et CC Richardson, "A bacteriophage T7 RNA polymerase/promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in *Aspergillus nidulans*," Gene. Dec. 1983;26(2-3):205-21.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease a with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81 (2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha—amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of gamma-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327 (6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts *Candida maltosa* and *Pichia guilliermondii*," J. Basic Microbiol. 1985; 25:141-4.

Kurtz et al., "Integrative transformation of *Candida albicans*, using a cloned Candida ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules, " Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et BH Robinson, "Approaches to DNA mutagenesis: an overview" Anal Biochem. Dec. 15, 1997;254 (2):157-78.

Wang, L & PG Schultz, "Expanding the genetic code," Chem Commun (Camb). Jan. 7, 2002;1:1-11.

Weissmann, C. "The cloning of interferon and other mistakes." in Interferon 3 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," Nature (1986) 321(6072):718.

Lohse et al., "Ribozyme-catalysed amino-acid transfer reactions", Nature (1996) 381:442-444.

Lu et al. "Site-specific incorporation of a phosphotyrosine mimetic reveals a role for tyrosine phosphorylation of SHP-2 in cell signaling" Mol Cell. (2001) 8(4):759-769.

Lyons et al., "Basic fibroblast growth factor promotes in vivo cerebral angiogenesis in chronic forebrain ischemia" Brain Res. (1991) 558:315-320.

Maggs et al., "Metabolic effects of troglitazone monotherapy in type 2 diabetes mellitus. A randomized, double-blind, placebo-controlled trial" Ann. Intern. Med. (1998) 128:176-85.

Mannucci et al., "Effect of metformin on glucagon-like peptide 1 (GLP-1) and leptin levels in obese nondiabetic subjects", Diabetes Care. (2001) 24(3):489-94.

Mattson et al., "Neurotrophic factor mediated protection from excitotoxicity and disturbances in calcium and free radical metabolism" Semin. Neurosci. (1993) 5:295-307.

McCorkle et al., "RNA's as Catalysts", Concepts Biochem. (1987) 64:221-226.

McKeehan et al., "The heparin sulfate-fibroblast growth factor family: diversity of structure and function.", Prog. Nucleic Acid Res. Mol. Biol. (1998) 59:135-176.

McWhirter et al., "A novel fibroblast growth factor gene expressed in the developing nervous system is a downstream target of the chimeric homeodomain oncoprotein E2A-Pbx1", Development (1997) 124:3221-3232.

Milleret et al., "Electron microscopic analysis of in vitro transposition intermediates of bacteriophage Mu DNA", Gene (1986) 48(1):101-8.

Mimura et al., "Effects of a new oral hypoglycaemic agent (CS-045) on metabolic abnormalities and insulin resistance in type 2 diabetes", Diabetes Med. (1994) 11:685-91.

Miyake et al., "Structure and expression of a novel member, FGF-16, on the fibroblast growth factor family", Biochem. Biophys. Res. Commun. (1998) 243:148-152.

Murakami et al., "Using a solid-phase ribozyme aminoacylation system to reprogram the genetic code", Chem Biol. (2003) 10(11):1077-84.

Needham-VanDevanter et al., "Characterization of an adduct between CC-1065 and a defined oligodeoxynucleotide duplex", Nucleic Acids Res., (1984) 12:6159-6168.

Nishimura et al., "Structure and expression of a novel human FGF, FGF-19, expressed in the fetal brain", Biochim. Biophys. Acta (1999) 1444:148-151.

Nolan et al., "Improvement in glucose tolerance and insulin resistance in obese subjects treated with troglitazone", New Eng. J. Med (1994) 331:1188-93.

Offord, "Protein engineering by chemical means?", Protein Eng., (1987) 1(3):151-157.

Ohbayashi et al., "Structure and expression of the mRNA encoding a novel fibroblast growth factor, FGF-18", J. Biol. Chem. (1998) 273:18161-18164.

Ohno et al., "Co-expression of yeast amber suppressor tRNATyr and tyrosyl-tRNA synthetase in *Escherichia coli*: possibility to expand the genetic code", J. Biochem. (Tokyo, Jpn.) (1998) 124:1065-1068.

Ohuchi et al., "The mesenchymal factor, FGF10, initiates and maintains the outgrowth of the chick limb bud through interaction with FGF8, an apical ectodermal factor", Development (1997) 124:2235-2244.

Olney, "Brain lesions, obesity, and other disturbances in mice treated with monosodium glutamate.", Science (1969) 164:719.

Ornitz et al., "Fibroblast growth factors", Genome Biol. (2001) 2(3):REVIEWS3005.

Ozawa et al., "Expression of the fibroblast growth factor family and their receptor family genes during mouse brain development", Mol. Brain Res. (1996) 41:279-288.

Pastrnak et al., "A New Orthogonal Suppressor tRNA/Aminoacyl-tRNA Synthetase Pair for Evolving an Organism with an Expanded Genetic Code", Helv. Chim. Acta (2000) 83:2277-2286.

Pearson et al., "The importance of silica type for reverse-phase protein separations", Anal Biochem. (1982) 124:217-230.

Peng et al., "Rapid purification of recombinant baculovirus using fluorescence-activated cell sorting", BioTechniques (1993) 14(2):274.

Pesenti et al., "Suramin prevents neovascularisation and tumour growth through blocking of basic fibroblast growth factor activity", British Journal of Cancer (1992) 66:367-372.

Plotnikov et al. "Structural basis for FGF receptor dimerization and activation", Cell. (1999) 98(5):641-650.

Reich-Slotky et al., "Chimeric molecules between keratinocyte growth factor and basic fibroblast growth factor define domains that confer receptor binding specificities", J. Biol. Chem. (1995) 270:29813-29818.

Reuss et al., "Fibroblast growth factors and their receptors in the central nervous system", Cell Tissue Res. (2003) 313:139-157.

Robertson et al., "A General and Efficient Route for Chemical Aminoacylation of Transfer RNAs", J. Am. Chem. Soc. (1991) 113:2722.

Sakamoto et al., "Site-specific incorporation of an unnatural amino acid into proteins in mammalian cells", Nucleic Acids Res. (2002) 30:4692-4699.

Saks et al., "An engineered Tetrahymena tRNAGln for in vivo incorporation of unnatural amino acids into proteins by nonsense suppression", J Biol Chem (1996) 271(38):23169-75.

Scheen et al., "Troglitazone: antihyperglycemic activity and potential role in the treatment of type 2 diabetes", Diabetes Care, (1999) 22(9):1568-1577.

Schumacher et al., "Induction of neoangiogenesis in ischemic myocardium by human growth factors: first clinical results of a new treatment of coronary heart disease", Circulation (1998) 97: 645-650.

Schwartz et al., "Effect of troglitazone in insulin-treated patients with type II diabetes mellitus. Troglitazone and Exogenous Insulin Study Group", New Engl. J. Med. (1998) 338:861-66.

Shafrir et al. (2002). "Regulation of muscle malonyl-CoA levels in the nutritionally insulin-resistant desert gerbil, *Psammomys obesus*", Diabetes Metab Res Rev (2002) 18(3): 217-23.

Smallwood et al., "Fibroblast growth factor (FGF) homologous factors: new members of the FGF family implicated in nervous system development", PNAS USA (1996) 93:9850-9857.

Smith et al., "Production of human beta interferon in insect cells infected with a baculovirus expression vector", Mol. Cell. Biol. (1983) 3:2156.

Spencer et al., "Rabbit liver growth hormone receptor and serum binding protein. Purification, characterization, and sequence", J. Biol. Chem., (1988) 263:7862-7867.

Tanaka et al., "Human androgen-induced growth factor in prostate and breast cancer cells: its molecular cloning and growth properties", FEBS Lett. (1995) 363:226-230/PNAS (1992) 89:8928-8932.

Tanaka et al., "Basic fibroblast growth factor increases regional cerebral blood flow and reduces infarct size after experimental ischemia in a rat model", Stroke (1995) 26:2154-2159.

Tilkins et al., "Transfection of Mammalian and Invertebrate Cells Using Cationic Lipids", Cell Biology: A Laboratory Handbook (1998) 4:145-154.

Truett et al., "Rat obesity gene fatty (fa) maps to chromosome 5: evidence for homology with the mouse gene diabetes (db)", PNAS USA (1991) 88:7806.

Uhl et al., "Basic fibroblast growth factor accelerates wound healing in chronically ischaemic tissue", Br. J. Surg. (1993) 80:977-980.

Van den Berghe et al., "Intensive insulin therapy in the critically ill patients", N. Engl J Med., (2001) 345(19):1359.

Wilke et al., Expression of fibroblast growth factor receptors (FGFR1, FGFR2, FGFR3) in the developing head and face, Dev. Dynam. (1997) 210:41-52.

Wilkie et al., "Functions of fibroblast growth factors and their receptors" Current Biology, (1995) 5:500-507.

Yoshida et al., "Characterization of the hst-1 gene and its product", Ann. NY Acad. Sci. (1991) 638:27-37.

Zander, "Additive glucose-lowering effects of glucagon-like peptide-1 and metformin in type 2 diabetes", Diabetes Care. (2001) 24(4):720-5.

Ahrén et al., "Inhibition of dipeptidyl peptidase IV improves metabolic control over a 4-week study period in type 2 diabetes", Diabetes Care, (2002) 25(5):869-75.

Arakawa et al., "Protein—solvent interactions in pharmaceutical formulations", Pharm. Res. (1991) 8(3):285-291.

Bailey, "Biguanides and NIDDM", Diabetes Care (1992) 15:755-72.

Bain et al., "Ribosome-mediated incorporation of a non-standard amino acid into a peptide through expansion of the genetic code", Nature (1992) 356(6369):537-9.

Baird et al., "The fibroblast growth factor family", Cancer Cells. (1991) 3(6):239-43.

Beaucage et al., "Deoxynucleoside Phosphoramidites—A New Class of Key Intermediates for Deoxypolynucleotide Synthesis", Tetrahedron Letts. (1981) 22(20):1859-1862.

Belluardo et al., "Comparative localization of fibroblast growth factor receptor-1, -2, and -3 mRNAs in the rat brain: in situ hybridization analysis", J Comp Neurol. (1997) 379(2):226-46.

Berkowitz et al., "Effect of troglitazone on insulin sensitivity and pancreatic beta-cell function in women at high risk for NIDDM", Diabetes (1996) 45(11):1572-9.

Biagini et al., "The concept of astrocyte-kinetic drug in the treatment of neurodegenerative diseases: evidence for L-deprenyl-induced activation of reactive astrocytes" Neurochem Int. (1994) 25(1):17-22.

Bray, "Drug treatment of obesity", Am J Clin Nutr. (1992) 55(2 Suppl):538S-544S.

Broadhead et al., "The Spray Drying of Pharmaceuticals," Drug Dev. Ind. Pharm, (1992) 18(11/12):1169-1206.

Burgess et al., "The Heparin Binding (Fibroblast) Growth Factor Family of Proteins", Annu. Rev. Biochem. (1989) 58:575-606.

Cameron et al., "Effects of monosodium glutamate-induced obesity in mice on carbohydrate metabolism in insulin secretion", Clin Exp Pharmacol Physiol. (1978) 5(1):41-51.

Cech, "The chemistry of self-splicing RNA and RNA enzymes", Science. Jun. 19, 1987;236(4808):1532-9.

Clissod et al., "Acarbose: A Preliminary Review of its Pharmacodynamic and Pharmacokinetic Properties, and Therapeutic Potential", Drugs (1988) 35:214-23.

Coulier et al., "The FGF6 gene within the FGF multigene family", Ann N Y Acad Sci. 1991;638:53-61.

Coleman et al., "Fat (fat) and tubby (tub): two autosomal recessive mutations causing obesity syndromes in the mouse", J Hered. (1990) 81(6):424-7.

Coleman, "Other Potentially Useful Rodents as Models for the Study of Human Diabetes Mellitus", Diabetes, (1982) 31 (Suppl 1 Pt 2):24-5.

Kurosu et al., "Regulation of fibroblast growth factor-23 signaling by Klotho", J Biol Chem. (2006) 281(10):6120-3.

Crossley et al., "The mouse Fgf8 gene encodes a family of polypeptides and is expressed in regions that direct outgrowth and patterning in the developing embryo", Development, (1995) 121(2):439-51.

Dawson et al., "Synthesis of native proteins by chemical ligation", Annu Rev Biochem. (2000) 69:923-60.

DeFronzo et al., "Efficacy of metformin in patients with non-insulin-dependent diabetes mellitus. The Multicenter Metformin Study Group", N Engl J Med. (1995) 333(9):541-9.

Dickson et al., "Expression, processing, and properties of int-2", Ann N Y Acad Sci. (1991) 638:18-26.

Dietrich et al., "Posttreatment with intravenous basic fibroblast growth factor reduces histopathological damage following fluid-percussion brain injury in rats" J Neurotrauma (1996) 13(6): 309-16.

Drummond et al., "Liposomal drug delivery systems for cancer therapy", Teicher B (ed): Cancer Drug Discovery and Development (2002) 191-213.

Edwards et al., "A bacterial amber suppressor in *Saccharomyces cerevisiae* is selectively recognized by a bacterial aminoacyl-tRNA synthetase", Mol Cell Biol. (1990) 10(4):1633-41.

Friedman et al., "Tackling a weighty problem", Cell (1992) 69:217-220.

Friesen et al., "The regulation of baculovirus gene expression" Curr Top Microbiol Immunol (1986) 131: 31-49.

Garber et al., "Efficacy of metformin in type II diabetes: results of a double-blind, placebo-controlled, dose-response trial", Am J. Med. (1997) 102:491-97.

Gemel et al., "Structure and sequence of human FGF8", Genomics (1996) 35:253-257.

Ghosh et al., "Molecular cloning and characterization of human FGF8 alternative messenger RNA forms", Cell Growth and Differentiation (1996) 7(10):1425-1434.

Giugliano et al., "Metformin improves glucose, lipid metabolism, and reduces blood pressure in hypertensive, obese women", Diabetes Care (1993) 16:1387-90.

Goldfarb et al., "Expression and possible functions of the FGF-5 gene", Ann. NY Acad. Sci (1991) 638:38-52.

Harmer et al., "The crystal structure of fibroblast growth factor (FGF) 19 reveals novel features of the FGF family and offers a structural basis for its unusual receptor affinity", Biochemistry (2004) 43:629-640.

Hecht et al., "'Chemical aminoacylation' of tRNA's", J Biol Chem. (1978) 253(13):4517-20.

Hecht, "Probing the synthetic capabilities of a center of biochemical catalysis", Acc. Chem. Res. (1992) 25(12):545-552.

Heckler et al., "Ribosomal binding and dipeptide formation by misacylated tRNA(Phe),S", Biochemistry. (1988) 27 (19)1254-62.

Hinke et al., "Metformin effects on dipeptidylpeptidase IV degradation of glucagon-like peptide-1", Biochem Biophys Res Commun. (2002) 291(5):1302-8.

Hoshikawa et al., "Structure and expression of a novel fibroblast growth factor, FGF-17, preferentially expressed in the embryonic brain", Biochem Biophys Res Commun. (1998) 244(1):187-91.

Hubinger et al., "The effect of etomoxir on insulin sensitivity in type 2 diabetic patients."Hormone Metab. Res. (1992) 24:115-18.

Illangakekare et al., "Aminoacyl-RNA Synthesis Catalyzed by an RNA", Science (1995) 267:643-647.

Inzucchi et al., "Efficacy and metabolic effects of metformin and troglitazone in type II diabetes mellitus.", New. Eng. J. Med. (1998) 338:867-72.

Itakura et al., "Expression in *Escherichia coli* of a chemically synthesized gene for the hormone somatostatin", Science (1997) 198:1056-1063.

Jung et al., "The management of obesity.", Clinical Endocrinology (199) 35:11-20.

Katoh et al., "FGF signaling network in the gastrointestinal tract (review)." Intl J. Oncology (2006) 29:163-168.

Kawamata et al., "Intracisternal basic fibroblast growth factor enhances functional recovery and up-regulates the expression of a molecular marker of neuronal sprouting following focal cerebral infarction."Proc.Natl. Acad. Sci.(1997) 94(15):8179-84.

Kourouklis et al., "Programmable ribozymes for mischarging tRNA with nonnatural amino acids and their applications to translation", Methods (2005) 36:239-4.

Kowal et al., "Exploiting unassigned codons in *Micrococcus luteus* for tRNA-based amino acid mutagenesis"Nucl. Acid. Res. (1997) 25:4685.

Kowal et al., "Twenty-first aminoacyl-tRNA synthetase-suppressor tRNA pairs for possible use in site-specific incorporation of amino acid analogues into proteins in eukaryotes and in eubacteria", PNAS. USA. (2001) 98:2268-2273.

Kumar et al., "Troglitazone, an insulin action enhancer, improves metabolic control in NIDDM patients" Diabetologia (1996) 39:701-709.

\* cited by examiner

Figure 7a
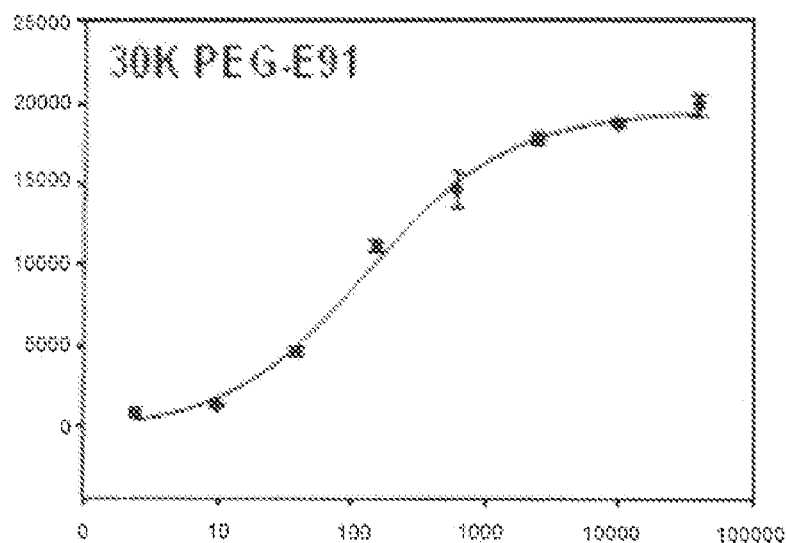
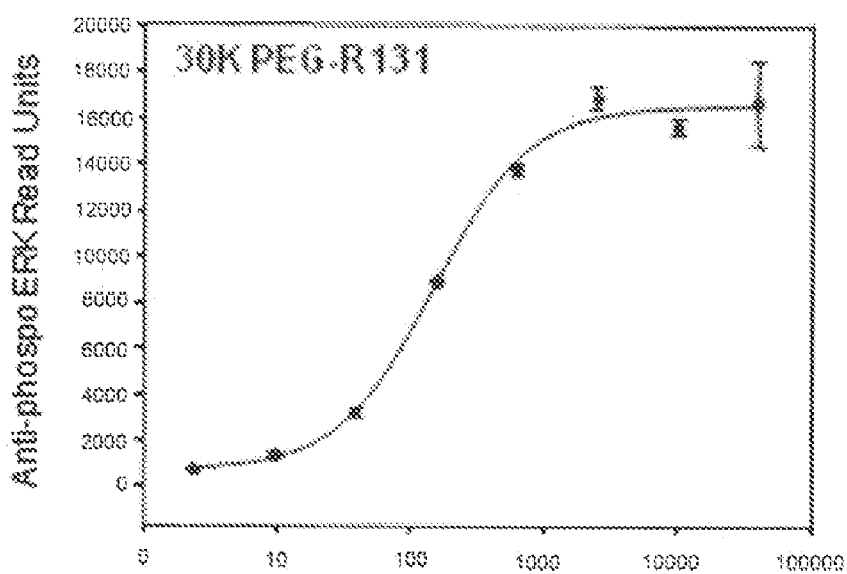

Figure 7b

| Protein | Fold loss of activity |
|---|---|
| HIS-FGF21 | 1 |
| 30KPEG-E91 | 4 |
| 30KPEG R131 | 4 |
| 30KPEG-Q108 | 6 |
| 30KPEG R77 | 6 |
| 30KPEG-R72 | 14 |
| 30KPEG H87 | 19 |
| 30KPEG L86 | 10 |
| 30KPEG R126 | 11 |
| 30KPEG E110 | 16 |
| 30KPEG Y83 | 17 |
| 30KPEG-P146 | 22 |
| 30KPEG R135 | 26 |
| 30KPEG R96 | 47 |
| 30KPEG R36 | 47 |
| 30KPEG Y104 | No agonist activity |
| 30KPEG L99 | No agonist activity |
| 30KPEG K56 | No agonist activity |
| 30KPEG Y22 | No agonist activity |

Expression of Untagged FGF-21

SDS-PAGE analysis of FGF-21 expressed in *E.coli*.

Purification: Untagged FGF-21-Y83pAF

Purification of untagged FGF-21-Y83pAF. A. Chromatogram of Q HP elution. B. SDS-PAGE analysis of FGF-21-Y83pAF elution fractions. C. SDS-PAGE analysis of FGF-21-Y83pAF Q HP elution pool.

N-His WT FGF21

N-His WT FGF21
Best-fit values
    Slope     348.5 ± 91.22
    Y-intercept when X=0.0  11.55 ± 30.17
    X-intercept when Y=0.0  -0.03315
    1/slope    0.002870
95% Confidence Intervals
    Slope     145.2 to 551.7
    Y-intercept when X=0.0  -55.67 to 78.77
    X-intercept when Y=0.0  -0.5647 to 0.1635
Goodness of Fit
    $r^2$     0.5934
    Sy.x      49.27

N-His WT FGF21
Best-fit values
 Slope     1079 ± 194.1
 Y-intercept when X=0.0  4.274 ± 64.19
 X-intercept when Y=0.0  -0.003959
 1/slope    0.0009265
95% Confidence Intervals
 Slope     646.9 to 1512
 Y-intercept when X=0.0  -138.7 to 147.3
 X-intercept when Y=0.0  -0.2567 to 0.1357
Goodness of Fit
 $r^2$     0.7556
 Sy.x     104.8

Figure 14
Periplasmic-derived WT FGF21
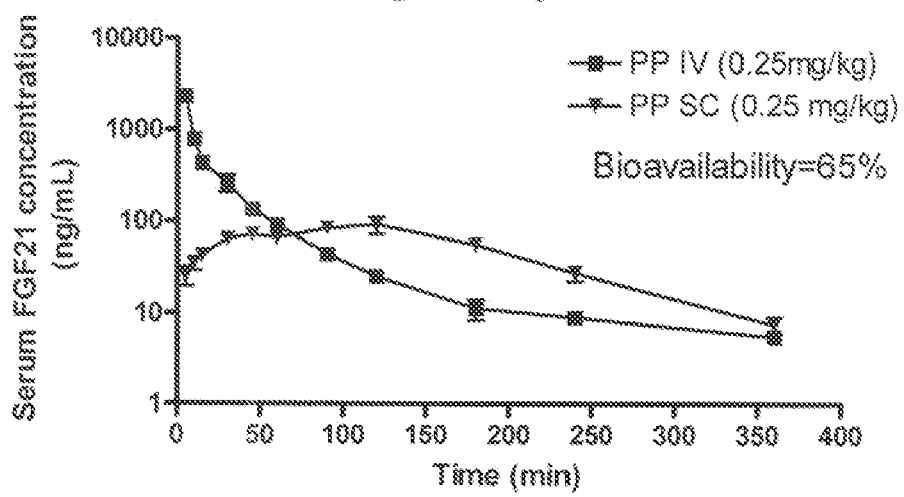
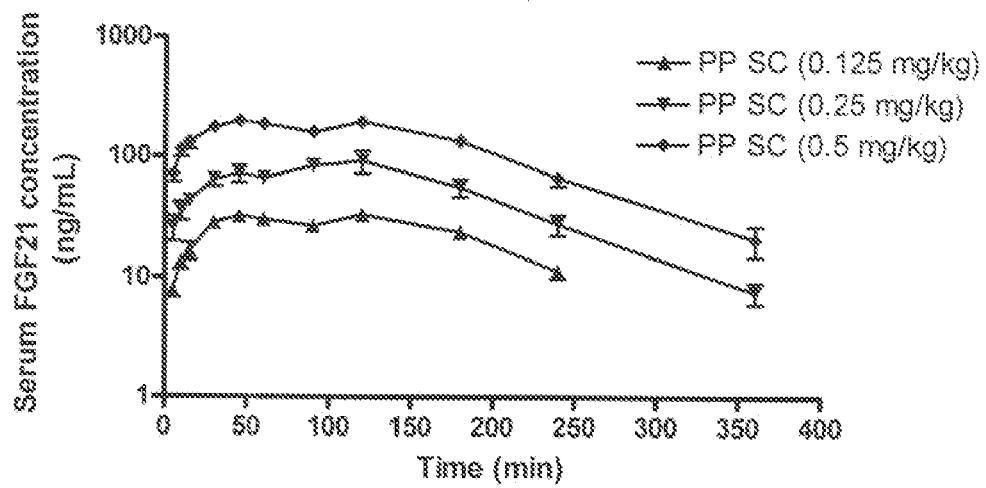

FGF-R-003
WT head-to-head comparison

FGF-R-003
WT head-to-head comparison

FGF-R-004 PEG PK part 1

*Diminished Bioavailability

FGF-R-004 PEG PK part 1

PEG PK comparison part 2

Figure 25 pVK10 FGF21 Sequence

Pharmacokinetic evaluation of Wild-type (WT) N-His 6 tagged FGF21

Figure 27
A.
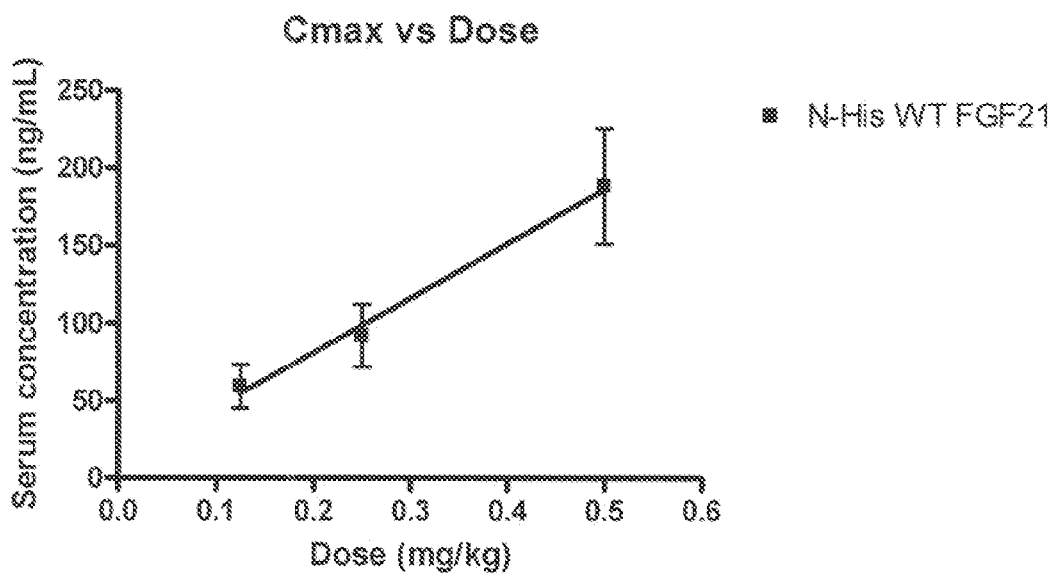
B.
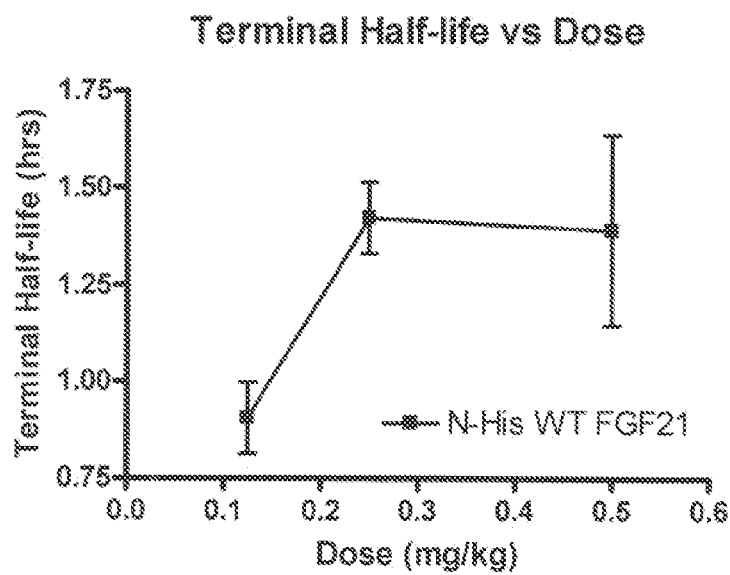

C.

Figure 28
A.
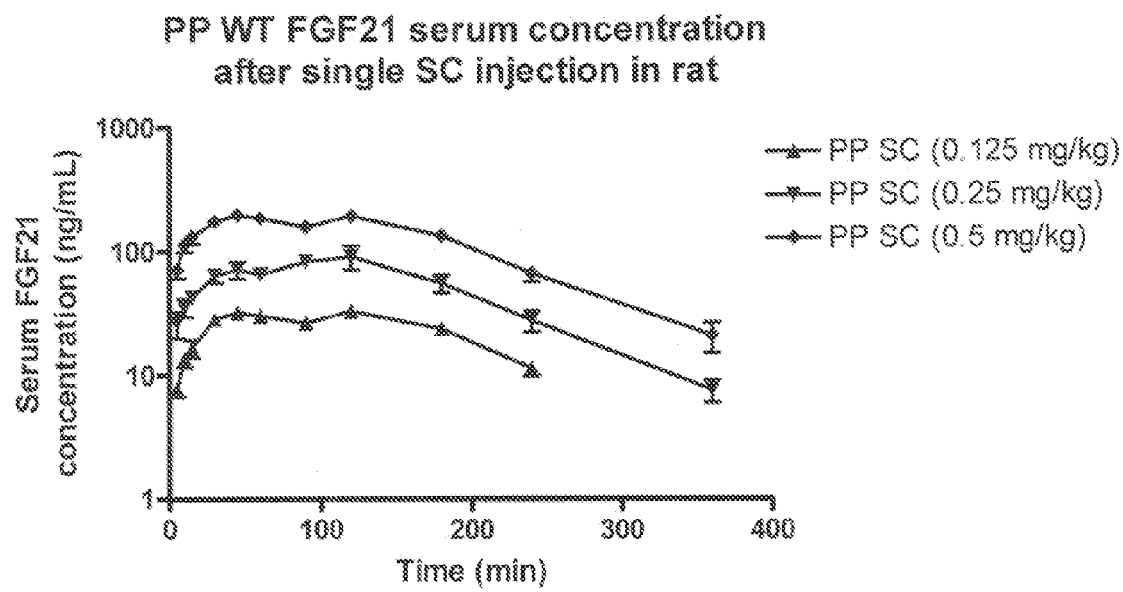
B.
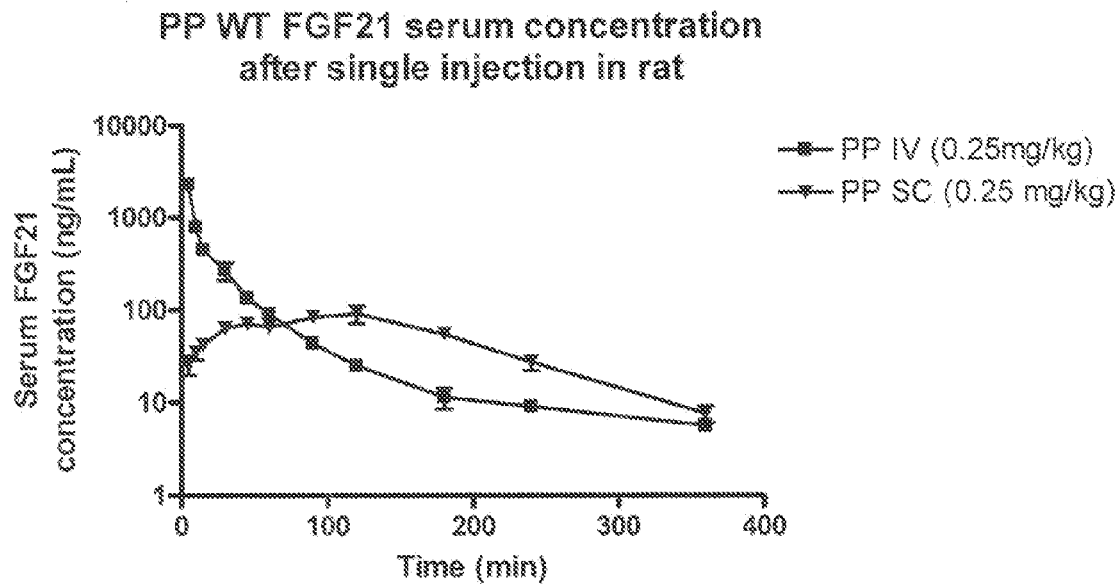

Figure 29
A.
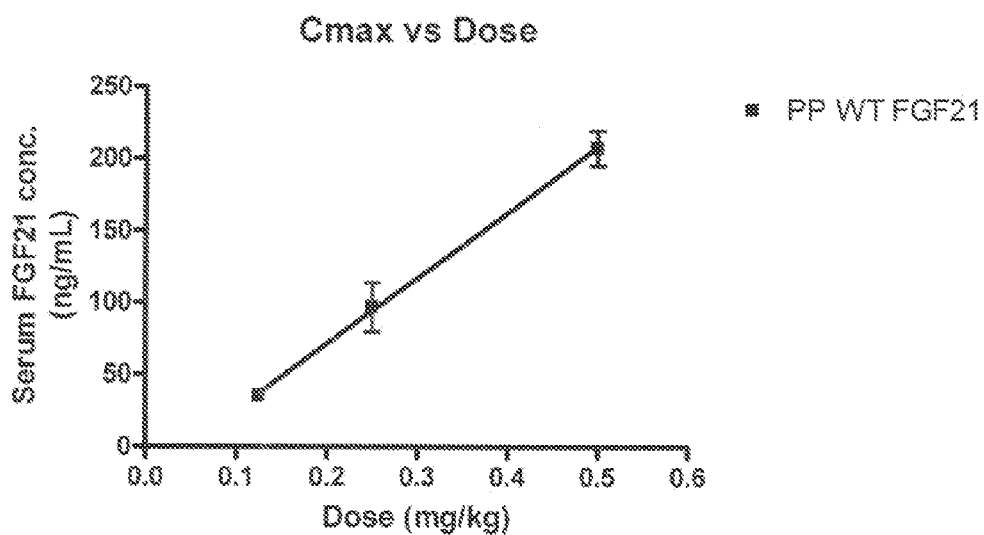
B.
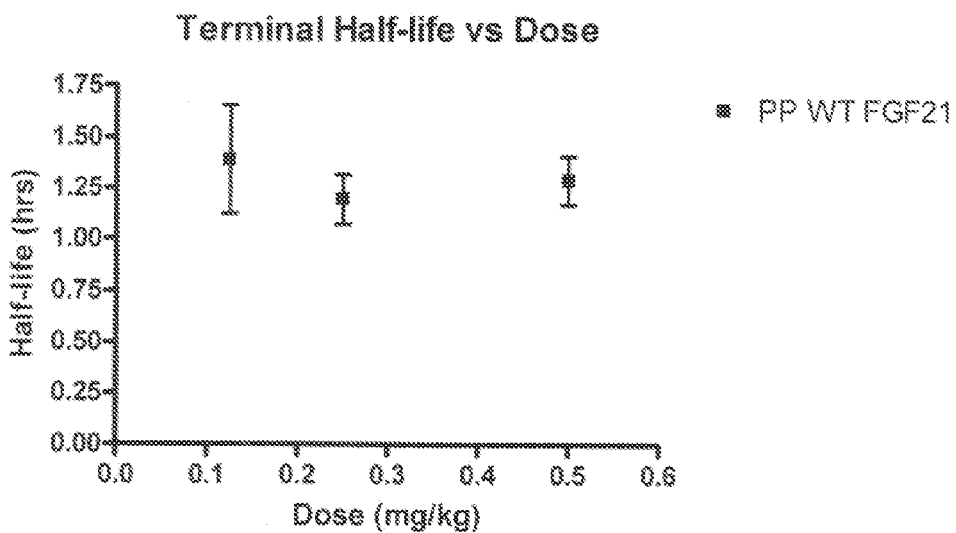

C.

A.

C.

Secretion of FGF21 in e.coli

MODIFIED FGF-21 POLYPEPTIDES AND THEIR USES

FIELD OF THE INVENTION

This invention relates to FGF-21 polypeptides optionally modified with at least one non-naturally-encoded amino acid.

BACKGROUND OF THE INVENTION

Fibroblast growth factors are large polypeptides widely expressed in developing and adult tissues (Baird et al., Cancer Cells, 3:239-243, 1991) and play crucial roles in multiple physiological functions including angiogenesis, mitogenesis, pattern formation, cellular differentiation, metabolic regulation and repair of tissue injury (McKeehan et al., Prog. Nucleic Acid Res. Mol. Biol. 59:135-176, 1998; Burgess, W. H. et al., Annu. Rev. Biochem. 58:575-606 (1989). The prototypic fibroblast growth factors (FGFs), FGF-1 and FGF-2, were originally isolated from brain and pituitary as mitogens for fibroblasts. FGF-3 was identified to be a common target for activation by the mouse mammary tumor virus (Dickson et al., Ann. N.Y. Acad. Sci. 638:18-26 (1991); FGF-4 to FGF-6 were identified as oncogene products (Yoshida et al., Ann. NY Acad. Sci. 638:27-37 (1991); Goldfarb et al., Ann. NY Acad. Sci 638:38-52 (1991); Coulier et al., Ann. NY Acad. Sci. 638:53-61 (1991)). FGF-10 was identified from rat lung by homology-based polymerase chain reaction (PCR) (Yamasaki et al., J. Biol. Chem. 271:15918-15921 (1996)). FGF-11 to FGF-14 (FGF homologous factors (FHFs) 1 to 4) were identified from human retina by a combination of random cDNA sequencing, database searches and homology-based PCR (Smallwood et al., Proc. Natl. Acad. Sci. USA 93:9850-9857 (1996)). FGF-15 was identified as a downstream target of a chimeric homeodomain oncoprotein (McWhirter et al., Development 124:3221-3232 (1997)). FGF-16, FGF-17, and FGF-18 were identified from rat heart and embryos by homology-based PCR, respectively (Miyake et al., Biochem. Biophys. Res. Commun. 243:148-152 (1998); Hoshikawa et al. Biochem. Biophys. Res. Commun. 244:187-191 (1998); Ohbayashi et al., J. Biol. Chem. 273: 18161-18164 (1998)). FGF-19 was identified from human fetal brain by database search (Nishimura et al., Biochim. Biophys. Acta 1444:148-151 (1999)). They have a conserved ~120-amino acid residue core with ~30 to 60% amino acid identity.

Animal models, overexpression, and analysis of naturally occurring mutations implicate fibroblast growth factors and their receptors in a wide range of diseases (e.g. Wilkie et al., Current Biology, (1995) 5:500-507; Pugh-Humphreys et al, In: The Cytokine Handbook, A. Thomson ed, 2nd edition, Academic Press, Harcourt Brace & co. publishers, London, pp 525-566) suggesting that regulation of activity could be used for treatment. For example, inhibition of fibroblast growth factor-2 by the compound Suramin prevents neovascularisation and tumor growth in mice (Pesenti et al., British Journal of Cancer, 66:367-372). Fibroblast growth factors also function in angiogenesis (Lyons, M. K., et al., Brain Res. (1991) 558:315-320), wound healing (Uhl, E., et al., Br. J. Surg. (1993) 80:977-980, 1993), astrogliosis, glial cell proliferation and differentiation (Biagini, G. et al., Neurochem. Int. (1994) 25:17-24), cerebral vasodilation (Tanaka, R. et al., Stroke (1995) 26:2154-2159), and neurotrophic/neuromodulatory processes.

Fibroblast growth factor also has multiple positive effects including blood flow and protection from calcium toxicity to improve outcome in cerebral ischemia (Mattson, M. P. et al., Semin. Neurosci. (1993) 5:295-307; Doetrocj. W. D. et al., J. Neurotrauma (1996) 13:309-316). Basic FGF treatment promotes neoangiogenesis in ischemic myocardium (Schumacher et al., Circulation (1998) 97: 645-650). Basic FGF enhances functional recovery and promotes neuronal sprouting following focal cerebral infarct (Kawamata et al., Proc. Natl. Acad. Sci. (1997) 94 (15):8179-84). According to the published literature, the FGF family consists of at least twenty-two members (Reuss et al., Cell Tissue Res. 313:139-157 (2003)).

Fibroblast growth factor 21 (FGF-21) has been reported to be preferentially expressed in the liver (Nishimura et al., Biochimica et Biophysica Acta, 1492:203-206 (2000); WO 01/36640; and WO 01/18172, which are incorporated by reference herein) and described as a treatment for ischemic vascular disease, wound healing, and diseases associated with loss of pulmonary, bronchia or alvelor cells or function and numerous other disorders. FGF-21 is expressed primarily in liver, kidney, and muscle tissue (see Example 2 of US Patent Publication No. 20040259780 which is incorporated by reference herein in its entirety). The FGF-21 gene is composed of 3 exons and is located on chromosome 19. Unlike other FGFs, FGF-21 does not have proliferative and tumorigenic effects (Genome Biol. 2001; 2(3): REVIEWS 3005).

US Patent Publication No. 20010012628, which is incorporated by reference in its entirety, describes a nucleotide and protein sequence for human FGF-21 (see SEQ ID NO: 1 and 2, respectively of US Patent Publication No. 20010012628). SEQ ID NO: 2 in the above-mentioned publication, referred to sbgFGF-19, is 209 amino acids in length and contains a 28 amino acid leader sequence at the N terminus. The human FGF-21 sequence presented as SEQ ID NO: 3 herein is the same sequence as SEQ ID NO: 2 of US Patent Publication No. 20010012628. This sequence has a single nucleotide polymorphism (SNP) with proline (P) at position 174, hereinafter referred to as the "209 amino acid P-form of FGF-21."

U.S. Pat. No. 6,716,626, which is incorporated by reference herein in its entirety, discuss human FGF-21 and homologous proteins in other mammals, particularly mice and rats. Mouse FGF shown as SEQ ID NO: 1 of U.S. Pat. No. 6,716,626 was highly expressed in liver and expressed in the testis and thymus, and it was suggested that human FGF-21 may play a role in development of and recovery from liver disease and/or disorders of testicular function or function of cells derived from the thymus. SEQ ID NO: 4 of U.S. Pat. No. 6,716,626 is 209 amino acids in length and contains a 28 amino acid leader sequence at the N terminus. The human FGF-21 sequence presented as SEQ ID NO: 6 herein is the same sequence as SEQ ID NO: 4 of U.S. Pat. No. 6,716,626. This sequence has a single nucleotide polymorphism (SNP) with leucine (L) at position 174, hereinafter referred to as the "209 amino acid L-form of FGF-21."

U.S. Patent Publication No. 20040259780, which is incorporated by reference herein in its entirety, discuss human FGF-21 and present a sequence that is 208 amino acids in length (SEQ ID NO: 2 of U.S. Patent Publication No. 20040259780) and contains a 27 amino acid leader sequence at the N terminus. The human FGF-21 sequence presented as SEQ ID NO: 7 herein is the same sequence as SEQ ID NO: 2 of U.S. Patent Publication No. 20040259780. This sequence has a single nucleotide polymorphism (SNP) with leucine (L) at position 173, herein after referred to as the "208 amino acid L-form of FGF-21."

FGF-21 has been shown to stimulate glucose-uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose-dependent manner, thus, providing the basis for the use of FGF-21 as a therapy for treating diabetes and obesity (WO 03/011213, which is incorporated by reference herein and Kharitonenkov et al. *J Clin Invest.* 2005 June; 115(6):1627-35). Kharitonenkov et al. *J Clin Invest.* 2005 June; 115(6):1627-35 also showed that transgenic mice expressing human FGF-21 are hypoglycemic, sensitive to insulin, and resistant to diet-induced obesity. Kharitonenkov et al. Endocrinology (in press) also show that FGF-21 lowered glucose, triglycerides, insulin, and glucagons in diabetic Rhesus monkeys.

In addition, FGF-21 has been shown to be effective in reducing the mortality and morbidity of critically ill patients (WO 03/059270, which is incorporated by reference herein). FGF-21 has been described in U.S. Patent Application 20050176631, which is incorporated by reference herein, to affect the overall metabolic state and may counter-act negative side-effects that can occur during the body's stress response to sepsis as well as systemic inflammatory response syndrome (SIRS) resulting from noninfectious pathologic causes. Thus, FGF-21 may be used to reduce the mortality and morbidity that occurs in critically ill patients. Critically ill patients include those patients who are physiologically unstable requiring continuous, coordinated physician, nursing, and respiratory care. This type of care necessitates paying particular attention to detail in order to provide constant surveillance and titration of therapy. Critically ill patients include those patients who are at risk for physiological decompensation and thus require constant monitoring such that the intensive care team can provide immediate intervention to prevent adverse occurrences. Critically ill patients have special needs for monitoring and life support which must be provided by a team that can provide continuous titrated care.

PEGylated FGF-21 polypeptides are described in WO 2005/091944, which is incorporated by reference herein. The FGF-21 polypeptide described in WO 2005/091944 is a 181 amino acid polypeptide. The mature, wild-type, or native human FGF-21 sequence indicated as SEQ ID NO: 1 of WO 2005/091944 lacks a leader sequence. This human FGF-21 is highly identical to mouse FGF-21 (~79% amino acid identity) and rat FGF-21 (~80% amino acid identity). The human FGF-21 sequence presented as SEQ ID NO: 5 herein is the same sequence as SEQ ID NO: 1 of WO 05/091944. This sequence has a single nucleotide polymorphism (SNP) with leucine (L) at position 146. One of ordinary skill in the art could readily use alternative mammalian FGF-21 polypeptide sequences or analogs, muteins, or derivatives that have sufficient homology to the human FGF-21 sequences for the uses described herein.

The human FGF-21 sequence presented as SEQ ID NO: 1 herein has a single nucleotide polymorphism (SNP) with proline (P) at position 146. A N-terminal His tag version of SEQ ID NO: 1 is shown as SEQ ID NO: 2 herein.

WO 2005/091944 describes the covalent attachment of one or more molecules of PEG to particular residues of an FGF-21 compound. The resulting compound was a biologically active, PEGylated FGF-21 compound with an extended elimination half-life and reduced clearance when compared to that of native FGF-21. The PEG molecules were covalently attached to cysteine or lysine residues. Substitutions were made at various positions with cysteine to allow attachment of at least one PEG molecule. PEGylation at one or more lysine residues (56, 59, 69, and 122) was described.

PEGylated FGF-21 compounds would be useful in treating subjects with disorders, including, but not limited to, type 2 diabetes, obesity, insulin resistance, hyperinsulinemia, glucose intolerance, hyperglycemia, and metabolic syndrome. It would be particularly advantageous to have PEGylated FGF-21 compounds that could increase efficacy by allowing for a longer circulating half-life and that would require fewer doses, increasing both the convenience to a subject in need of such therapy and the likelihood of a subject's compliance with dosing requirements. Metabolic syndrome can be defined as a cluster of at least three of the following signs: abdominal fat—in most men, a 40-inch waist or greater; high blood sugar—at least 110 milligrams per deciliter (mg/dL) after fasting; high triglycerides—at least 150 mg/dL in the bloodstream; low HDL—less than 40 mg/dL; and, blood pressure of 130/85 of higher.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. There has been research on the formulation of a therapeutic FGF-21 compound, but it has been problematic for many reasons, one of which is because proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.*, 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N-CHR-COOH$. The alpha amino moiety ($H_2N-$) of one amino acid joins to the carboxyl moiety ($-COOH$) of an adjacent amino acid to form amide linkages, which can be represented as $-(NH-CHR-CO)_n-$, where the subscript "n" can equal hundreds or thousands. The fragment represented by R can contain reactive sites for protein biological activity and for attachment of PEG derivatives.

For example, in the case of the amino acid lysine, there exists an $-NH_2$ moiety in the epsilon position as well as in the alpha position. The epsilon $-NH_2$ is free for reaction under conditions of basic pH. Much of the art in the field of protein derivatization with PEG has been directed to developing PEG derivatives for attachment to the epsilon —NH$_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —NH$_2$ can also react with —N(H)—. Similarly, the side chain of the amino acid cysteine bears a free sulfhydryl group, represented structurally as —SH. In some instances, the PEG derivatives directed at the epsilon —NH$_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into FGF-21 that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —NH$_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which have enabled the incorporation of non-genetically encoded amino acids to proteins in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *Chem Bio Chem* 3(11):1135-1137; J. W. Chin, et al., (2002), *PNAS United States of America* 99:11020-11024; and, L. Wang, & P. G. Schultz, (2002), *Chem. Comm.*, 1:1-11. All references are incorporated by reference in their entirety. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —NH$_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2]cycloaddition reaction in aqueous conditions in the presence of a catalytic amount of copper. See, e.g. Tornoe, et al., (2002) *J. Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of FGF-21 polypeptides, and also addresses the production of an FGF-21 polypeptide with improved biological or pharmacological properties, such as improved therapeutic half-life.

SUMMARY OF THE INVENTION

This invention provides FGF-21 polypeptides comprising one or more non-naturally encoded amino acids.

In some embodiments, the FGF-21 polypeptide comprises one or more post-translational modifications. In some embodiments, the FGF-21 polypeptide is linked to a linker, polymer, or biologically active molecule. In some embodiments, the FGF-21 polypeptide is linked to a bifunctional polymer, bifunctional linker, or at least one additional FGF-21 polypeptide.

In some embodiments, the non-naturally encoded amino acid is linked to a water soluble polymer. In some embodiments, the water soluble polymer comprises a poly(ethylene glycol) moiety. In some embodiments, the non-naturally encoded amino acid is linked to the water soluble polymer with a linker or is bonded to the water soluble polymer. In some embodiments, the poly(ethylene glycol) molecule is a bifunctional polymer. In some embodiments, the bifunctional polymer is linked to a second polypeptide. In some embodiments, the second polypeptide is a FGF-21 polypeptide.

In some embodiments, the FGF-21 polypeptide comprises at least two amino acids linked to a water soluble polymer comprising a poly(ethylene glycol) moiety. In some embodiments, at least one amino acid is a non-naturally encoded amino acid.

In some embodiments, one or more non-naturally encoded amino acids are incorporated in one or more of the following positions in FGF-21: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, one or more non-naturally encoded amino acids are incorporated in one or more positions from before position 1 (i.e. at the N-terminus) through the C terminus in SEQ ID NOs: 34-36. In some embodiments, one or more non-naturally encoded amino acids are incorporated in one or more of the following positions in FGF-21: 10, 52, 117, 126, 131, 162, 87, 77, 83, 72, 69, 79, 91, 96, 108, and 110 (SEQ ID NO: 1 or the corresponding amino acids of SEQ ID NOs: 2-7). In some embodiments, one or more non-naturally encoded amino acids are incorporated in one or more of the following positions in FGF-21: 10, 52, 77, 117, 126, 131, 162 (SEQ ID NO: 1 or the corresponding amino acids of SEQ ID NOs: 2-7). In some embodiments, one or more non-naturally encoded amino acids are incorporated in one or more of the following positions in FGF-21: 87, 77, 83, 72 (SEQ ID NO: 1 or the corresponding amino acids of SEQ ID NOs: 2-7). In some embodiments, one or more non-naturally encoded amino acids are incorporated in one or more of the following positions in FGF-21: 69, 79, 91, 96, 108, and 110 (SEQ ID NO: 1 or the corresponding amino acids of SEQ ID NOs: 2-7). In some embodiments, one or more non-natural amino acids are incorporated in the leader or signal sequence of SEQ ID NOs: 3, 4, 6, 7, or other FGF-21 sequence. In some embodiments, leader sequences may be chosen from SEQ ID NOs: 39, 40, 41, 42, 43, or 44. In some embodiments, FGF-21 secretion constructs are cloned into pVK7ara (Nde/Eco) with a leader sequences chosen from SEQ ID NOs: 39, 40, 41, 42, 43, or 44.

In some embodiments, the non-naturally occurring amino acid at one or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, the non-naturally occurring amino acid at one or more positions from before position 1 (i.e. at the N-terminus) through the C terminus in SEQ ID NOs: 34-36 is linked to a water soluble polymer. In some embodiments, the non-naturally occurring amino acid at one or more of these positions is linked to a water soluble polymer, including but not limited to, positions: 10, 52, 117, 126, 131, 162, 87, 77, 83, 72, 69, 79, 91, 96, 108, and 110 (SEQ ID NO: 1 or the corresponding amino acids of SEQ ID NOs: 2-7). In some embodiments, the non-naturally occurring amino acid at one or more of these positions is linked to a water soluble polymer, including but not limited to, positions: 10, 52, 77, 117, 126, 131, 162 (SEQ ID NO: 1 or the corresponding amino acids of SEQ ID NOs: 2-7). In some embodiments, the non-naturally occurring amino acid at one or more of these positions is linked to a water soluble polymer: 87, 77, 83, 72 (SEQ ID NO: 1 or the corresponding amino acids of SEQ ID NOs: 2-7). In some embodiments, the non-naturally occurring amino acid at one or more of these positions is linked to a water soluble polymer: 69, 79, 91, 96, 108, and 110 (SEQ ID NO: 1 or the corresponding amino acids of SEQ ID NOs: 2-7). In some embodiments, the one or more non-naturally occurring amino acids in the leader or signal sequence of SEQ ID NOs: 3, 4, 6, 7, 39, 40, 41, 42, 43, 44, or other FGF-21 sequence is linked to a water soluble polymer. In some embodiments, the one or more non-naturally occurring amino acids in the leader or signal sequence of SEQ ID NOs: 3, 4, 6, 7, or other FGF-21 sequence is linked to a water soluble polymer.

In some embodiments, the FGF-21 polypeptide comprises a substitution, addition or deletion that modulates affinity of the FGF-21 polypeptide for a FGF-21 polypeptide receptor or binding partner, including but not limited to, a protein, polypeptide, small molecule, or nucleic acid. In some embodiments, the FGF-21 polypeptide comprises a substitution, addition, or deletion that increases the stability of the FGF-21 polypeptide when compared with the stability of the corresponding FGF-21 without the substitution, addition, or deletion. In some embodiments, the FGF-21 polypeptide comprises a substitution, addition, or deletion that modulates the immunogenicity of the FGF-21 polypeptide when compared with the immunogenicity of the corresponding FGF-21 without the substitution, addition, or deletion. In some embodiments, the FGF-21 polypeptide comprises a substitution, addition, or deletion that modulates serum half-life or circulation time of the FGF-21 polypeptide when compared with the serum half-life or circulation time of the corresponding FGF-21 without the substitution, addition, or deletion.

In some embodiments, the FGF-21 polypeptide comprises a substitution, addition, or deletion that increases the aqueous solubility of the FGF-21 polypeptide when compared to aqueous solubility of the corresponding FGF-21 without the substitution, addition, or deletion. In some embodiments, the FGF-21 polypeptide comprises a substitution, addition, or deletion that increases the solubility of the FGF-21 polypeptide produced in a host cell when compared to the solubility of the corresponding FGF-21 without the substitution, addition, or deletion. In some embodiments, the FGF-21 polypeptide comprises a substitution, addition, or deletion that increases the expression of the FGF-21 polypeptide in a host cell or increases synthesis in vitro when compared to the expression or synthesis of the corresponding FGF-21 without the substitution, addition, or deletion. The FGF-21 polypeptide comprising this substitution retains agonist activity and retains or improves expression levels in a host cell. In some embodiments, the FGF-21 polypeptide comprises a substitution, addition, or deletion that increases protease resistance of the FGF-21 polypeptide when compared to the protease resistance of the corresponding FGF-21 without the substitution, addition, or deletion. U.S. Pat. No. 6,716,626 indicated that potential sites that may be substituted to alter protease cleavage include, but are not limited to, a monobasic site within 2 residues of a proline. In some embodiments, the FGF-21 polypeptide comprises a substitution, addition, or deletion that modulates signal transduction activity of the FGF-21 receptor when compared with the activity of the receptor upon interaction with the corresponding FGF-21 polypeptide without the substitution, addition, or deletion. In some embodiments, the FGF-21 polypeptide comprises a substitution, addition, or deletion that modulates its binding to another molecule such as a receptor when compared to the binding of the corresponding FGF-21 polypeptide without the substitution, addition, or deletion.

In some embodiments, the FGF-21 polypeptide comprises a substitution, addition, or deletion that increases compatibility of the FGF-21 polypeptide with pharmaceutical preservatives (e.g., m-cresol, phenol, benzyl alcohol) when compared to compatibility of the corresponding FGF-21 without the substitution, addition, or deletion. This increased compatibility would enable the preparation of a preserved pharmaceutical formulation that maintains the physiochemical properties and biological activity of the protein during storage. WO 2005/091944, which is incorporated by reference in its entirety, discusses the following examples of FGF-21 muteins with enhanced pharmaceutical stability: the substitution with a charged and/or polar but uncharged amino acid for one of the following: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152, alanine 154, glutamine 156, glycine 161, serine 163, glycine 170, or serine 172 of SEQ ID NO: 1 of WO 05/091944. A FGF-21 polypeptide of the present invention may include one or more of these substitutions at the corresponding position in the polypeptide and/or may include one or more other substitutions, additions, or deletions. In some embodiments, one or more non-natural amino acids are substituted at one or more of the following positions: glycine 42, glutamine 54, arginine 77, alanine 81, leucine 86, phenylalanine 88, lysine 122, histidine 125, arginine 126, proline 130, arginine 131, leucine 139, alanine 145, proline/leucine 146, isoleucine 152, alanine 154, glutamine 156, glycine 161, serine 163, glycine 170, serine 172 (SEQ ID NO: 1 or the corresponding amino acids in SEQ ID NOs: 2-7). In some embodiments, one or more non-natural amino acids are substituted at one or more of the following positions: glutamate 91, arginine 131, glutamine 108, arginine 77, arginine 72, histidine 87, leucine 86, arginine 126, glutamate 110, tyrosine 83, proline 146, arginine 135, arginine 96, arginine 36, (SEQ ID NO: 1 or the corresponding amino acids in SEQ ID NOs: 2-7).

WO 05/091944 describes additional muteins of FGF-21 with enhanced pharmaceutical stability. Such muteins include the substitution of a cysteine for two or more of the following in FGF-21 (see SEQ ID NO: 1 of WO 05/091944): arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139. FGF-21 polypeptides of the present invention may include one or more of these substitutions at the corresponding position in the polypeptide and/or may include one or more other substitutions, additions, or deletions. In some embodiments, one or more non-natural amino acids are substituted at one or more of the following positions: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139 (SEQ ID NO: 1 or the corresponding amino acids in SEQ ID NOs: 2-7).

WO 05/091944 further describes specific muteins of FGF-21 with engineered disulfide bonds (amino acids substituted with cysteine), in addition to the naturally occurring one at Cys75-Cys93, are as follows: Gln76Cys-Ser109Cys, Cys75-Ser85Cys, Cys75-Ala92Cys, Phe73Cys-Cys93, Ser123Cys-His125Cys, Asp102Cys-Tyr104Cys, Asp127Cys-Gly132Cys, Ser94Cys-Glu110Cys, Pro115Cys-His117Cys, Asn121Cys-Asp127Cys, Leu100Cys-Asp102Cys, Phe95Cys-Tyr107Cys, Arg19CysPro138Cys, Tyr20Cys-Leu139Cys, Tyr22Cys-Leu137Cys, Arg77Cys-Asp79Cys, Pro90Cys-Ala92Cys, Glu50Cys-Lys69Cys, Thr23Cys-Asp25Cys, Ala31Cys-Gly43Cys, Gln28Cys-Gly43Cys, Thr23Cys-Gln28Cys, Val41Cys-Leu82Cys, Leu58Cys-Val62Cys, Gln54Cys-Leu66Cys, Ile35Cys-Gly67Cys, Gly67Cys-Arg72Cys, Ile35Cys-Gly84Cys, Arg72Cys-Gly84Cys, or Arg77Cys-Ala81Cys, where the numbering is based on SEQ ID NO: 1 of WO 05/091944. Additional muteins with engineered disulfide bonds are Tyr22Cys-Leu139Cys; Asp24Cys-Arg135Cys; Leu118Cys-Gly132Cys; His117Cys-Pro130Cys; His17Cys-Ala129Cys; Leu82Cys-Pro119Cys; Gly80Cys-Ala129Cys; Gly43Cys-Pro124Cys; Gly42Cys-Arg126Cys; Gly42Cys-Pro124Cys; Gln28Cys-Pro124Cys; Gln27Cys-Ser123Cys; Ala26Cys-Lys122Cys; or Asp25Cys-Lys122Cys, where the numbering is based on SEQ ID NO: 1 of WO 05/091944. Additional muteins with engineered disulfide bonds are Leu118Cys-Ala134Cys; Leu21Cys-Leu33Cys; Ala26Cys-Lys122Cys; Leu21Cys-Leu33Cys/Leu118Cys-Ala134Cys, where the numbering is based on SEQ ID NO: 1 of WO 05/091944. FGF-21 polypeptides of the present invention may include one or more of these substitutions at the corresponding position(s) in the polypeptide and/or may include one or more other substitutions, additions, or deletions. FGF-21 polypeptides of the present invention may include one or more of these substitutions at the corresponding position(s) in the polypeptide (SEQ ID NO: 1 or the corresponding amino acids in SEQ ID NOs: 2-7). In some embodiments, FGF-21 polypeptides of the present invention may include one or more of these substitutions at the corresponding positions from before position 1 (i.e. at the N-terminus) through the C terminus in SEQ ID NOs: 34-36.

WO 05/091944 describes additional muteins of FGF-21 that were PEGylated. These muteins had one of the following substitutions: D25C, D38C, L58C, K59C, P60C, K69C, D79C, H87C, E91C, E101C, D102C, L114C, L116C, K122C, R126C, P130C, P133C, P140C. FGF-21 polypeptides of the present invention may include one or more of these substitutions at the corresponding position in the polypeptide and/or may include one or more other substitutions, additions, or deletions. In some embodiments, one or more non-natural amino acids are substituted at one or more of the following positions: 25, 38, 58, 59, 60, 69, 79, 87, 91, 101, 102, 114, 116, 122, 126, 130, 133, 140 (SEQ ID NO: 1 or the corresponding amino acids in SEQ ID NOs: 2-7). In some embodiments, FGF-21 polypeptides of the present invention may include one or more of these substitutions at the corresponding positions from before position 1 (i.e. at the N-terminus) through the C terminus in SEQ ID NOs: 34-36.

WO 05/091944 describes cysteine substitutions at the following positions: 19, 21, 26, 28, 29, 30, 36, 39, 42, 50, 56, 61, 64, 65, 68, 70, 71, 77, 81, 85, 86, 90, 92, 94, 98, 107, 108, 112, 113, 123, and 124. WO 05/091944 indicates cysteine substitutions at the following positions: 24, 27, 37, 40, 44, 46, 49, 57, 88, 89, 106, 110, 111, 115, 120, and 139. WO 05/091944 also describes cysteine substitutions at the following positions: 18, 45, 47, 48, 78, 83, 99, 103, 125, 128, 131, 132, and 138. WO 05/091944 also describes cysteine substitutions at the following positions: 25, 38, 58, 59, 60, 69, 79, 87, 91, 101, 102, 114, 116, 122, 126, 130, 133, and 140.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non-naturally encoded, with a linker, polymer, or other molecule under suitable conditions; etc.

In some embodiments, one or more amino acid substitutions in the FGF-21 polypeptide may be with one or more naturally occurring or non-naturally occurring amino acids. In some embodiments the amino acid substitutions in the FGF-21 polypeptide may be with naturally occurring or non-naturally occurring amino acids, provided that at least one substitution is with a non-naturally encoded amino acid. In some embodiments, one or more amino acid substitutions in the FGF-21 polypeptide may be with one or more naturally occurring amino acids, and additionally at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

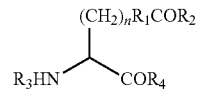

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

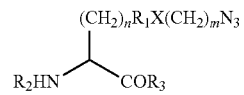

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

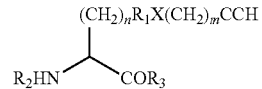

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a FGF-21 polypeptide agonist, partial agonist, antagonist, partial antagonist, or inverse agonist. In some embodiments, the FGF-21 polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the FGF-21 polypeptide agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that hybridizes under stringent conditions to SEQ ID NO: 8-14. The present invention also provides isolated nucleic acids comprising a polynucleotide that hybridizes under stringent conditions to SEQ ID NO: 8-14 wherein the polynucleotide comprises at least one selector codon. The present invention also provides isolated nucleic acids comprising a polynucleotide that encodes the polypeptides shown as SEQ ID NOs.: 1-7. The present invention also provides isolated nucleic acids comprising a polynucleotide that encodes the polypeptides shown as SEQ ID NOs.: 1-7 with one or more non-naturally encoded amino acids. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making a FGF-21 polypeptide linked to a water soluble polymer. In some embodiments, the method comprises contacting an isolated FGF-21 polypeptide comprising a non-naturally encoded amino acid with a water soluble polymer comprising a moiety that reacts with the non-naturally encoded amino acid. In some embodiments, the non-naturally encoded amino acid incorporated into the FGF-21 polypeptide is reactive toward a water soluble polymer that is otherwise unreactive toward any of the 20 common amino acids. In some embodiments, the non-naturally encoded amino acid incorporated into the FGF-21 polypeptide is reactive toward a linker, polymer, or biologically active molecule that is otherwise unreactive toward any of the 20 common amino acids.

In some embodiments, the FGF-21 polypeptide linked to the water soluble polymer is made by reacting a FGF-21 polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage.

In some embodiments, the FGF-21 polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the FGF-21 polypeptide linked to the water soluble polymer is made by reacting a FGF-21 polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the FGF-21 polypeptide linked to the water soluble polymer is made by reacting a FGF-21 polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the FGF-21 polypeptide comprises a polyalkylene glycol moiety. In some embodiments, the non-naturally encoded amino acid residue incorporated into the FGF-21 polypeptide comprises a carbonyl group, an aminooxy group, a hydrazide group, a hydrazine, a semicarbazide group, an azide group, or an alkyne group. In some embodiments, the non-naturally encoded amino acid residue incorporated into the FGF-21 polypeptide comprises a carbonyl moiety and the water soluble polymer comprises an aminooxy, hydrazide, hydrazine, or semicarbazide moiety. In some embodiments, the non-naturally encoded amino acid residue incorporated into the FGF-21 polypeptide comprises an alkyne moiety and the water soluble polymer comprises an azide moiety. In some embodiments, the non-naturally encoded amino acid residue incorporated into the FGF-21 polypeptide comprises an azide moiety and the water soluble polymer comprises an alkyne moiety.

The present invention also provides compositions comprising a FGF-21 polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the FGF-21 polypeptide comprising a selector codon. In some embodiments, the cells comprise an orthogonal RNA synthetase and/or an orthogonal tRNA for substituting a non-naturally encoded amino acid into the FGF-21 polypeptide.

The present invention also provides methods of making a FGF-21 polypeptide comprising a non-naturally encoded amino acid. In some embodiments, the methods comprise culturing cells comprising a polynucleotide or polynucleotides encoding a FGF-21 polypeptide, an orthogonal RNA synthetase and/or an orthogonal tRNA under conditions to permit expression of the FGF-21 polypeptide; and purifying the FGF-21 polypeptide from the cells and/or culture medium.

The present invention also provides methods of increasing therapeutic half-life, serum half-life or circulation time of FGF-21 polypeptides. The present invention also provides methods of modulating immunogenicity of FGF-21 polypeptides. In some embodiments, the methods comprise substituting a non-naturally encoded amino acid for any one or more amino acids in naturally occurring FGF-21 polypeptides and/ or linking the FGF-21 polypeptide to a linker, a polymer, a water soluble polymer, or a biologically active molecule.

The present invention also provides methods of treating a patient in need of such treatment with an effective amount of a FGF-21 molecule of the present invention. In some embodiments, the methods comprise administering to the patient a therapeutically-effective amount of a pharmaceutical composition comprising a FGF-21 polypeptide comprising a non-naturally-encoded amino acid and a pharmaceutically acceptable carrier. In some embodiments, the non-naturally encoded amino acid is linked to a water soluble polymer.

The present invention also provides FGF-21 polypeptides comprising a sequence shown in SEQ ID NO: 1-7 or any other FGF-21 polypeptide sequence, except that at least one amino acid is substituted by a non-naturally encoded amino acid. The present invention also provides FGF-21 polypeptides comprising a sequence shown as SEQ ID NO: 1, 2, 4, and 5. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a FGF-21 polypeptide comprising the sequence shown in SEQ ID NO: 1-7 or any other FGF-21 polypeptide sequence, wherein at least one amino acid is substituted by a non-naturally encoded amino acid. The present invention also provides pharmaceutical compositions comprising a pharmaceutically acceptable carrier and a FGF polypeptide comprising the sequence shown in SEQ ID NO: 1-7. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the FGF-21 polypeptide via a saccharide moiety.

The present invention also provides a FGF-21 polypeptide comprising a water soluble polymer linked by a covalent bond to the FGF-21 polypeptide at a single amino acid. In some embodiments, the water soluble polymer comprises a poly(ethylene glycol) moiety. In some embodiments, the amino acid covalently linked to the water soluble polymer is a non-naturally encoded amino acid present in the polypeptide.

The present invention provides a FGF-21 polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a FGF-21 polypeptide comprising a linker, polymer, or biologically active molecule that is attached to one or more non-naturally encoded amino acid wherein said non-naturally encoded amino acid is ribosomally incorporated into the polypeptide at pre-selected sites.

Included within the scope of this invention is the FGF-21 leader or signal sequence joined to an FGF-21 coding region, as well as a heterologous signal sequence joined to an FGF-21 coding region. The heterologous leader or signal sequence selected should be one that is recognized and processed, e.g. by host cell secretion system to secrete and possibly cleaved by a signal peptidase, by the host cell. Leader sequences of the present invention may be chosen from the following: the three leucine leader from SEQ ID NO: 3 and SEQ ID NO: 6 (amino acid positions 1-28), the two leucine leader from SEQ ID NO: 4 and SEQ ID NO: 7 (amino acid positions 1-27), the His tag from SEQ ID NO: 2 (amino acid positions 1-10), SEQ ID NO: 39, SEQ ID NO: 40, SEQ ID NO: 41, SEQ ID NO: 42, SEQ ID NO: 43, SEQ ID NO: 44. A method of treating a condition or disorder with the FGF-21 of the present invention is meant to imply treating with FGF-21 with or without a signal or leader peptide.

The present invention also provides methods of inducing an increase in glucose uptake in adipocyte cells, said method comprising administering FGF-21 to said cells in an amount effective to induce an increase in glucose uptake. Said increase in glucose uptake may cause an increase in energy expenditure by faster and more efficient glucose utilization.

In another embodiment, conjugation of the FGF-21 polypeptide comprising one or more non-naturally occurring amino acids to another molecule, including but not limited to PEG, provides substantially purified FGF-21 due to the unique chemical reaction utilized for conjugation to the non-natural amino acid. Conjugation of FGF-21 comprising one or more non-naturally encoded amino acids to another molecule, such as PEG, may be performed with other purification techniques performed prior to or following the conjugation step to provide substantially pure FGF-21.

BRIEF DESCRIPTION OF THE DRAWINGS

FIG. 7b—A table showing the average fold loss of activity for each of the pegylated FGF21 variants listed.

FIG. 14—Data from Example 28, Pharmacokinetic properties of FGF-21 compounds in rats.

FIG. 25—pVK10-FGF21 vector sequence.

FIG. 28a—Serum concentration-time profiles of three doses of PP WT FGF21 in rats. Rats were given a single administration of test article subcutaneously. N=4 animals per group. Symbols indicate means of measured serum concentrations, error bars indicate standard error.

FIG. 28b—Serum concentration-time profiles of PP WT FGF21 dosed either subcutaneously or intravenously at 0.25 mg/kg. Rats were given a single administration of test article subcutaneously. N=4 animals per group. Symbols indicate means of measured serum concentrations, error bars indicate standard error. The total bioavailability is ~65%

DEFINITIONS

Figure 1:
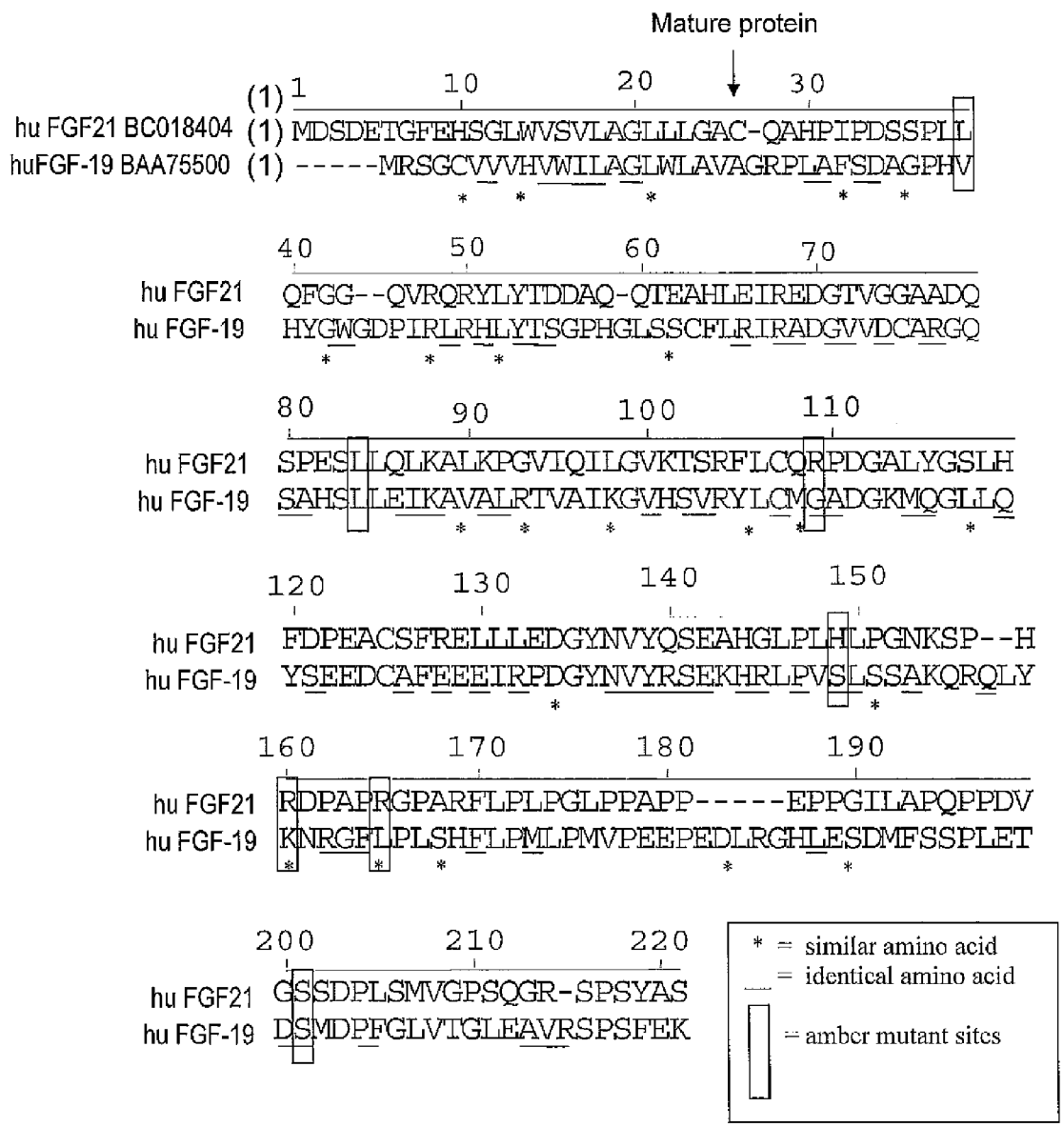
FIG. 1—Amber mutations in FGF-21 and corresponding sites in FGF-19 are shown.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "FGF-21" or "FGF-21 polypeptide" is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a FGF-21 polypeptide that may be substantially or essentially free of components that normally accompany or interact with the protein as found in its naturally occurring environment, i.e. a native cell, or host cell in the case of recombinantly produced FGF-21 polypeptides. FGF-21 polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the FGF-21 polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the FGF-21 polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" FGF-21 polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the FGF-21 polypeptide has been secreted, including medium either before or after a proliferation step. The term also may encompass buffers or reagents that contain host cell lysates, such as in the case where the FGF-21 polypeptide is produced intracellularly and the host cells are lysed or disrupted to release the FGF-21 polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

The term "anti-diabetic agent" shall mean any drug that is useful in treating, preventing, or otherwise reducing the severity of any glucose metabolism disorder, or any complications thereof, including any of the conditions, disease, or complications described herein. Anti-diabetic agents include insulin, thiazolidinediones, sulfonylureas, benzoic acid derivatives, alpha-glucosidase inhibitors, or the like. Other general categories of anti-diabetic agents which may be part of a subject composition include (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C. §355(a) ("regulatory approved drug"); any agent that is or was subject to a human drug application under 21 U.S.C. §379(g) ("human drug"). (All references to statutory code for this definition refer to such code as of the original filing date of this application.) Other anti-diabetic agents are disclosed herein, and are known to those of skill in the art. It is preferred that the inventive antidiabetic compositions, as used herein, are capable of reducing HbA1c levels by at least a 10% change from the baseline, and it is more particularly preferred that the inventive anti-diabetic compositions, as used herein, are capable of reducing HbA1c levels by at least a 50% change from the baseline. Antidiabetic agents include insulin potentiators, such as including but not limited to, small molecule insulin potentiators, Taurine, Alpha Lipoic Acid, an extract of Mulberry, Chromium, Glutamine, *Enicostemma littorale* Blume, *Scoparia dulcis*, an extract of Tarragon, *Andrographis paniculata*, Isomalt, Trehalose or D-Mannose which may further potentiate the secretion or activity of insulin.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "FGF-21 polypeptide," "fibroblast growth factor 21" or "FGF-21" and unhyphenated forms thereof shall include those polypeptides and proteins that have at least one biological activity of a fibroblast growth factor 21, as well as FGF-21 analogs, FGF-21 isoforms, FGF-21 mimetics, FGF-21 fragments, hybrid FGF-21 proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "FGF-21 polypeptide" and "FGF-21" encompass FGF-21 polypeptides comprising one or more amino acid substitutions, additions or deletions.

Substitutions in a wide variety of amino acid positions in naturally-occurring FGF-21 have been described. Substitutions including but not limited to, those that modulate pharmaceutical stability, increase agonist activity, increase protease resistance, convert the polypeptide into an antagonist, etc. and are encompassed by the term "FGF-21 polypeptide" or "FGF-21."

For sequences of FGF-21 that lack a leader sequence, see SEQ ID NO: 1, SEQ ID NO: 2 and SEQ ID NO: 5 herein. For sequences of FGF-21 with a leader sequence, see SEQ ID NO: 3, SEQ ID NO: 4, SEQ ID NO: 6 and SEQ ID NO: 7 herein. In some embodiments, FGF-21 polypeptides of the invention are substantially identical to SEQ ID NOs: 1-7 or any other sequence of a FGF-21 polypeptide. Multiple polymorphisms of FGF-21 have been identified. Leucine or proline have been described at the same position in U.S. Patent Publication No. 20010012628 and U.S. Pat. No. 6,716,626. N-terminal leader or signal sequences that differ by 1 amino acid (leucine) are shown in U.S. Pat. No. 6,716,626 and U.S. Patent Publication No. 20040259780. Nucleic acid molecules encoding FGF-21 and FGF-21 polypeptides including mutants and methods to express and purify FGF-21 polypeptides are well known and include, but are not limited to, those disclosed in U.S. Pat. No. 6,716,626; U.S. Patent Publication Nos. 2005/0176631, 2005/0037457, 2004/0185494, 2004/0259780, 2002/0164713, and 2001/0012628; WO 01/36640; WO 03/011213; WO 03/059270; WO 04/110472; WO 05/061712; WO 05/072769; WO 05/091944; WO 05/113606; WO 06/028595; WO 06/028714; WO 06/050247; WO 06/065582; WO 06/078463, which are incorporated by reference in their entirety herein.

The term "FGF-21 polypeptide" also includes the pharmaceutically acceptable salts and prodrugs, and prodrugs of the salts, polymorphs, hydrates, solvates, biologically-active fragments, biologically active variants and stereoisomers of the naturally-occurring FGF-21 as well as agonist, mimetic, and antagonist variants of the naturally-occurring FGF-21 and polypeptide fusions thereof. Fusions comprising additional amino acids at the amino terminus, carboxyl terminus, or both, are encompassed by the term "FGF-21 polypeptide." Exemplary fusions include, but are not limited to, e.g., methionyl FGF-21 in which a methionine is linked to the N-terminus of FGF-21 resulting from the recombinant expression of the mature form of FGF-21 lacking the leader or signal peptide or portion thereof (a methionine is linked to the N-terminus of FGF-21 resulting from the recombinant expression), fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13. Chimeric molecules comprising FGF-21 and one or more other molecules, including but not limited to, keratinocyte growth factor (KGF) may be generated (Reich-Slotky, R. et al., J. Biol. Chem. 270:29813-29818 (1995)). The chimeric molecule can contain specific regions or fragments of one or both of the FGF-21 and KGF molecules. Any such fragments can be prepared from the proteins by standard biochemical methods, or by expressing a polynucleotide encoding the fragment. FGF-21, or a fragment thereof, can be produced as a fusion protein comprising human serum albumin (HSA) or a portion thereof. Such fusion constructs are suitable for enhancing expression of the FGF-21, or fragment thereof, in an eukaryotic host cell. Exemplary HSA portions include the N-terminal polypeptide (amino acids 1-369, 1-419, and intermediate lengths starting with amino acid 1), as disclosed in U.S. Pat. No. 5,766,883, and PCT publication WO 97/24445, which is incorporated by reference herein. Other chimeric polypeptides can include a HSA protein with FGF-21, or fragments thereof, attached to each of the C-terminal and N-terminal ends of the HSA. Such HSA constructs are disclosed in U.S. Pat. No. 5,876,969, which is incorporated by reference herein. Mammalian cell expression of FGF-21 is described in WO 2005/091944 which is incorporated by reference herein.

Various references disclose modification of polypeptides by polymer conjugation or glycosylation. The term "FGF-21 polypeptide" includes polypeptides conjugated to a polymer such as PEG and may be comprised of one or more additional derivitizations of cysteine, lysine, or other residues. In addition, the FGF-21 polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer conjugation of FGF-21 and other polypeptides has been reported. See, e.g. WO 2005/091944 which is incorporated by reference herein. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092, which is incorporated by reference herein, discloses modification of granulocyte colony stimulating factor (G-CSF) and other polypeptides so as to introduce at least one additional carbohydrate chain as compared to the native polypeptide.

The term "FGF-21 polypeptide" also includes glycosylated FGF-21, such as but not limited to, polypeptides glycosylated at any amino acid position, N-linked or O-linked glycosylated forms of the polypeptide. Variants containing single nucleotide changes are also considered as biologically active variants of FGF-21 polypeptide. In addition, splice variants are also included. The term "FGF-21 polypeptide" also includes FGF-21 polypeptide heterodimers, homodimers, heteromultimers, or homomultimers of any one or more FGF-21 polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

All references to amino acid positions in FGF-21 described herein are based on the position in SEQ ID NO: 1, unless otherwise specified (i.e., when it is stated that the comparison is based on SEQ ID NO: 2, 3, 4, 5, 6, 7, or other FGF-21 sequence). For example, the amino acid at position 77 of SEQ ID NO: 1, is an arginine and the corresponding arginine is located in SEQ ID NO: 2 at position 87. Those of skill in the art will appreciate that amino acid positions corresponding to positions in SEQ ID NO: 1 can be readily identified in any other FGF-21 molecule such as SEQ ID NO: 2, 3, 4, 5, 6, and 7. Those of skill in the art will appreciate that amino acid positions corresponding to positions in SEQ ID NO: 1, 2, 3, 4, 5, 6, 7 or any other FGF-21 sequence can be readily identified in any other FGF-21 molecule such as FGF-21 fusions, variants, fragments, etc. For example, sequence alignment programs such as BLAST can be used to align and identify a particular position in a protein that corresponds with a position in SEQ ID NO: 1, 2, 3, 4, 5, 6, 7 or other FGF-21 sequence. Substitutions, deletions or additions of amino acids described herein in reference to SEQ ID NO: 1, 2, 3, 4, 5, 6, 7, or other FGF-21 sequence are intended to also refer to substitutions, deletions or additions in corresponding positions in FGF-21 fusions, variants, fragments, etc. described herein or known in the art and are expressly encompassed by the present invention.

The term "FGF-21 polypeptide" or "FGF-21" encompasses FGF-21 polypeptides comprising one or more amino acid substitutions, additions or deletions. FGF-21 polypeptides of the present invention may be comprised of modifications with one or more natural amino acids in conjunction with one or more non-natural amino acid modification. Exemplary substitutions in a wide variety of amino acid positions in naturally-occurring FGF-21 polypeptides have been described, including but not limited to substitutions that modulate pharmaceutical stability, that modulate one or more of the biological activities of the FGF-21 polypeptide, such as but not limited to, increase agonist activity, increase solubility of the polypeptide, decrease protease susceptibility, convert the polypeptide into an antagonist, etc. and are encompassed by the term "FGF-21 polypeptide." In some embodiments, the FGF-21 antagonist comprises a non-naturally encoded amino acid linked to a water soluble polymer that is present in a receptor binding region of the FGF-21 molecule.

In some embodiments, the FGF-21 polypeptides further comprise an addition, substitution or deletion that modulates biological activity of the FGF-21 polypeptide. For example, the additions, substitutions or deletions may modulate one or more properties or activities of FGF-21. For example, the additions, substitutions or deletions may modulate affinity for the FGF-21 polypeptide receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, FGF-21 polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "FGF-21 polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water soluble polymers of a variety of lengths such as poly(ethylene glycol) or polydextran, or polypeptides of various lengths.

A "non-naturally encoded amino acid" refers to an amino acid that is not one of the common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, toxins, prokaryotic and eukaryotic cells, viruses, polysaccharides, nucleic acids and portions thereof obtained or derived from viruses, bacteria, insects, animals or any other cell or cell type, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Publication No. 188,256; U.S. Pat. Nos. 4,671, 958, 4,659,839, 4,414,148, 4,699,784; 4,680,338; and 4,569, 789 which are incorporated by reference herein. A "multifunctional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the FGF-21 and its receptor or FGF-21.

Where substituent groups are specified by their conventional chemical formulas, written from left to right, they equally encompass the chemically identical substituents that would result from writing the structure from right to left, for example, the structure —CH$_2$O— is equivalent to the structure —OCH$_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, —(CH$_2$)$_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —SO$_2$, =S, —COOH, —NR$_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—($C_1$-$C_{10}$ aryl), —(CH$_2$)$_m$—O—(—(CH$_2$)$_m$—O—($C_1$-$C_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —CH$_2$CH$_2$— and —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to FGF-21 polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered binding to one or more binding partners, and altered receptor dimerization or multimerization. The water soluble polymer may or may not have its own biological activity, and may be utilized as a linker for attaching FGF-21 to other substances, including but not limited to one or more FGF-21 polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly(alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified FGF-21 relative to its non-modified form. Serum half-life is measured by taking blood samples at various time points after administration of FGF-21, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of FGF-21, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al (1997) *Nuc. Acids Res.* 25:3389-3402, and Altschul et al (1990) *J. Mol. Biol.* 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the FGF-21 polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

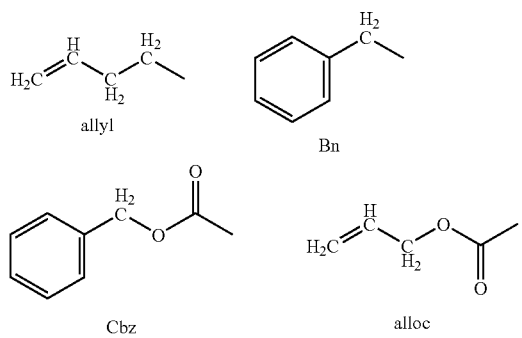

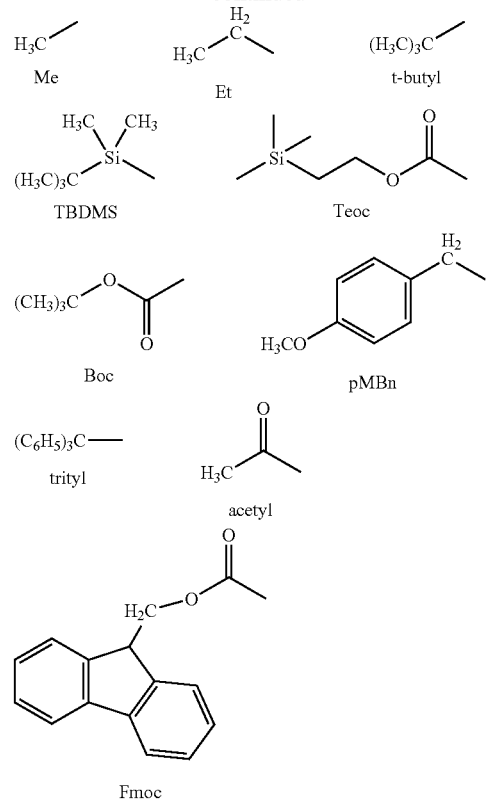

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^3H$ and $^{14}C$ are incorporated, may be useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

FGF-21 molecules comprising at least one unnatural amino acid are provided in the invention. In certain embodiments of the invention, the FGF-21 polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2]cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified FGF-21 polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on FGF-21 comprising at least one non-naturally encoded amino acid. Introduction of at least one non-naturally encoded amino acid into FGF-21 can allow for the application of conjugation chemistries that involve specific chemical reactions, including, but not limited to, with one or more non-naturally encoded amino acids while not reacting with the commonly occurring 20 amino acids. In some embodiments, FGF-21 comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2]cycloaddition reaction (see, e.g., Padwa, A. in *Comprehensive Organic Synthesis*, Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2]cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *J. Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2]cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2]cycloaddition product.

It is well established in the art that PEG can be used to modify the surfaces of biomaterials (see, e.g., U.S. Pat. No. 6,610,281; Mehvar, R., J. Pharm Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2]cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Fibroblast Growth Factors

Because of their potent activities for promoting growth, proliferation, survival and differentiation of a wide variety of cells and tissue types, FGFs continue to be pursued as therapeutic agents for a number of different indications, including wound healing, such as musculo-skeletal conditions, for example, bone fractures, ligament and tissue repair, tendonitis, bursitis, etc.; skin conditions, for example, burns, cuts, lacerations, bed sores, slow healing ulcers, etc.; tissue protection, repair, and the induction of angiogenesis during myocardial infarction and ischemia, in the treatment of neurological conditions, for example, neuro-degenerative disease and stroke, in the treatment of eye disease, including macular degeneration, and the like.

The fibroblast growth factor (FGF) proteins identified to date belong to a family of signaling molecules that regulate growth and differentiation of a variety of cell types. The significance of FGF proteins to human physiology and pathology relates in part to their key roles in embryogenesis, in blood vessel development and growth, and in bone growth. In vitro experiments have demonstrated a role for FGF in regulating cell growth and division of endothelial cells, vascular smooth muscle cells, fibroblasts, and cardiac and skeletal myocytes. Other members of the FGF family and their biological roles are described in Crossley et al., Development 121:439-451 (1995); Ohuchi et al., Development 124:2235-2244 (1997); Gemel et al., Genomics 35:253-257 (1996); and Ghosh et al., Cell Growth and Differentiation 7:1425-1434 (1996).

FGF proteins are also significant to human health and disease because of a role in cancer cell growth. For example, FGF-8 was identified as an androgen-induced growth factor in breast and prostate cancer cells. (Tanaka et al., FEBS Lett. 363:226-230 (1995) and P.N.A.S. 89:8928-8932 (1992)).

The role of FGF in normal development is being elucidated in part through studies of FGF receptors. Wilke, T. et al., Dev. Dynam. 210:41-52 (1997) found that FGFR1, FGFR2, and FGFR3 transcripts were localized to specific regions of the head during embryonic development in chickens. The expression pattern correlated with areas affected by human FGFR mutations in Crouzon syndrome, a condition of abnormal intramembranous bone formation. Belluardo, N. et al., Jour. Comp. Neur. 379:226-246 (1997) studied localization of FGFR 1, 2, and 3 mRNAs in rat brain, and found cellular specificity in several brain regions. Furthermore, FGFR1 and FGFR2 mRNAs were expressed in astroglial reactive cells after brain lesion, supporting a role of certain FGF's in brain disease and injury. Ozawa, K. et al., Mol. Brain Res. 41:279-288 (1996) reported that FGF1 and FGF-5 expression increased after birth, whereas FGF3, FGF-6, FGF-7, and FGF-8 genes showed higher expression in late embryonic stages than in postnatal stages. A cofactor, Klotho beta (Klb), may also be involved with signal transduction of FGF-21 and its receptor. Klb has been reported to increase the ability of FGFR1 and FGFR4 to bind FGF21. Klb is a single-pass transmembrane protein and although the role of the full transmembrane form is unknown, it has been shown in regards to FGF23 that Klotho enhanced FGF23 binding and increased phosphorylation of FGF receptor while Klotho beta has been shown to enhance FGF-21 binding (H. Kurosu, Y. Ogawa, M. Miyoshi, M. Yamamoto, A. Nandi, K. P. Rosenblatt, M. G. Baum, S. Schiavi, M.-C. Hu, O. W. Moe, M. Kuro-o, Regulation of fibroblast growth factor-23 signaling by Klotho. J. Biol. Chem. 281, 6120-6123 (2006) incorporated herein by reference).

Katoh et al. (International Journal of Oncology (2006) 29:163-168) describe the FGF family and phylogenetic analyses of the family members. Katoh et al. also discuss signaling pathway network in the gastrointestinal tract.

Plotnikov et al. (Cell (1999) 98:641-650) describe the crystal structure of FGF2 with FGF receptor 1 (FGFR1) and the 2-fold symmetric dimer that is formed between two of these complexes. Plotnikov et al. provide a model for dimerization of the receptor and induction of dimerization by FGF and heparin.

Additional members of the FGF family are likely to be discovered in the future. New members of the FGF family can be identified through computer-aided secondary and tertiary structure analyses of the predicted protein sequences, and by selection techniques designed to identify molecules that bind to a particular target.

Thus, the description of the FGF family is provided for illustrative purposes and by way of example only and not as a limit on the scope of the methods, compositions, strategies and techniques described herein. Further, reference to FGF-21 in this application is intended to use the generic term as an example of any member of the FGF family. Thus, it is understood that the modifications and chemistries described herein with reference to FGF-21 polypeptides or protein can be equally applied to any member of the FGF family, including those specifically listed herein.

III. General Recombinant Nucleic Acid Methods for Use with the Invention

In numerous embodiments of the present invention, nucleic acids encoding a FGF-21 polypeptide of interest will be isolated, cloned and often altered using recombinant methods. Such embodiments are used, including but not limited to, for protein expression or during the generation of variants, derivatives, expression cassettes, or other sequences derived from a FGF-21 polypeptide. In some embodiments, the sequences encoding the polypeptides of the invention are operably linked to a heterologous promoter.

A nucleotide sequence encoding an FGF-21 polypeptide comprising a non-naturally encoded amino acid may be synthesized on the basis of the amino acid sequence of the parent polypeptide, including but not limited to, having the amino acid sequence shown in SEQ ID NO: 1-7 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression. A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology volume 152* Academic Press, Inc., San Diego, Calif. (Berger); Sambrook et al., *Molecular Cloning—A Laboratory Manual (2nd Ed.), Vol.* 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, PCT-mediated mutagenesis, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, In vitro mutagenesis, *Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl.*

Acids Res. 13: 8749-8764 (1985); Taylor et al., *The rapid generation of oligonucleotide-directed mutations at high frequency using phosphorothioate-modified DNA, Nucl. Acids Res.* 13: 8765-8785 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *5'-3' Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide,* (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Different base/base mismatches are corrected with different efficiencies by the methyl-directed DNA mismatch-repair system of E. coli, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond. A* 317: 415-423 (1986); Nambiar et al., *Total synthesis and cloning of a gene coding for the ribonuclease S protein, Science* 223: 1299-1301 (1984); Sakmar and Khorana, *Total synthesis and expression of a gene for the alpha-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shotgun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA,* 83:7177-7181 (1986); Arnold, *Protein engineering for unusual environments, Current Opinion in Biotechnology* 4:450-455 (1993); Sieber, et al., Nature Biotechnology, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique,* third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture;* Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, Flexi-Prep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, *Gene* 8:81 (1979); Roberts, et al., *Nature,* 328:731 (1987); Schneider, E., et al., *Protein Expr. Purif.* 6(1):10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the FGF-21 polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' *Exonucleases in phosphorothioate-based oligonucleotide-directed mutagenesis. Nucleic Acids Res* 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code. Selection of Efficient Suppressors of Four-base Codons and Identification of "Shifty" Four-base Codons with a Library Approach in Escherichia coli, J. Mol. Biol.* 307:755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.* 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature*

*Biotechnology,* 20:177-182. See, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11585-6; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a FGF-21 polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a FGF-21 polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the common amino acids (including but not limited to, azido, ketone, aldehyde and aminooxy groups) to form stable conjugates. For example, a FGF-21 polypeptide that includes a non-naturally encoded amino acid containing an azido functional group can be reacted with a polymer (including but not limited to, poly (ethylene glycol) or, alternatively, a second polypeptide containing an alkyne moiety to form a stable conjugate resulting for the selective reaction of the azide and the alkyne functional groups to form a Huisgen [3+2]cycloaddition product.

The generic structure of an alpha-amino acid is illustrated as follows (Formula I):

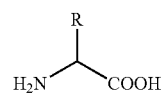

I

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Pat. Nos. 7,045,337 and 7,083,970, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

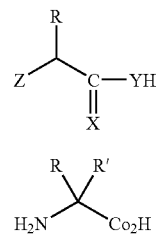

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation*, PNAS 99:19-24, which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-amino-phenylalanine and reductive amination.

In one embodiment, compositions of a FGF-21 polypeptide that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2]cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Structure and Synthesis of Non-Natural Amino Acids: Carbonyl, Carbonyl-Like, Masked Carbonyl, Protected Carbonyl Groups, and Hydroxylamine Groups In some embodiments the present invention provides FGF-21 linked to a water soluble polymer, e.g., a PEG, by an oxime bond.

Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. No. 7,083,970 and U.S. Pat. No. 7,045,337, which are incorporated by reference herein in their entirety.

Some embodiments of the invention utilize FGF-21 polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42: 6735-6746 (2003), incorporated by reference. Other carbonyl- or dicarbonyl-containing amino acids can be similarly prepared by one of ordinary skill in the art. Further, non-limiting examplary syntheses of non-natural amino acid that are included herein are presented in FIGS. 4, 24-34 and 36-39 of U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

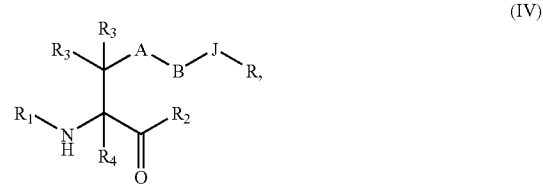

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$ —N=N—, and —C(R')$_2$—N(R')—N(R')—, where each R' is independently H, alkyl, or substituted alkyl;

J is

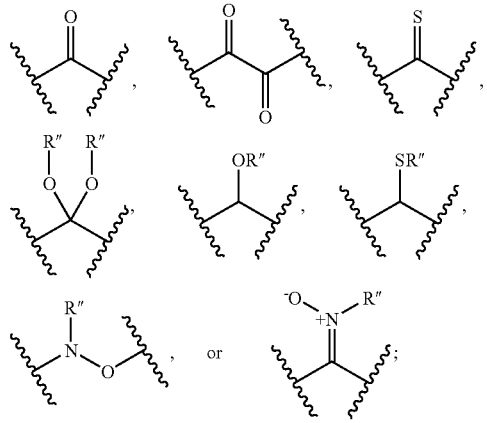

R is H, alkyl, substituted alkyl, cycloalkyl, or substituted cycloalkyl;

each R" is independently H, alkyl, substituted alkyl, or a protecting group, or when more than one R" group is present, two R" optionally form a heterocycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —(CH$_2$)$_4$— and each $R_3$ is H, B is not —NHC(O)(CH$_2$CH$_2$)—; and that when A and B are absent and each $R_3$ is H, R is not methyl.

In addition, having the structure of Formula (V) are included:

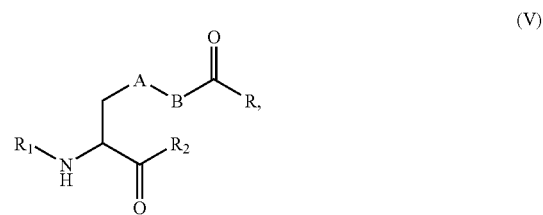

(V)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$ —N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

with a proviso that when A is phenylene, B is present; and that when A is —(CH$_2$)$_4$—, B is not —NHC(O)(CH$_2$CH$_2$)—; and that when A and B are absent, R is not methyl.

In addition, amino acids having the structure of Formula (VI) are included:

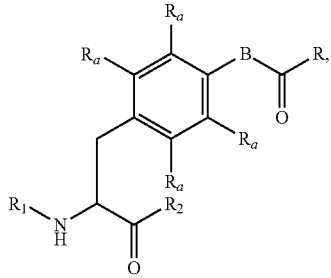

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

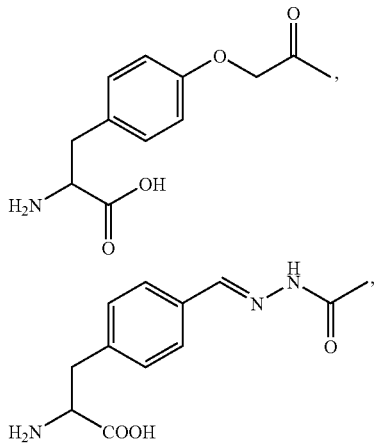

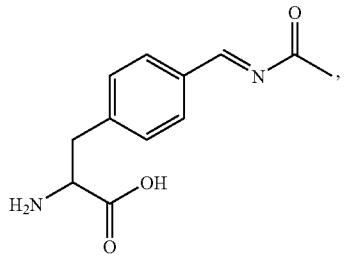

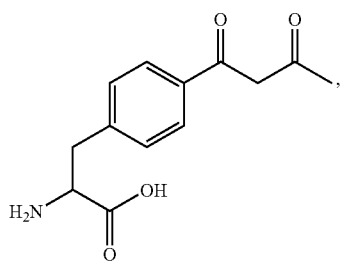

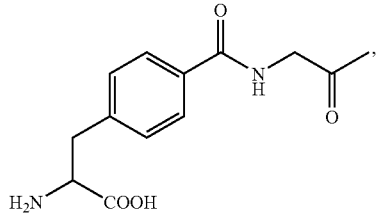

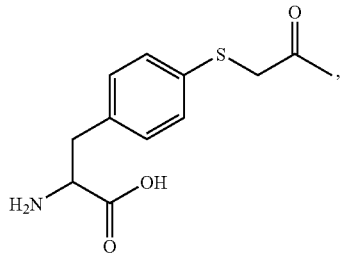

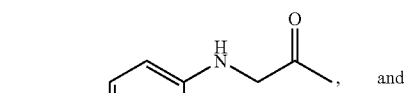, and

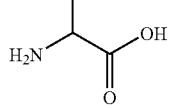

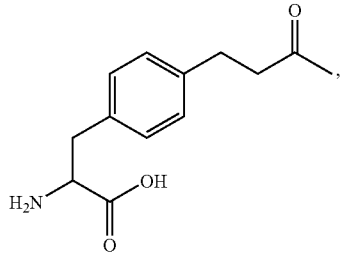

wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

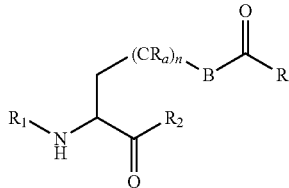
(VII)

wherein

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$ —N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8;

with a proviso that when A is —(CH$_2$)$_4$—, B is not —NHC(O)(CH$_2$CH$_2$)—.

In addition, the following amino acids are included:

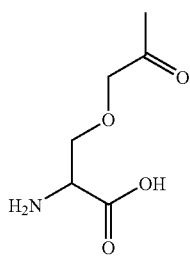
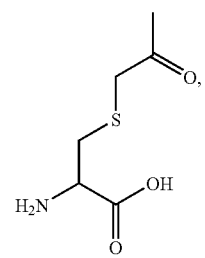

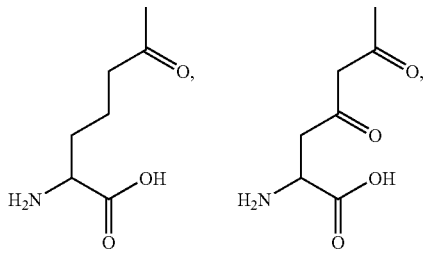

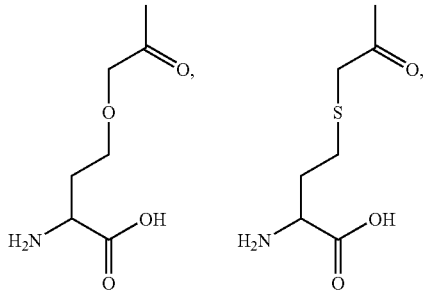

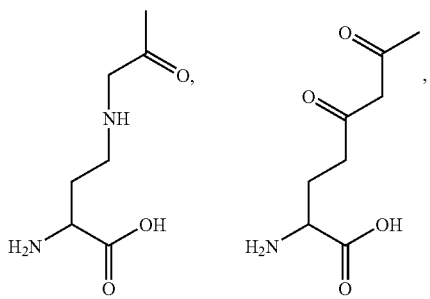

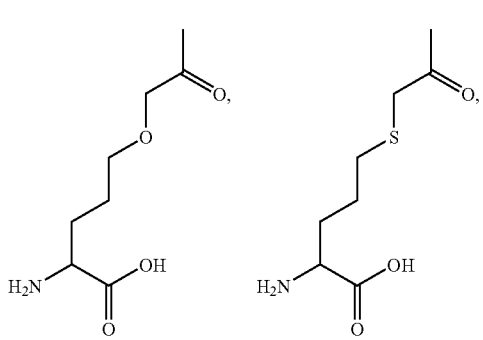

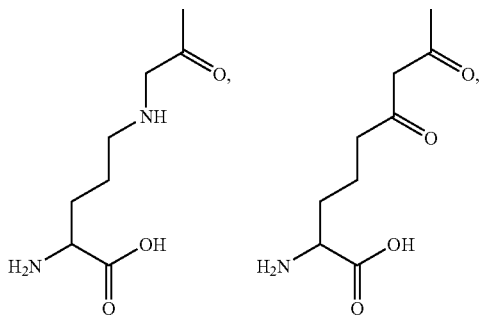

-continued

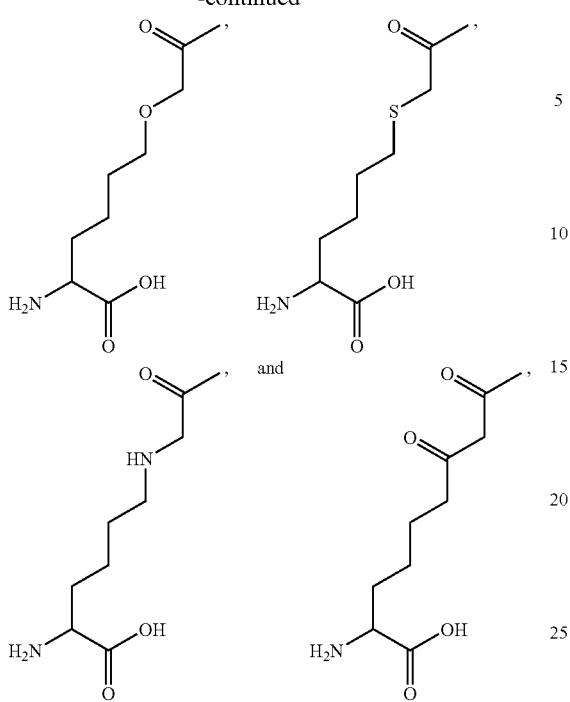

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

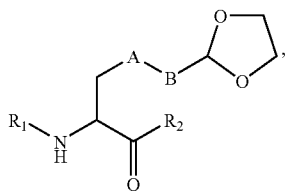

(VIII)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN (R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide.

In addition, the following amino acids having the structure of Formula (IX) are included:

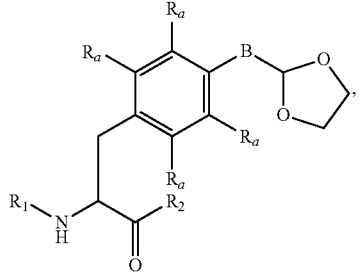

(IX)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN (R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

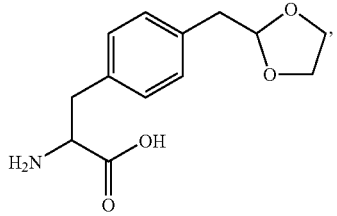
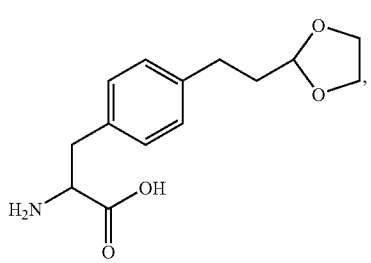
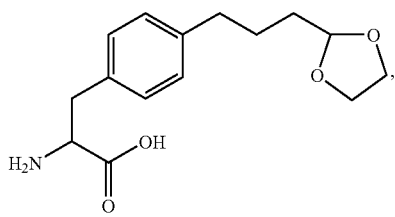
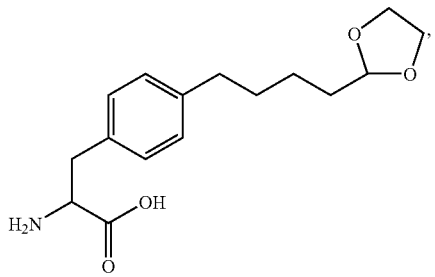
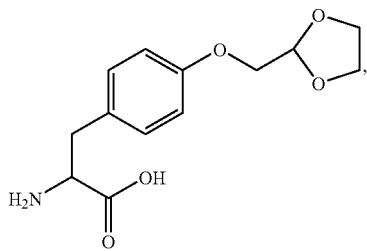
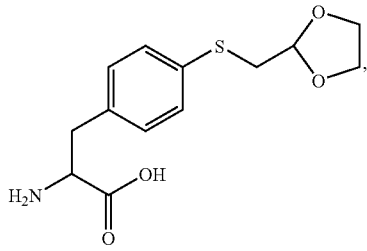
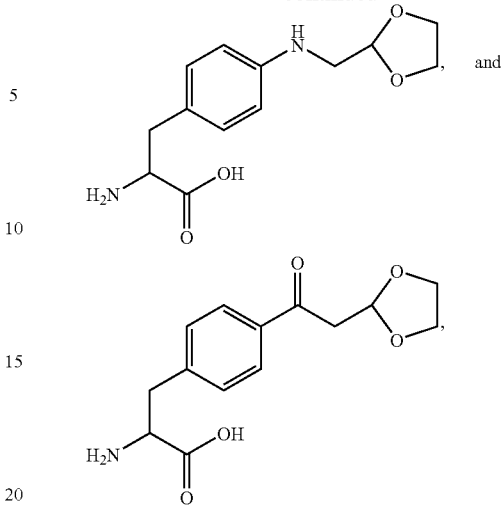

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

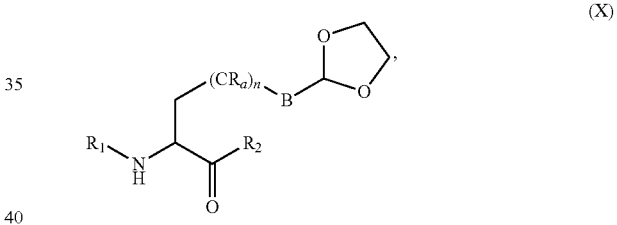

(X)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
each $R_a$ is independently selected from the group consisting of H, halogen, alkyl, substituted alkyl, —N(R')$_2$, —C(O)$_k$R' where k is 1, 2, or 3, —C(O)N(R')₂, —OR', and —S(O)ₖR', where each R' is independently H, alkyl, or substituted alkyl; and n is 0 to 8.

In addition, the following amino acids are included:

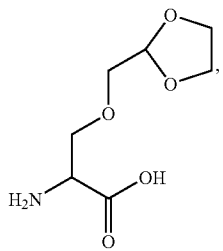 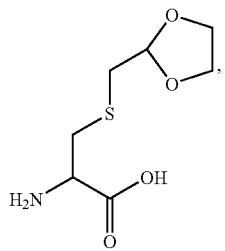

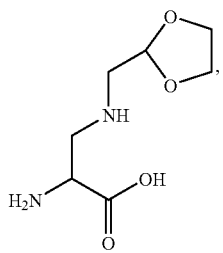 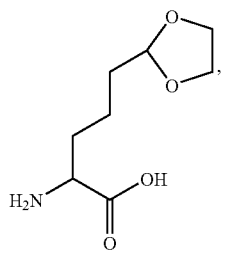

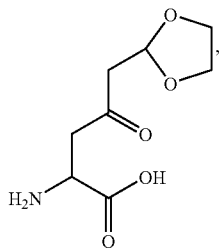 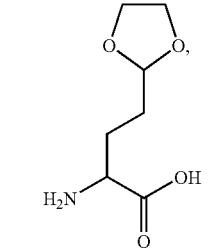

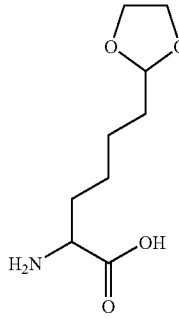 and 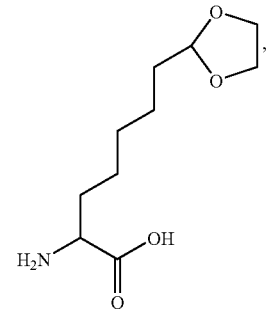

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

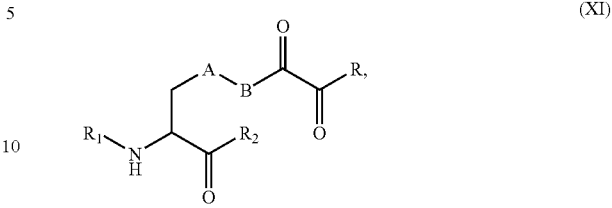

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)ₖ— where k is 1, 2, or 3, —S(O)ₖ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)ₖN(R')—, —N(R')C(O)N(R')—, —N(R')C(S)N(R')—, —N(R')S(O)ₖN(R')—, —N(R')—N=, —C(R')=N—, —C(R')=N—N(R')—, —C(R')=N—N=, —C(R')₂—N=N—, and —C(R')₂—N(R')—N(R')—, where each R' is independently H, alkyl, or substituted alkyl; R is H, alkyl, substituted alkyl, cycloalkyl, or substituted cycloalkyl;

R₁ is optional, and when present, is H, an amino protecting group, resin, amino acid, polypeptide, or polynucleotide; and R₂ is optional, and when present, is OH, an ester protecting group, resin, amino acid, polypeptide, or polynucleotide.

In addition, the following amino acids having the structure of Formula (XII) are included:

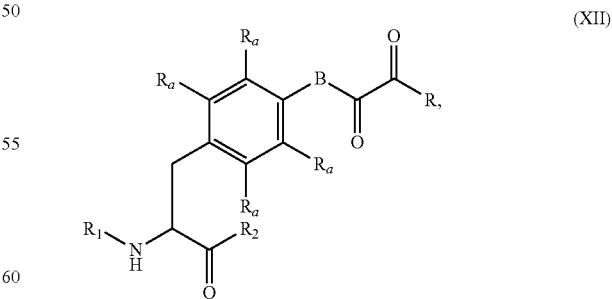

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl; R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;
wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

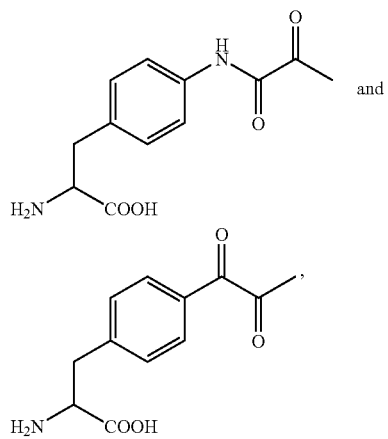

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

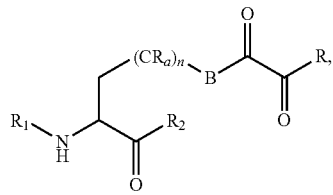

(XIII)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

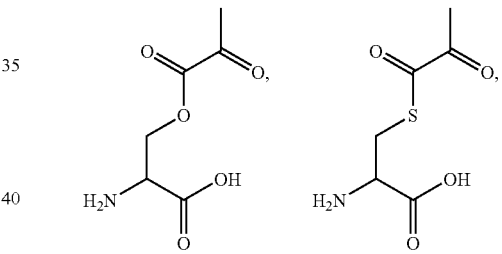

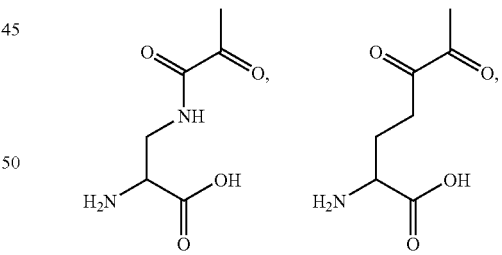

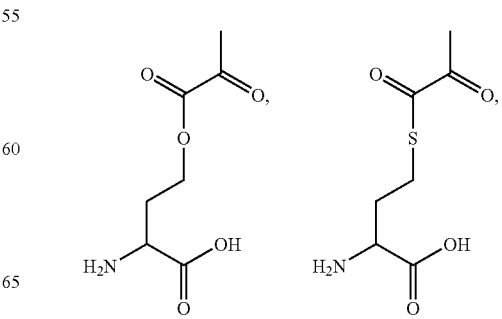

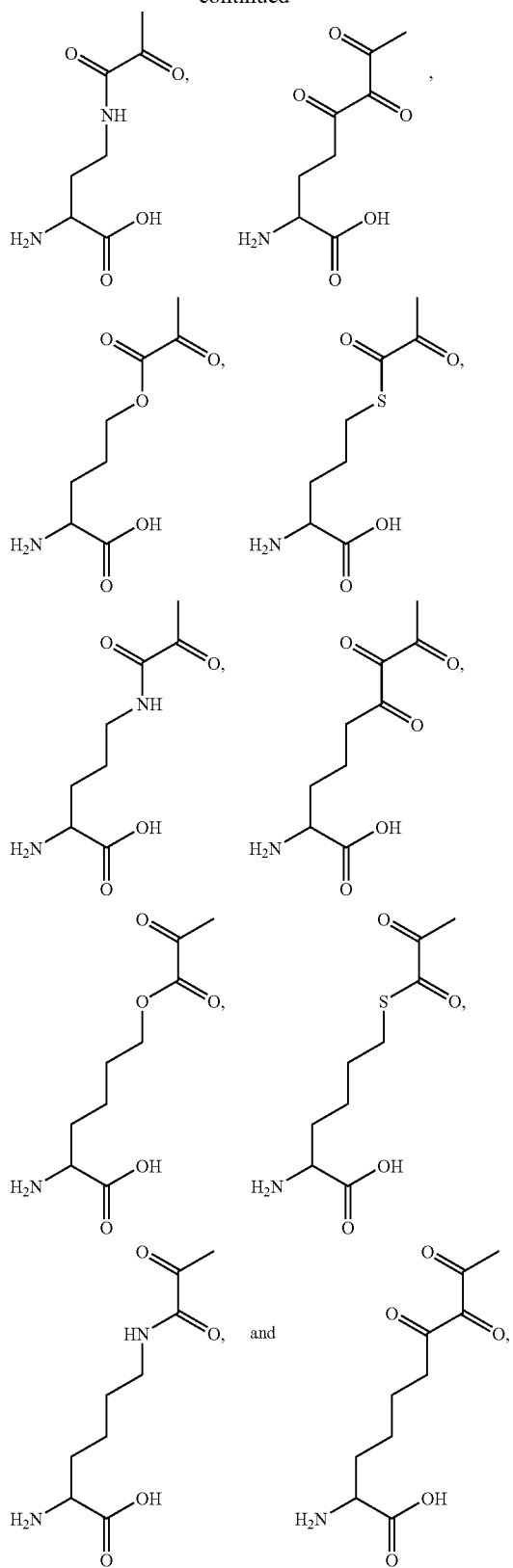

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

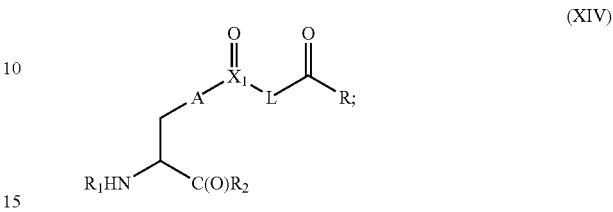

(XIV)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

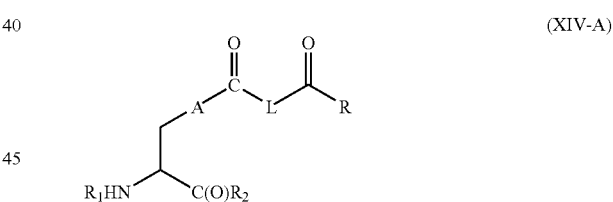

(XIV-A)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-B) are included:

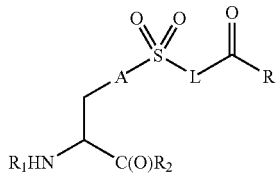

(XIV-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
L is alkylene, substituted alkylene, N(R')(alkylene) or N(R') (substituted alkylene), where R' is H, alkyl, substituted alkyl, cycloalkyl, or substituted cycloalkyl.

In addition, the following amino acids having the structure of Formula (XV) are included:

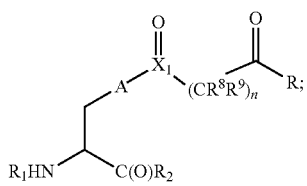

(XV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-A) are included:

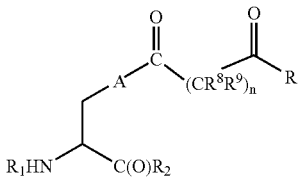

(XV-A)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-B) are included:

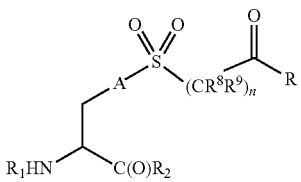

(XV-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XVI) are included:

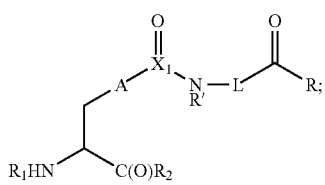

(XVI)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-A) are included:

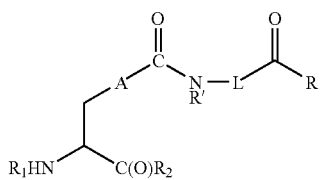

(XVI-A)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-B) are included:

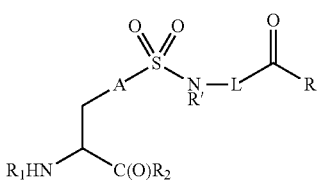

(XVI-B)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

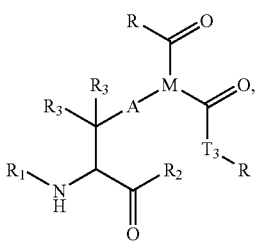

(XVII)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

-continued

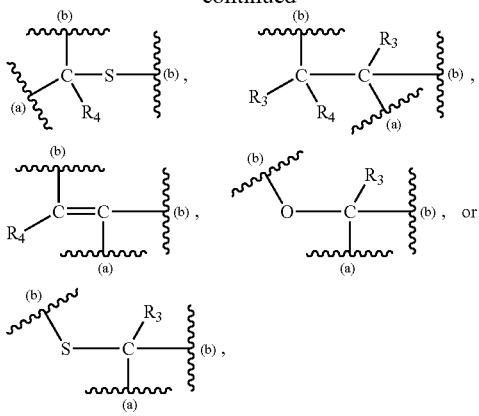

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, amino acids having the structure of Formula (XVIII) are included:

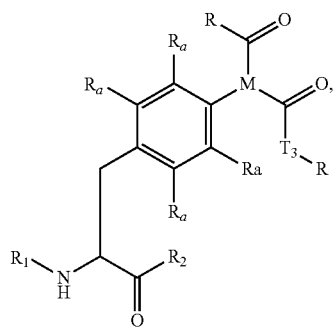

(XVIII)

wherein:

M is —C($R_3$)—,

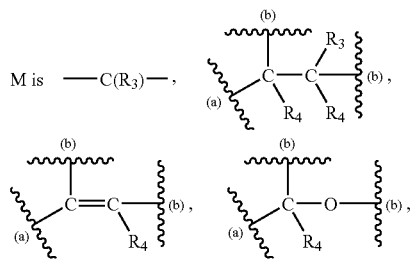

-continued

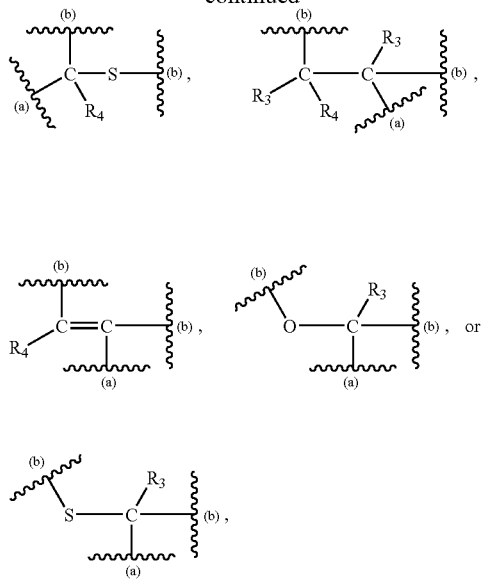

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, amino acids having the structure of Formula (XIX) are included:

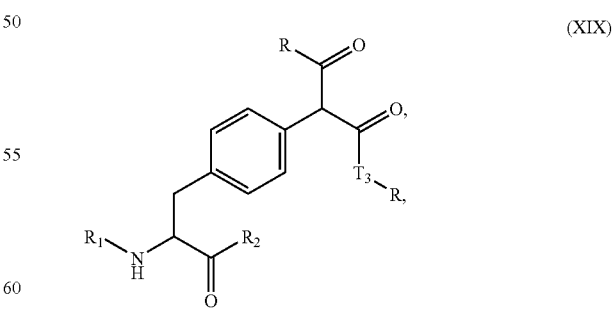

(XIX)

wherein:

R is H, halogen, alkyl, substituted alkyl, cycloalkyl, or substituted cycloalkyl; and $T_3$ is O, or S.

In addition, amino acids having the structure of Formula (XX) are included:

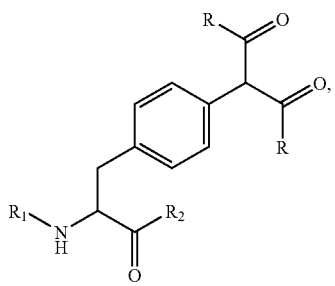

(XX)

wherein:
R is H, halogen, alkyl, substituted alkyl, cycloalkyl, or substituted cycloalkyl.

In addition, the following amino acids having structures of Formula (XXI) are included:

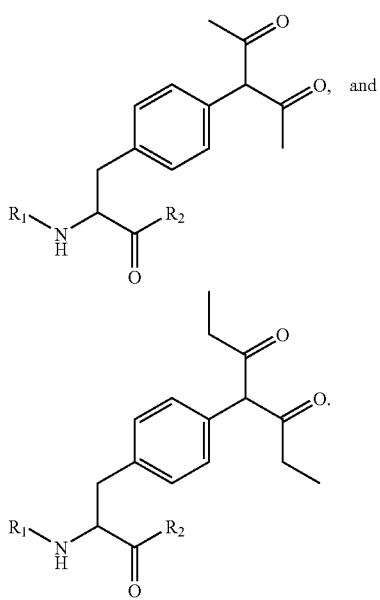

and

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Structure and Synthesis of Non-Natural Amino Acids: Hydroxylamine-Containing Amino Acids U.S. Provisional Patent Application No. 60/638,418 is incorporated by reference in its entirety. Thus, the disclosures provided in Section V (entitled "Non-natural Amino Acids"), Part B (entitled "Structure and Synthesis of Non-Natural Amino Acids: Hydroxylamine-Containing Amino Acids"), in U.S. Provisional Patent Application No. 60/638,418 apply fully to the methods, compositions (including Formulas I-XXP), techniques and strategies for making, purifying, characterizing, and using non-natural amino acids, non-natural amino acid polypeptides and modified non-natural amino acid polypeptides described herein to the same extent as if such disclosures were fully presented herein. U.S. Patent Publication Nos. 2006/0194256, 2006/0217532, and 2006/0217289 and WO 2006/069246 entitled "Compositions containing, methods involving, and uses of non-natural amino acids and polypeptides," are also incorporated herein by reference in their entirety.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.,* 38, 4660-4669; King, F. E. & Kidd, D. A. A. (1949) *A New Synthesis of Glutamine and of γ-Dipeptides of Glutamic Acid from Phthylated Intermediates. J. Chem. Soc.,* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.*

53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference herein.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

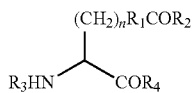

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., *Biochemistry* 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al, *Bioconjug. Chem.* 3: 262-268 (1992); Geoghegan, K. & Stroh, J., *Bioconjug Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

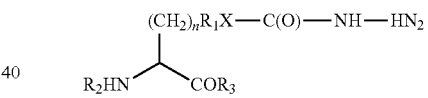

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

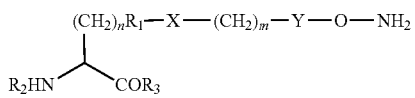

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid, have been isolated from natural sources (Rosenthal, G., *Life Sci.* 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing FGF-21 polypeptide can be carried out at room temperature under aqueous conditions by the addition of Cu(II) (including but not limited to, in the form of a catalytic amount of $CUSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2]cycloaddition reaction between an azide and an alkyne is desired, the FGF-21 polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azidophenylalanine).

Exemplary water soluble polymers containing an aryl ester and a phosphine moiety can be represented as follows:

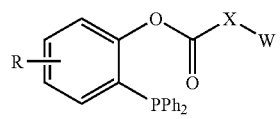

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2$R', —$S(O)_2$NR'R", —CN and —$NO_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

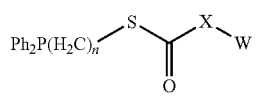

wherein n is 1-10; X can be O, N, S or not present, Ph is phenyl, and W is a water soluble polymer.

Exemplary alkyne-containing amino acids can be represented as follows:

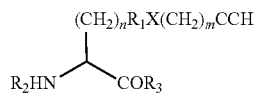

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is O, m is 1 and the propargyloxy group is positioned in the para position relative to the alkyl side chain (i.e., O-propargyl-tyrosine). In some embodiments, n is 1, R$_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one of ordinary skill in the art.

Exemplary azide-containing amino acids can be represented as follows:

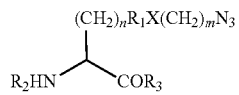

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned Para to the alkyl side chain. In some embodiments, n is 0-4 and R$_1$ and X are not present, and m=0. In some embodiments, n is 1, R$_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into FGF-21 polypeptides and then reacted with water soluble polymers comprising an aldehyde functionality. In some embodiments, a water soluble polymer, drug conjugate or other payload can be coupled to a FGF-21 polypeptide comprising a beta-substituted aminothiol amino acid via formation of the thiazolidine.

F. Additional Reactive Groups

Additional reactive groups and non-naturally encoded amino acids that can be incorporated into FGF-21 polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein Arrays" which is incorporated by reference herein; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly Design-Path™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, those identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6\>Manα1-6\>Manβ1-4GlcNAcβ1-4GlcNAcβ1-Asn<br>Manα1-3/ Manα1-3/ |
| Hybrid | Manα1-6\>Manβ1-4GlcNAcβ1-4GlcNAcβ1-Asn<br>GlcNAcβ1-2—Manα1-3/ |
| Complex | GlcNAcβ1-2—Manα1-6\>Manβ1-4GlcNAcβ1-4GlcNAcβ1-Asn<br>GlcNAcβ1-2—Manα1-3/ |
| Xylose | Manα1-6\>Manβ1-4GlcNAcβ1-4GlcNAcβ1-Asn<br>Xylβ1-2/ |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.*, 118:8150-8151; Mahal, et al., (1997) *Science*, 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2]cycloaddition reaction (see, e.g., Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry,* (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *J. Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2]cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like.

These molecules can be added to an unnatural amino acid with an alkynyl group, including but not limited to, p-propargyloxyphenylalanine, or azido group, including but not limited to, p-azido-phenylalanine, respectively.

V. In Vivo Generation of FGF-21 Polypeptides Comprising Non-Naturally-Encoded Amino Acids The FGF-21 polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O-RS, or portions thereof, are encoded by polynucleotide sequences and include amino acid sequences disclosed in U.S. Pat. Nos. 7,045,337 and 7,083, 970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

An example of an azide-specific O-tRNA/aminoacyl-tRNA synthetase system is described in Chin, J. W., et al., *J. Am. Chem. Soc.* 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Pat. No. 7,083,970 which is incorporated by reference herein. Exemplary O-tRNA sequences suitable for use in the present invention include, but are not limited to, nucleotide sequences SEQ ID NOs: 1-3 as disclosed in U.S. Pat. No. 7,083,970) which is incorporated by reference herein. Other examples of O-tRNA/aminoacyl-tRNA synthetase pairs specific to particular non-naturally encoded amino acids are described in U.S. Pat. No. 7,045,337 which is incorporated by reference herein. O-RS and O-tRNA that incorporate both keto- and azide-containing amino acids in *S. cerevisiae* are described in Chin, J. W., et al., *Science* 301: 964-967 (2003).

Several other orthogonal pairs have been reported. Glutaminyl (see, e.g., Liu, D. R., and Schultz, P. G. (1999) *Proc. Natl. Acad. Sci. U.S.A.* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem.* (Tokyo, Jpn.) 124:1065-1068; and, Kowal, A. K., et al., (2001) *Proc. Natl. Acad. Sci. U.S.A.* 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) *Proc. Natl. Acad. Sci. U.S.A.* 98:2268-2273) and tyrosyl (see, e.g., Edwards, H., and Schimmel, P. (1990) *Mol. Cell. Biol.* 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) *Nucleic Acids Res.* 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the FGF-21 polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Pat. No. 7,045,337, which is incorporated by reference herein. Methods for selecting an orthogonal tRNA-tRNA synthetase pair for use in in vivo translation system of an organism are also described in U.S. Pat. Nos. 7,045,337 and 7,083,970 which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O-RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O—RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in FGF-21 Polypeptides

The present invention contemplates incorporation of one or more non-naturally-occurring amino acids into FGF-21 polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

A variety of biochemical and structural approaches can be employed to select the desired sites for substitution with a non-naturally encoded amino acid within the FGF-21 polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing an FGF-21 molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of FGF-21 polypeptides can be identified using point mutation analysis, alanine scanning, saturation mutagenesis and screening for biological activity, or homolog scanning methods known in the art. Residues that are critical for FGF-21 bioactivity, residues that are involved with pharmaceutical stability, antibody epitopes, or receptor or heparin binding residues may be mutated. U.S. Pat. Nos. 5,580,723; 5,834,250; 6,013,478; 6,428,954; and 6,451,561, which are incorporated by reference herein, describe methods for the systematic analysis of the structure and function of polypeptides such as FGF-21 by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

A lot of data has already been collected using the methods presented in this application and potential and beneficial sites of mutation have been found and successfully tested, as described in the examples provided later in this specification. Finding additional information regarding structure and activity of mutants, even those which include some details regarding formulation and/or testing that has not been specifically described in the examples, of FGF-21 polypeptides that contain deletions can also be examined to determine regions of the protein that are likely to be tolerant of substitution with a non-naturally encoded amino acid. In a similar manner, protease digestion and monoclonal antibodies can be used to identify regions of FGF-21 that are responsible for binding the FGF-21 receptor. Once residues that are likely to be intolerant to substitution with non-naturally encoded amino acids have been eliminated, the impact of proposed substitutions at each of the remaining positions can be examined. Models may be generated from the three-dimensional crystal structures of other FGF family members and FGF receptors. Protein Data Bank (PDB, available on the World Wide Web at rcsb.org) is a centralized database containing three-dimensional structural data of large molecules of proteins and nucleic acids. Models may be made investigating the secondary and tertiary structure of polypeptides, if three-dimensional structural data is not available. Thus, those of ordinary skill in the art can readily identify amino acid positions that can be substituted with non-naturally encoded amino acids.

In some embodiments, the FGF-21 polypeptides of the invention comprise one or more non-naturally occurring amino acids positioned in a region of the protein that does not disrupt the structure of the polypeptide.

Exemplary residues of incorporation of a non-naturally encoded amino acid may be those that are excluded from potential receptor binding regions, may be fully or partially solvent exposed, have minimal or no hydrogen-bonding interactions with nearby residues, may be minimally exposed to nearby reactive residues, may be on one or more of the exposed faces, may be a site or sites that are juxtaposed to a second FGF-21, or other molecule or fragment thereof, may be in regions that are highly flexible, or structurally rigid, as predicted by the three-dimensional, secondary, tertiary, or quaternary structure of FGF-21, bound or unbound to its receptor, or coupled or not coupled to another biologically active molecule, or may modulate the conformation of the FGF-21 itself or a dimer or multimer comprising one or more FGF-21, by altering the flexibility or rigidity of the complete structure as desired.

The family of FGF proteins have a common β-trefoil or α-sheet structure as identified by crystallography (Harmer et al., Biochemistry 43:629-640 (2004)). One of ordinary skill in the art recognizes that such analysis of FGF-21 enables the determination of which amino acid residues are surface exposed compared to amino acid residues that are buried within the tertiary structure of the protein. Therefore, it is an embodiment of the present invention to substitute a non-naturally encoded amino acid for an amino acid that is a surface exposed residue.

In some embodiments, one or more non-naturally encoded amino acids are incorporated at any position in FGF-21: 1-181 from SEQ ID NO: 1 or the corresponding amino acids in SEQ ID NOs: 2-7. In some embodiments, one or more non-naturally encoded amino acids are incorporated in one or more of the following positions in FGF-21: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, one or more non-naturally encoded amino acids are incorporated in one or more of the following positions in FGF-21:10, 52, 117, 126, 131, 162, 87, 77, 83, 72, 69, 79, 91, 96, 108, and 110 (SEQ ID NO: 1 or the corresponding amino acids of SEQ ID NOs: 2-7). In some embodiments, one or more non-naturally encoded amino acids are incorporated in one or more of the following positions in FGF-21:10, 52, 77, 117, 126, 131, and 162 (SEQ ID NO: 1 or the corresponding amino acids of SEQ ID NOs: 2-7). In some embodiments, one or more non-naturally encoded amino acids are incorporated in one or more of the following positions in FGF-21: 87, 77, 83, 72 (SEQ ID NO: 1 or the corresponding amino acids of SEQ ID NOs: 2-7). In some embodiments, one or more non-naturally encoded amino acids are incorporated in one or more of the following positions in FGF-21: 69, 79, 91, 96, 108, and 110 (SEQ ID NO: 1 or the corresponding amino acids of SEQ ID NOs: 2-7).

In one embodiment, the non-naturally occurring amino acid is at the 91 position in FGF-21 (SEQ ID NO: 1 or the corresponding amino acids of SEQ ID NOs: 2-7). In one embodiment, the non-naturally occurring amino acid is at the 131 position in FGF-21 (SEQ ID NO: 1 or the corresponding amino acids of SEQ ID NOs: 2-7). In one embodiment, the non-naturally occurring amino acid is at the 108 position in FGF-21 (SEQ ID NO: 1 or the corresponding amino acids of SEQ ID NOs: 2-7). In one embodiment, the non-naturally occurring amino acid is at the 77 position in FGF-21 (SEQ ID NO: 1 or the corresponding amino acids of SEQ ID NOs: 2-7). In one embodiment, the non-naturally occurring amino acid is at the 72 position in FGF-21 (SEQ ID NO: 1 or the corresponding amino acids of SEQ ID NOs: 2-7). In one embodiment, the non-naturally occurring amino acid is at the 87 position in FGF-21 (SEQ ID NO: 1 or the corresponding amino acids of SEQ ID NOs: 2-7). In one embodiment, the non-naturally occurring amino acid is at the 86 position in FGF-21 (SEQ ID NO: 1 or the corresponding amino acids of SEQ ID NOs: 2-7). In one embodiment, the non-naturally occurring amino acid is at the 126 position in FGF-21 (SEQ ID NO: 1 or the corresponding amino acids of SEQ ID NOs: 2-7). In one embodiment, the non-naturally occurring amino acid is at the 110 position in FGF-21 (SEQ ID NO: 1 or the corresponding amino acids of SEQ ID NOs: 2-7). In one embodiment, the non-naturally occurring amino acid is at the 83 position in FGF-21 (SEQ ID NO: 1 or the corresponding amino acids of SEQ ID NOs: 2-7). In one embodiment, the non-naturally occurring amino acid is at the 146 position in FGF-21 (SEQ ID NO: 1 or the corresponding amino acids of SEQ ID NOs: 2-7). In one embodiment, the non-naturally occurring amino acid is at the 135 position in FGF-21 (SEQ ID NO: 1 or the corresponding amino acids of SEQ ID NOs: 2-7). In one embodiment, the non-naturally occurring amino acid is at the 96 position in FGF-21 (SEQ ID NO: 1 or the corresponding amino acids of SEQ ID NOs: 2-7). In one embodiment, the non-naturally occurring amino acid is at the 36 position in FGF-21 (SEQ ID NO: 1 or the corresponding amino acids of SEQ ID NOs: 2-7).

In another embodiment, there is a non-naturally occurring amino acid at 91 and one other non-naturally occurring amino acid at one of the following positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 91 and one other non-naturally occurring amino acid at one of the following positions: 131, 108, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at position 91 and position 131 (SEQ ID NO: 1 or the corresponding amino acids in SEQ ID NOs: 2-7). In another embodiment, there is a non-naturally occurring amino acid at position 91 and position 77 (SEQ ID NO: 1 or the corresponding amino acids in SEQ ID NOs: 2-7). In another embodiment, there is a non-naturally occurring amino acid at position 91 and position 108 (SEQ ID NO: 1 or the corresponding amino acids in SEQ ID NOs: 2-7). In another embodiment, there is a non-naturally occurring amino acid at position 131 and position 108 (SEQ ID NO: 1 or the corresponding amino acids in SEQ ID NOs: 2-7). In another embodiment, there is a non-naturally occurring amino acid at position 131 and position 77 (SEQ ID NO: 1 or the corresponding amino acids in SEQ ID NOs: 2-7). In another embodiment, there is a non-naturally occurring amino acid at position 131 (SEQ ID NO: 1 or the corresponding amino acids in SEQ ID NOs: 2-7). In another embodiment, there is a non-naturally occurring amino acid at position 108 (SEQ ID NO: 1 or the corresponding amino acids in SEQ ID NOs: 2-7). In another embodiment, there is a non-naturally occurring amino acid at position 77 (SEQ ID NO: 1 or the corresponding amino acids in SEQ ID NOs: 2-7). In another embodiment, there is a non-naturally occurring amino acid at position 72 (SEQ ID NO: 1 or the corresponding amino acids in SEQ ID NOs: 2-7). In another embodiment, there is a non-naturally occurring amino acid at position 87 (SEQ ID NO: 1 or the corresponding amino acids in SEQ ID NOs: 2-7). In another embodiment, there is a non-naturally occurring amino acid at position 86 (SEQ ID NO: 1 or the corresponding amino acids in SEQ ID NOs: 2-7) linked. In another embodiment, there is a non-naturally occurring amino acid at position 126 (SEQ ID NO: 1 or the corresponding amino acids in SEQ ID NOs: 2-7). In another embodiment, there is a non-naturally occurring amino acid at position 110 (SEQ ID NO: 1 or the corresponding amino acids in SEQ ID NOs: 2-7). In another embodiment, there is a non-naturally occurring amino acid at position 83 (SEQ ID NO: 1 or the corresponding amino acids in SEQ ID NOs: 2-7).

In another embodiment, there is a non-naturally occurring amino acid at 91 and one or more other non-naturally occurring amino acids at one or more of the following positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 91 and one or more other non-naturally occurring amino acid at one or more of the following positions: 131, 108, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at 131 and one other non-naturally occurring amino acid at one or more of the following positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 131 and one other non-naturally occurring amino acid at one or more of the following positions: 131, 108, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at position 108 and two or more other non-naturally occurring amino acids at two or more of the following positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at position 108 and two or more other non-naturally occurring amino acids at two or more of the following positions: 131, 108, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at 77 and one other non-naturally occurring amino acid at one or more of the following positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 77 and one other non-naturally occurring amino acid at one or more of the following positions: 131, 108, 77, 72, 87, 86, 126, 110, 83, 146, 135, 96, and 36 (SEQ ID NO: 1 or the corresponding amino acids of SEQ ID NOs: 2-7).

An examination of the crystal structure of FGF-21 or FGF family member(s) and its interaction with the FGF receptor can indicate which certain amino acid residues have side chains that are fully or partially accessible to solvent. The side chain of a non-naturally encoded amino acid at these positions may point away from the protein surface and out into the solvent. In some embodiments, the non-naturally occurring amino acid at one or more of these positions is linked to a water soluble polymer, including but not limited to, positions:

before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, the non-naturally occurring amino acid at one of these positions is linked to a water soluble polymer, including positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, the non-naturally occurring amino acid at two or more of these positions is linked to a water soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, the non-naturally occurring amino acid at one or more of these positions is linked to a water soluble polymer, including but not limited to, positions: 10, 52, 117, 126, 131, 162, 87, 77, 83, 72, 69, 79, 91, 96, 108, and 110 (SEQ ID NO: 1 or the corresponding amino acids of SEQ ID NOs: 2-7). In some embodiments, the non-naturally occurring amino acid at one or more of these positions is linked to a water soluble polymer: 10, 52, 77, 117, 126, 131, 162, (SEQ ID NO: 1 or the corresponding amino acids of SEQ ID NOs: 2-7). In some embodiments, the non-naturally occurring amino acid at one or more of these positions is linked to a water soluble polymer: 87, 77, 83, 72 (SEQ ID NO: 1 or the corresponding amino acids of SEQ ID NOs: 2-7). In some embodiments, the non-naturally occurring amino acid at one or more of these positions is linked to a water soluble polymer: 69, 79, 91, 96, 108, and 110 (SEQ ID NO: 1 or the corresponding amino acids of SEQ ID NOs: 2-7). In some embodiments, the non-naturally occurring amino acid at one or more of these positions is linked to a water soluble polymer: 91, 131, 108, 77, 72, 87, 86, 126, 110, 83, 146, 135, 96, and 36 (SEQ ID NO: 1 or the corresponding amino acids of SEQ ID NOs: 2-7). In another embodiment, where a non-naturally occurring amino acid occurs at amino acid 91 (SEQ ID NO: 1 or the corresponding amino acids of SEQ ID NOs: 2-7) the non-naturally occurring amino acid is linked to a water soluble polymer.

In another embodiment, there is a non-naturally occurring amino acid at 91 linked to a water soluble polymer and one other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 91 and one or more other non-naturally occurring amino acid at one of the following positions and these non-naturally occurring amino acids are linked to a water soluble polymer: 131, 108, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 91 linked to a water soluble polymer and one or more other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 91 linked to a water soluble polymer and one or more other non-naturally occurring amino acids which are linked to a water soluble polymer: 131, 108, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 91 linked to a water soluble polymer and two or more other non-naturally occurring amino acid at two or more of the following positions and these non-naturally occurring amino acids are linked to a water soluble polymer: before position 1

(i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 91 linked to a water soluble polymer and two or more other non-naturally occurring amino acid at two or more of the following positions and these non-naturally occurring amino acids are linked to a water soluble polymer: 131, 108, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at 131 linked to a water soluble polymer and one other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 131 and one or more other non-naturally occurring amino acid at one of the following positions and these non-naturally occurring amino acids are linked to a water soluble polymer: 91, 108, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 131 linked to a water soluble polymer and one or more other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7).

In another embodiment, there is a non-naturally occurring amino acid at 131 linked to a water soluble polymer and one or more other non-naturally occurring amino acids which are linked to a water soluble polymer: 91, 108, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 131 linked to a water soluble polymer and two or more other non-naturally occurring amino acid at two or more of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 131 linked to a water soluble polymer and two or more other non-naturally occurring amino acid at two or more of the following positions and these non-naturally occurring amino acids are linked to a water soluble polymer: 91, 108, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at 108 linked to a water soluble polymer and one other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 108 and one or more other non-naturally occurring amino acid at one of the following positions and these non-naturally occurring amino acids are linked to a water soluble polymer: 91, 131, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 108 linked to a water soluble polymer and one or more other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 108 linked to a water soluble polymer and one or more other non-naturally occurring amino acids which are linked to a water soluble polymer: 91, 131, 77, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 108 linked to a water soluble polymer and two or more other non-naturally occurring amino acid at two or more of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 108 linked to a water soluble polymer and two or more other non-naturally occurring amino acid at two or more of the following positions and these non-naturally occurring amino acids are linked to a water soluble polymer: 91, 131, 77, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at 77 linked to a water soluble polymer and one other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 77 and one or more other non-naturally occurring amino acid at one of the following positions and these non-naturally occurring amino acids are linked to a water soluble polymer: 91, 131, 108, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 77 linked to a water soluble polymer and one or more other non-naturally occurring amino acid at one of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 77 linked to a water soluble polymer and one or more other non-naturally occurring amino acids which are linked to a water soluble polymer: 91, 131, 108, 72, 87, 86, 126, 110, 83, 146, 135, 96, and 36 (SEQ ID NO: 1 or the corresponding amino acids of SEQ ID NOs: 2-7). In another embodiment, there is a non-naturally occurring amino acid at 77 linked to a water soluble polymer and two or more other non-naturally occurring amino acid at two or more of the following positions and these non-naturally occurring amino acids are linked to a water soluble polymer: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In another embodiment, there is a non-naturally occurring amino acid at 77 linked to a water soluble polymer and two or more other non-naturally occurring amino acid at two or more of the following positions and these non-naturally occurring amino acids are linked to a water soluble polymer: 91, 131, 108, 72, 87, 86, 126, 110, 83, 146, 135, 96, and 36 (SEQ ID NO: 1 or the corresponding amino acids of SEQ ID NOs: 2-7).

In another embodiment, there is a non-naturally occurring amino acid at position 91 and position 131 (SEQ ID NO: 1 or the corresponding amino acids in SEQ ID NOs: 2-7) and one or more of these positions is linked to a water soluble polymer. In another embodiment, there is a non-naturally occurring amino acid at position 91 and position 77 (SEQ ID NO: 1 or the corresponding amino acids in SEQ ID NOs: 2-7) and one or more of these positions is linked to a water soluble polymer. In another embodiment, there is a non-naturally occurring amino acid at position 91 and position 108 (SEQ ID NO: 1 or the corresponding amino acids in SEQ ID NOs: 2-7) and one or more of these positions is linked to a water soluble polymer. In another embodiment, there is a non-naturally occurring amino acid at position 131 and position 108 (SEQ ID NO: 1 or the corresponding amino acids in SEQ ID NOs: 2-7) and one or more of these positions is linked to a water soluble polymer. In another embodiment, there is a non-naturally occurring amino acid at position 131 and position 77 (SEQ ID NO: 1 or the corresponding amino acids in SEQ ID NOs: 2-7) and one or more of these positions is linked to a water soluble polymer. In another embodiment, there is a non-naturally occurring amino acid at position 91 (SEQ ID NO: 1 or the corresponding amino acids in SEQ ID NOs: 2-7) linked to a water soluble polymer. In another embodiment, there is a non-naturally occurring amino acid at position 131 (SEQ ID NO: 1 or the corresponding amino acids in SEQ ID NOs: 2-7) linked to a water soluble polymer. In another embodiment, there is a non-naturally occurring amino acid at position 108 (SEQ ID NO: 1 or the corresponding amino acids in SEQ ID NOs: 2-7) linked to a water soluble polymer. In another embodiment, there is a non-naturally occurring amino acid at position 77 (SEQ ID NO: 1 or the corresponding amino acids in SEQ ID NOs: 2-7) linked to a water soluble polymer. In another embodiment, there is a non-naturally occurring amino acid at position 72 (SEQ ID NO: 1 or the corresponding amino acids in SEQ ID NOs: 2-7) linked to a water soluble polymer. In another embodiment, there is a non-naturally occurring amino acid at position 87 (SEQ ID NO: 1 or the corresponding amino acids in SEQ ID NOs: 2-7) linked to a water soluble polymer. In another embodiment, there is a non-naturally occurring amino acid at position 86 (SEQ ID NO: 1 or the corresponding amino acids in SEQ ID NOs: 2-7) linked to a water soluble polymer. In another embodiment, there is a non-naturally occurring amino acid at position 126 (SEQ ID NO: 1 or the corresponding amino acids in SEQ ID NOs: 2-7) linked to a water soluble polymer. In another embodiment, there is a non-naturally occurring amino acid at position 110 (SEQ ID NO: 1 or the corresponding amino acids in SEQ ID NOs: 2-7) linked to a water soluble polymer. In another embodiment, there is a non-naturally occurring amino acid at position 83 (SEQ ID NO: 1 or the corresponding amino acids in SEQ ID NOs: 2-7) linked to a water soluble polymer.

A wide variety of non-naturally encoded amino acids can be substituted for, or incorporated into, a given position in a FGF-21 polypeptide. In general, a particular non-naturally encoded amino acid is selected for incorporation based on an examination of the three dimensional crystal structure of a FGF-21 polypeptide or other FGF family member with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the FGF-21 polypeptide (e.g., the introduction of 4-azidophenylalanine if one wants to effect a Huisgen [3+2]cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the FGF-21 polypeptide to affect other biological traits of the FGF-21 polypeptide. In some cases, the other additions, substitutions or deletions may increase the stability (including but not limited to, resistance to proteolytic degradation) of the FGF-21 polypeptide or increase affinity of the FGF-21 polypeptide for its receptor. In some cases, the other additions, substitutions or deletions may increase the pharmaceutical stability of the FGF-21 polypeptide. In some cases, the other additions, substitutions or deletions may increase the solubility (including but not limited to, when expressed in E. coli or other host cells) of the FGF-21 polypeptide. In some embodiments additions, substitutions or deletions may increase the polypeptide solubility following expression in E. coli or other recombinant host cells. In some embodiments sites are selected for substitution with a naturally encoded or non-natural amino acid in addition to another site for incorporation of a non-natural amino acid that results in increasing the polypeptide solubility following expression in E. coli or other recombinant host cells. In some embodiments, the FGF-21 polypeptides comprise another addition, substitution or deletion that modulates affinity for the FGF-21 polypeptide receptor, binding proteins, or associated ligand, modulates signal transduction after binding to the FGF-21 receptor, modulates circulating half-life, modulates release or bio-availability, facilitates purification, or improves or alters a particular route of administration. In some embodiments, the FGF-21 polypeptides comprise an addition, substitution or deletion that increases the affinity of the FGF-21 variant for its receptor. Similarly, FGF-21 polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, FGF-21 size reduction, or other traits of the polypeptide.

In some embodiments, the substitution of a non-naturally encoded amino acid generates an FGF-21 antagonist. In some embodiments, a non-naturally encoded amino acid is substituted or added in a region involved with receptor binding. In some embodiments, a non-naturally encoded amino acid is substituted or added in a region involved with heparin binding. In some embodiments, FGF-21 antagonists comprise at least one substitution that cause FGF-21 to act as an antagonist. In some embodiments, the FGF-21 antagonist comprises a non-naturally encoded amino acid linked to a water soluble polymer that is present in a receptor binding region of the FGF-21 molecule.

In some cases, 1, 2, 3, 4, 5, 6, 7, 8, 9, 10, or more amino acids are substituted with one or more non-naturally-encoded amino acids. In some cases, the FGF-21 polypeptide further includes 1, 2, 3, 4, 5, 6, 7, 8, 9, 10, or more substitutions of one or more non-naturally encoded amino acids for naturally-occurring amino acids. For example, in some embodiments, one or more residues in FGF-21 are substituted with one or more non-naturally encoded amino acids. In some cases, the one or more non-naturally encoded residues are linked to one or more lower molecular weight linear or branched PEGs, thereby enhancing binding affinity and comparable serum half-life relative to the species attached to a single, higher molecular weight PEG.

In some embodiments, up to two of the following residues of FGF-21 are substituted with one or more non-naturally-encoded amino acids.

VII. Expression in Non-Eukaryotes and Eukaryotes

To obtain high level expression of a cloned FGF-21 polynucleotide, one typically subclones polynucleotides encoding a FGF-21 polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing FGF-21 polypeptides of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the FGF-21 polypeptides of the invention, host cells for expression are selected based on their ability to use the orthogonal components. Exemplary host cells include Gram-positive bacteria (including but not limited to *B. brevis, B. subtilis,* or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

I. Expression Systems Culture, and Isolation

FGF-21 polypeptides may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding a FGF-21 polypeptide. Such yeasts include, but are not limited to, ascosporogenous yeasts (*Endomycetales*), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium,* and *Filobasidiella*. Yeasts belonging to the Fungi Imperfecti (Blastomycetes) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis,* and *Candida*, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa,* and *H. polymorpha*.

The selection of suitable yeast for expression of FGF-21 polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a FGF-21 polypeptide, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIO-TECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica; A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora, Penicillium, Tolypocladium* (WO 91/00357), each incorporated by reference herein.

Control sequences for yeast vectors are known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073); and other glycolytic enzymes, such as pyruvate decarboxylase, triose-phosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/07862; WO 98/37208; and WO 98/26080; European Patent Applications EP 0 946

736; EP 0 732 403; EP 0 480 480; WO 90/10277; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein. WO 2005/091944 which is incorporated by reference herein describes the expression of FGF-21 in yeast.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a FGF-21 polypeptide, are included in the progeny intended by this definition.

The selection of suitable insect cells for expression of FGF-21 polypeptides is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528; 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographa californica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlue-Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKTNS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression in THE MOLECULAR BIOLOGY OF BACULOVIRUSES* (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those of ordinary skill in the art. See Miller et al., BIOESSAYS (1989) 11(4):91; SUMMERS AND SMITH, TEXAS AGRICULTURAL EXPERIMENT STATION BULLETIN NO. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

*E. Coli, Pseudomonas* species, and other Prokaryotes Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981)

9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce FGF-21 polypeptides at high levels. Examples of such vectors are known to those of ordinary skill in the art and include the pET29 series from Novagen, and the pPOP vectors described in WO99/05297, which is incorporated by reference herein. Such expression systems produce high levels of FGF-21 polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an E. coli operator region (EP Pub. No. 267 851).

In addition to a functioning promoter sequence, an efficient ribosome binding site is also useful for the expression of foreign genes in prokaryotes. In E. coli, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of E. coli 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in Escherichia coli", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a FGF-21 polypeptide, are included in the progeny intended by this definition.

The selection of suitable host bacteria for expression of FGF-21 polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable E. coli hosts include, but are not limited to, strains of BL21, DH10B, or derivatives thereof. In another embodiment of the methods of the present invention, the E. coli host is a protease minus strain including, but not limited to, OMP– and LON–. The host cell strain may be a species of *Pseudomonas*, including but not limited to, *Pseudomonas fluorescens, Pseudomonas aeruginosa*, and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the World Wide Web at dow.com).

Once a recombinant host cell strain has been established (i.e., the expression construct has been introduced into the host cell and host cells with the proper expression construct are isolated), the recombinant host cell strain is cultured under conditions appropriate for production of FGF-21 polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the FGF-21 polypeptide accumulates intracellularly) or harvesting of culture supernatant in either batch or continuous formats. For production in prokaryotic host cells, batch culture and cell harvest are preferred.

The FGF-21 polypeptides of the present invention are normally purified after expression in recombinant systems. The FGF-21 polypeptide may be purified from host cells or culture medium by a variety of methods known to the art. FGF-21 polypeptides produced in bacterial host cells may be poorly soluble or insoluble (in the form of inclusion bodies). In one embodiment of the present invention, amino acid substitutions may readily be made in the FGF-21 polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the FGF-21 polypeptides. When handling inclusion bodies of FGF-21 polypeptide, it may be advantageous to minimize the homogenization time on repetitions in order to maximize the yield of inclusion bodies without loss due to factors such as solubilization, mechanical shearing or proteolysis.

Insoluble or precipitated FGF-21 polypeptide may then be solubilized using any of a number of suitable solubilization agents known to the art. The FGF-21 polypeptide may be solubilized with urea or guanidine hydrochloride. The volume of the solubilized FGF-21 polypeptide should be minimized so that large batches may be produced using conveniently manageable batch sizes. This factor may be significant in a large-scale commercial setting where the recombinant host may be grown in batches that are thousands of liters in volume. In addition, when manufacturing FGF-21 polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the FGF-21 polypeptide inclusion bodies in place of the harsher denaturing agent guanidine hydrochloride. The use of urea significantly reduces the risk of damage to stainless steel equipment utilized in the manufacturing and purification process of FGF-21 polypeptide while efficiently solubilizing the FGF-21 polypeptide inclusion bodies.

In the case of soluble FGF-21 protein, the FGF-21 may be secreted into the periplasmic space or into the culture medium. For example, FGF-21 was secreted into the periplasmic space of W3110-B2 cells by using plasmids encoding constructs including eight different leader sequences, including those listed in SEQ ID NOs: 39-44, and transforming these into W3110-B2 cells, the cells were then grown at 37° C. until OD reached about 0.8, at which point the expression was induced with 0.01% arabinose. Five hours later the periplasmic release samples were prepped from the cultures and run on the gels (FIG. 33) showing overall expression (total lysates) and periplasmic secretions (soluble fraction).

In addition, soluble FGF-21 may be present in the cytoplasm of the host cells. It may be desired to concentrate soluble FGF-21 prior to performing purification steps. Standard techniques known to those of ordinary skill in the art may be used to concentrate soluble FGF-21 from, for example, cell lysates or culture medium. In addition, standard techniques known to those of ordinary skill in the art may be used to disrupt host cells and release soluble FGF-21 from the cytoplasm or periplasmic space of the host cells.

When FGF-21 polypeptide is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved FGF-21 polypeptide may be purified from the cleaved fusion sequence by methods known to those of ordinary skill in the art. Such methods will be determined by the identity and properties of the fusion sequence and the FGF-21 polypeptide, as will be apparent to one of ordinary skill in the art. Methods for purification may include, but are not limited to, size-exclusion chromatography, hydrophobic interaction chromatography, ion-exchange chromatography or dialysis or any combination thereof.

The FGF-21 polypeptide may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. The FGF-21 polypeptide may be separated from the precipitated DNA using standard well known methods including, but not limited to, centrifugation or filtration. Removal of host nucleic acid molecules is an important factor in a setting where the FGF-21 polypeptide is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human FGF-21 polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the FGF-21 polypeptide of the present invention includes separating deamidated and clipped forms of the FGF-21 polypeptide variant from the intact form.

Any of the following exemplary procedures can be employed for purification of FGF-21 polypeptides of the invention: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, peptides comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins or peptides comprising unnatural amino acids) are used as purification reagents, including but not limited to, for affinity-based purification of proteins or peptides comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production. Antibodies generated against polypeptides of the present invention may be obtained by administering the polypeptides or epitope-bearing fragments, or cells to an animal, preferably a non-human animal, using routine protocols. One of ordinary skill in the art could generate antibodies using a variety of known techniques. Also, transgenic mice, or other organisms, including other mammals, may be used to express humanized antibodies. The above-described antibodies may be employed to isolate or to identify clones expressing the polypeptide or to purify the polypeptides. Antibodies against polypeptides of the present invention may also be employed to treat diseases.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use as a vaccine, a polypeptide or a nucleic acid vector will be normally provided as a vaccine formulation (composition). The formulation may further comprise a suitable carrier. Since a polypeptide may be broken down in the stomach, it may be administered parenterally (for instance, subcutaneous, intramuscular, intravenous, or intra-dermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The vaccine formulation may also include adjuvant systems for enhancing the immunogenicity of the formulation which are known to those of ordinary skill in the art. The dosage will depend on the specific activity of the vaccine and can be readily determined by routine experimentation.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice* 3rd Edition Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins or peptides can possess a conformation different from the desired conformations of the relevant polypeptides. In one aspect of the invention, the expressed protein or polypeptide is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of FGF-21 polypeptide, the FGF-21 polypeptide thus produced may be misfolded and thus lacks or has reduced biological activity. The bioactivity of the protein may be restored by "refolding". In general, misfolded FGF-21 polypeptide is refolded by solubilizing (where the FGF-21 polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. FGF-21 polypeptide may be refolded using standard methods known in the art, such as those described in U.S. Pat. Nos. 4,511,502, 4,511,503, and 4,512,922, which are incorporated by reference herein. The FGF-21 polypeptide may also be cofolded with other proteins to form heterodimers or heteromultimers.

After refolding, the FGF-21 may be further purified. Purification of FGF-21 may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, FGF-21 may be exchanged into different buffers and/or concentrated by any of a variety of methods known to the art, including, but not limited to, diafiltration and dialysis. FGF-21 that is provided as a single purified protein may be subject to aggregation and precipitation.

The purified FGF-21 may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the FGF-21, the FGF-21 is sufficiently pure for use as a pharmaceutical product or for further processing, such as conjugation with a water soluble polymer such as PEG.

Certain FGF-21 molecules may be used as therapeutic agents in the absence of other active ingredients or proteins (other than excipients, carriers, and stabilizers, serum albumin and the like), or they may be complexed with another protein or a polymer.

General Purification Methods Any one of a variety of isolation steps may be performed on the cell lysate, extract, culture medium, inclusion bodies, periplasmic space of the host cells, cytoplasm of the host cells, or other material, comprising FGF-21 polypeptide or on any FGF-21 polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the FGF-21 polypeptide may be reduced and denatured by first denaturing the resultant purified FGF-21 polypeptide in urea, followed by dilution into TRIS buffer containing a reducing agent (such as DTT) at a suitable pH. In another embodiment, the FGF-21 polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured FGF-21 polypeptide mixture may then be further isolated or purified.

As stated herein, the pH of the first FGF-21 polypeptide mixture may be adjusted prior to performing any subsequent isolation steps. In addition, the first FGF-21 polypeptide mixture or any subsequent mixture thereof may be concentrated using techniques known in the art. Moreover, the elution buffer comprising the first FGF-21 polypeptide mixture or any subsequent mixture thereof may be exchanged for a buffer suitable for the next isolation step using techniques known to those of ordinary skill in the art.

Ion Exchange Chromatography In one embodiment, and as an optional, additional step, ion exchange chromatography may be performed on the first FGF-21 polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Anion or cation exchange column chromatography may be performed on the FGF-21 polypeptide at any stage of the purification process to isolate substantially purified FGF-21 polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding FGF-21 over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, preferably having an FGF-21 binding pH range of about 2.5 to about 6.0. Alternatively, the strong cation exchanger may have an FGF-21 binding pH range of about pH 2.5 to about pH 5.5. The cation exchange matrix may be a strong cation exchanger having an FGF-21 binding pH of about 3.0. Alternatively, the cation exchange matrix may be a strong cation exchanger, preferably having an FGF-21 binding pH range of about 6.0 to about 8.0. The cation exchange matrix may be a strong cation exchanger preferably having an FGF-21 binding pH range of about 8.0 to about 12.5. Alternatively, the strong cation exchanger may have an FGF-21 binding pH range of about pH 8.0 to about pH 12.0.

Prior to loading the FGF-21, the cation exchange matrix may be equilibrated, for example, using several column volumes of a dilute, weak acid, e.g., four column volumes of 20 mM acetic acid, pH 3. Following equilibration, the FGF-21 may be added and the column may be washed one to several times, prior to elution of substantially purified FGF-21, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified FGF-21 may be eluted by contacting the cation exchanger matrix with a buffer having a sufficiently low pH or ionic strength to displace the FGF-21 from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes.

Following adsorption of the FGF-21 polypeptide to the cation exchanger matrix, substantially purified FGF-21 polypeptide may be eluted by contacting the matrix with a buffer having a sufficiently high pH or ionic strength to displace the FGF-21 polypeptide from the matrix. Suitable buffers for use in high pH elution of substantially purified FGF-21 polypeptide may include, but not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the FGF-21 polypeptide to isolate substantially purified FGF-21 polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{1-8}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the FGF-21 polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, and triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques Hydrophobic interaction chromatography (HIC) may be performed on the FGF-21 polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.).

Briefly, prior to loading, the HIC column may be equilibrated using standard buffers known to those of ordinary skill in the art, such as an acetic acid/sodium chloride solution or HEPES containing ammonium sulfate. Ammonium sulfate may be used as the buffer for loading the HIC column. After loading the FGF-21 polypeptide, the column may then washed using standard buffers and conditions to remove unwanted materials but retaining the FGF-21 polypeptide on the HIC column. The FGF-21 polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the FGF-21 molecules. The eluant may then be concentrated, for example, by filtration such as diafiltration or ultrafiltration. Diafiltration may be utilized to remove the salt used to elute the FGF-21 polypeptide.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first FGF-21 polypeptide mixture or any subsequent mixture thereof, to remove any excess salts and to replace the buffer with a suitable buffer for the next isolation step or even formulation of the final drug product.

The yield of FGF-21 polypeptide, including substantially purified FGF-21 polypeptide, may be monitored at each step described herein using techniques known to those of ordinary skill in the art. Such techniques may also be used to assess the yield of substantially purified FGF-21 polypeptide following the last isolation step. For example, the yield of FGF-21 polypeptide may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In specific embodiments of the present invention, the yield of FGF-21 after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the FGF-21 in the starting material for each purification step.

Purity may be determined using standard techniques, such as SDS-PAGE, or by measuring FGF-21 polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of FGF-21 polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The FGF-21 polypeptide fractions which are within the IPC limits are pooled.

DEAE Sepharose (Pharmacia) material consists of diethylaminoethyl (DEAE)-groups which are covalently bound to the surface of Sepharose beads. The binding of FGF-21 polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and FGF-21 polypeptide is eluted with a buffer with increased ionic strength. The column is packed with DEAE Sepharose fast flow. The column volume is adjusted to assure a FGF-21 polypeptide load in the range of 3-10 mg FGF-21 polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, FGF-21 polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

Additional methods that may be employed include, but are not limited to, steps to remove endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, Limulus Amebocyte Lysate (LAL) assays. The Endosafe™-PTS assay is a colorimetric, single tube system that utilizes cartridges preloaded with LAL reagent, chromogenic substrate, and control standard endotoxin along with a handheld spectrophotometer. Alternate methods include, but are not limited to, a Kinetic LAL method that is turbidmetric and uses a 96 well format.

A wide variety of methods and procedures can be used to assess the yield and purity of a FGF-21 protein comprising one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art.

Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

VIII. Expression in Alternate Systems

Several strategies have been employed to introduce unnatural amino acids into proteins in non-recombinant host cells, mutagenized host cells, or in cell-free systems. These systems are also suitable for use in making the FGF-21 polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem*, 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.*, 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.*, 428:68 (1998); J. C. van Hest, K. L. Kiick and D. A. Tirrell, *J. Am. Chem. Soc.*, 122:1282 (2000); and, K. L. Kiick and D. A. Tirrell, *Tetrahedron*, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S, Nishimura, *J. Biol. Chem.*, 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these non-cognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature*, 192: 1227-1232 (1961); Hofmann, K., Bohn, H. *Studies on polypeptides. XXXVI. The effect of pyrazole-imidazole replacements on the S-protein activating potency of an S-peptide fragment, J. Am. Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science*, 238(4832): 1401-1403 (1987); Kaiser, E. T., Lawrence D. S., Rokita, S. E. *The chemical modification of enzymatic specificity, Annu Rev Biochem*, 54:565-595 (1985); Kaiser, E. T., Lawrence, D. S. *Chemical mutation of enyzme active sites, Science*, 226 (4674):505-511 (1984); Neet, K. E., Nanci A, Koshland, D. E. *Properties of thiol-subtilisin, J Biol. Chem*, 243(24):6392-6401 (1968); Polgar, L. et M. L. Bender. *A new enzyme containing a synthetically formed active site. Thiol-subtilisin. J. Am. Chem Soc*, 88:3153-3154 (1966); and, Pollack, S. J., Nakayama, G. Schultz, P. G. *Introduction of nucleophiles and spectroscopic probes into antibody combining sites, Science*, 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem*, 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci*, 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science*, 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc*, 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.*, vol. 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res*, 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science*, 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{CCCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Stephan in Scientist 2005 Oct. 10; pages 30-33 describes additional methods to incorporate non-naturally encoded amino acids into proteins. Lu et al. in Mol. Cell. 2001 October; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, Science, 268:439 (1995); and, D. A. Dougherty, Curr. Opin. Chem. Biol., 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, J. Biol. Chem., 271:19991 (1996); the incorporation of biotinylated amino acids to identify surface-exposed residues in ion channels, see, e.g., J. P. Gallivan, H. A. Lester and D. A. Dougherty, Chem. Biol., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, Cell, 96:89 (1999); and, T. Lu, A. Y. Ting, J. Mainland, L. Y. Jan, P. G. Schultz and J. Yang, Nat. Neurosci., 4:239 (2001).

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties.

In one attempt to site-specifically incorporate para-F-Phe, a yeast amber suppressor tRNAPheCUA/phenylalanyl-tRNA synthetase pair was used in a p-F-Phe resistant, Phe auxotrophic Escherichia coli strain. See, e.g., R. Furter, Protein Sci., 7:419 (1998).

It may also be possible to obtain expression of a FGF-21 polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering*, 74:309-316 (2001); Kim, D. M. and J. R. Swartz, *Biotechnology Letters*, 22, 1537-1542, (2000); Kim, D. M., and J. R. Swartz, *Biotechnology Progress*, 16, 385-390, (2000); Kim, D. M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of FGF-21 polypeptides comprising a non-naturally encoded amino acid includes the mRNA-peptide fusion technique. See, e.g., R. Roberts and J. Szostak, *Proc. Natl. Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of FGF-21 polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci. (USA)* 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

IX. Macromolecular Polymers Coupled to FGF-21 Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to FGF-21 polypeptides of the present invention to modulate biological properties of the FGF-21 polypeptide, and/or provide new biological properties to the FGF-21 molecule. These macromolecular polymers can be linked to the FGF-21 polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100, 000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated FGF-21 polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:FGF-21 polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of FGF-21 polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the FGF-21 polypeptide by the formula:

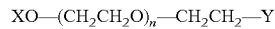

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a FGF-21 polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the FGF-21 polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the FGF-21 polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the FGF-21 polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—($CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(-YCHZ_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

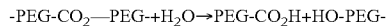

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof. (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.
Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900, 461). All of the above references and patents are incorporated herein by reference.

In certain embodiments of the present invention, the polymer derivatives of the invention comprise a polymer backbone having the structure:

wherein:
X is a functional group as described above; and
n is about 20 to about 4000.
In another embodiment, the polymer derivatives of the invention comprise a polymer backbone having the structure:

wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

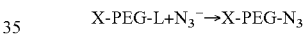

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

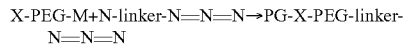

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

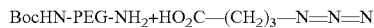

$$BocHN\text{-}PEG\text{-}NH_2 + HO_2C\text{-}(CH_2)_3\text{-}N=N=N$$

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

X-A-POLY-B-C—C—R wherein:
R can be either H or an alkyl, alkene, alkyoxy, or aryl or substituted aryl group;
B is a linking moiety, which may be present or absent; POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

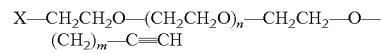

$$X\text{—}CH_2CH_2O\text{—}(CH_2CH_2O)_n\text{—}CH_2CH_2\text{—}O\text{—}(CH_2)_m\text{—}C\equiv CH$$

wherein:
X is a functional group as described above;
n is about 20 to about 4000; and
m is between 1 and 10.
Specific examples of each of the heterobifunctional PEG polymers are shown below.

The acetylene-containing PEG derivatives of the invention can be prepared using methods known to those of ordinary skill in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

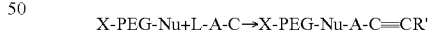

$$X\text{-}PEG\text{-}Nu + L\text{-}A\text{-}C \rightarrow X\text{-}PEG\text{-}Nu\text{-}A\text{-}C\equiv CR'$$

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:
PEG is poly(ethylene glycol) and X is a capping group such as alkoxy or a functional group as described above; and
R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water soluble polymers can be linked to the FGF-21 polypeptides of the invention. The water soluble polymers may be linked via a non-naturally encoded amino acid incorporated in the FGF-21 polypeptide or any functional group or substituent of a non-naturally encoded or naturally encoded amino acid, or any functional group or substituent added to a non-naturally encoded or naturally encoded amino acid. Alternatively, the water soluble polymers are linked to a FGF-21 polypeptide incorporating a non-naturally encoded amino acid via a naturally-occurring amino acid (including but not limited to, cysteine, lysine or the amine group of the N-terminal residue). In some cases, the FGF-21 polypeptides of the invention comprise 1, 2, 3, 4, 5, 6, 7, 8, 9, non-natural amino acids, wherein one or more non-naturally-encoded amino acid(s) are linked to water soluble polymer(s) (including but not limited to, PEG and/or oligosaccharides). In some cases, the FGF-21 polypeptides of the invention further comprise 1, 2, 3, 4, 5, 6, 7, 8, 9, 10, or more naturally-encoded amino acid(s) linked to water soluble polymers. In some cases, the FGF-21 polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the FGF-21 polypeptide relative to the unconjugated form.

The number of water soluble polymers linked to a FGF-21 polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of FGF-21 is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

Peg Derivatives Containing a Strong Nucleophilic Group (i.e., Hydrazide, Hydrazine, Hydroxylamine or Semicarbazide)

In one embodiment of the present invention, a FGF-21 polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

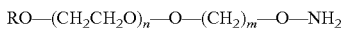

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

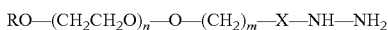

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

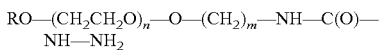

where R is a simple alkyl (methyl, ethyl, propyl, etc.), m is 2-10 and n is 100-1,000.

In another embodiment of the invention, a FGF-21 polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

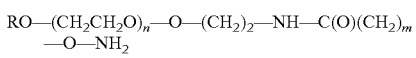

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

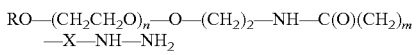

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

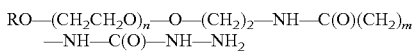

where R is a simple alkyl (methyl, ethyl, propyl, etc.), m is 2-10 and n is 100-1,000.

In another embodiment of the invention, a FGF-21 polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, a FGF-21 polypeptide comprising a non-naturally encoded amino acid is modified with a PEG derivative having a branched structure. For instance, in some embodiments, the hydrazine- or hydrazide-terminal PEG derivative will have the following structure:

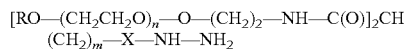

where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

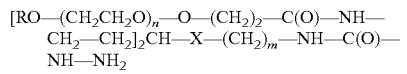

where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

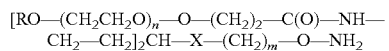

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the FGF-21 polypeptide can modulate the binding of the FGF-21 polypeptide to the FGF-21 polypeptide receptor. In some embodiments, the linkages are arranged such that the FGF-21 polypeptide binds the FGF-21 polypeptide receptor with a $K_d$ of about 400 nM or lower, with a $K_d$ of 150 nM or lower, and in some cases with a $K_d$ of 100 nM or lower, as measured by an equilibrium binding assay, such as that described in Spencer et al., *J. Biol. Chem.*, 263:7862-7867 (1988) for FGF-21.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor V111 (WO 94/15625), hemoglobin (WO 94/09027), oxygen carrying molecule (U.S. Pat. No. 4,412,989), ribonuclease and superoxide dismutase (Veronese at al, *App. Biochem. Biotech.* 11: 141-52 (1985)). All references and patents cited are incorporated by reference herein.

PEGylation (i.e., addition of any water soluble polymer) of FGF-21 polypeptides containing a non-naturally encoded amino acid, such as p-azido-L-phenylalanine, is carried out by any convenient method. For example, FGF-21 polypeptide is PEGylated with an alkyne-terminated mPEG derivative. Briefly, an excess of solid mPEG(5000)-O—CH$_2$—C≡CH is added, with stirring, to an aqueous solution of p-azido-L-Phe-containing FGF-21 polypeptide at room temperature. Typically, the aqueous solution is buffered with a buffer having a p$K_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated FGF-21 polypeptide variants from free mPEG(5000)-O—CH$_2$—C≡CH and any high-molecular weight complexes of the pegylated FGF-21 polypeptide which may form when unblocked PEG is activated at both ends of the molecule, thereby crosslinking FGF-21 polypeptide variant molecules. The conditions during hydrophobic interaction chromatography are such that free mPEG(5000)-O—CH$_2$—C≡CH flows through the column, while any crosslinked PEGylated FGF-21 polypeptide variant complexes elute after the desired forms, which contain one FGF-21 polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

If necessary, the PEGylated FGF-21 polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, Ariz. in PROTEIN PURIFICATION METHODS, A PRACTICAL APPROACH (Harris & Angal, Eds.) IRL Press 1989, 293-306). The purity of the FGF-21-PEG conjugate can be assessed by proteolytic degradation (including but not limited to, trypsin cleavage) followed by mass spectrometry analysis. Pepinsky R B., et al., *J. Pharmcol. & Exp. Ther.* 297(3):1059-66 (2001).

A water soluble polymer linked to an amino acid of a FGF-21 polypeptide of the invention can be further derivatized or substituted without limitation.

Azide-Containing PEG Derivatives

In another embodiment of the invention, a FGF-21 polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

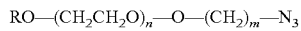

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

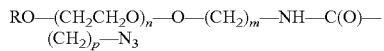

where R is a simple alkyl (methyl, ethyl, propyl, etc.), m is 2-10, p is 2-10 and n is 100-1,000 (i.e., average molecular weight is between 5-40 kDa).

In another embodiment of the invention, a FGF-21 polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

[RO—(CH$_2$CH$_2$O)$_n$—O—(CH$_2$)$_2$—NH—C(O)]$_2$CH (CH$_2$)$_m$—X—(CH$_2$)$_p$N$_3$ where R is a simple alkyl (methyl, ethyl, propyl, etc.), m is 2-10, p is 2-10, and n is 100-1,000, and
X is optionally an O, N, S or carbonyl group (C=O), in each case that can be present or absent.

Alkyne-Containing PEG Derivatives

In another embodiment of the invention, a FGF-21 polypeptide is modified with a PEG derivative that contains an alkyne moiety that will react with an azide moiety present on the side chain of the non-naturally encoded amino acid.

In some embodiments, the alkyne-terminal PEG derivative will have the following structure:

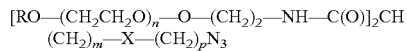

where R is a simple alkyl (methyl, ethyl, propyl, etc.), m is 2-10 and n is 100-1,000 (i.e., average molecular weight is between 5-40 kDa).

In another embodiment of the invention, a FGF-21 polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

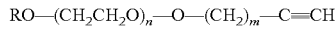

where R is a simple alkyl (methyl, ethyl, propyl, etc.), m is 2-10, p is 2-10 and n is 100-1,000.

In another embodiment of the invention, a FGF-21 polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

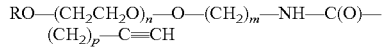

where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, a FGF-21 polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

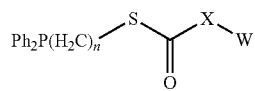

wherein n is 1-10; X can be O, N, S or not present, Ph is phenyl, and W is a water soluble polymer.

In some embodiments, the PEG derivative will have the structure:

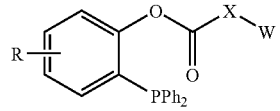

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Other PEG Derivatives and General PEGylation Techniques

Other exemplary PEG molecules that may be linked to FGF-21 polypeptides, as well as PEGylation methods include, but are not limited to, those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949;

2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Additional polymer and PEG derivatives are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Enhancing Affinity for Serum Albumin

Various molecules can also be fused to the FGF-21 polypeptides of the invention to modulate the half-life of FGF-21 polypeptides in serum. In some embodiments, molecules are linked or fused to FGF-21 polypeptides of the invention to enhance affinity for endogenous serum albumin in an animal.

For example, in some cases, a recombinant fusion of a FGF-21 polypeptide and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., J, *Immunol. Methods* 201:115-123 (1997)), or albumin-binding peptides such as those described in, e.g., Dennis, et al., *J. Biol. Chem.* 277:35035-35043 (2002).

In other embodiments, the FGF-21 polypeptides of the present invention are acylated with fatty acids. In some cases, the fatty acids promote binding to serum albumin. See, e.g., Kurtzhals, et al., *Biochem. J.* 312:725-731 (1995).

In other embodiments, the FGF-21 polypeptides of the invention are fused directly with serum albumin (including but not limited to, human serum albumin). Those of skill in the art will recognize that a wide variety of other molecules can also be linked to FGF-21 in the present invention to modulate binding to serum albumin or other serum components.

X. Glycosylation of FGF-21 Polypeptides

The invention includes FGF-21 polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to FGF-21 polypeptides either in vivo or in vitro. In some embodiments of the invention, a FGF-21 polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the FGF-21 polypeptide. See, e.g., H. Liu, et al. *J. Am. Chem. Soc.* 125:1702-1703 (2003).

In some embodiments of the invention, a FGF-21 polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a FGF-21 polypeptide comprising an azide or alkynyl-containing non-naturally encoded amino acid can then be modified by, including but not limited to, a Huisgen [3+2]cycloaddition reaction with, including but not limited to, alkynyl or azide derivatives, respectively. This method allows for proteins to be modified with extremely high selectivity.

XI. FGF-21 Dimers and Multimers

The present invention also provides for FGF-21 and FGF-21 analog combinations such as homodimers, heterodimers, homomultimers, or heteromultimers (i.e., trimers, tetramers, etc.) where FGF-21 containing one or more non-naturally encoded amino acids is bound to another FGF-21 or FGF-21 variant thereof or any other polypeptide that is not FGF-21 or FGF-21 variant thereof, either directly to the polypeptide backbone or via a linker. Due to its increased molecular weight compared to monomers, the FGF-21 dimer or multimer conjugates may exhibit new or desirable properties, including but not limited to different pharmacological, pharmacokinetic, pharmacodynamic, modulated therapeutic half-life, or modulated plasma half-life relative to the monomeric FGF-21. In some embodiments, FGF-21 dimers of the invention will modulate signal transduction of the FGF-21 receptor. In other embodiments, the FGF-21 dimers or multimers of the present invention will act as a FGF-21 receptor antagonist, agonist, or modulator.

In some embodiments, one or more of the FGF-21 molecules present in a FGF-21 containing dimer or multimer comprises a non-naturally encoded amino acid linked to a water soluble polymer.

In some embodiments, the FGF-21 polypeptides are linked directly, including but not limited to, via an Asn-Lys amide linkage or Cys-Cys disulfide linkage. In some embodiments, the FGF-21 polypeptides, and/or the linked non-FGF-21 molecule, will comprise different non-naturally encoded amino acids to facilitate dimerization, including but not limited to, an alkyne in one non-naturally encoded amino acid of a first FGF-21 polypeptide and an azide in a second non-naturally encoded amino acid of a second molecule will be conjugated via a Huisgen [3+2]cycloaddition. Alternatively, FGF-21, and/or the linked non-FGF-21 molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two FGF-21 polypeptides, and/or the linked non-FGF-21 molecule, are linked via a linker. Any hetero- or homo-bifunctional linker can be used to link the two molecules, and/or the linked non-FGF-21 molecules, which can have the same or different primary sequence. In some cases, the linker used to tether the FGF-21, and/or the linked non-FGF-21 molecules together can be a bifunctional PEG reagent. The linker may have a wide range of molecular weight or molecular length. Larger or smaller molecular weight linkers may be used to provide a desired spatial relationship or conformation between FGF-21 and the linked entity or between FGF-21 and its receptor, or between the linked entity and its binding partner, if any. Linkers having longer or shorter molecular length may also be used to provide a desired space or flexibility between FGF-21 and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more FGF-21 polypeptide, formed by reactions with water soluble activated polymers that have the structure:

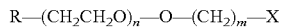

R—(CH$_2$CH$_2$O)$_n$—O—(CH$_2$)$_m$—X wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of FGF-21 Polypeptide Activity and Affinity of FGF-21 Polypeptide for the FGF-21 Polypeptide Receptor FGF-21 has been shown to stimulate glucose uptake and enhance insulin sensitivity in 3T3-L1 adipocytes, an in vitro model utilized for the study of adipose tissue metabolism as shown in Example 3 of U.S. Patent Publication No. 20040259780 which is incorporated by reference in its entirety. A characteristic of Type 2 diabetes is the deficiency of glucose uptake in various tissue types including adipose tissue. Thus, FGF-21 is useful for treating Type 2 diabetes by lowering blood glucose levels. Moreover, FGF-21 is useful for treating obesity by increasing energy expenditure by faster and more efficient glucose utilization. Additionally, FGF-21 has been shown to stimulate glucose uptake in 3T3-L1 adipocytes in an insulin independent manner, indicating that it is useful for treating Type 1 diabetes as well. See U.S. Patent Publication No. 20040259780. FGF-21 is shown to stimulate glucose uptake in 3T3-L1 adipocytes in a concentration dependent manner at a sub-optimal concentration of insulin (5 nM) and in the absence of insulin in U.S. Patent Publication No. 20040259780. Additionally, FGF-21 induces glucose uptake in an ex vivo tissue model, described in in U.S. Patent Publication No. 20040259780.

Glucose uptake in 3T3-1 adipocytes may be assessed using the following method. 3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, 2 days after cells reached confluency (referred as day 0), cells are exposed to differentiation medium (DM) containing 10% fetal bovine serum, 10 μg/ml of insulin, 1 μM dexamethasone, and 0.5 μM isobutylmethylxanthine, for 48 hours. Cells then are maintained in post differentiation medium containing 10% fetal bovine serum, and 10 μg/ml of insulin. In vitro potency may be measured with the glucose uptake assay which are known to those of ordinary skill in the art. In vitro potency can be defined as the measure of glucose uptake of a FGF-21 compound in a cell-based assay and is a measure of the biological potency of the FGF compound. It can be expressed as the EC$_{50}$ which is the effective concentration of compound that results in 50% activity in a single dose-response experiment.

Glucose Transport Assay—Insulin Dependent—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM NaPO$_4$, 0.9 mM CaCl$_2$, 0.9 mM MgSO$_4$, pH 7.4) warmed to 37° C. and containing 0.2% BSA, incubated in Leibovitz's L-15 medium containing 0.2% BSA for 2 hours at 37° C. in room air, washed twice again with KRP containing, 0.2% BSA buffer, and incubated in KRP, 0.2% BSA buffer in the absence (Me$_2$SO only) or presence of wortmannin for 30 minutes at 37° C. in room air. Insulin is then added to a final concentration of 100 nM for 15 minutes, and the uptake of 2-deoxy-D-[$^{14}$C]glucose is measured for the last 4 minutes. Nonspecific uptake, measured in the presence of 10 μM cytochalasin B, is subtracted from all values. Protein concentrations are determined with the Pierce bicinchoninic acid assay. Uptake is measured routinely in triplicate or quadruplicate for each experiment. The effect of acute and chronic pretreatment of 3T3-L1 adipocytes with FGF-21 in the presence of insulin may be investigated.

Glucose Transport Assay—Insulin Independent—3T3-L1 fibroblast are plated in 96-well plates and differentiated into fat cells (adipocytes) for 2 weeks. After differentiation they are starved in serum-free medium and treated with FGF-21 for 24 hours. Upon treatment, cells are washed twice with KRBH buffer, containing 0.1% BSA. Glucose uptake is performed in the presence of labeled glucose (without insulin) in KPBH buffer. FGF-21 has been shown to stimulate glucose uptake in 3T3-L1 adipocytes in a concentration dependent manner at a sub-optimal concentration of insulin (5 nM) and in the absence of insulin (see US Patent Publication No. 2004259780). Additionally, FGF-21 polypeptides of the present invention may be shown to induce glucose uptake in an ex vivo tissue model.

In the ex vivo glucose transport model, the glucose transport assay is described as follows: Krebs-Henseleit Buffer Stock Solutions—Stock 1: NaCl (1.16 M); KCl (0.046 M); $KH_2PO_4$ (0.0116 M); $NaHCO_3$ (0.0253 M). Stock 2: $CaCl_2$ (0.025 M); $MgSO_4$ ($2H_2O$) (0.0116 M). BSA: Use ICN Cohn Fraction V, fatty acid free BSA directly without dialysing. Media Preparation: Add 50 ml of Krebs stock 1 to 395 ml of $dH_2O$ and gas with 95% $O_2$/5% $CO_2$ for 1 hour. Add 50 ml of stock 2 and bring to 500 ml with $dH_2O$. Add 500 mg of ICN fatty acid free BSA. Preincubation and Incubation Media: 32 mM Mannitol, 8 mM Glucos. Wash Media: 40 mM Mannitol, 2 mM Pyruvate. Transport Media: 39 mM Mannitol, 1 mM 2-DG; 32 mM Mannitol, 8 mM 3-O-MG. Insulin Solution: (Porcine Insulin [Lilly] 100,000,000 µU/ml) at a final concentration of 2000 µU/ml or 13.3 nM. Radioactive Label Media Preparation: Specific activities used: 2DG=1.5 mCi/ml; 3-O-MG=437 µCi/ml; or, Mannitol=8 µCi/m. Rats are anesthetized with 0.1 cc Nembutal per 100 g body weight. Muscle tissue is excised and rinsed in 0.9% saline then placed in pre-incubation media (2 ml) at 29° C. for 1 hour. The muscle tissue is transferred to incubation media (2 ml; same as pre-incubation except including insulin or test compound) and incubated for 30 minutes (depends upon experimental conditions). The muscle tissue is then transferred to wash media (2 ml) for 10 minutes at 29° C., then transferred to label media (1.5 ml) for 10 min (3-O-MG) or 20 min (2DG). The muscle tissue is trimmed, weighed and placed in polypropylene tubes on dry ice. 1 ml of 1 N KOH is added to the tubes which are then placed in a 70° C. water bath for 10-15 minutes, vortexing the tubes every few minutes. The tubes are cooled on ice and 1 ml of 1 N HCl is added, then mixed well. 200 µl of supernatant is then put in duplicate scintillation vials and counted on a scintillation counter compared to known radioactive standards.

For contraction, the muscles are first incubated for 1 hour in preincubation/incubation media. After 1 hour, one muscle of each pair (one pair per rat) is pinned to the stimulation apparatus and the other muscle is transferred to a new flask of incubation media. The contracted muscle is stimulated by 200 msec trains of 70 Hz with each impulse in a train being 0.1 msec. The trains are delivered at 1/sec at 10-15V for 2×10 minutes with a 1 minute rest in between. At the end of the stimulation period, the muscle is removed from the stimulation apparatus and placed in wash media for 10 minutes, followed by label media as outlined above.

The FGF receptor can be prepared using techniques and methods that are known to one of ordinary skill in the art. FGF-21 polypeptide activity can be determined using standard or known in vitro or in vivo assays. For a non-PEGylated or PEGylated FGF-21 polypeptide comprising a non-natural amino acid, the affinity of FGF-21 for its receptor can be measured by using a BIAcore™ biosensor (Pharmacia).

Regardless of which methods are used to create the FGF-21 polypeptides, the FGF-21 polypeptides are subject to assays for biological activity. In general, the test for biological activity should provide analysis for the desired result, such as increase or decrease in biological activity (as compared to modified FGF-21), different biological activity (as compared to modified FGF-21), receptor or binding partner affinity analysis, conformational or structural changes of the FGF-21 itself or its receptor (as compared to the modified FGF-21), or serum half-life analysis.

The above compilation of references for assay methodologies is not exhaustive, and those of ordinary skill in the art will recognize other assays useful for testing for the desired end result.

XIII. Measurement of Potency, Functional In Vivo Half-Life, and Pharmacokinetic Parameters An important aspect of the invention is the prolonged biological half-life that is obtained by construction of the FGF-21 polypeptide with or without conjugation of the polypeptide to a water soluble polymer moiety. The rapid post administration decrease of FGF-21 polypeptide serum concentrations has made it important to evaluate biological responses to treatment with conjugated and non-conjugated FGF-21 polypeptide and variants thereof. The conjugated and non-conjugated FGF-21 polypeptide and variants thereof of the present invention may have prolonged serum half-lives also after administration via, e.g. subcutaneous or i.v. administration, making it possible to measure by, e.g. ELISA method or by a primary screening assay. ELISA or RIA kits from commercial sources may be used. Measurement of in vivo biological half-life is carried out as described herein.

The potency and functional in vivo half-life of an FGF-21 polypeptide comprising a non-naturally encoded amino acid can be determined according to protocols known to those of ordinary skill in the art.

Pharmacokinetic parameters for a FGF-21 polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a FGF-21 polypeptide comprising a non-naturally encoded amino acid not conjugated to a water soluble polymer and about 4 days for a FGF-21 polypeptide comprising a non-naturally encoded amino acid and conjugated to a water soluble polymer. Pharmacokinetic data for FGF-21 without a non-naturally encoded amino acid can be compared directly to the data obtained for FGF-21 polypeptides comprising a non-naturally encoded amino acid.

Pharmacokinetic parameters can also be evaluated in a primate, e.g., cynomolgus monkeys. Typically, a single injection is administered either subcutaneously or intravenously, and serum FGF-21 levels are monitored over time.

The specific activity of FGF-21 polypeptides in accordance with this invention can be determined by various assays known in the art. The biological activity of the FGF-21 polypeptide muteins, or fragments thereof, obtained and purified in accordance with this invention can be tested by methods described or referenced herein or known to those of ordinary skill in the art.

Polypeptides of the present invention may be used to treat mammals suffering from non-insulin dependent Diabetes Mellitus (NIDDM: Type 2), insulin dependent diabetes (Type 1), as well as obesity, inadequate glucose clearance, hyperglycemia, hyperinsulinemia, and the like. FGF-21 is effective in animal models of diabetes and obesity, as shown in US Patent Publication No. 20040259780, which is incorporated by reference herein in its entirety. As metabolic profiles differ among various animal models of obesity and diabetes, analysis of multiple models have been undertaken to separate the effects of hyperinsulinemia, hyperglycemia and obesity. The diabetes (db/db) and obese (ob/ob) mice are characterized by massive obesity, hyperphagia, variable hyperglycemia, insulin resistance, hyperinsulinemia and impaired thermogenesis (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299-340). However, diabetes is much more severe in the db/db model (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299-340). Zucker (fa/fa) rats are severely obese, hyperinsulinemic, and insulin resistant (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299-340), and the fa/fa mutation may be the rat equivalent of the murine db mutation (Friedman et al., Cell 69:217-220, 1992; Truett et al., Proc. Natl. Acad. Sci. USA 88:7806, 1991). Tubby (tub/tub) mice are characterized by obesity, moderate insulin resistance and hyperinsulinemia without significant hyperglycemia (Coleman et al., J. Heredity 81:424, 1990).

The monosodium glutamate (MSG) model for chemically-induced obesity (Olney, Science 164:719, 1969; Cameron et al., Cli. Exp. Pharmacol. Physiol. 5:41, 1978), in which obesity is less severe than in the genetic models and develops without hyperphagia, hyperinsulinemia and insulin resistance, may also be examined. Finally, the streptozotocin (STZ) model for chemically-induced diabetes may be tested to examine the effects of hyperglycemia in the absence of obesity. STZ-treated animals are deficient in insulin and severely hyperglycemic (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299-340).

FGF-21 polypeptides of the invention can be evaluated in an in vivo septic shock model in ob/ob mice. See U.S. Patent Publication No. 20050176631, which is incorporated by reference in its entirety herein.

XIV. Administration and Pharmaceutical Compositions

The polypeptides or proteins of the invention (including but not limited to, FGF-21, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a FGF-21 polypeptide modified to include one or more unnatural amino acids to a natural amino acid FGF-21 polypeptide), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

FGF-21 polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The FGF-21 polypeptide, may be used alone or in combination with other suitable components such as a pharmaceutical carrier. The FGF-21 polypeptide may be used in combination with other agents, including but not limited to, an oral anti-diabetic agent.

The term "anti-diabetic agent" shall mean any drug that is useful in treating, preventing, or otherwise reducing the severity of any glucose metabolism disorder, or any complications thereof, including any of the conditions, disease, or complications described herein. Anti-diabetic agents include insulin, thiazolidinediones, sulfonylureas, benzoic acid derivatives, alpha-glucosidase inhibitors, or the like. Other general categories of anti-diabetic agents which may be part of a subject composition include (with defined terms being in quotation marks): "drug articles" recognized in the official United States Pharmacopoeia or official National Formulary (or any supplement thereto); "new drug" and "new animal drug" approved by the FDA of the U.S. as those terms are used in Title 21 of the United States Code; any drug that requires approval of a government entity, in the U.S. or abroad ("approved drug"); any drug that it is necessary to obtain regulatory approval so as to comply with 21 U.S.C.sctn.355(a) ("regulatory approved drug"); any agent that is or was subject to a human drug application under 21 U.S.C.sctn.379(g) ("human drug"). (All references to statutory code for this definition refer to such code as of the original filing date of this application.) Other anti-diabetic agents are disclosed herein, and are known to those of skill in the art. Current drugs or anti-diabetic agents used for managing Type 2 diabetes that are well-known in the art include a number of categories: the biguanides, thiazolidinediones, the sulfonylureas, benzoic acid derivatives and glucosidase inhibitors. These drugs usually have distinct modes of action. The biguanides, e.g., metformin, are believed to prevent excessive hepatic gluconeogenesis. The thiazolidinediones are believed to act by increasing the rate of peripheral glucose disposal. The sulfonylureas, e.g., tolbutamide and glyburide, and the benzoic acid derivatives, e.g. repaglinide, lower plasma glucose by stimulating insulin secretion. The alpha-glucosidase inhibitors competitively inhibit alpha-glucosidase, which metabolizes carbohydrates, thereby delaying carbohydrate absorption and attenuating post-prandial hyperglycemia. In addition, there are a number of proposed therapies for treatment of diabetes that have not yet been approved for human use.

Current drugs or anti-diabetic agents used for managing diabetes and its precursor syndromes, such as insulin resistance, that are well-known in the art include five classes of compounds: the biguanides, e.g., metformin; thiazolidinediones; the sulfonylureas, e.g., tolbutamide and glyburide; benzoic acid derivatives, e.g. repaglinide; and glucosidase inhibitors. In addition to these agents, a number of other therapies may be used in combination with the FGF-21 polypeptides of the present invention to improve glucose control, including but not limited to DPP-4 inhibitors. Certain of these anti-diabetic agents have been approved for human use. The lead DPP-4 compounds tested in clinical trials include Vildagliptin (Galvus) (LAF237), Sitagliptin (Januvia), Saxagliptin and Alogliptin (Sitagliptin). Januvia was approved for the treatment of type 2 diabetes in the United States on Oct. 17, 2006, for use as monotherapy, or combination therapy, with either metformin or a thiazolidinedione. Administration of the first generation Novartis compound 1-[[[2-[(5-cyanopyridin-2-yl)amino]ethyl]amino]acetyl]-2-cyano-(S)-pyrrolidine (NVP DPP728) over a 4 week period to 93 patients with Type 2 diabetes (mean HbA1c of 7.4%) reduced levels of plasma glucose, insulin, and HbA1c over the 4 week study period. See *Inhibition of Dipeptidyl Peptidase IV Improves Metabolic Control Over a 4-Week Study Period in Type 2 Diabetes. Diabetes Care.* 2002 May; 25(5):869-875. Patients receiving metformin have also been noted to exhibit additive glucose lowering benefits following institution of GLP-1 therapy. See *Additive glucose-lowering effects of glucagon-like peptide-1 and metformin in type 2 diabetes. Diabetes Care.* 2001 April; 24(4):720-5. In a study of 10 obese non-diabetic male patients, metformin administration was associated with increased levels of circulating GLP-1 following oral glucose-loading, and in experiments using pooled human plasma, metformin (0.1-0.5 microg/ml) significantly inhibited degradation of GLP-1(7-36)amide after a 30-min incubation at 37 degrees C., in the presence or absence of DPP-4. The authors of this study raised the possibility that metformin may inhibit the enzymatic breakdown of GLP-1 both in vitro and in vivo. See *Effect of metformin on glucagon-like peptide 1 (GLP-1) and leptin levels in obese nondiabetic subjects. Diabetes Care.* 2001 March; 24(3):489-94. Analysis of the relationship between DPP-4, and GLP-1 degradation using biochemical analyses in vitro. Demuth and colleagues found no effect of metformin on the DPP-4-mediated degradation of GLP-1 using a variety of sources of human DPP-4. See *Metformin Effects on Dipeptidylpeptidase IV Degradation of Glucagon-like Peptide-1. Biochem Biophys Res Commun.* 2002 Mar. 15, 291(5):1302-8.

Among biguanides useful as diabetic therapeutic agents, metformin has proven particularly successful. Metformin (N,N-dimethylimidodicarbonimidicdiamide; 1,1-dimethylbiguanide; N,N-dimethylbiguanide; N,N-dimethyldiguanide; N'-dimethylguanylguanidine) is an anti-diabetic agent that acts by reducing glucose production by the liver and by decreasing intestinal absorption of glucose. It is also believed to improve the insulin sensitivity of tissues elsewhere in the body (increases peripheral glucose uptake and utilization). Metformin improves glucose tolerance in impaired glucose tolerance (IGT) subjects and Type 2 diabetic subjects, lowering both pre- and post-prandial plasma glucose. Metformin is generally not effective in the absence of insulin. Bailey, *Diabetes Care* 15.755-72 (1992).

The efficacy of metformin has been shown in several trials. In one study of moderately obese Type 2 diabetics, HbA1c levels improved from 8.6% to 7.1% after 29 weeks of metformin therapy alone or in combination with sulfonylurea. DeFronzo et al., New Engl. J. Med. 333:541-49 (1995). Metformin also had a favorable effect on serum lipids, lowering mean fasting serum triglycerides, total cholesterol, and LDL cholesterol levels and showing no adverse effects on other lipid levels. In another trial, metformin improved glycemic control in NIDDM subjects in a dose-related manner. After 14 weeks, metformin 500 and 2000 mg daily reduced HbA1c by 0.9% and 2.0%, respectively. Garber et al., *Am J. Med.* 102: 491-97 (1997). Metformin may also have a beneficial therapeutic effect on insulin resistant non-diabetics. One study indicated that treatment of hypertensive obese non-diabetic women with metformin decreased blood pressure, fasting and glucose-stimulated plasma insulin fibrinogen. Giugliano et al., *Diabetes Care* 16:1387-90 (1993).

Metformin is commonly administered as metformin HCl. This as well as all other useful forms of metformin are contemplated for use with FGF-21 polypeptides of the present invention. Generally, a fixed dosage regimen is individualized for the management of hyperglycemia in diabetes with metformin HCl or any other pharmacologic agent. Individualization of dosage is made on the basis of both effectiveness and tolerance, while generally not exceeding the maximum recommended daily dose of 2550 mg.

Thiazolidinediones contemplated for use in the practice of the present invention include troglitazone, and the like. Such compounds are well-known, e.g., as described in U.S. Pat. Nos. 5,223,522, 5,132,317, 5,120,754, 5,061,717, 4,897,405, 4,873,255, 4,687,777, 4,572,912, 4,287,200, and 5,002,953; and Current Pharmaceutical Design 2:85-101 (1996). Troglitazone is an oral antihyperglycemic agent that increases glucose transport possibly by activation of peroxisome proliferator-activated receptor-γ (PPARγ). By such activation, troglitazone may enhance expression of GLUT4 glucose transporters, resulting in increased insulin-stimulated glucose uptake. Troglitazone may also attenuate gluconeogenesis and/or activation of glycolysis.

HbA1c is a blood test that measures the amount of glycosylated which is generally higher when a patient has experienced periods of increased blood glucose. The test provides an estimate of the last 2-3 months of diabetes management for a patient. Glycemic control resulting from troglitazone therapy reduces HbA1c by approximately 1 to 2%. Mimura et al., Diabetes Med. 11:685-91 (1994); Kumar et al., Diabetologia 39:701-09 (1996). Effects may not occur for a few weeks after beginning therapy. Troglitazone may also decrease insulin requirements. In one trial of patients with NIDDM and using exogenous insulin, mean HbA1c fell by 0.8% and 1.4% for doses of 200 and 600 mg troglitazone, respectively. Insulin requirements were reduced by up to 29%. Schwartz et al., New Engl. J. Med. 338:861-66 (1998). In another study of NIDDM diabetics using 400 and 600 mg troglitazone, fasting and post-prandial glucose levels were decreased, and hyperinsulinemic euglycemic clam indicated that glucose disposal was approximately 45% above pretreatment levels. Maggs et al., Ann. Intern. Med. 128:176-85 (1998).

In one study, 400 mg of troglitazone increased glucose disposal rates in obese patients with either impaired or normal glucose tolerance. Nolan et al., New Eng. J. Med 331:1188-93 (1994). In another study of women with IGT and a history of gestational diabetes, 600 mg troglitazone improved insulin homeostasis, including improving insulin sensitivity and lowering circulating insulin concentrations, but glucose tolerance was unchanged. Berkowitz et al., Diabetes 45:172-79 (1996). Thiazolidinediones may be used with at-risk populations for NIDDM, such as women with POCS or GDM, to prevent or delay the onset of NIDDM. U.S. Pat. No. 5,874,454. Effective amounts of troglitazone, when used alone, range from about 10 mg up to about 800 mg per daily dose and a commensurate range is contemplated for use in the present invention. In addition to being used with metformin, troglitazone may be used in combination with insulin and a sulfonylurea agent. See, for example, U.S. Pat. No. 5,859,037.

Sulfonylureas generally operate by lowering plasma glucose by increasing the release of insulin from the pancreas. Specifically, sulfonylureas act by blocking the ATP-sensitive potassium channels. The sulfonylurea glimepiride may also increase insulin sensitivity by stimulating translocation of GLUT4 transporters. Sulfonylureas are typically prescribed when HbA1c is above 8%. See also U.S. Pat. Nos. 5,258,185, 4,873,080.

The sulfonylureas are a class of compounds that are well-known in the art, e.g., as described in U.S. Pat. Nos. 3,454,635, 3,669,966, 2,968,158, 3,501,495, 3,708,486, 3,668,215, 3,654,357, and 3,097,242. Exemplary sulfonylureas contemplated for use in certain embodiments of the present invention (with typical daily dosages indicated in parentheses) include acetohexamide (in the range of about 250 up to about 1500 mg), chlorpropamide (in the range of about 100 up to about 500 mg), tolazimide (in the range of about 100 up to about 1000 mg), tolbutamide (in the range of about 500 up to about 3000 mg), gliclazide (in the range of about 80 up to about 320 mg), glipizide (in the range of about 5 up to about 40 mg), glipizide GITS (in the range of about 5 up to about 20 mg), glyburide (in the range of about 1 up to about 20 mg), micronized glyburide (in the range of about 0.75 up to about 12 mg), glimeperide (in the range of about 1 up to about 8 mg), AG-EE 623 ZW, and the like. Glimepiride is the first anti-diabetic agent in this class to be approved for use with insulin, and there may be less risk of hypoglycemia associated with its use A variety of alpha-glucosidase inhibitors may used with the present invention to treat and/or prevent diabetes. Such inhibitors competitively inhibit alpha-glucosidase, which metabolizes carbohydrates, thereby delaying carbohydrate absorption and attenuating post-prandial hyperglycemia. Clissod et al., Drugs 35:214-23 (1988). The decrease in glucose may be shown through decreased HbA1c levels. Exemplary alpha-glucosidase inhibitors contemplated for use in the practice of the present invention include acarbose, miglitol, and the like. Effective dosages of both acarbose and miglitol are in the range of about 25 up to about 300 mg daily.

Alpha-glucosidase inhibitors may be used with polypeptides of the present invention in combination with sulfonylureas. Alpha-glucosidase inhibitors in combination with sulfonylureas alone have been shown to decrease HbA1c levels generally, from about 0.5 to 1.0%. In addition, alpha-glucosidase inhibitors have been shown to be effective in reducing the post-prandial rise in blood glucose. Lefevre et al., Drugs 44:29-38 (1992).

A variety of benzoic acid derivatives may used with polypeptides of the present invention to treat and/or prevent diabetes. These agents, also known as meglitinides, are non-sulfonylurea hypoglycemic agents having insulin secretory capacity. For example, repaglinide appears to bind to ATP-sensitive potassium channels on pancreatic beta cells and thereby increases insulin secretion. Exemplary benzoic acid derivatives contemplated for use in the practice of the present invention include repaglinide and the like. For repaglinide, the effective daily dosage may be in the range of about 0.5 mg up to about 16 mg, and the agent may be taken before each meal.

A number of agents are presently under investigation as potential anti-diabetics in humans. Any of such agents may be used with polypeptides of the present invention for treatment and/or prevention of metabolic disorders, and in particular of diabetes, if they become available for therapeutic use.

Another category of anti-diabetic agents that is inhibitors of carnitine palmitoyl-transferase I (CPT-I), such as etomoxir, which in an additional embodiment of the invention may be used with the modified FGF-21 polypeptides to modulate blood glucose. Etomoxir irreversibly inhibits carnitine palmitoyl-transferase I, which is necessary for fatty acid oxidation. Such inhibition may reduce fasting hyperglycemia, because products of fatty acid oxidation stimulate hepatic gluconeogenesis. Etomoxir may improve insulin sensitivity in Type 2 diabetics. Hubinger et al., Hormone Metab. Res. 24:115-18 (1992).

Other known anti-diabetic agents include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone, Rivoglitazone (CS-011), FK-614, the compound described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG-131(T-131), THR-0921), α-glucosidase inhibitors (e.g., voglibose, acarbose, miglitol, emiglitate etc.), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Vidagliptin (LAF237), P32/98, Sitagliptin (MK-431), P93/01, PT-100, Saxagliptin (BMS-477118), T-6666, TS-021), .beta.3 agonists (e.g., AJ-9677), GPR40 agonists, glucagon-like polypeptides (I) (glp I), (glp2), or other diabetogenic peptide hormones, GLP-1 receptor agonists [e.g., GLP-1, GLP-1MR agent, N,N-2211, AC-2993 (exendin-4), BIM-51077, Aib(8,35)hGLP-1 (7,37) NH.sub.2, CJC-[131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11.beta.-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/2273.5 etc.), glucokinase activators (e.g., R.sup.o-28-1675), GIP (Glucose-dependent insulinotropic peptide) and the like can be mentioned.

The FGF-21 polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of FGF-21 can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, FGFs, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human FGF-21 polypeptides of the invention can be administered directly to a mammalian subject. Administration is by any of the routes normally used for introducing FGF-21 polypeptide to a subject. The FGF-21 polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. FGF-21 polypeptides of the invention can be prepared in a mixture in a unit dosage injectable form (including but not limited to, solution, suspension, or emulsion) with a pharmaceutically acceptable carrier. FGF-21 polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; and/or nonionic surfactants including but not limited to Tween™ (including but not limited to, Tween 80 (polysorbate 80) and Tween 20 (polysorbate 20), Pluronics™ and other pluronic acids, including but not limited to, and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof PEO-PPO-PEO and PPO-PEO-PPO are commercially available under the trade names Pluronics™, R-Pluronis™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated FGF-21 against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof.

FGF-21 polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped FGF-21 polypeptides can be prepared by methods described in, e.g., DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al, *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the FGF-21 polypeptide of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available FGF-21 polypeptide products approved for use in humans. Generally, a PEGylated FGF-21 polypeptide of the invention can be administered by any of the routes of administration described above.

In some embodiments, modified FGF-21 polypeptides of the present invention modulate the effect of an anti-diabetic agent. In another embodiment of the present invention, modified FGF-21 polypeptides may be coadministered with an anti-diabetic agent. In another embodiment of the present invention, modified FGF-21 polypeptides may be administered before treatment with an anti-diabetic agent. In another embodiment of the present invention, modified FGF-21 polypeptides may be administered following treatment with an anti-diabetic agent. In another embodiment of the present invention, modified FGF-21 polypeptides are coadministered with metformin. In another embodiment of the present invention, therapeutic treatment with modified FGF-21 polypeptides of the invention and metformin increase the ability of metformin to modulate plasma glucose, in the presence or absence of insulin. In combination therapy, metformin has been used with sulfonylureas, alpha-glucosidase inhibitors, troglitazeon, and insulin. Metformin combined with a sulfonylurea increases insulin sensitivity and may lower plasma glucose. Alternatively, metformin with repaglinide may be more effective than glipizide, and at least as effective as glyburide, in maintaining glycemic control over many months. Metformin with troglitazone improves glucose control in excess of either agent alone. Inzucchi et al., New. Eng. J. Med. 338:867-72 (1998). In some embodiments, the FGF-21 polypeptides of the present invention are coadministered with Klotho beta. In some embodiments, the FGF-21 polypeptides of the present invention are coadministered with Klotho beta that includes one or more non-naturally encoded amino acids. In some embodiments, the FGF-21 polypeptides of the present invention are coadministered with Klotho beta and an anti-diabetic agent. In some embodiments, the FGF-21 polypeptides of the present invention are coadministered with an anti-diabetic agent. In some embodiments, FGF-21 polypeptides of the present invention are used in combination with one or more of the following: Taurine, Alpha Lipoic Acid, an extract of Mulberry, Chromium, Glutamine, *Enicostemma littorale* Blume, Scoparia dulcis, an extract of *Tarragon* and *Andrographis paniculata*. In some embodiments, FGF-21 polypeptides of the present invention are used in combination with one or more of the following: insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone, Rivoglitazone (CS-011), FK-614, the compound described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG-131 (T-131), THR-0921), α-glucosidase inhibitors (e.g., voglibose, acarbose, miglitol, emiglitate etc.), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Vidagliptin (LAF237), P32/98, Sitagliptin (MK-431), P93/01, PT-100, Saxagliptin (BMS-477118), T-6666, TS-021), .beta.3 agonists (e.g., AJ-9677), GPR40 agonists, glucagon-like polypeptides (I) (glp I), (glp2), or other diabetogenic peptide hormones, GLP-1 receptor agonists [e.g., GLP-1, GLP-1MR agent, N,N-2211, AC-2993 (exendin-4), BIM-51077, Aib(8,35)hGLP-1 (7,37) NH.sub.2, CJC-[131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11.beta.-hydroxysteroid dehydrogenase inhibitors (e.g., BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/2273.5 etc.), glucokinase activators (e.g., R.sup.o-28-1675), GIP (Glucose-dependent insulinotropic peptide).

In some embodiments, polypeptides of the present invention are used in combination with insulin potentiators such as, including but not limited to, Taurine, Alpha Lipoic Acid, an extract of Mulberry, Chromium, Glutamine, Enicostemma littorale Blume, Scoparia dulcis, an extract of Tarragon and Andrographis paniculata. In another embodiment, the present invention may comprise one or more of Isomalt, Trehalose or D-Mannose to further potentiate the secretion or activity of insulin. In an additional embodiment, the insulin potentiator and polypeptides of the present invention are used in addition to another anti-diabetic agent.

One way in which the therapeutic efficacy of the polypeptides and combined therapies including the present invention's polypeptides may be determined is through a reduction in patient HbA1c levels. In one embodiment, polypeptides of the present invention lower HbA1c levels by at least a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or at least 50% change from HbA1c levels two months prior to beginning therapy with modified FGF-21 polypeptides, from three months prior to beginning therapy with modified FGF-21 polypeptides, or by percentage changes from a baseline. In another embodiment, polypeptides of the present invention administered to a patient also being treated with an anti-diabetic agent modulate the ability of the anti-diabetic agent to lower blood glucose. In another embodiment, polypeptides of the present invention administered to a patient also being treated with an anti-diabetic agent lower HbA1c levels by at least a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, or at least 50% change from HbA1c levels two months prior to beginning therapy with modified FGF-21 polypeptides, from three months prior to beginning therapy with modified FGF-21 polypeptides, or by percentage changes from a baseline or from a pre-treatment baseline.

In another embodiment, modified FGF-21 polypeptides of the present invention modulate the ability of Troglitazone to decrease insulin requirements. In another embodiment, Additional embodiment, modified FGF-21 polypeptides of the present invention when administered to a patient being treated with Troglitazone further decrease said patient's insulin requirements. Troglitazone used in combination with the present invention may be used to delay or prevent Type 2 diabetes in certain embodiments of the present invention.

In one embodiment of the present invention, modified FGF-21 polypeptides are coadministered with a sulfonylurea. In another embodiment of the present invention, modified FGF-21 polypeptides are administered before treatment with a sulfonylurea. In another embodiment of the present invention, modified FGF-21 polypeptides are administered after treatment with a sulfonylurea. In some embodiments of the present invention, treatment with a therapeutic dose of modified FGF-21 polypeptides modulates serum glucose. In another embodiment, FGF-21 polypeptides of the present invention are administered with Klotho beta which modulates the effects of the polypeptides on blood glucose. In another embodiment, FGF-21 polypeptides of the present invention are administered with Klotho beta which decreases blood glucose more than use of modified FGF-21 polypeptides alone. In another embodiment, these changes are measured using HbA1c tests. In another embodiment, FGF-21 polypeptides of the present invention and Klotho beta are administered to a patient being treated with an anti-diabetic agent which decreases blood glucose more than use of the anti-diabetic agent alone.

XV. Therapeutic Uses of FGF-21 Polypeptides of the Invention

The FGF-21 polypeptides of the invention are useful for treating a wide range of disorders.

FGF-21 polypeptides of the invention may be used to treat mammals suffering from non-insulin dependent Diabetes Mellitus (NIDDM: Type 2), insulin dependent diabetes (Type 1), as well as obesity, inadequate glucose clearance, hyperglycemia, hyperinsulinemia, and any other disease or condition that may be mediated by FGF-21. Glucose intolerance can be defined as an exceptional sensitivity to glucose. Hyperglycemia is defined as an excess of sugar (glucose) in the blood. Hyperinsulinemia is defined as a higher-than-normal level of insulin in the blood. Insulin resistance is defined as a state in which a normal amount of insulin produces a subnormal biologic response. Obesity, in terms of the human subject, can be defined as that body weight over 20 percent above the ideal body weight for a given population (R. H. Williams, Textbook of Endocrinology, 1974, p. 904-916).

Diabetes mellitus is characterized in two broad groups based on clinical manifestations, namely, the non-insulin-dependent or maturity onset form, also known as Type 2; and the insulin-dependent or juvenile onset form, also known as Type 1. Clinically, the majority of Type 2, maturity onset diabetics are obese, with manifestations of clinical symptoms of the disease usually appearing at an age over 40. In contrast, Type 1, juvenile onset patients are not over-weight relative to their age and height, with rapid onset of the disease at an early age, often before 30, although Type 1 diabetes can occur at any age.

Diabetes mellitus is a metabolic disorder in humans with a prevalence of approximately one percent in the general population, with one-fourth of these being the Type 1 (Foster, D. W., Harrison's Principles of Internal Medicine, Chap. 114, pp. 661-678, 10th Ed., McGraw-Hill, New York). The disease manifests itself as a series of hormone-induced metabolic abnormalities that eventually lead to serious, long-term and debilitating complications involving several organ systems including the eyes, kidneys, nerves, and blood vessels. Pathologically, the disease is characterized by lesions of the basement membranes, demonstrable under electron microscopy.

Non-insulin-dependent Diabetes Mellitus (NIDDM: Type 2) is a debilitating disease characterized by high-circulating blood glucose, insulin and corticosteroid levels. The incidence of Type 2 diabetes is high and rising and is becoming a leading cause of mortality, morbidity and healthcare expenditure throughout the world (Amos et al., Diabetic Med. 14:S1-85, 1997).

The causes of Type 2 diabetes are not well understood. Type 2 diabetes is characterized by excess glucose production in spite of the availability of insulin, and circulating glucose levels remain excessively high as a result of inadequate glucose clearance. It is thought that both resistance of target tissues to the action of insulin and decreased insulin secretion ("β-cell failure") occur. Major insulin-responsive tissues for glucose homeostasis are liver, in which insulin stimulates glycogen synthesis and inhibits gluconeogenesis; muscle, in which insulin stimulates glucose uptake and glycogen stimulates glucose uptake and inhibits lipolysis. Thus, as a consequence of the diabetic condition, there are elevated levels of glucose in the blood, and prolonged high blood sugar which is indicative of a condition which will cause blood vessel and nerve damage.

Currently, there are various pharmacological approaches for the treatment of Type 2 diabetes (Scheen et al., Diabetes Care, 22(9):1568-1577, 1999). They act via different modes of action: 1) sulfonyulureas essentially stimulate insulin secretion; 2) biguanides (metformin) act by promoting glucose utilization, reducing hepatic glucose production and diminishing intestinal glucose output; 3) α-glucosidase inhibitors (acarbose, miglitol) slow down carbohydrate digestion and consequently absorption from the gut and reduce postprandial hyperglycemia; 4) thiazol-idinediones (troglitazone) enhance insulin action, thus promoting glucose utilization in peripheral tissues; and 5) insulin stimulates tissue glucose utilization and inhibits hepatic glucose output. The above mentioned pharmacological approaches may be utilized individually or in combination therapy. However, each approach has its limitations and adverse effects.

Obesity is a chronic disease that is highly prevalent in modern society and is associated not only with a social stigma, but also with decreased life span and numerous medical problems including adverse psychological development, dermatological disorders such as infections, varicose veins, exercise intolerance, diabetes mellitus, insulin resistance, hypertension, hypercholesterolemia, and coronary heart disease. Rissanen et al., British Medical Journal, 301: 835-837 (1990).

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Jung and Chong, Clinical Endocrinology, 35: 11-20 (1991); Bray, Am. J. Clin. Nutr., 55: 538S-544S (1992).

Considering the high prevalence of obesity in our society and the serious consequences associated therewith as discussed above, any therapeutic drug potentially useful in reducing weight of obese persons could have a profound beneficial effect on their health. There is a need in the art for a drug that will reduce total body weight of obese subjects toward their ideal body weight without significant adverse side effects and that will help the obese subject maintain the reduced weight level.

It is therefore desirable to provide a treatment regimen that is useful in returning the body weight of obese subjects toward a normal, ideal body weight. It is further desirable to provide a therapy for obesity that results in maintenance of the lowered body weight for an extended period of time.

Obesity is highly correlated with insulin resistance and diabetes in experimental animals and humans. Indeed, obesity and insulin resistance, the latter of which is generally accompanied by hyperinsulinemia or hyperglycemia, or both, are hallmarks of Type 2 diabetes. In addition, Type 2 diabetes is associated with a two- to four-fold risk of coronary artery disease. Despite decades of research on these serious health problems, the etiology of obesity and insulin resistance is unknown.

Type 1 diabetics characteristically show very low or immeasurable plasma insulin with elevated glucagon. Regardless of what the exact etiology is, most Type 1 patients have circulating antibodies directed against their own pancreatic cells including antibodies to insulin, to islet of Langerhans cell cytoplasm and to the enzyme glutamic acid decarboxylase. An immune response specifically directed against beta cells (insulin producing cells) leads to Type 1 diabetes. This specificity is supported by the above clinical picture, since beta cells secrete insulin while alpha cells secrete glucagon.

Current therapeutic regimens for Type 1 diabetes include modifications to the diet in order to minimize hyper-glycemia resulting from the lack of natural insulin, which in turn, is the result of damaged beta cells. Diet is also modified with regard to insulin administration to counter the hypoglycemic effects of the hormone. Whatever the form of treatment, parenteral administration of insulin is required for all Type 1 diabetics, hence the term "insulin-dependent" diabetes.

Thus, there is a need for an effective therapy of Type 2 diabetes that has fewer adverse effects than the available pharmaceutical approaches. Moreover, an effective alternative therapy to insulin could be useful for the treatment of Type 1 diabetes. The present invention provides a pharmacological therapy which stimulates glucose uptake and enhances insulin sensitivity in peripheral tissues and has fewer adverse effects than current treatment regimens for Type 2 diabetes. In addition, the present invention provides an alternative treatment for Type 1 diabetes. Furthermore, the present invention is useful for treating obesity by increasing energy expenditure by faster and more efficient glucose utilization.

The present invention provides a method for treating a mammal exhibiting one or more of Type 1 diabetes, Type 2 diabetes, obesity, insulin resistance, hyperinsulinemia, glucose intolerance, or hyperglycemia, comprising administering to said mammal in need of such treatment a therapeutically effective amount of the FGF-21 polypeptide of the invention.

The method of treating may be sufficient to achieve in said mammal at least one of the following modifications: reduction in body fat stores, decrease in insulin resistance, reduction of hyperinsulinemia, increase in glucose tolerance, and reduction of hyperglycemia.

In another aspect, the present invention relates to a method of treating a domestic animal including but not limited to, cattle, pigs, sheep, horses, and the like, comprising administering an effective amount of FGF-21 or variant thereof, in order to reduce body fat stores. The reduction of body fat stores on a long term, or permanent basis in domestic animals would obviously be of considerable economic benefit to man, particularly since animals supply a major portion of man's diet; and the animal fat may end up as de novo fat deposits in man.

Fibroblast growth factor 21 (FGF-21) may be used to reduce the morbidity and mortality associated with critically ill patients. See U.S. Patent Publication No. 20050176631 which is incorporated by reference herein in its entirety. Critically ill patients requiring intensive care for an extended period of time have a high risk of death and substantial mortality. A common cause for admittance of patients to intensive care units (ICUs) is systemic inflammatory response syndrome (SIRS) associated with infectious insults (sepsis) as well as noninfectious pathologic causes such as pancreatitis, ischemia, multiple trauma and tissue injury, hemorrhagic shock, and immune-mediated organ injury. The present invention also encompasses a method of reducing mortality and morbidity in critically ill patients suffering from systemic inflammatory response syndrome (SIRS) associated with infectious insults as well as noninfectious pathologic causes which comprises administering to the critically ill patients a therapeutically effective amount of FGF-21. Examples of conditions that involve SIRS include sepsis, pancreatitis, ischemia, multiple trauma and tissue injury, hemorrhagic shock, immune-mediated organ injury, acute respiratory distress syndrome (ARDS), shock, renal failure, and multiple organ dysfunction syndrome (MODS). The present invention also encompasses a method of reducing mortality and morbidity in critically ill patients suffering from respiratory distress.

A frequent complication of SIRS is the development of organ system dysfunction, including acute respiratory distress syndrome (ARDS), shock, renal failure, and multiple organ dysfunction syndrome (MODS), all of which amplify the risk of an adverse outcome. While many specialists believe that some type of nutritional support is beneficial to critically ill patients to help restore metabolic stability, the benefits and specifics of such support remain controversial due to the lack of well-controlled randomized clinical trials.

Because hyperglycemia and insulin resistance are common in critically ill patients given nutritional support, some ICUs administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe, et al. N Engl J Med., 345(19):1359, 2001).

The present invention encompasses a method of reducing the mortality and morbidity in these critically ill patients through the administration of FGF-21. The critically ill patients encompassed by the present invention generally experience an unstable hypermetabolic state. This unstable metabolic state is due to changes in substrate metabolism which may lead to relative deficiencies in some nutrients. Generally there is increased oxidation of both fat and muscle.

The critically ill patients wherein the administration of FGF-21 can reduce the risk of mortality and morbidity are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

Systemic inflammatory response syndrome (SIRS) describes an inflammatory process associated with a large number of clinical conditions and includes, but is not limited to, more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a $PaCO_2$ of less than 32 mm Hg; and (4) an alteration in the white blood cell count, such as a count greater than 12,000/cu mm, a count less than 4,000/cu mm, or the presence of more than 10% immature neutrophils. These physiologic changes should represent an acute alteration from baseline in the absence of other known causes for such abnormalities, such as chemotherapy, induced neutropenia, and leukopenia.

Sepsis is defined as a SIRS arising from infection. Noninfectious pathogenic causes of SIRS may include pancreatitis, ischemia, multiple trauma and tissue injury, including but not limited to, crushing injuries or severe burns, hemorrhagic shock, immune-mediated organ injury, and the exogenous administration of such putative mediators of the inflammatory process as tumor necrosis factor and other cytokines.

Septic shock and multi-organ dysfunction are major contributors to morbidity and mortality in the ICU setting. Sepsis is associated with and mediated by the activation of a number of host defense mechanisms including the cytokine network, leukocytes, and the complement cascade, and coagulation/fibrinolysis systems including the endothelium. Disseminated intravascular coagulation (DIC) and other degrees of consumption coagulopathy associated with fibrin deposition within the microvasculature of various organs, are manifestations of sepsis/septic shock. The downstream effects of the host defense response on target organs is an important mediator in the development of the multiple organ dysfunction syndrome (MODS) and contributes to the poor prognosis of patients with sepsis, severe sepsis and sepsis complicated by shock.

Respiratory distress denotes a condition wherein patients have difficulty breathing due to some type of pulmonary dysfunction. Often these patients exhibit varying degrees of hypoxemia that may or may not be refractory to treatment with supplemental oxygen. Respiratory distress may occur in patients with impaired pulmonary function due to direct lung injury or may occur due to indirect lung injury such as in the setting of a systemic process. In addition, the presence of multiple predisposing disorders substantially increases the risk, as does the presence of secondary factors such as chronic alcohol abuse, chronic lung disease, and a low serum pH.

Some causes of direct lung injury include pneumonia, aspiration of gastric contents, pulmonary contusion, fat emboli, near-drowning, inhalation injury, high altitude and reperfusion pulmonary edema after lung transplantation or pulmonary embolectomy. Some causes of indirect lung injury include sepsis, severe trauma with shock and multiple transfusions; cardiopulmonary bypass, drug overdose, acute pancreatitis, and transfusions of blood products.

One class of pulmonary disorders that causes respiratory distress are associated with the syndrome known as Cor Pulmonale. These disorders are associated with chronic hypoxemia resulting in raised pressure within the pulmonary circulation called pulmonary hypertension. The ensuing pulmonary hypertension increases the work load of the right ventricle, thus leading to its enlargement or hypertrophy. Cor Pulmonale generally presents as right heart failure defined by a sustained increase in right ventricular pressures and clinical evidence of reduced venous return to the right heart.

Chronic obstructive pulmonary diseases (COPDs) which include emphysema and chronic bronchitis also cause respiratory distress and are characterized by obstruction to air flow. COPDs are the fourth leading cause of death and claim over 100,000 lives annually.

Acute respiratory distress syndrome (ARDS) is generally progressive and characterized by distinct stages. The syndrome is generally manifested by the rapid onset of respiratory failure in a patient with a risk factor for the condition. Arterial hypoxemia that is refractory to treatment with supplemental oxygen is a characteristic feature. There may be alveolar filling, consolidation, and atelectasis occurring in dependent lung zones; however, non-dependent areas may have substantial inflammation. The syndrome may progress to fibrosing alveolitis with persistent hypoxemia, increased alveolar dead space, and a further decrease in pulmonary compliance. Pulmonary hypertension which results from damage to the pulmonary capillary bed may also develop.

The severity of clinical lung injury varies. Both patients with less severe hypoxemia as defined by a ratio of the partial pressure of arterial oxygen to the fraction of inspired oxygen as 300 or less and patients with more severe hypoxemia as defined by a ratio of 200 or less are encompassed by the present invention. Generally, patients with a ratio 300 or less are classified as having acute lung injury and patients with having a ratio of 200 or less are classified as having acute respiratory distress syndrome.

The acute phase of acute lung injury is characterized by an influx of protein-rich edema fluid into the air spaces as a consequence of increased vascular permeability of the alveolar-capillary barrier. The loss of epithelial integrity wherein permeability is altered can cause alveolar flooding, disrupt normal fluid transport which affects the removal of edema fluid from the alveolar space, reduce the production and turnover of surfactant, lead to septic shock in patients with bacterial pneumonia, and cause fibrosis. Sepsis is associated with the highest risk of progression to acute lung injury.

In conditions such as sepsis, where hypermetabolism occurs, there is an accelerated protein breakdown both to sustain gluconeogenesis and to liberate the amino acids required for increased protein synthesis. Hyperglycemia may be present and high concentrations of triglycerides and other lipids in serum may be present.

For patients with compromised respiratory function, hypermetabolism may affect the ratio of carbon dioxide production to oxygen consumption. This is known as the respiratory quotient (R/Q) and in normal individuals is between about 0.85 and about 0.90. Excess fat metabolism has a tendency to lower the R/Q whereas excess glucose metabolism raises the R/Q. Patients with respiratory distress often have difficulty eliminating carbon dioxide and thus have abnormally high respiratory quotients.

The critically ill patients encompassed by the present invention also generally experience a particular stress response characterized by a transient down-regulation of most cellular products and the up-regulation of heat shock proteins. Furthermore, this stress response involves the activation of hormones such as glucagon, growth hormone, cortisol, and pro- and anti-inflammatory cytokines. While this stress response appears to have a protective function, the response creates additional metabolic instability in these critically ill patients. For example, activation of these specific hormones causes elevations in serum glucose which results in hyperglycemia. In addition, damage to the heart and other organs may be exacerbated by adrenergic stimuli. Further, there may be changes to the thyroid which may have significant effects on metabolic activity.

Average quantities of the FGF-21 may vary and in particular should be based upon the recommendations and prescription of a qualified physician. The exact amount of FGF-21 is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one of ordinary skill in the art based upon therapy with FGF-21.

Pharmaceutical compositions of the invention may be manufactured in a conventional manner.

EXAMPLES

The following examples are offered to illustrate, but do not limit the claimed invention.

Example 1

This example describes one of the many potential sets of criteria for the selection of sites of incorporation of non-naturally encoded amino acids into FGF-21.

FIG. 1 shows the sequence homology between FGF-21 (Protein accession number BC018404) and FGF-19 (Protein accession number BAA75500) as determined using Vector NTI (Invitrogen; Carlsbad, Calif.). The amino acids marked with an asterisk are similar between the two molecules. The amino acids that are underlined are identical between the two polypeptides. Seven different FGF-21 polypeptides were generated by substituting a naturally encoded amino acid with a non-naturally encoded amino acid. Each polypeptide had one of the amino acids marked with a rectangle in FIG. 1 substituted with para-acetylphenylalanine. The polypeptides generated lacked the leader sequence shown in FIGS. 1 and 3 and were His tagged at the N terminus with 6 histidine residues. SEQ ID NO.: 1 is a 181 amino acid sequence of human FGF-21 (P form) without the leader sequence. SEQ ID NO.: 2 is the sequence of human FGF-21 (P form) without the leader sequence and with a His tag at the N terminus. Each of the polypeptides generated had a non-naturally encoded amino acid substitution at one of the following positions 10, 52, 77, 117, 126, 131, and 162 of SEQ ID NO: 1.

Figure 2:
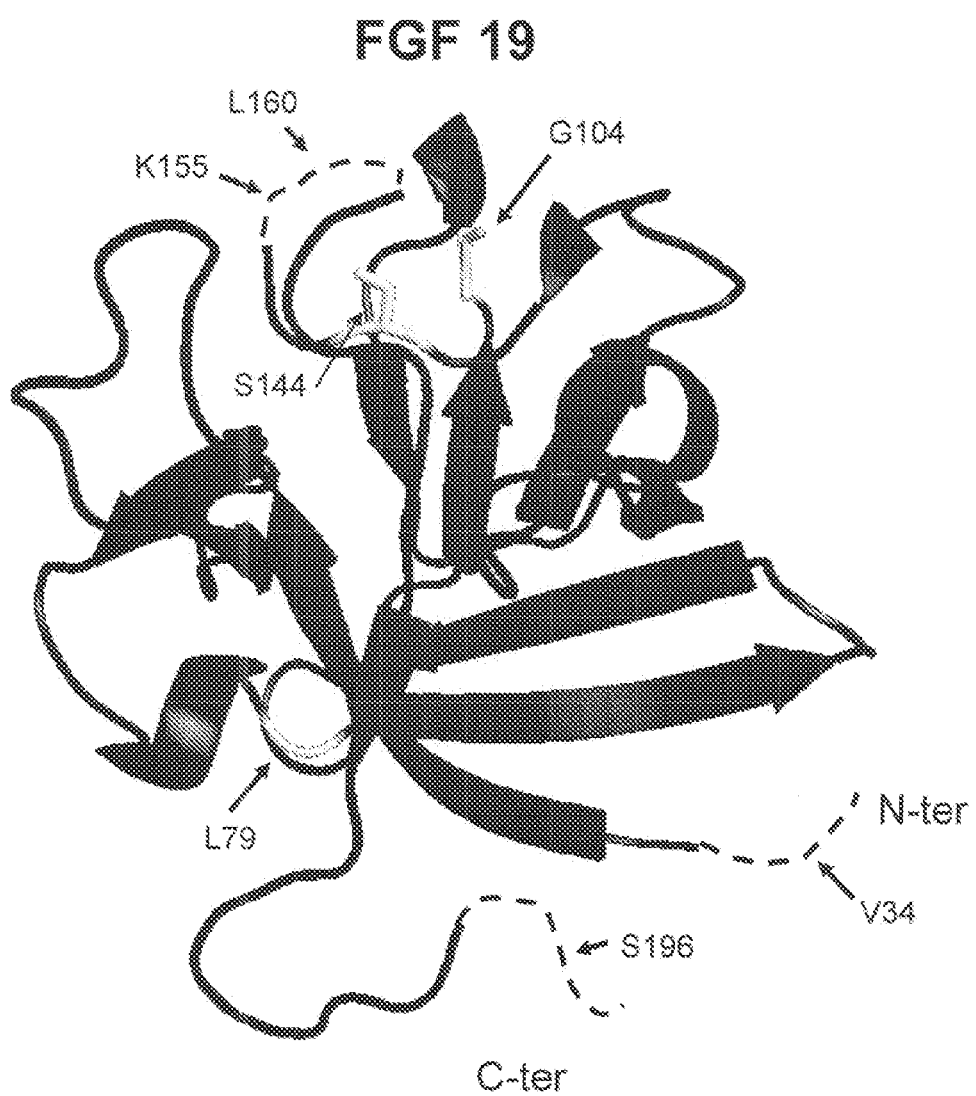
FIG. 2—The structure of human FGF-19 is shown.

FIG. 2 shows the structure of human FGF-19 that was obtained from the Protein Data Bank (PDB) (Bernstein et al. *J. Mol. Biol.* 1997, 112, pp 535) (1PWA) and was labeled using the PyMOL software (DeLano Scientific; Palo Alto, Calif.). The amino acids corresponding to V34, L79, G104, S144, K155, L160, and S196 of FGF-19 were substituted with para-acetylphenylalanine in FGF-21 polypeptides of the invention. The dashed line indicates regions that were not resolved in the original structure.

Figure 3:
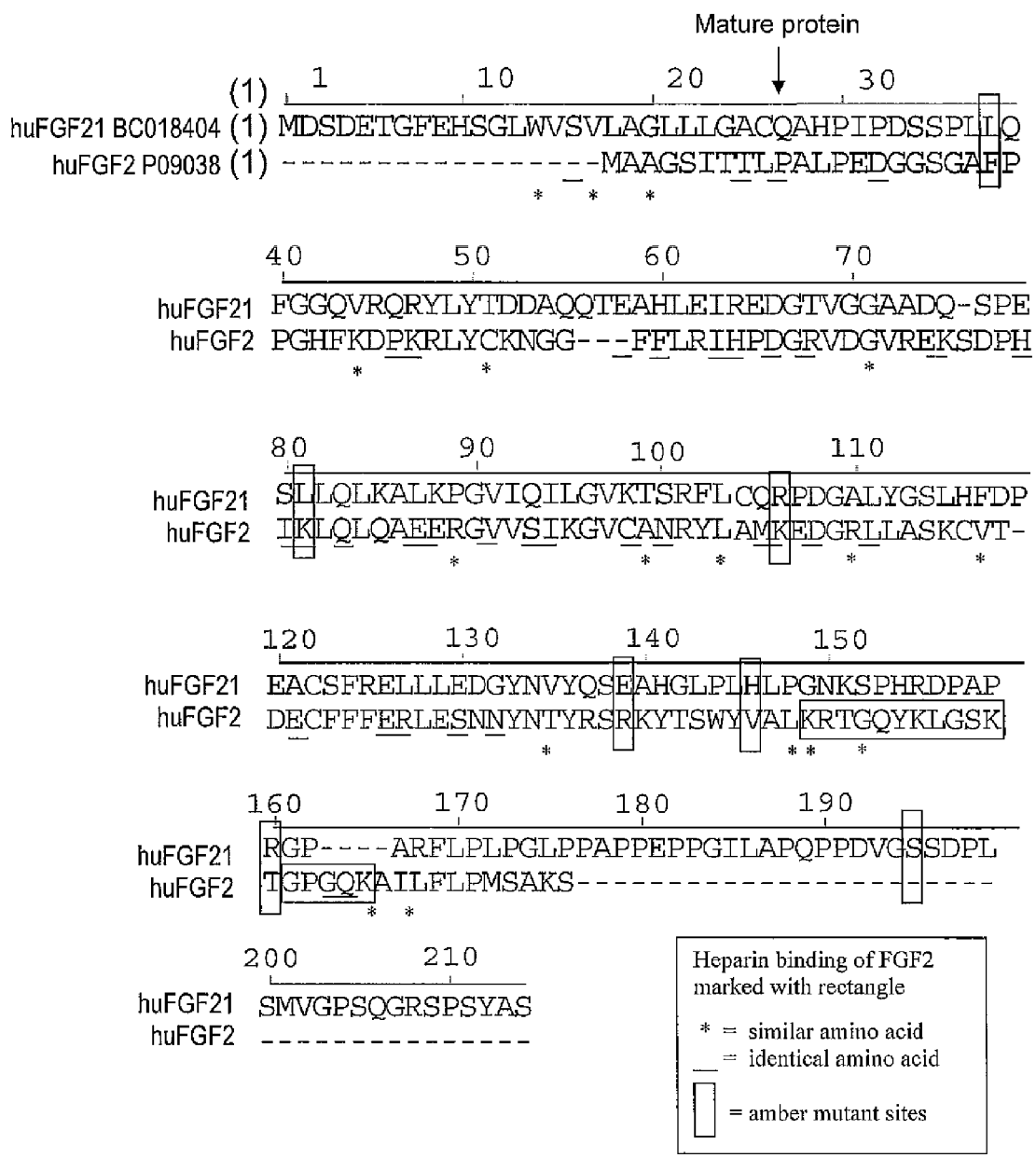
FIG. 3—Amber mutations in FGF-21 and corresponding sites in FGF-2 are shown.

FIG. 3 shows the sequence homology between FGF-21 (Protein accession number BC018404) and FGF-2 (Protein accession number BAA75500) as determined using Vector NTI (Invitrogen; Carlsbad, Calif.). The amino acids marked with an asterisk are similar between the two molecules. The amino acids that are underlined are identical between the two polypeptides. The 7 amino acids shown in FIG. 1 as sites for substitution are also placed in a rectangle in FIG. 3.

Figure 4:
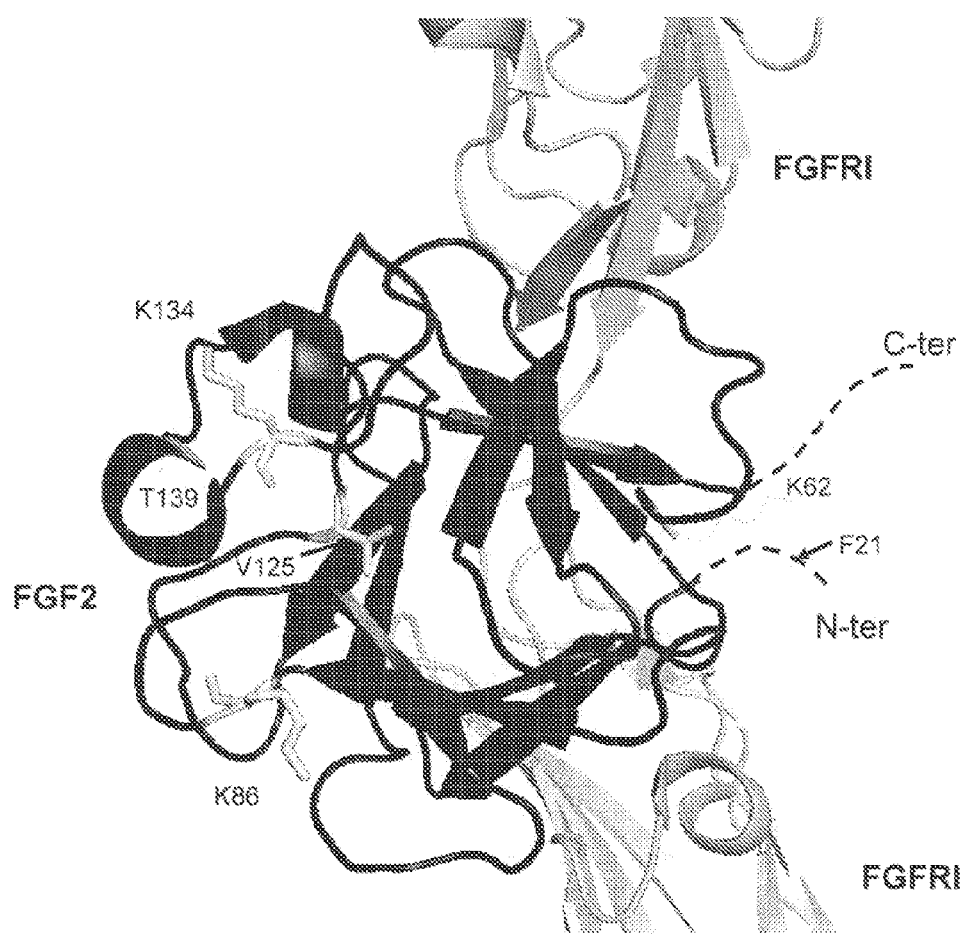
FIG. 4—The structure of human FGF-19 is shown.

FIG. 4 shows the structure of human FGF-2 structure that was obtained from PDB (1CVS) and was labeled using the PyMOL software (DeLano Scientific; Palo Alto, Calif.). The gray structures are human FGF receptor 1 (FGFR1) and the black is human FGF2. Plotnikov, A N et al. Cell. 1999 Sep. 3; 98(5):641-50 describe the crystal structure of FGF2 bound to FGF receptor. The amino acids corresponding to F21, K62, K86, V125, K134, T139 of FGF-2 were substituted with para-acetylphenylalanine in FGF-21 polypeptides of the invention. The dashed line indicates regions that were not resolved in the original structure.

Another set of criteria for the selection of preferred sites of incorporation of non-naturally encoded amino acids is the following. Ten crystal structures from the Protein Data Bank were used to model the structure of FGF-21: 1PWA (human FGF-19); 1IJT (human FGF-4); 1NUN (human FGF10-FGF Receptor 2b Complex); 1G82 (human FGF-9 dimer with FGF Receptor and heparin); 1IHK (human FGF-9); 1BAR (bovine FGF-1); 1QQK (rat FGF-7); 1K5U (human FGF-1); 1FQ9 (human FGF-2 with FGF Receptor 1 and heparin); and 2FDB (human FGF-8b with FGF Receptor 2c). The coordinates for these structures are available from the Protein Data Bank (PDB) (Bernstein et al. *J. Mol. Biol.* 1997, 112, pp 535). A comparison of the crystal structures indicated that they were all very similar in the core structure. However, the N- and C-termini were found to be highly divergent between these FGF molecules, and therefore the termini could not be modeled. The modeling identified two residues, Y22 and Y104, which were highly conserved and were involved with receptor binding. Two potential heparin binding sites were also identified involving R36 and E37. The amino acid positions identified for the receptor binding and heparin binding residues correspond to SEQ ID NO: 1.

As a result, residues were identified that 1) would not interfere with binding to the FGF receptor or heparin, 2) would not be present in the interior of the protein, and 3) would be in regions that were fairly consistent between the crystal structures. In some embodiments, one or more non-naturally encoded amino acids are incorporated at, but not limited to, one or more of the following positions of FGF-21: 87, 77, 83, 72, 69, 79, 91, 96, 108, and 110 of SEQ ID NO: 1 or the corresponding amino acids in SEQ ID NOs: 2-7). In some embodiments, one or more non-naturally encoded amino acids are incorporated at, but not limited to, one or more of the following positions of FGF-21: 87, 77, 83, 72 of SEQ ID NO: 1 or the corresponding amino acids in SEQ ID NOs: 2-7). In some embodiments, one or more non-naturally encoded amino acids are incorporated at, but not limited to, one or more of the following positions of FGF-21: 69, 79, 91, 96, 108, and 110 of SEQ ID NO: 1 or the corresponding amino acids in SEQ ID NOs: 2-7).

The following criteria were used to evaluate each position of FGF-21 for the introduction of a non-naturally encoded amino acid: the residue (a) should not interfere with binding of the FGF-21 Receptor based on structural analysis, b) should not be affected by alanine or homolog scanning mutagenesis (c) should be surface exposed and exhibit minimal van der Waals or hydrogen bonding interactions with surrounding residues, (d) should be either deleted or variable in FGF-21 variants, (e) would result in conservative changes upon substitution with a non-naturally encoded amino acid and (f) could be found in either highly flexible regions or structurally rigid regions.

Additional or different crystal structures for members of the FGF family such as structures for FGF-23 and/or FGF-19 may also be used to select sites for incorporation of one or more non-naturally encoded amino acids into FGF-21. For example, the crystal structure of human FGF-19 (PDB ID 2P23) and/or crystal structure of human FGF-19 (PDB ID 2P23) and/or human FGF-23 (PDB ID 2P39) may provide additional information to select sites for incorporation of non-naturally encoded amino acids into FGF-21. Such sites may be in different regions of the protein, including but not limited to, the N- and C-termini, receptor binding and heparin binding regions. In addition, further calculations can be performed on the FGF-21 molecule, utilizing the Cx program (Pintar et al. (2002) *Bioinformatics*, 18, pp 980) to evaluate the extent of protrusion for each protein atom.

In some embodiments, one or more non-naturally encoded amino acids are incorporated in one or more of the following positions in FGF-21: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). In some embodiments, one or more non-naturally encoded amino acids are incorporated in one or more of the following positions in FGF-21: 10, 52, 117, 126, 131, 162, 87, 77, 83, 72, 69, 79, 91, 96, 108, and 110 (SEQ ID NO: 1 or the corresponding amino acids of SEQ ID NOs: 2-7). In some embodiments, one or more non-naturally encoded amino acids are incorporated in one or more of the following positions in FGF-21: 10, 52, 77, 117, 126, 131, and 162 (SEQ ID NO: 1 or the corresponding amino acids of SEQ ID NOs: 2-7). In some embodiments, one or more non-naturally encoded amino acids are incorporated in one or more of the following positions in FGF-21: 87, 77, 83, 72 (SEQ ID NO: 1 or the corresponding amino acids of SEQ ID NOs: 2-7). In some embodiments, one or more non-naturally encoded amino acids are incorporated in one or more of the following positions in FGF-21: 69, 79, 91, 96, 108, and 110 (SEQ ID NO: 1 or the corresponding amino acids of SEQ ID NOs: 2-7).

Example 2

This example details cloning and expression of a FGF-21 polypeptide including a non-naturally encoded amino acid in *E. coli*. This example also describes one method to assess the biological activity of modified FGF-21 polypeptides.

Methods for cloning FGF-21 are known to those of ordinary skill in the art. Polypeptide and polynucleotide sequences for FGF-21 and cloning of FGF-21 into host cells are detailed in U.S. Pat. No. 6,716,626; U.S. Patent Publication Nos. 2005/0176631, 2005/0037457, 2004/0185494, 2004/0259780, 2002/0164713, and 2001/0012628; WO 01/36640; WO 03/011213; WO 03/059270; WO 04/110472; WO 05/061712; WO 05/072769; WO 05/091944; WO 05/113606; WO 06/028595; WO 06/028714; WO 06/050247; WO 06/065582; WO 06/078463, which are incorporated by reference in their entirety herein.

cDNA encoding the P form of FGF-21 without the leader sequence is shown as SEQ ID NO: 8. This polypeptide is shown as SEQ ID NO: 1.

cDNA encoding a His tagged P form of FGF-21 without a leader sequence is shown as SEQ ID NO: 9. This polypeptide is shown as SEQ ID NO: 2.

cDNA encoding the P form of FGF-21 with a leader sequence containing 3 leucines together is shown as SEQ ID NO: 10. This polypeptide is shown as SEQ ID NO: 3.

cDNA encoding the P form of FGF-21 with a leader sequence containing 2 leucines together is shown as SEQ ID NO: 11. This polypeptide is shown as SEQ ID NO: 4.

cDNA encoding the L form of FGF-21 without the leader sequence is shown as SEQ ID NO: 12. This polypeptide is shown as SEQ ID NO: 5.

cDNA encoding the L form of FGF-21 with a leader sequence containing 3 leucines together is shown as SEQ ID NO: 13. This polypeptide is shown as SEQ ID NO: 6.

cDNA encoding the L form of FGF-21 with a leader sequence containing 2 leucines together is shown as SEQ ID NO: 14. This polypeptide is shown as SEQ ID NO: 7.

An introduced translation system that comprises an orthogonal tRNA (O-tRNA) and an orthogonal aminoacyl tRNA synthetase (O-RS) is used to express FGF-21 containing a non-naturally encoded amino acid. The O-RS preferentially aminoacylates the O-tRNA with a non-naturally encoded amino acid. In turn the translation system inserts the non-naturally encoded amino acid into FGF-21, in response to an encoded selector codon. Suitable O-RS and O-tRNA sequences are described in WO 2006/068802 entitled "Compositions of Aminoacyl-tRNA Synthetase and Uses Thereof" (E9; SEQ ID NO: 15) and WO 2007/021297 entitled "Compositions of tRNA and Uses Thereof" (F13; SEQ ID NO: 16), which are incorporated by reference in their entirety herein.

TABLE 2

O-RS and O-tRNA sequences.

| | | |
|---|---|---|
| SEQ ID NO: 17 | *M. jannaschii* mtRNA$_{CUA}^{Tyr}$ | tRNA |
| SEQ ID NO: 18 | HLAD03; an optimized amber supressor tRNA | tRNA |
| SEQ ID NO: 19 | HL325A; an optimized AGGA frameshift supressor tRNA | tRNA |
| SEQ ID NO: 20 | Aminoacyl tRNA synthetase for the incorporation of p-azido-L-phenylalanine p-Az-PheRS(6) | RS |

TABLE 2-continued

O-RS and O-tRNA sequences.

| | | |
|---|---|---|
| SEQ ID NO: 21 | Aminoacyl tRNA synthetase for the incorporation of p-benzoyl-L-phenylalanine p-BpaRS(1) | RS |
| SEQ ID NO: 22 | Aminoacyl tRNA synthetase for the incorporation of propargyl-phenylalanine Propargyl-PheRS | RS |
| SEQ ID NO: 23 | Aminoacyl tRNA synthetase for the incorporation of propargyl-phenylalanine Propargyl-PheRS | RS |
| SEQ ID NO: 24 | Aminoacyl tRNA synthetase for the incorporation of propargyl-phenylalanine Propargyl-PheRS | RS |
| SEQ ID NO: 25 | Aminoacyl tRNA synthetase for the incorporation of p-azido-phenylalanine p-Az-PheRS(1) | RS |
| SEQ ID NO: 26 | Aminoacyl tRNA synthetase for the incorporation of p-azido-phenylalanine p-Az-PheRS(3) | RS |
| SEQ ID NO: 27 | Aminoacyl tRNA synthetase for the incorporation of p-azido-phenylalanine p-Az-PheRS(4) | RS |
| SEQ ID NO: 28 | Aminoacyl tRNA synthetase for the incorporation of p-azido-phenylalanine p-Az-PheRS(2) | RS |
| SEQ ID NO: 29 | Aminoacyl tRNA synthetase for the incorporation of p-acetyl-phenylalanine (LW1) | RS |
| SEQ ID NO: 30 | Aminoacyl tRNA synthetase for the incorporation of p-acetyl-phenylalanine (LW5) | RS |
| SEQ ID NO: 31 | Aminoacyl tRNA synthetase for the incorporation of p-acetyl-phenylalanine (LW6) | RS |
| SEQ ID NO: 32 | Aminoacyl tRNA synthetase for the incorporation of p-azido-phenylalanine (AzPheRS-5) | RS |
| SEQ ID NO: 33 | Aminoacyl tRNA synthetase for the incorporation of p-azido-phenylalanine (AzPheRS-6) | RS |

The transformation of *E. coli* with plasmids containing the modified FGF-21 gene and the orthogonal aminoacyl tRNA synthetase/tRNA pair (specific for the desired non-naturally encoded amino acid) allows the site-specific incorporation of non-naturally encoded amino acid into the FGF-21 polypeptide.

Wild type mature FGF-21 was amplified by PCR from a cDNA synthesis reaction derived from healthy human liver polyA+ mRNA (Biochain) using standard protocols and cloned into pET30 (NcoI-BamHI). Following sequence confirmation, FGF-21 including an N-terminal HHHHHHSGG sequence was subcloned into a suppression vector containing an amber suppressor tyrosyl tRNA$^{Tyr/CUA}$ from *Methanococcus jannaschii* (Mj tRNA$^{Tyr/CUA}$) under constitutive control of a synthetic promoter derived from the *E. coli* lipoprotein promoter sequence (Miller, J. H., Gene, 1986), as well as well as the orthogonal tyrosyl-tRNA-synthetase (MjTyrRS) under control of the *E. coli* GlnRS promoter. Expression of FGF-21 was under control of the T7 promoter. Amber mutations were introduced using standard quick change mutation protocols (Stratagene; La Jolla, Calif.). All constructs were sequence verified.

Suppression with Para-Acetyl-Phenylalanine (pAcF)

Plasmids (pVK3-HisFGF21) were transformed into the W3110 B2 strain of *E. coli* in which expression of the T7 polymerase was under control of an arabinose-inducible promoter. Overnight bacterial cultures were diluted 1:100 into shake flasks containing 2×YT culture media and grown at 37° C. to an OD$_{600}$ of ~0.8. Protein expression was induced by the addition of arabinose (0.2% final), and para-acetyl-phenylalanine (pAcF) to a final concentration of 4 mM. Cultures were incubated at 37° C. for 4 hours. Cells were pelleted and resuspended in B-PER lysis buffer (Pierce) 100 ul/OD/ml+ 10 ug/ml DNase and incubated at 37° C. for 30 min. Cellular material was removed by centrifugation and the supernatant removed. The pellet was re-suspended in an equal amount of SDS-PAGE protein loading buffer. All samples were loaded on a 4-12% PAGE gel with MES and DTT. Methods for purification of FGF-21 are known to those of ordinary skill in the art and are confirmed by SDS-PAGE, Western Blot analyses, or electrospray-ionization ion trap mass spectrometry and the like.

Figure 5:
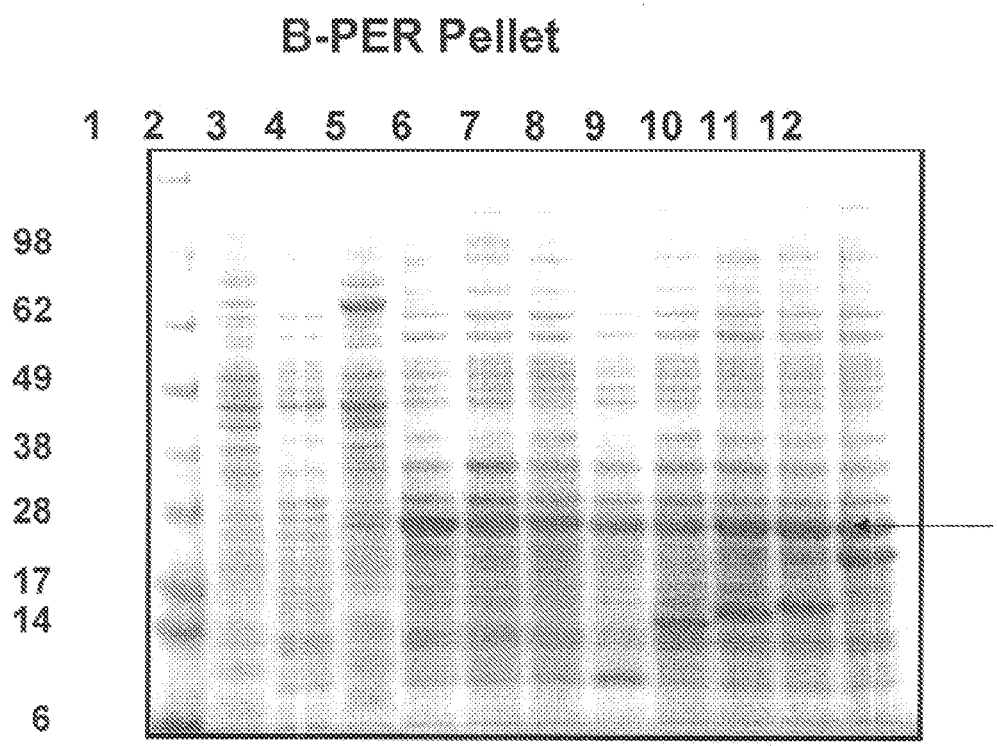
FIG. 5—Expression of N-terminal His tagged FGF-21 and suppression at 7 amber sites are shown.

Expression of N-terminal His tagged FGF-21 and suppression at 7 amber sites is shown as FIG. 5. The FGF-21 polypeptide is marked with an arrow. FIG. 5 shows the B-PER pellet samples—Lane 1: Marker; Lane 2: VK3-FGF21 preinduction, supernatant; Lane 3: VK-FGF21 preinduction, pellet; Lane 4: VK3-FGF21 0.2% arabinose, supernatant; Lane 5: VK3-FGF21 0.2% arabinose, pellet; Lane 6: VK3-FGF21-pAcF-L10, 0.2% arabinose; Lane 7: VK3-FGF21-pAcF-L52, 0.2% arabinose; Lane 8: VK3-FGF21-pAcF-R77, 0.2% arabinose; Lane 9: VK3-FGF21-pAcF-H117, 0.2% arabinose; Lane 10: VK3-FGF21-pAcF-R126, 0.2% arabinose; Lane 11: VK3-FGF21-pAcF-R131, 0.2% arabinose; Lane 12: VK3-FGF21-pAcF-S162, 0.2% arabinose. The position numbers indicated for the amino acid substitution are based on SEQ ID NO: 1.

Figure 6:
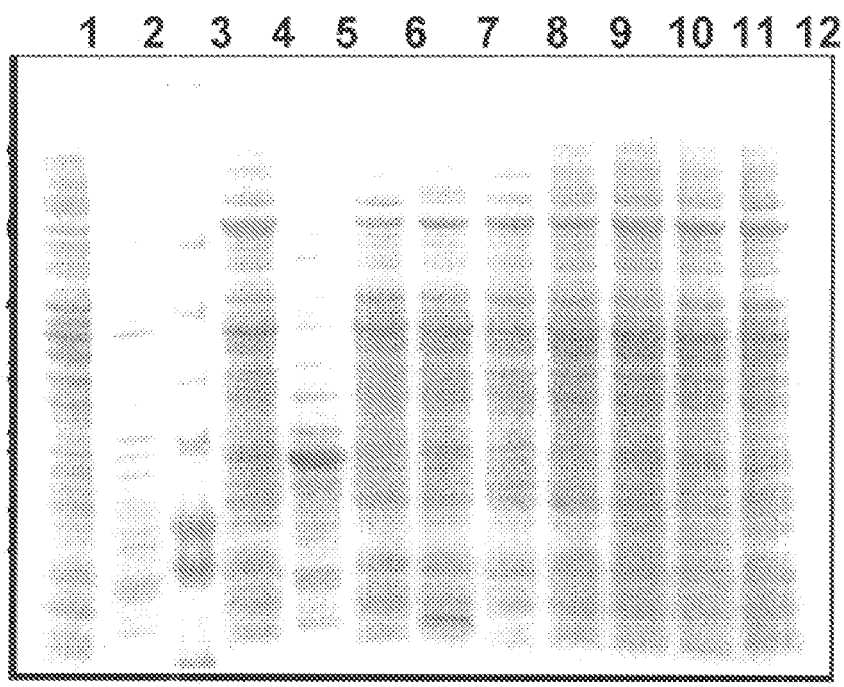
FIG. 6—BPER supernatant samples from the expression of N-terminal His tagged FGF-21 and suppression at 7 amber sites are shown.

FIG. 6 shows the B-PER supernatant samples—Lane 1: VK3-FGF21 preinduction, supernatant; Lane 2: VK3-FGF21 preinduction, pellet; Lane 3: Marker; Lane 4: VK3-FGF21 0.2% arabinose, supernatant; Lane 5: VK3-FGF21 0.2% arabinose, pellet; Lane 6: VK3-FGF21-pAcF-L10, 0.2% arabinose; Lane 7: VK3-FGF21-pAcF-L52, 0.2% arabinose; Lane 8: VK3-FGF21-pAcF-R77, 0.2% arabinose; Lane 9: VK3-FGF21-pAcF-H117, 0.2% arabinose; Lane 10: VK3-FGF21-pAcF-R126, 0.2% arabinose; Lane 11: VK3-FGF21-pAcF-R131, 0.2% arabinose; Lane 12: VK3-FGF21-pAcF-S162, 0.2% arabinose. The position numbers indicated for the amino acid substitution are based on SEQ ID NO: 1.

His-tagged mutant FGF-21 proteins can be purified using methods known to those of ordinary skill in the art. The ProBond Nickel-Chelating Resin (Invitrogen, Carlsbad, Calif.) may be used via the standard His-tagged protein purification procedures provided by the manufacturer.

pVK10 (FIG. 24) was developed for use with the untagged FGF-21 protein, having a sequence given in FIG. 25. This was the vector used to make R36am and Y83am mutants and there is further data on this non-His tagged FGF-21 mutant proteins and their purification later in the examples and shown throughout the figures.

Differentiation of 3T3-L1 to Adipocytes and Glucose Uptake Assay

To assess the biological activity of FGF-21 polypeptides, the following assay may be performed. Mouse 3T3-L1 fibroblasts (ATCC #CL-173) are seeded in a 10 cm dish with DMEM containing 10% bovine calf serum. The cells are kept at a density not higher the 70% for expansion. Before starting differentiation to adipocytes, the cells are allowed to go to 100% confluence; the medium has to be changed every 2 days. The cells are counted and seeded at 25,000 cells/well in a 96 well/plate (cells can also be plated on Cytostar-T 96 well/plate) and incubated for another 48 hours. Differentiation is induced by adding the following medium after removing the previous culture medium: DMEM supplemented with 10% FBS (Fetal Calf Serum), 1 μM dexamethasone (DBX), 0.5 mM 3-isobutyl-1-methylxanthine (IBMX), and 5 μg/mL insulin. An alternative way to induce differentiation is to treat the cells with 1 μM Rosiglitazone and incubate for 6 days before changing medium to DMEM/10% FBS, since this is a faster way to induce 3T3-L1 fibroblasts to differentiate into adipocytes. A third possibility is to combine the two procedures to shorten time for differentiation.

After adding DBX/IBMX/insulin containing medium to cells, the cells are incubated for 48 hours. The medium is changed to DMEM/10% FBS/5 μg/mL insulin, and the cells are incubated for 48 hours. Thereafter the medium is changed to DMEM/10% FBS and the medium is replaced with fresh medium every 2 days. The cells will differentiate between 7-14 days. Differentiated cells accumulate lipid droplets. The cells can be stained with OIL RED O. Once the 95% adipocytes contain lipid droplets, the cells can be used for the glucose uptake assay.

Differentiated 3T3-L1 are treated with FGF-21 (1 μg/mL) in DMEM supplemented with 0.1% fatty acid free-BSA for 18 hours to starve the cells. The cells are then washed 3 times with Kreb's-Ringer HEPES buffer (KRH=0.118M NaCl, 5 mM KCl, 2.54 mM $CaCl_2$, 1.19 mM $KH_2PO_4$, 1.19 mM $MgSO_4$, and 20 mM HEPES) supplemented with 0.1% FAF-BSA. The labeling mix is prepared by adding 4 μCi, 0.1 mM of 2-deoxyD-[1-$^3$H]-glucose to KRH/0.1% FAF-BSA buffer. The cells are added and incubated for 1 hour at 37° C. The reaction is stopped by washing the cells twice with ice-cold PBS containing 20 μM cytochalasin B. The plate is blotted to eliminate any residual buffer. Scintillitaion liquid is added to each well and samples are counted on a TopCounter.

An alternative way to measure glucose uptake is to load the differentiated 3T3-L1 cells with a non-radioactive substrate as 2-NBDG and read with a fluorescence plate reader. An indirect procedure for measuring glucose uptake is to measure the expression GLUT1 or GLUT4 on the cell membrane surface. GLUT1 and GLUT4 are glucose transporters that are translocated on the cell membrane surface from the internal vesicles upon insulin or FGF-21 stimulation. An ELISA on live cells can be developed.

Example 3

This example details introduction of a carbonyl-containing amino acid and subsequent reaction with an aminooxy-containing PEG.

This Example demonstrates a method for the generation of a FGF-21 polypeptide that incorporates a ketone-containing non-naturally encoded amino acid that is subsequently reacted with an aminooxy-containing PEG of approximately 5,000 MW. Each of the residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7) is separately substituted with a non-naturally encoded amino acid having the following structure:

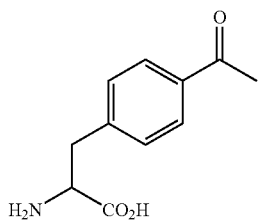

The sequences utilized for site-specific incorporation of p-acetyl-phenylalanine into FGF-21 are SEQ ID NO: 1 (FGF-21), and SEQ ID NO: 16 or 17 (muttRNA, *M. jannaschii* mtRNA$_{CUA}^{Tyr}$), and 15, 29, 30 or 31 (TyrRS LW1, 5, or 6) described in Example 2 above.

Once modified, the FGF-21 polypeptide variant comprising the carbonyl-containing amino acid is reacted with an aminooxy-containing PEG derivative of the form:

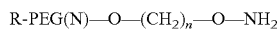
R-PEG(N)—O—(CH$_2$)$_n$—O—NH$_2$ where R is methyl, n is 3 and N is approximately 5,000 MW. The purified FGF-21 containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-FGF-21 is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

R-PEG(N)—O—(CH$_2$)$_2$—NH—C(O)(CH$_2$)$_n$—O—NH$_2$ where R=methyl, n=4 and N is approximately 20,000 MW. The reaction, purification, and analysis conditions are as described in Example 3.

Example 5

This example details the introduction of two distinct non-naturally encoded amino acids into FGF-21 polypeptides.

This example demonstrates a method for the generation of a FGF-21 polypeptide that incorporates non-naturally encoded amino acid comprising a ketone functionality at two positions among the following residues: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7). The FGF-21 polypeptide is prepared as described in Examples 1 and 2, except that the selector codon is introduced at two distinct sites within the nucleic acid.

Example 6

This example details conjugation of FGF-21 polypeptide to a hydrazide-containing PEG and subsequent in situ reduction.

A FGF-21 polypeptide incorporating a carbonyl-containing amino acid is prepared according to the procedure described in Examples 2 and 3. Once modified, a hydrazide-containing PEG having the following structure is conjugated to the FGF-21 polypeptide:

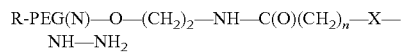
R-PEG(N)—O—(CH$_2$)$_2$—NH—C(O)(CH$_2$)$_n$—X—NH—NH$_2$ where R=methyl, n=2 and N=10,000 MW and X is a carbonyl (C=O) group. The purified FGF-21 containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into a FGF-21 polypeptide and derivatization with mPEG-azide.

The following residues, before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7), are each substituted with the following non-naturally encoded amino acid:

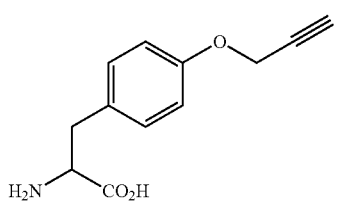

The sequences utilized for site-specific incorporation of p-propargyl-tyrosine into FGF-21 are SEQ ID NO: 1 (FGF-21), SEQ ID NO: 16 or 17 (muttRNA, *M. jannaschii* mtRNA$_{CUA}^{Tyr}$), and 22, 23 or 24 described in Example 2 above. The FGF-21 polypeptide containing the propargyl tyrosine is expressed in *E. coli* and purified using the conditions described in Example 3.

The purified FGF-21 containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition, including but not limited to, by similar procedures described in Example 3.

In this Example, the PEG will have the following structure:

R-PEG(N)—O—(CH$_2$)$_2$—NH—C(O)(CH$_2$)$_n$—N$_3$ where R is methyl, n is 4 and N is 10,000 MW.

Example 8

This example details substitution of a large, hydrophobic amino acid in a FGF-21 polypeptide with propargyl tyrosine.

A Phe, Trp or Tyr residue present within one the following regions of FGF-21: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7) is substituted with the following non-naturally encoded amino acid as described in Example 7:

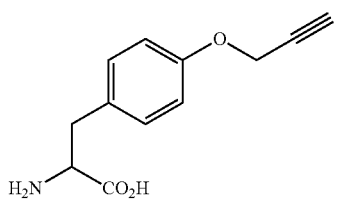

Once modified, a PEG is attached to the FGF-21 polypeptide variant comprising the alkyne-containing amino acid. The PEG will have the following structure:

Me-PEG(N)—O—(CH$_2$)$_2$—N$_3$ and coupling procedures would follow those in Example 7. This will generate a FGF-21 polypeptide variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a FGF-21 polypeptide homodimer, heterodimer, homomultimer, or heteromultimer separated by one or more PEG linkers.

The alkyne-containing FGF-21 polypeptide variant produced in Example 7 is reacted with a bifunctional PEG derivative of the form:

N$_3$—(CH$_2$)$_n$—C(O)—NH—(CH$_2$)$_2$—O-PEG(N)—O—(CH$_2$)$_2$—NH—C(O)—(CH$_2$)$_n$—N$_3$ where n is 4 and the PEG has an average MW of approximately 5,000, to generate the corresponding FGF-21 polypeptide homodimer where the two FGF-21 molecules are physically separated by PEG. In an analogous manner a FGF-21 polypeptide may be coupled to one or more other polypeptides to form heterodimers, homomultimers, or heteromultimers. Coupling, purification, and analyses will be performed as in Examples 7 and 3.

Example 10

This example details coupling of a saccharide moiety to a FGF-21 polypeptide.

One residue of the following is substituted with the non-naturally encoded amino acid below: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182 (i.e., at the carboxyl terminus of the protein) (SEQ ID NO: 1 or the corresponding amino acids in SEQ ID NOs: 2-7) as described in Example 3.

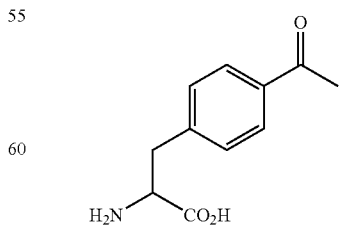

Once modified, the FGF-21 polypeptide variant comprising the carbonyl-containing amino acid is reacted with a β-linked aminooxy analogue of N-acetylglucosamine (GlcNAc). The FGF-21 polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated FGF-21 polypeptide (5 mg/mL) with UDP-galactose (16 mM) and β-1,4-galactosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated FGF-21 polypeptide antagonist.

A residue, including but not limited to, those involved in FGF-21 receptor binding is substituted with the following non-naturally encoded amino acid as described in Example 3.

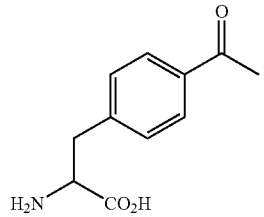

Once modified, the FGF-21 polypeptide variant comprising the carbonyl-containing amino acid will be reacted with an aminooxy-containing PEG derivative of the form:

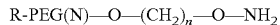

R-PEG(N)—O—(CH$_2$)$_n$—O—NH$_2$ where R is methyl, n is 4 and N is 20,000 MW to generate a FGF-21 polypeptide antagonist comprising a non-naturally encoded amino acid that is modified with a PEG derivative at a single site within the polypeptide. Coupling, purification, and analyses are performed as in Example 3.

Example 12

Generation of a FGF-21 Polypeptide Homodimer, Heterodimer, Homomultimer, or Heteromultimer in Which the FGF-21 Molecules Are Linked Directly A FGF-21 polypeptide variant comprising the alkyne-containing amino acid can be directly coupled to another FGF-21 polypeptide variant comprising the azido-containing amino acid. In an analogous manner a FGF-21 polypeptide may be coupled to one or more other polypeptides to form heterodimers, homomultimers, or heteromultimers. Coupling, purification, and analyses are performed as in Examples 3, 6, and 7.

Example 13

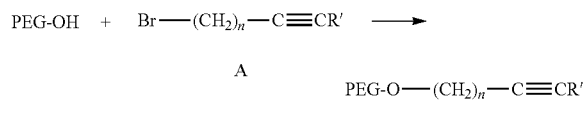

The polyalkylene glycol (P—OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

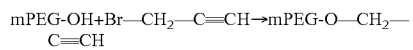

mPEG-OH+Br—CH$_2$—C≡CH→mPEG-O—CH$_2$—C≡CH mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford propargyl-O-PEG.

Example 15

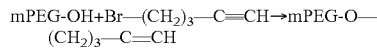

mPEG-OH+Br—(CH$_2$)$_3$—C≡CH→mPEG-O—(CH$_2$)$_3$—C≡CH

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added CH$_2$Cl$_2$ (25 mL) and the organic layer was separated, dried over anhydrous Na$_2$SO$_4$, and the volume was reduced to approximately 2 mL. This CH$_2$Cl$_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

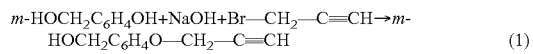

*m*-HOCH$_2$C$_6$H$_4$OH+NaOH+Br—CH$_2$—C≡CH→*m*-HOCH$_2$C$_6$H$_4$O—CH$_2$—C≡CH   (1)

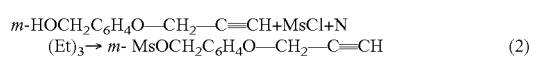

*m*-HOCH$_2$C$_6$H$_4$O—CH$_2$—C≡CH+MsCl+N(Et)$_3$→*m*-MsOCH$_2$C$_6$H$_4$O—CH$_2$—C≡CH   (2)

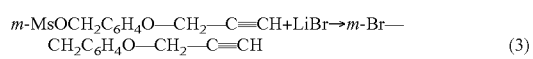

*m*-MsOCH$_2$C$_6$H$_4$O—CH$_2$—C≡CH+LiBr→*m*-Br—CH$_2$C$_6$H$_4$O—CH$_2$—C≡CH   (3)

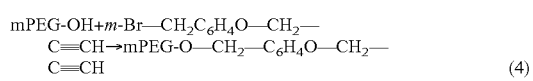

mPEG-OH+*m*-Br—CH$_2$C$_6$H$_4$O—CH$_2$—C≡CH→mPEG-O—CH$_2$—C$_6$H$_4$O—CH$_2$—C≡CH   (4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over $MgSO_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a white precipitate, which was collected to yield the PEG derivative.

Example 17

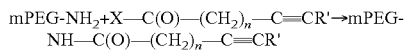

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

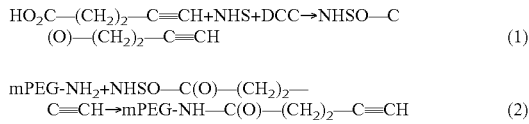

4-pentynoic acid (2.943 g, 3.0 mmol) was dissolved in $CH_2Cl_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-$NH_2$ with a molecular weight of 5,000 Da (mPEG-$NH_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added $CH_2Cl_2$ (50 mL) and the organic layer was separated, dried over anhydrous $Na_2SO_4$, and the volume was reduced to approximately 2 mL. This $CH_2Cl_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

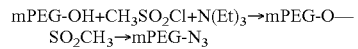

The mPEG-OH (MW=3,400, 25 g, 10 mmol) in 150 mL of toluene was azeotropically distilled for 2 hours under nitrogen and the solution was cooled to room temperature. 40 mL of dry $CH_2Cl_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with $CH_2Cl_2$ (50 mL). The organic fraction was washed with NaCl solution and dried over anhydrous $MgSO_4$. The volume was reduced to 20 ml and the product was precipitated by addition to 150 ml of cold dry ether.

Example 20

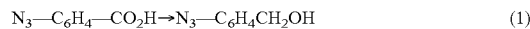 (1)

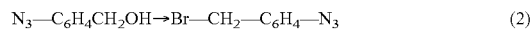 (2)

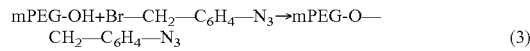 (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in $CH_2Cl_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a precipitate, which was collected to yield mPEG-O—$CH_2$—$C_6H_4$—$N_3$.

Example 21

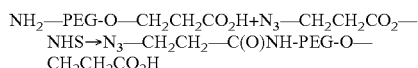

$NH_2$—PEG-O—$CH_2CH_2CO_2H$ (MW 3,400 Da, 2.0 g) was dissolved in a saturated aqueous solution of $NaHCO_3$ (10 mL) and the solution was cooled to 0° C. 3-azido-1-N-hydroxysuccinimido propionate (5 equiv.) was added with vigorous stirring. After 3 hours, 20 mL of $H_2O$ was added and the mixture was stirred for an additional 45 minutes at room temperature. The pH was adjusted to 3 with 0.5 $NH_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the omega-carboxy-azide PEG derivative.

Example 22

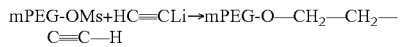

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 $NH_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxy-polyethylene glycol (mPEG).

Example 23

Azide- and acetylene-containing amino acids can be incorporated site-selectively into proteins using the methods described in L. Wang, et al., (2001), Science 292:498-500, J. W. Chin et al., Science 301:964-7 (2003)), J. W. Chin et al., (2002), Journal of the American Chemical Society 124:9026-9027; J. W. Chin, & P. G. Schultz, (2002), Chem Bio Chem 3(11):1135-1137; J. W. Chin, et al., (2002), PNAS United States of America 99:11020-11024: and, L. Wang, & P. G. Schultz, (2002), Chem. Comm., 1:1-11. Once the amino acids were incorporated, the cycloaddition reaction is carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 24

This example describes the synthesis of p-Acetyl-D,L-phenylalanine (pAF) and m-PEG-hydroxylamine derivatives.

The racemic pAF is synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures are completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which is stirred at room temperature (RT) for 1 hour, methoxy-polyethylene glycol amine (m-PEG-$NH_2$, 7.5 g, 0.25 mmol, Mt. 30 K, from BioVectra) and Diisopropylethylamine (0.1 mL, 0.5 mmol) is added. The reaction is stirred at RT for 48 hours, and then is concentrated to about 100 mL. The mixture is added dropwise to cold ether (800 mL). The t-Boc-protected product precipitated out and is collected by filtering, washed by ether 3×100 mL. It is further purified by re-dissolving in DCM (100 mL) and precipitating in ether (800 mL) twice. The product is dried in vacuum yielding 7.2 g (96%), confirmed by NMR and Nihydrin test.

The deBoc of the protected product (7.0 g) obtained above is carried out in 50% TFA/DCM (40 mL) at 0° C. for 1 hour and then at RT for 1.5 hour. After removing most of TFA in vacuum, the TFA salt of the hydroxylamine derivative is converted to the HCl salt by adding 4N HCl in dioxane (1 mL) to the residue. The precipitate is dissolved in DCM (50 mL) and re-precipitated in ether (800 mL). The final product (6.8 g, 97%) is collected by filtering, washed with ether 3×100 mL, dried in vacuum, stored under nitrogen. Other PEG (5K, 20K) hydroxylamine derivatives are synthesized using the same procedure.

Example 25

Analysis of ERK1/2 Phosphorylation Induced by FGF-21 WT and 30K PEG Analogs

Seed 293-stably transfected with human Klotho beta at 100,000 cells/well (DMEM+10% FBS) in a poly-Lys coated plate. The following day cells are 100% confluent, media is aspirated off and replaced with fresh media and incubate overnight. After 24 hours cells are stimulated with the appropriate 30K PEG FGF-21 analogs using as standard FGF21WT. Each individual compound is prepared by diluting them in PBS/1% BSA. Cells are treated in triplicate for 10 min @37° C. in the incubator. After 10 min incubation media is carefully aspirated off from each well and 40 ul of cold 1× Cell Signaling Lysis Buffer containing protease/phosphatase inhibitors (PI cocktail, Na3VN4 and PMSF) are added to each well to produce cell lysates. 96 well/plate is placed on ice for 20 minutes and then spun down at 4000 rpm for 10 min. Cell lysates are frozen down @−80° C. Later on each sample is thawed out and 10 ul of cell lysates is added to MSD treated plate coated with antibody capturing both the unphosphorylated and phosphorylated forms of ERK1/2. Incubation with primary antibody occurs for 2 hrs, then plate is washed several times with specific buffer followed by addition of secondary antibody. After 1 hour incubation plate is washed again several times. Buffer for reading is added to each well. Plate is transferred to MSD reading machine. The curve that is produced is based on the anti-phosphorylated ERK1/2 reading units and EC50 is calculated using Sigma Plot. The fold loss of activity is calculated by dividing EC50 of the 30 K pegylated specific compound with the EC50 of the WT.

Example 26

Cellular ERK 1/2 Phosphorylation Assay (pERK) Protocol and MSD Analysis

293 βKlotho-4 cells were maintained in DMEM+10% FBS+P/S+0.5 mg/mL Geneticin. When the cells reached 50-90% confluency, they were trypsinized, and seeded 100,000 cells/well in poly-D-lys coated 96-well plates in DMEM+10% FBS+P/S.

The following day when the cells were ~100% confluent, they were checked to be sure that the media was still red, then the media was aspirated off 200 uL/well of serial dilutions of FGF-21 variants (in PBS+1% BSA) were pipetted into the 96-well plate. The 96-well plate was then placed in 37° C., 5% CO2 incubator for exactly 9 minutes. The FGF-21 treatments were then completely aspirated off and 40 uL/well of freshly made 1× Cell Signaling Lysis Buffer+1× Sigma Protease Inhibitor Cocktail+2 mM Sodium Orthovanadate+1 mM PMSF+1×MSD Phosphatase Inhibitor I+1×MSD Phosphatase Inhibitor II+1×MSD Protease Inhibitor Cocktail+2 mM MSD PMSF was added. The dish was placed on ice, and set aside for 25 minutes, while, pipette each well up and down with a P20 pipettor to mix the lysates. After mixing wells, place the whole ice bucket and dish on 4 C shaker for the remainder of the time. After 25 minutes, spin down the plate at 4000 rpm, 10 min, at 4 C. Transfer the supernatants to a cold round-bottom 96-well plate on ice.

MSD Analysis

This assay was performed using the Meso Scale Discovery MULTI-SPOT Assay System whole-cell lysate kit Phospho (T/Y 202/204; 185/187)/Total—ERK1/2/Assay.

All MSD reagents were thawed to room temperature and all necessary buffers were made per kit instructions. To each well, 150 uL of Blocker A was added to a phosphoERK-totalERK Duplex plate and it was allowed to block for 1 hr at room temperature on a shaker. The plate was then washed 4× with 160 uL/well of 1× Wash Buffer. 16 uL/well of Lysis Buffer+protease and phosphatase inhibitors (made earlier for the cell stimulations) were added and 10 uL/well were transferred from the cold lysate supernatant plate to the MSD plate wells (total volume then became 26 uL/well). The MSD plate incubated for 3 hrs at room temperature on a shaker the plate was then washed 4× with 160 uL/well of 1× Wash Buffer. 25 uL/well of Detection Antibody (diluted 50× in Antibody Dilution Buffer) were added and set to incubate for 1 hr at room temperature on a shaker. The plate was again washed 4× with 160 uL/well of 1× Wash Buffer and 150 uL/well of 1× Read Buffer T was added after which the plate was immediately read on MSD Sector Imager 2400 machine.

BCA Quantification

The Pierce BCA Protein Assay Kit was used. BSA standard was diluted in a 96-well plate from a top concentration of 2 mg/mL, with 2× dilutions down the columns in 1× Cell Signaling Lysis Buffer. (last set of wells were buffer, no BSA) 25 uL/well of the BSA standards were pipetted in duplicate to two MaxiSorp 96-well plates. 3× dilutions of lysates were made in 1× Cell Signaling Lysis Buffer and 25 uL/well were added to the MaxiSorp plates. The Working Reagent was made as per the Pierce Kit instruction sheet 200 uL were pipette into each well in the MaxiSorp plates. The plates incubated at room temperature and were read at $\lambda$=562 nm on the plate reader.

Data Analysis

Figure 7A:
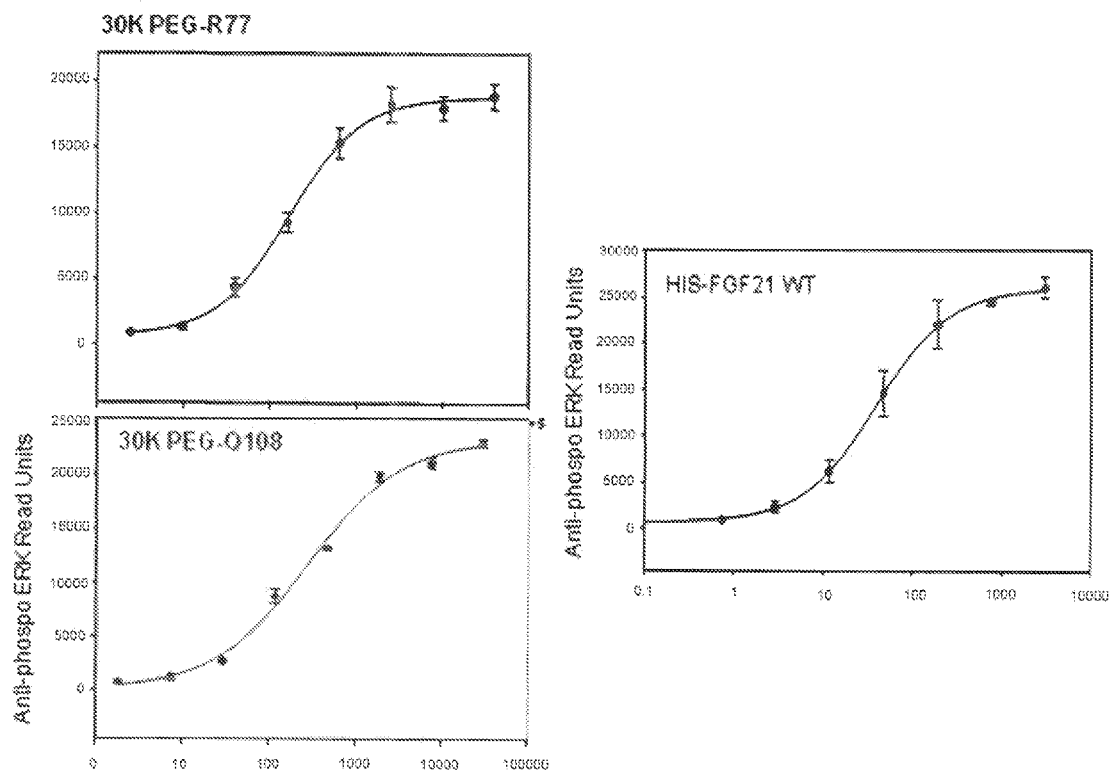
FIG. 7a—SigmaPlot calculating the EC50 values for serial dilutions of FGF21 variants 30K PEG-391, 30K PEG-477, 30K PEG-R131, 30K PEG-Q108, HIS-FGF21 (His-tagged wild type).
Figure 8:
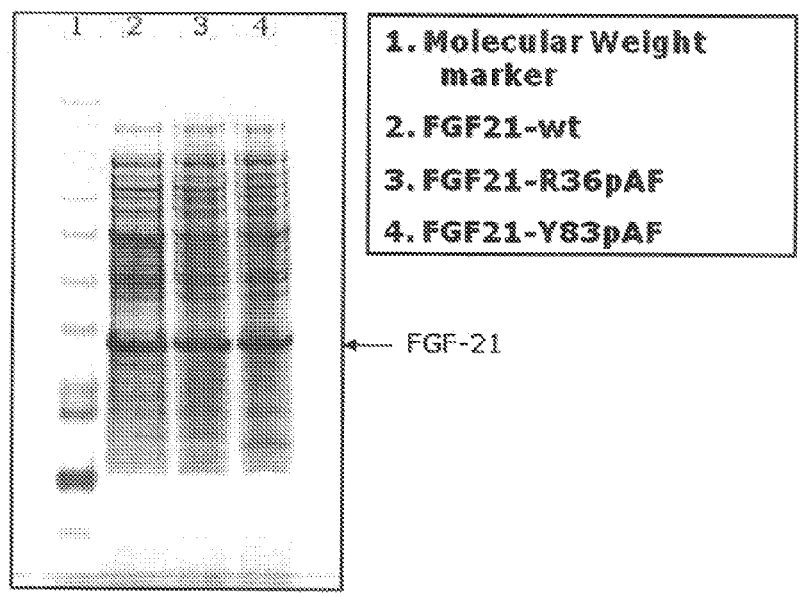
FIG. 8—An SDS-PAGE analysis of non-His-tagged FGF-21 expressed in *E. coli*.
Figure 9:
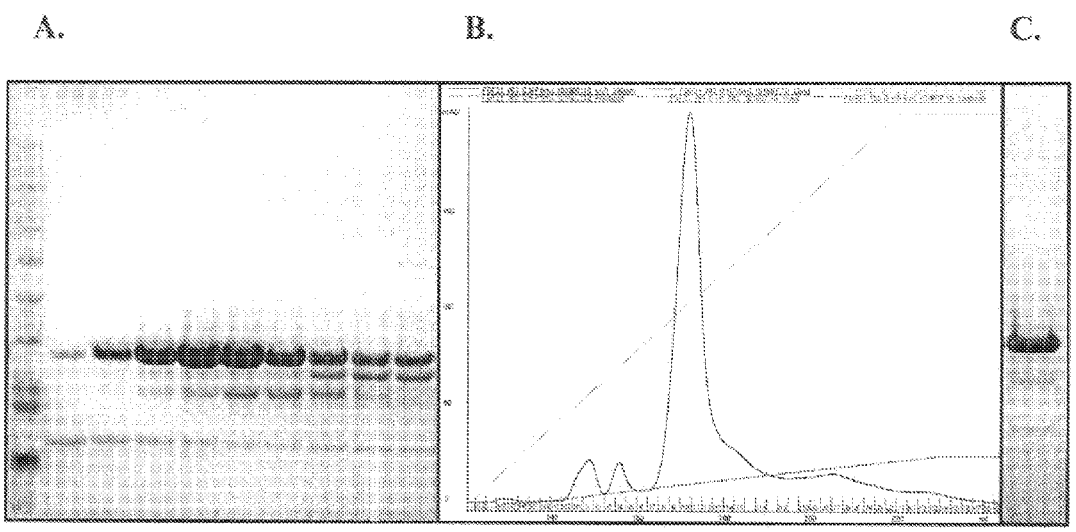
FIG. 9—(A) SDS-PAGE analysis of FGF-21-Y83pAF elution fractions. (B) Chromatogram of Q HP elution of untagged FGF-21-Y83pAF. (C) SDS-PAGE analysis of FGF-21-Y832pAFQ HP elution pool.
Figure 10:
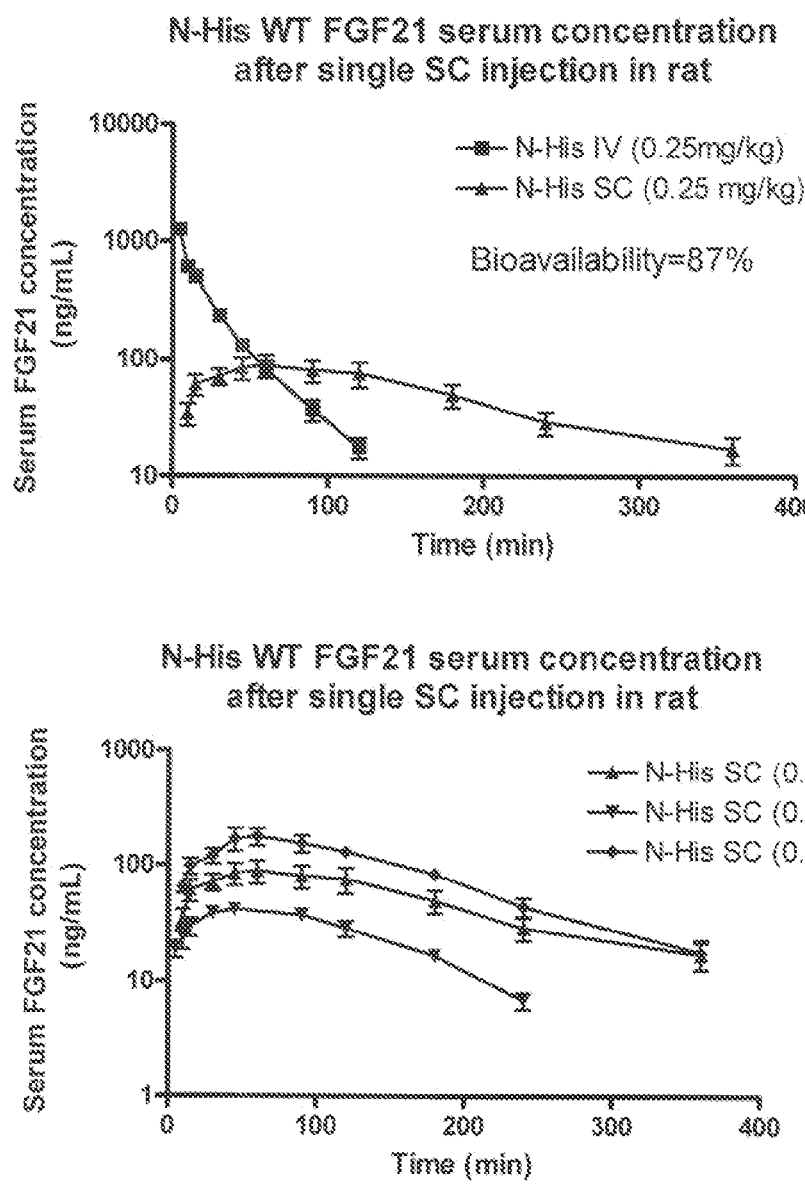
FIG. 10—Data from Example 28, Pharmacokinetic properties of FGF-21 compounds in rats.
Figure 11:
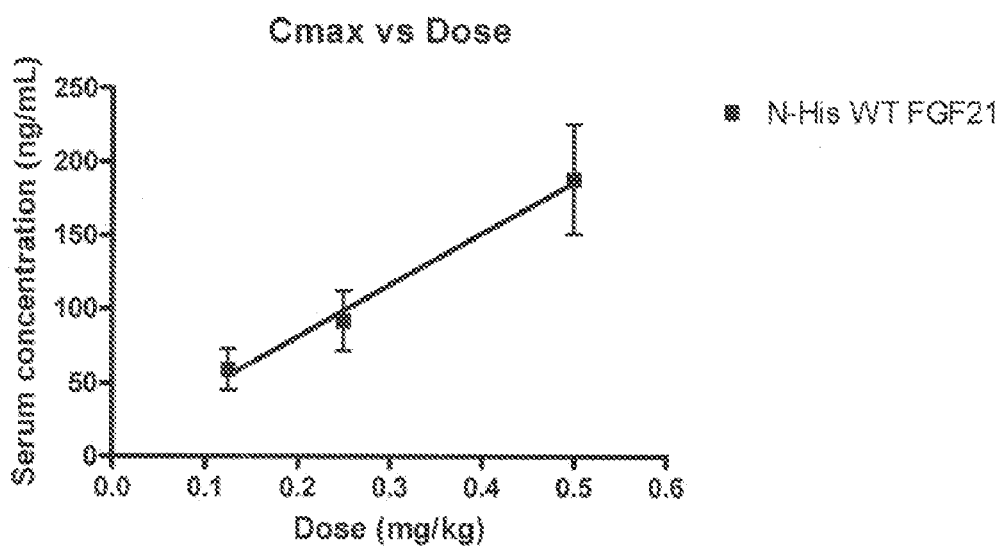
FIG. 11—Data from Example 28, Pharmacokinetic properties of FGF-21 compounds in rats.
Figure 12:
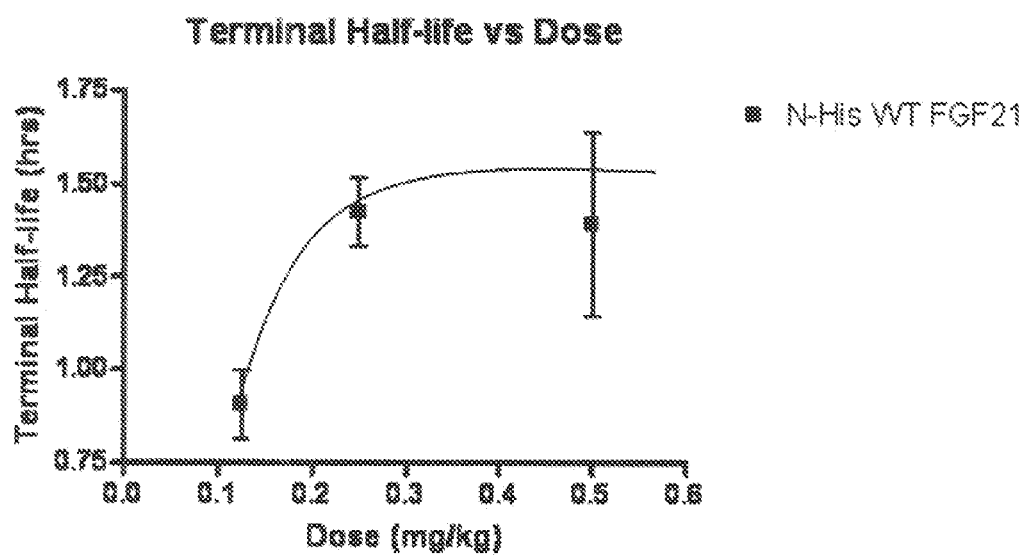
FIG. 12—Data from Example 28, Pharmacokinetic properties of FGF-21 compounds in rats.
Figure 13:
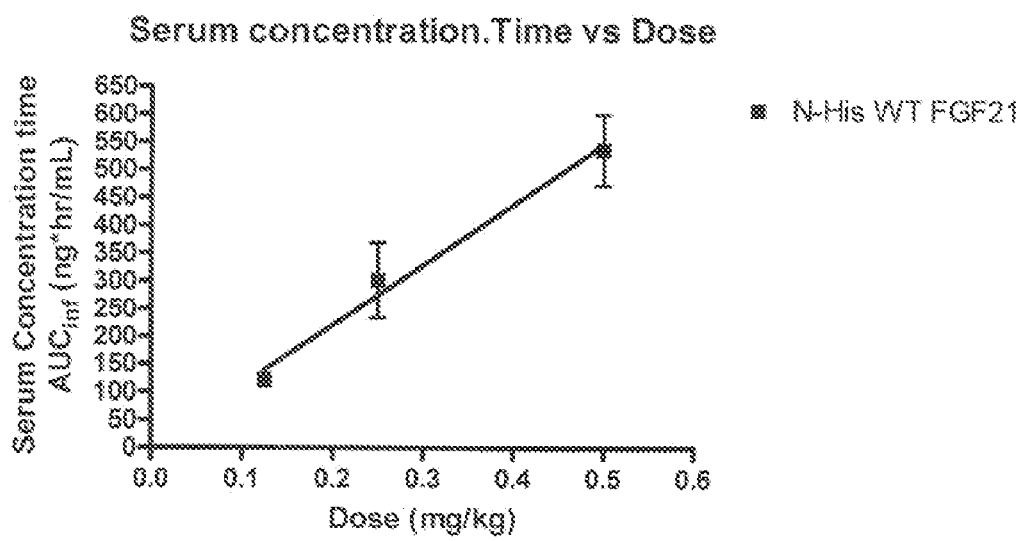
FIG. 13—Data from Example 28, Pharmacokinetic properties of FGF-21 compounds in rats.
Figure 15:
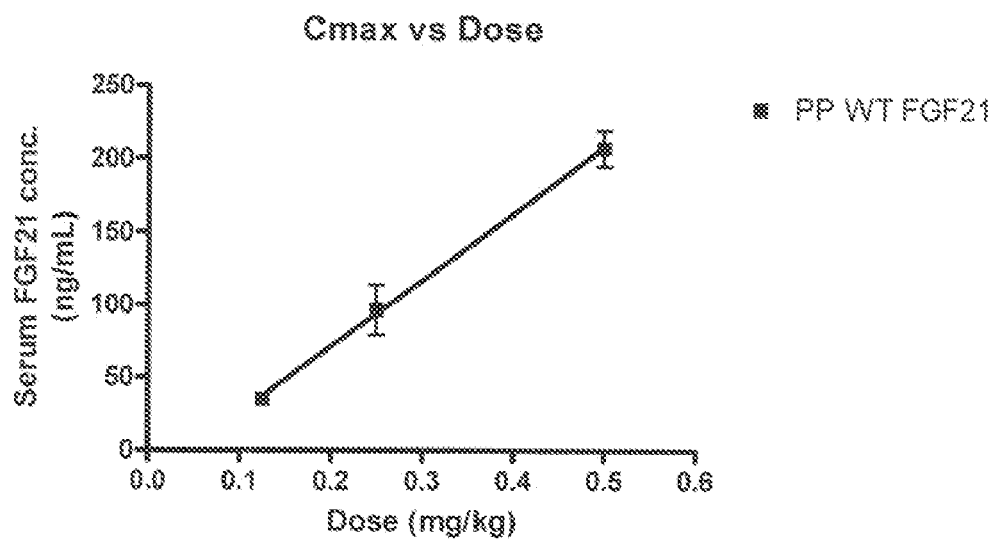
FIG. 15—Data from Example 28, Pharmacokinetic properties of FGF-21 compounds in rats.
Figure 16:
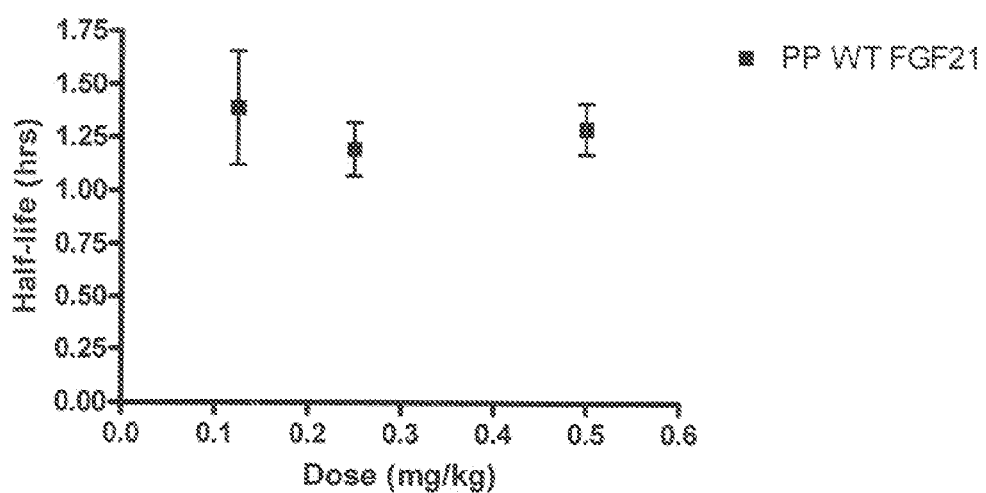
FIG. 16—Data from Example 28, Pharmacokinetic properties of FGF-21 compounds in rats.
Figure 17:
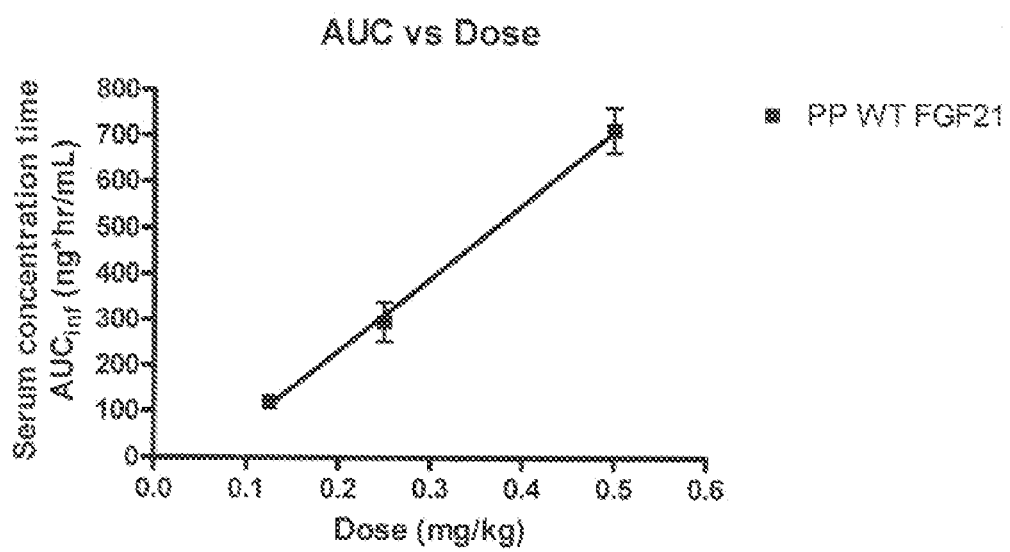
FIG. 17—Data from Example 28, Pharmacokinetic properties of FGF-21 compounds in rats.
Figure 18:
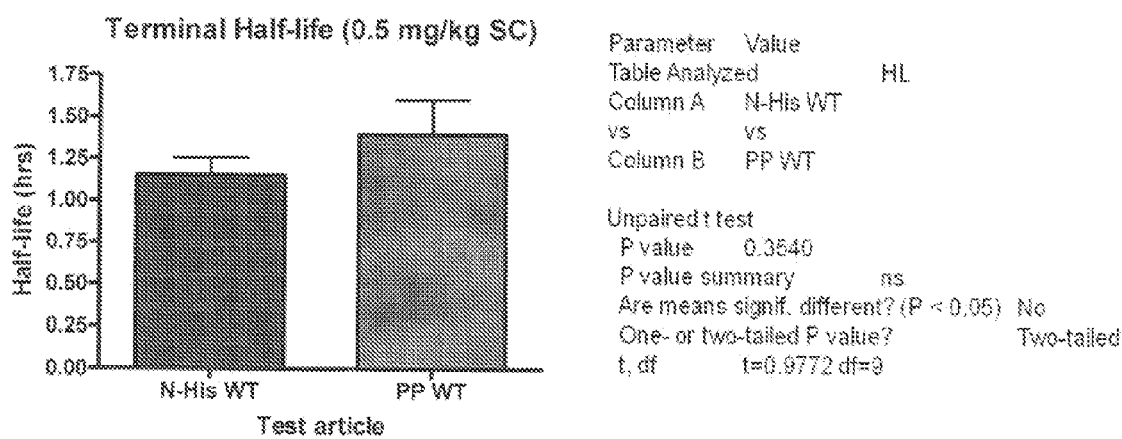
FIG. 18—Data from Example 28, Pharmacokinetic properties of FGF-21 compounds in rats.
Figure 19:
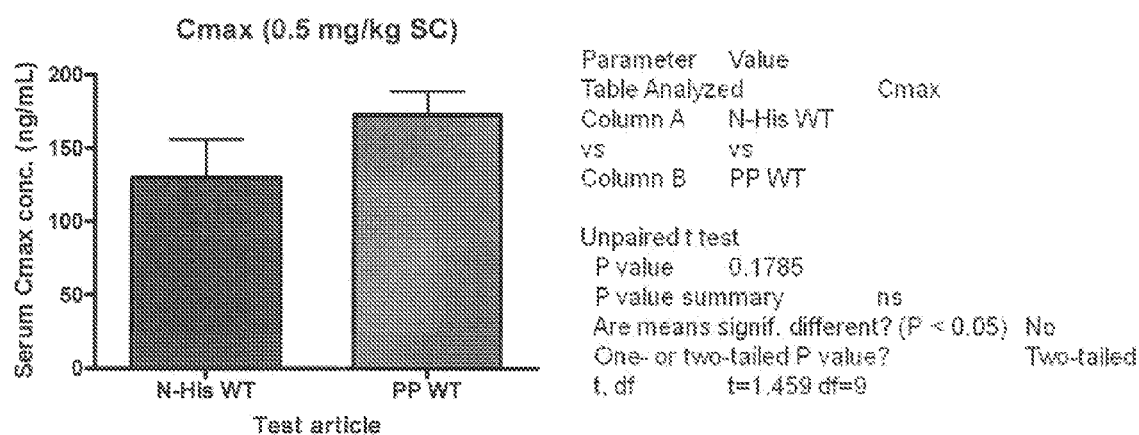
FIG. 19—Data from Example 28, Pharmacokinetic properties of FGF-21 compounds in rats.
Figure 20:
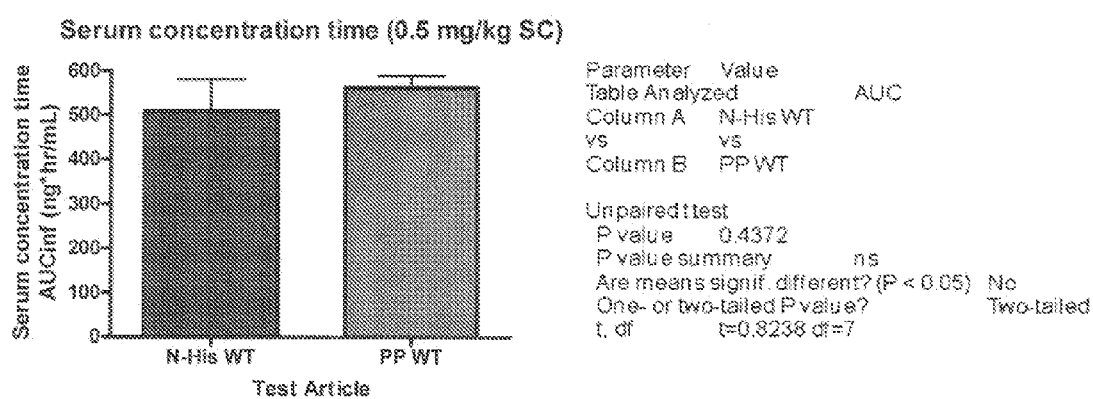
FIG. 20—Data from Example 28, Pharmacokinetic properties of FGF-21 compounds in rats.
Figure 21:
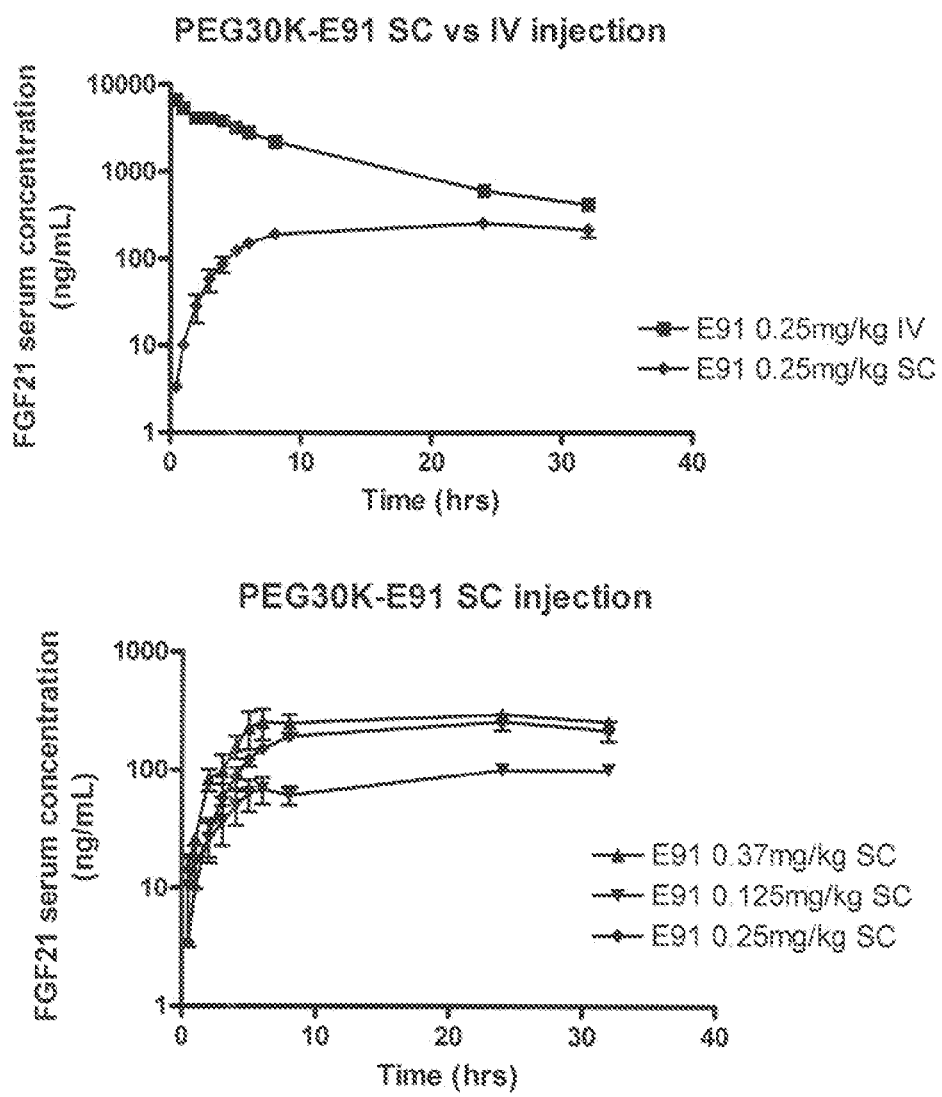
FIG. 21—Data from Example 28, Pharmacokinetic properties of FGF-21 compounds in rats.
Figure 22:
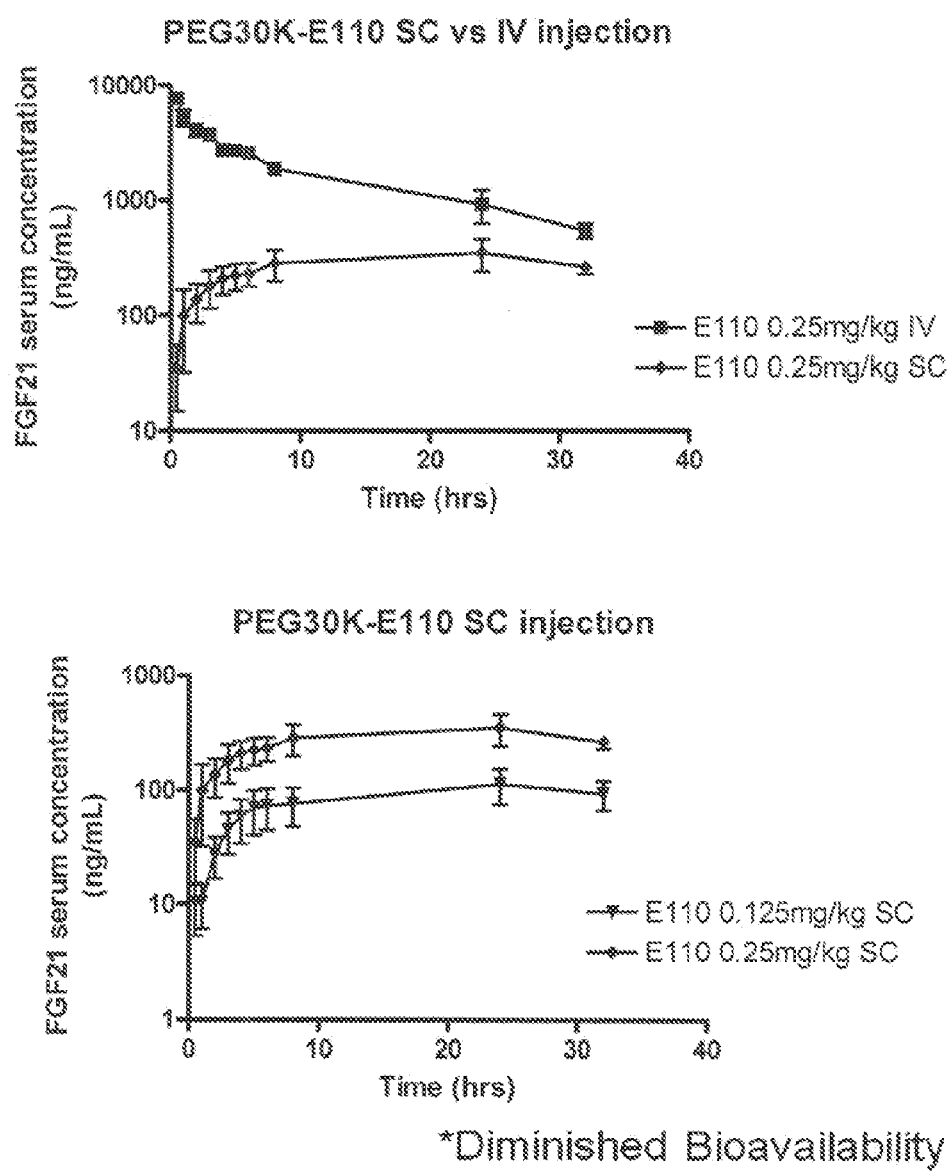
FIG. 22—Data from Example 28, Pharmacokinetic properties of FGF-21 compounds in rats.
Figure 23:
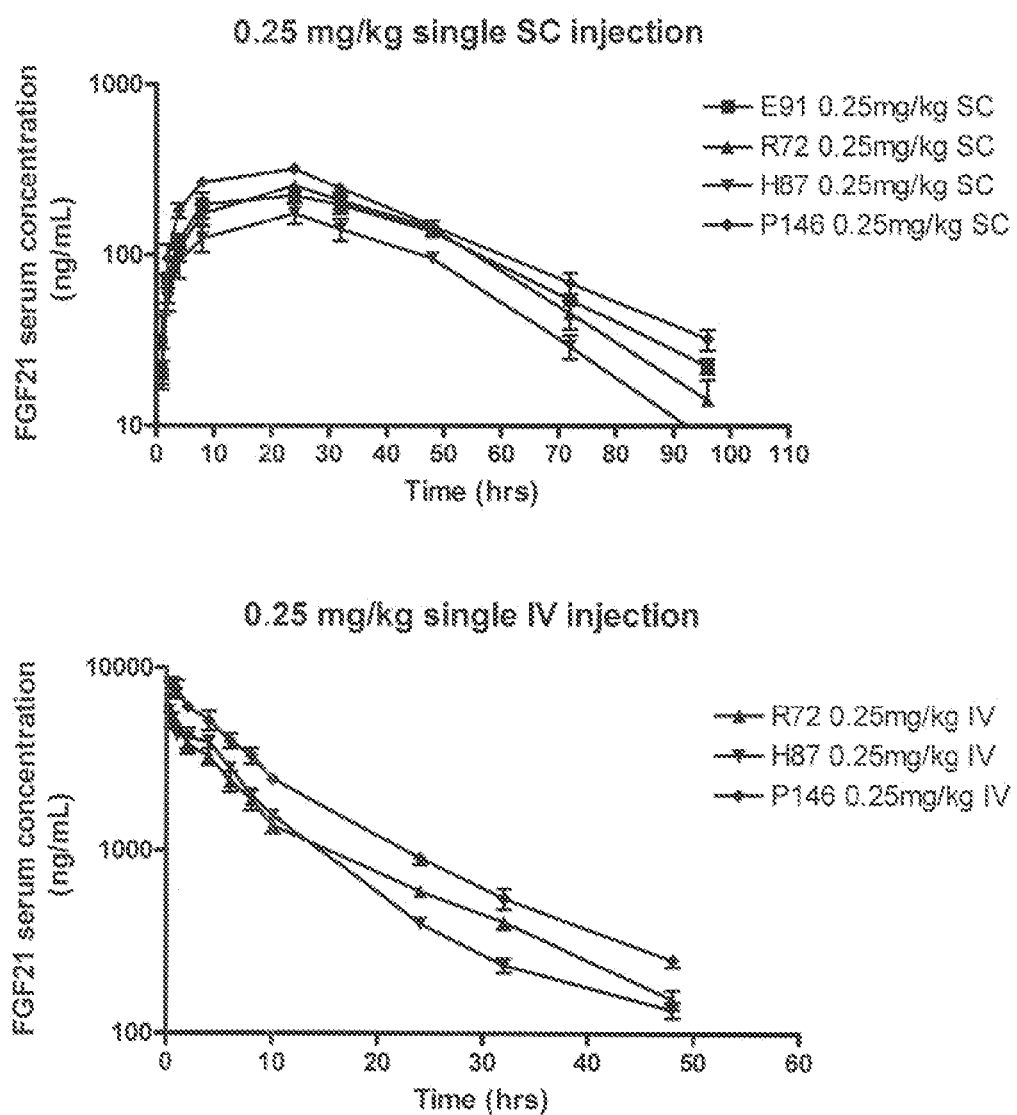
FIG. 23—Data from Example 28, Pharmacokinetic properties of FGF-21 compounds in rats.
Figure 24:
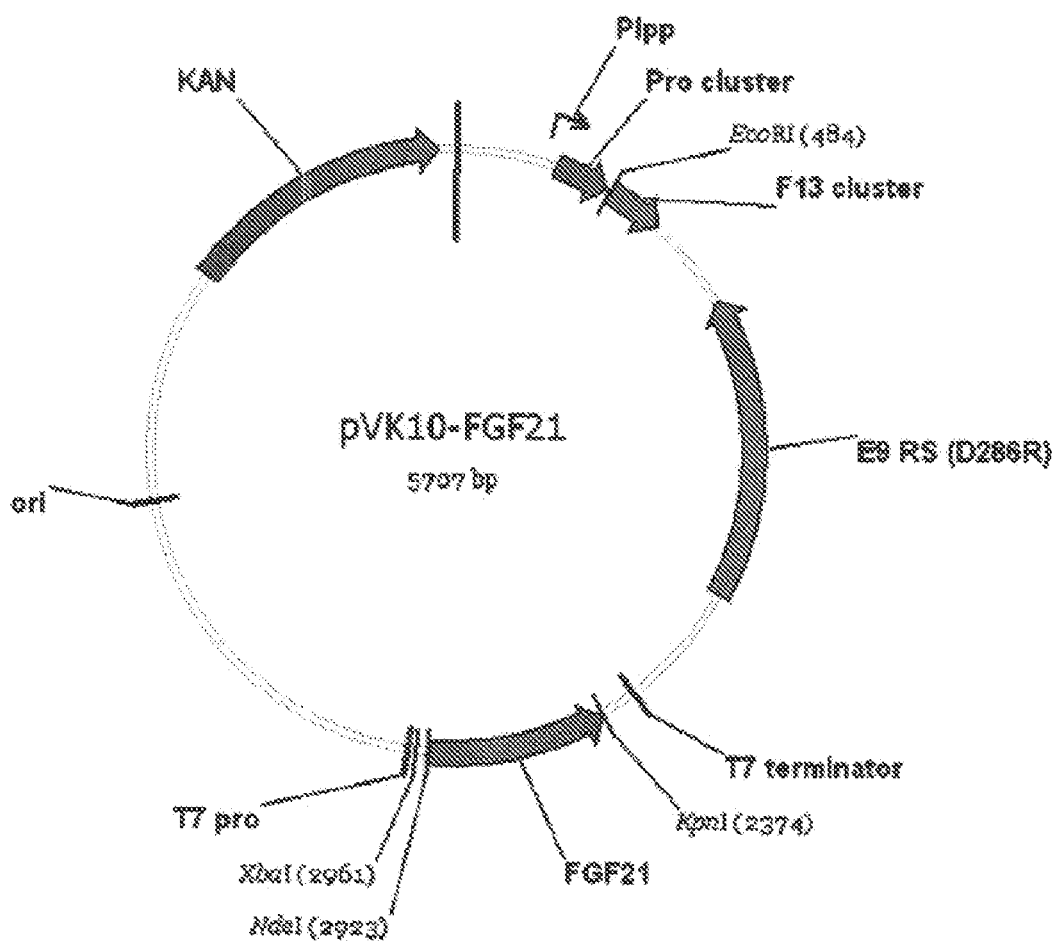
FIG. 24—pVK10-FGF21 vector map.
Figure 26:
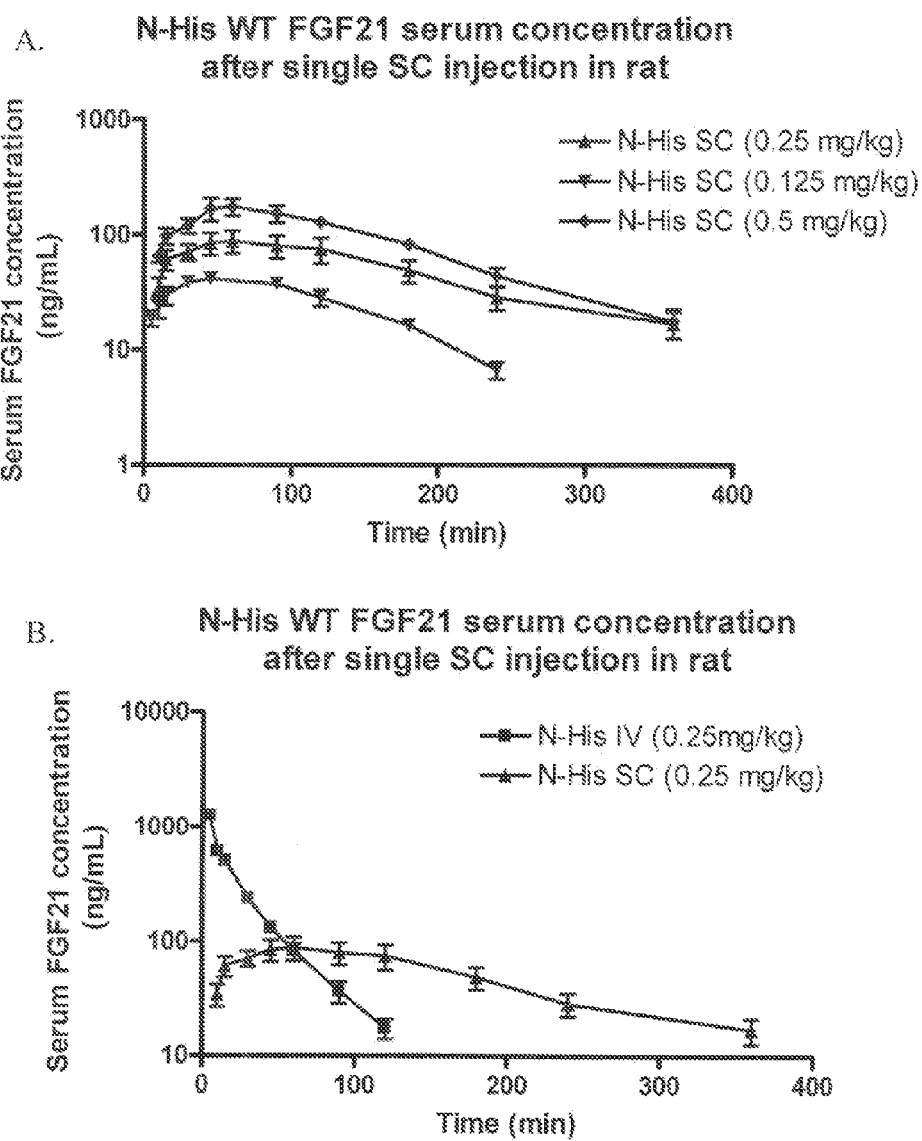
FIG. 26a—Serum concentration-time profiles of three doses of N-6His WT FGF21 in rats. Rats were given a single administration of test article subcutaneously. N=4 animals per group. Symbols indicate means of measured serum concentrations, error bars indicate standard error.
FIG. 26b—Serum concentration-time profiles of N-6His WT FGF21 dosed either subcutaneously or intravenously at 0.25 mg/kg. Rats were given a single administration of test article subcutaneously. N=4 animals per group. Symbols indicate means of measured serum concentrations, error bars indicate standard error. Total bioavailability is ~87%
Figure 27:
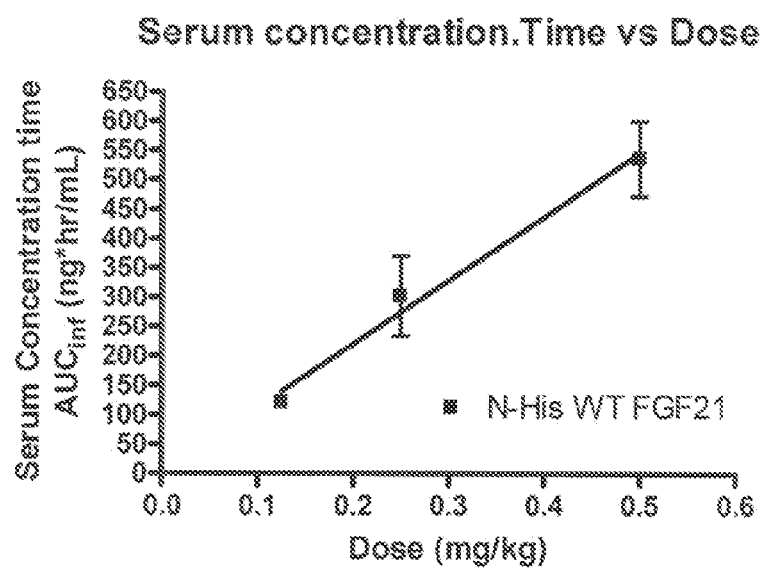
FIG. 27a—Dose relationship to serum concentration of test article at Cmax. Cmax values are reported as observed not theoretical. N=4 animals per treatment group. The linear regression value is 0.59 with a slope of 348.5±91.22.
FIG. 27b—Dose relationship to terminal half-life of test article. N=4 animals per treatment group. The linear regression value could not be calculated due to an apparent saturation of clearance above 0.25 mg/kg.
FIG. 27c—Dose relationship to serum concentration AUC. AUC values are reported as observed calculated to infinity. N=4 animals per treatment group. The linear regression value is 0.75 with a slope of 1079±194.1
Figure 29:
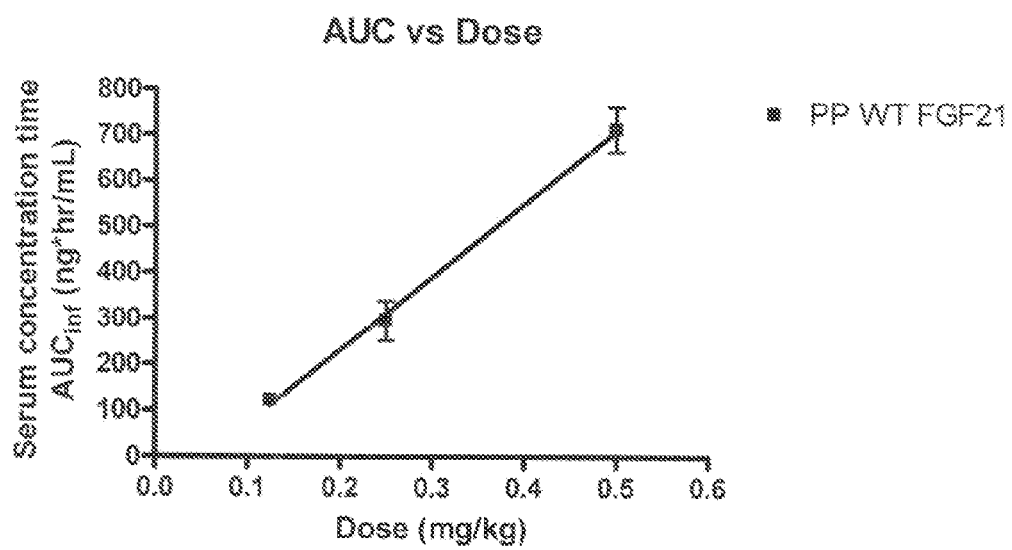
FIG. 29a—Dose relationship to serum concentration of test article at Cmax. Cmax values are reported as observed not theoretical. N=4 animals per treatment group. The linear regression value is 0.92 with a slope of 454.2±42.42.
FIG. 29b—Dose relationship to terminal half-life of test article. N=4 animals per treatment group. The linear regression value could not be calculated due to an apparent saturation of clearance above 0.125 mg/kg.
FIG. 29c—Dose relationship to serum concentration AUC. AUC values are reported as observed calculated to infinity. N=4 animals per treatment group. The linear regression value is 0.93 with a slope of 1585±137.1
Figure 30:
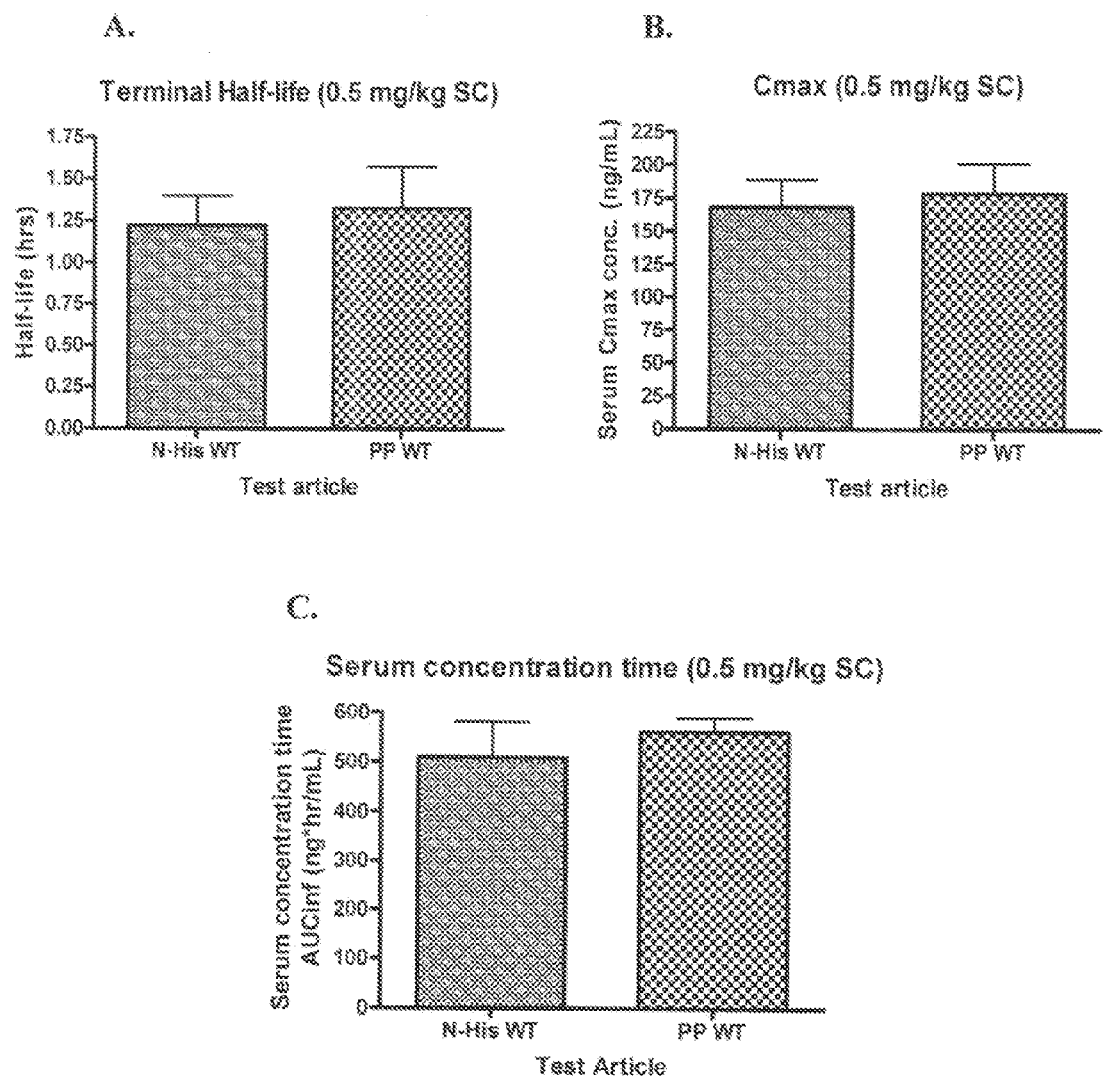
FIG. 30a—Comparison of calculated terminal half-life for PP versus N6-His WT FGF21 compounds dosed at 0.5 mg/kg subcutaneously in rats. The calculated p value using a two-tailed t-test is 0.7715. N=3-4 animals per group FIG. 30b—Comparison of Cmax values for PP versus N6-His WT FGF21 compounds dosed at 0.5 mg/kg subcutaneously in rats. The calculated p value using a two-tailed t-test is 0.7652. N=3-4 animals per group FIG. 30c—Comparison of AUCinf for PP versus N6-His WT FGF21 compounds dosed at 0.5 mg/kg subcutaneously in rats. The calculated p value using a two-tailed t-test is 0.4372
Figure 31:
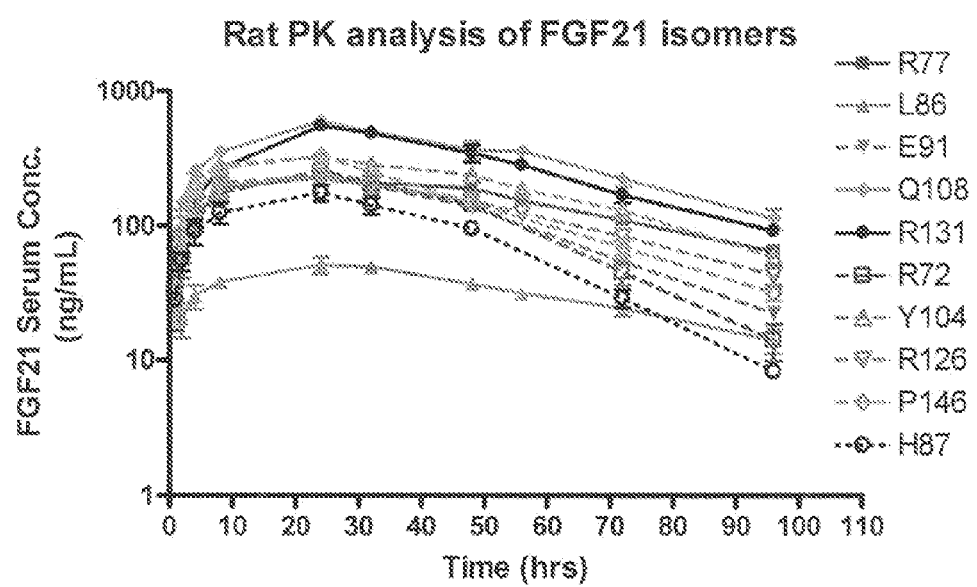
FIG. 31a—PK profiles of ten PEGylated N6-His tagged FGF21 isomers.
FIG. 31b—Absorption profiles for PEGylated FGF21 isomers after 0.25 mg/kg subcutaneous injection.
FIG. 31c—Elimination profiles for PEGylated FGF21 isomers after 0.25 mg/kg subcutaneous injection.
Figure 31:
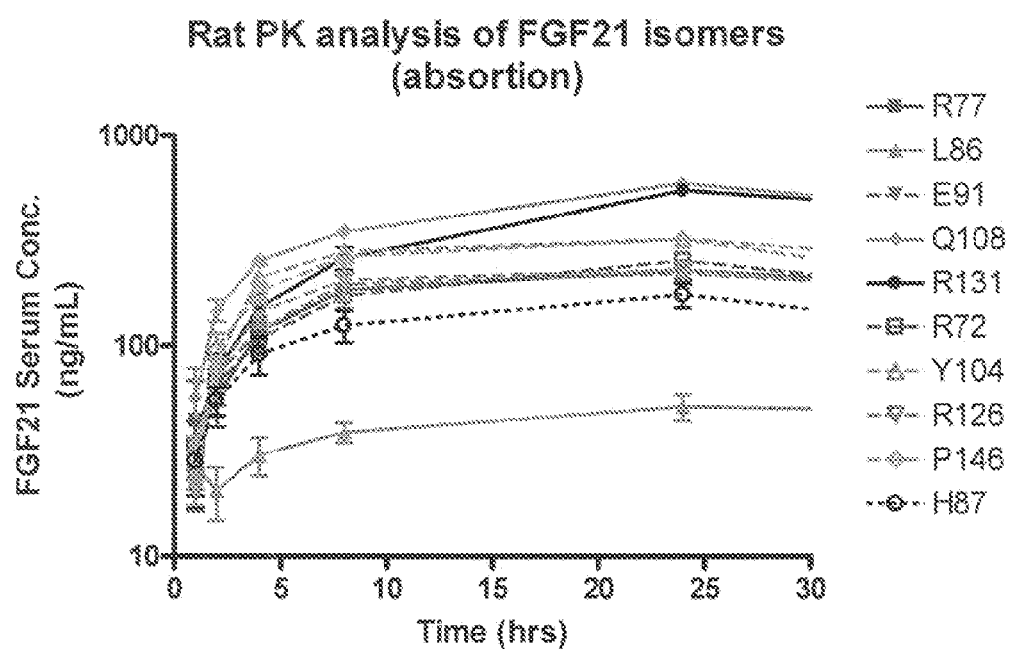
Figure 31:
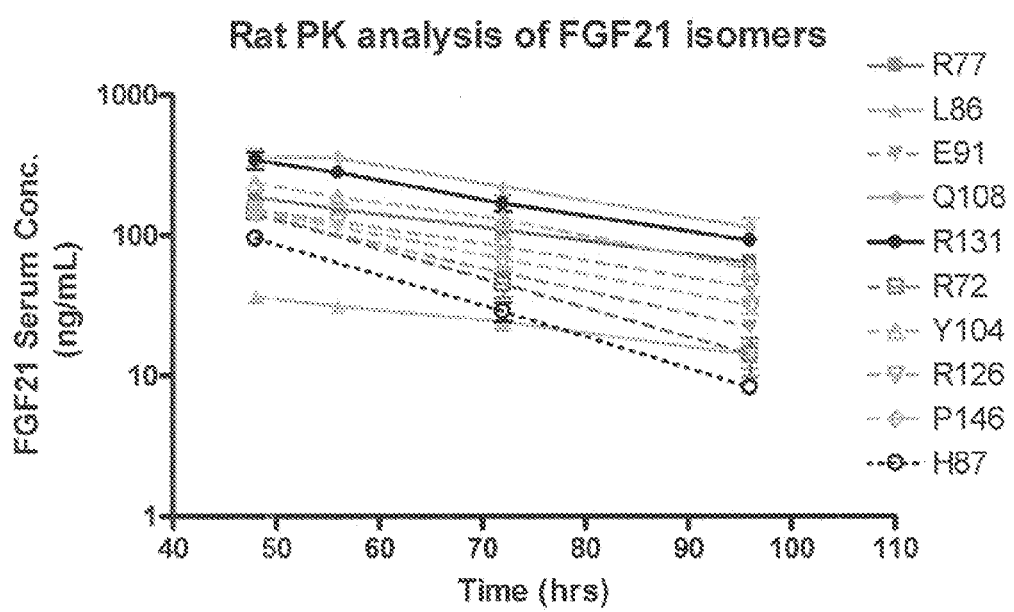
Figure 32:
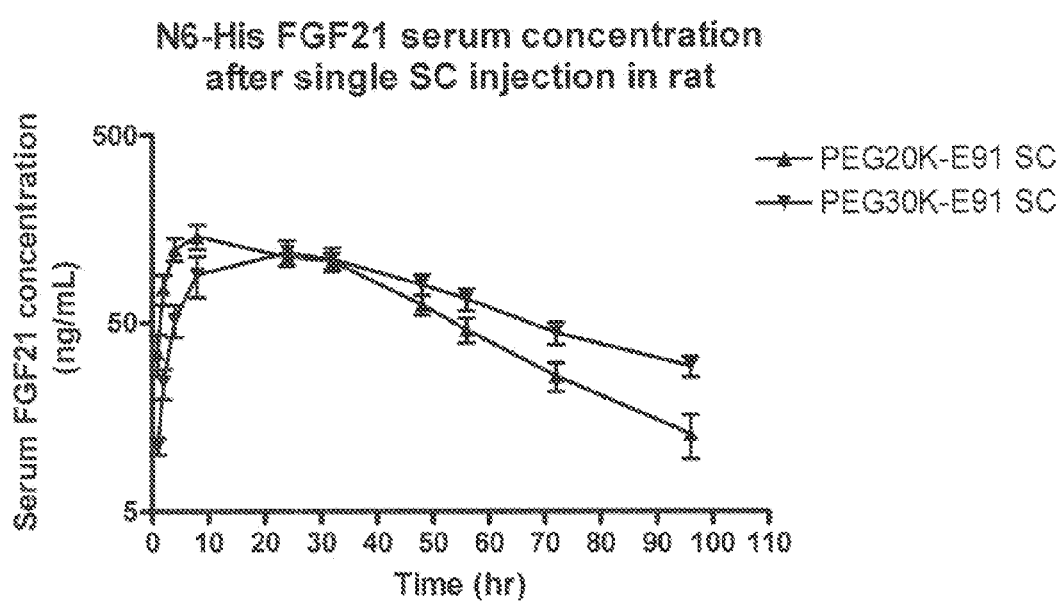
FIG. 32—Pharmacokinetic comparison of 20 and 30 kDa PEGylation.
Figure 33:
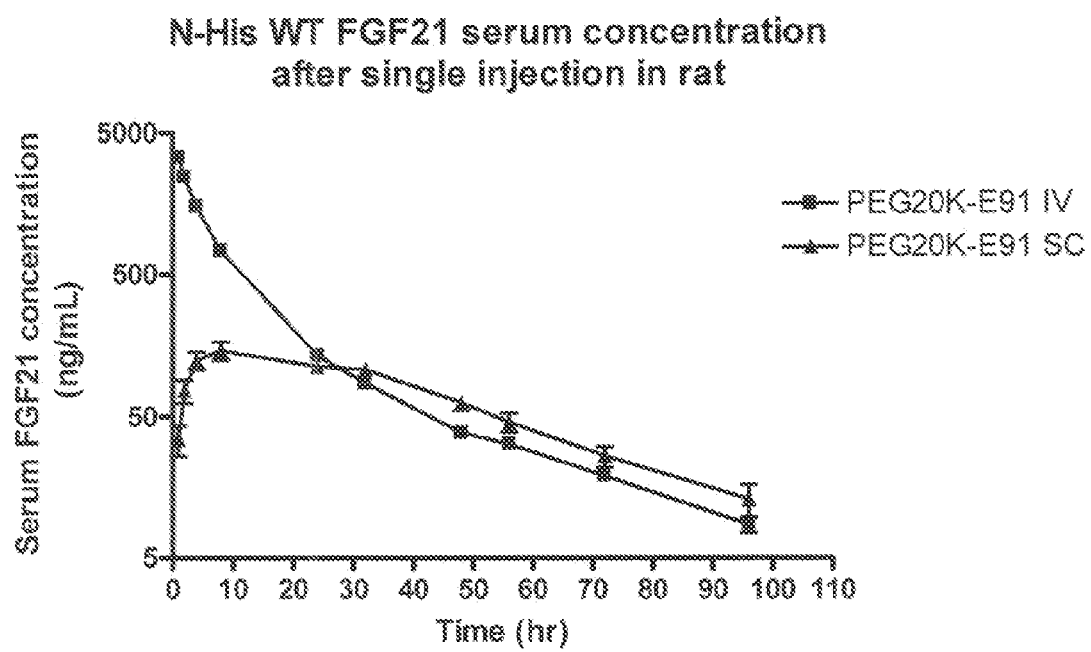
FIG. 33—Plasma concentration time curves for rats dosed either intravenously or subcutaneously with 0.25 mg/kg of 20 KPEG-pAF91(N-6-His)FGF21. A single dose was administered to each animal. N=4 animals per group. Symbols indicate means of measured plasma concentrations, bars indicate standard deviation. Total bioavailability is ~30%.
Figure 34:
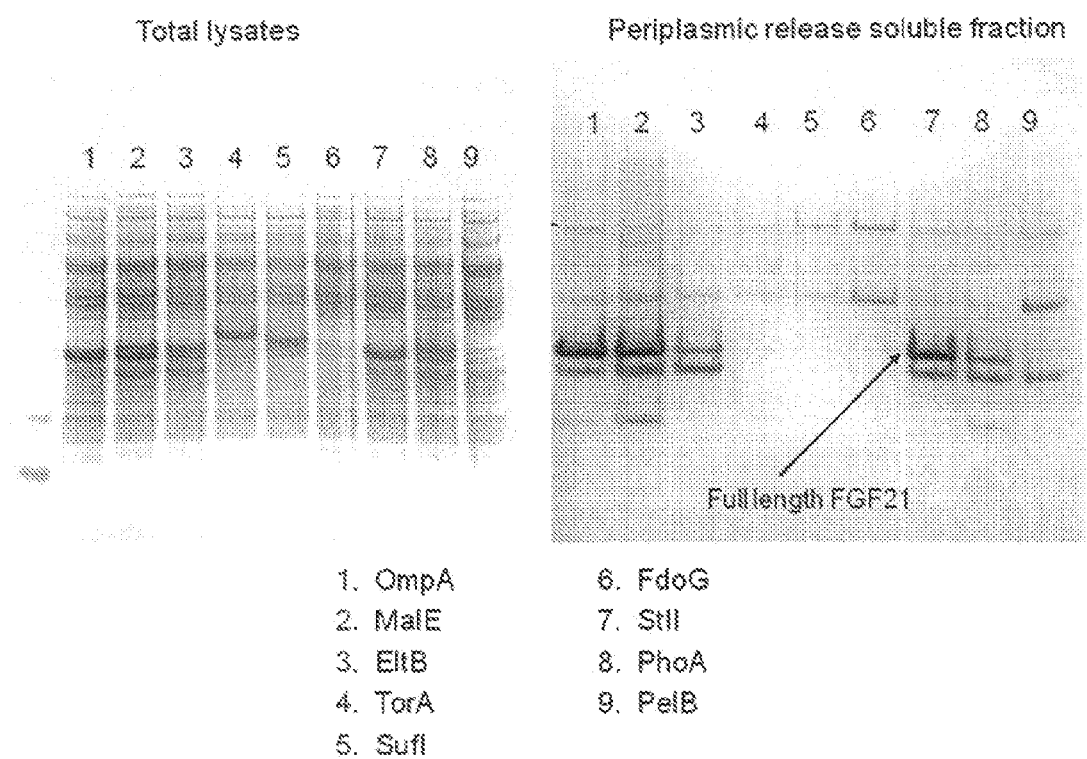
FIG. 34—Two gels showing the secretion of FGF21 in *e. coli* and showing of the leaders used that OmpA, MalE, and StII worked very well, as demonstrated by the periplasmic release soluble fraction in the second gel.

The concentrations were calculated for all lysates with the BCA Kit. When lysates are all similar in concentration, then do not normalize for the MSD analysis. For MSD analysis, average replicate points, calculate standard deviation, and CV values. Use SigmaPlot to calculate the EC50 values for serial dilutions of FGF-21 variants, and use Fold Above WT EC50 as the ranking criteria for the variants. Results can be seen in FIGS. 7a and 7b of this application.

Example 27

FGF-21 Untagged Downstream Process

Inclusion Body Prep Solubilization

Cell paste was resuspended by mixing to a final 10% solid in 4° C. inclusion body (IB) Buffer I (50 mM Tris pH 8.0; 100 mM NaCl; 1 mM EDTA; 1% Triton X-100; 4° C.). Cells were lysed by passing resuspended material through a micro fluidizer a total of two times, then it was centrifuged (10,000 g; 15 min; 4° C.) and the supernatant was decanted. The IB pellet was washed by resuspending in an additional volume of IB buffer I (50 mM Tris pH 8.0; 100 mM NaCl; 1 mM EDTA; 1% Triton X-100; 4° C.) and resuspended material was passed through micro fluidizer a total of two times, then it was centrifuged (10,000 g; 15 min; 4° C.) and the supernatant was decanted. The IB pellet was resuspended in one volume of buffer II (50 mM Tris pH 8.0; 100 mM NaCl; 1 mM EDTA; 4° C.), then it was centrifuged (10,000 g; 15 min; 4° C.) and the supernatant was decanted. IB pellet was then resuspended in ½ volume of buffer II (50 mM Tris pH 8.0; 100 mM NaCl; 1 mM EDTA; 4° C.). IB was aliquoted into appropriate containers, then it was centrifuged (10,000 g; 15 min; 4° C.) and the supernatant was decanted. Inclusion bodies were solubilized (this is the point at which they could otherwise be stored at −80° C. until further use.)

Inclusion Body Solubilization

Inclusion bodies were solubilized to a final concentration between 10-15 mg/mL in solubilization buffer (20 mM Tris, pH 8.0; 8M Urea; 10 mM β-ME) and incubated solubilized IB at room temperature under constant mixing for 1 hour. Insoluble material was removed by filtration (0.45 μm PES filter) and the protein concentration was adjusted (not always necessary) by dilution with additional solubilization buffer (when protein concentration is high).

Refold

Refolded by dilution to a final protein concentration of 0.5 mg/mL in 20 mM Tris, pH 8.0; 4° C. Allowed to refold for 18 to 24 hours at 4° C.

Purification

Filtered refold reaction through a 0.45 μM PES filter. Loaded material over a Q HP column (GE Healthcare) equilibrated in Buffer A (20 mM Tris, pH 7.5). Eluted FGF-21 with a linear gradient over 20CV to 100% Buffer B (20 mMTris, pH 7.5; 250 mM NaCl). Pooled monomeric FGF-21.

Pegylation and Purification

Took Q HP pool and buffer exchange into 20 mM Tris, pH 8.0; 2M urea; 1 mM EDTA. Dropped pH to 4.0 with 50% glacial acetic acid. Concentrate sample down to 4.0±1.0 mg/mL. Add 12:1 molar excess PEG and a final concentration of 1% Acetic Hydrazide, pH 4.0 to sample. Incubate at 28° C. for 48-72 hours. Add a final of 50 mM Tris base to PEG reaction and dilute 10 fold with RO water. Make sure conductivity is <1 mS/cm and pH is between 8.0-9.0. Load material over a Source 30Q column (GE Healthcare) equilibrated in Buffer A (20 mM Tris, pH 8.0). Elute PEG-FGF-21 with a linear gradient over 20CV to 100% B (20 mM Tris, pH 8.0; 100 mM NaCl). Pool PEG-FGF-21 and buffer exchange into 20 mM Tris, pH 7.4; 150 mM NaCl. Concentrate PEG material between 1-2 mg/mL and filter sterilize using 0.22 μm PES filter. Store at 4° C. For prolonged storage, flash freeze and store at −80° C.

Example 28

Pharmacokinetic Properties of FGF-21 Compounds in Rats

This protocol was used in order to provide data (found in FIGS. 11-23) on the pharmacokinetic properties of Native and PEG-modified FGF-21 compounds produced by Ambrx's proprietary technology in catheterized rats. The pharmacokinetics of test articles were assayed by ELISA specific for human FGF-21 from serum samples obtained at specific time points after drug dosing.

Test Articles:
1. Ambrx compound PEG-R77 FGF-21 will be used at 0.25 mg/ml diluted in 1×PBS.
2. Ambrx compound PEG-Y104 FGF-21 will be used at 0.25 mg/ml diluted in 1×PBS.
3. Ambrx compound PEG-R126 FGF-21 will be used at 0.25 mg/ml diluted in 1×PBS.

Test Article Quality/Formulation:
Stock Concentrations=
1.0 mg/mL PEG-R77 FGF-21
1.16 mg/mL PEG-Y104 FGF-21
1.08 mg/mL PEG-R126 FGF-21

Animals:
Twelve (12) male Sprague-Dawley (SD) rats weighing approximately 250-275 grams at study initiation will have had jugular vein catheters surgically placed prior to arriving at Ambrx. Animals were received from CRL in good condition and will have acclimated to the study location for at least 3 days prior to the start of the study. Rats will be weighed on the day of test article administration. Animals will be housed in standard, pathogen-free conditions with food and water ad libitum.

Animal Groups All compounds will be administered subcutaneously
Group 1 (n=4): PEG-R77 SC injection (0.25 mg/kg).
Group 2 (n=4): PEG-Y104 SC injection (0.25 mg/kg).
Group 3 (n=4): PEG-R126 SC injection (0.25 mg/kg).

Animals are weighed prior to administration of test article. Compounds are formulated so as to be administered at 1×BW in μL. Subcutaneous administration of test article is injected into the dorsal scapular region. Animals will receive a single injection of test article (time=0). At specific time points (see below), whole blood will be drawn from the animals, collected into SST microtainer collection tubes. Serum will be allowed to clot for 30 minutes prior to centrifugation. Serum will be transferred to polypropylene titer tubes, sealed with microstrips, and stored at −800 C until analyzed by ELISA to determine FGF-21 serum concentrations.

Data Collection/End Point:
Each animal will be used for a complete PK time course. Approximately 0.25 mL of whole blood will be drawn from the jugular vein catheters. Immediately after the blood collection, the catheters will be flushed with 0.1 mL of saline. The following collection time points for animals receiving test article material are required based on the anticipated pharmacokinetic profile of the test articles:
Pre-bleed, 1, 2, 4, 8, 24, 32 48, 56, 72, and 96 hours post-dose.

Termination:
All animals will be euthanized following the completion of the study Results:
Results are given in the table below and in the figures accompanying this application.

| FGF21 PEG Isomer PK properties-IV | | | | | | | | | |
|---|---|---|---|---|---|---|---|---|---|
| PEG 30K | | Intravenous 0.25 mg/kg | | | | | | | |
| Isomer | | R72 | R77 | H87 | E91 | Y104 | E110 | R126 | P146 |
| Lambda_z | 1/hr | 0.057 | | 0.043 | | | 0.044 | | 0.052 |
| Lambda_z_lower | hr | 8 | | 8 | | | 8 | | 8 |
| Lambda_z_upper | hr | 48 | | 48 | | | 48 | | 48 |
| HL_Lambda_z | hr | 12.27 | | 16.44 | | | 15.61 | | 13.67 |
| Tmax | hr | 0.25 | | 0.25 | | | 0.25 | | 0.3125 |
| Cmax | ng/mL | 5998.6 | | 5802.3 | | | 7821.4 | | 8655.8 |
| C0 | ng/mL | 6861.4 | | 6662.5 | | | 9280.1 | | 9149.9 |
| AUCINF_obs | hr * ng/mL | 53714.9 | | 52962.1 | | | 69435.8 | | 86554.6 |
| Vz_obs | mL/kg | 82.46 | | 113.10 | | | 81.65 | | 58.06 |
| Cl_obs | mL/hr/kg | 4.65 | | 4.74 | | | 3.61 | | 2.92 |
| MRTINF_obs | hr | 14.49 | | 13.81 | | | 16.18 | | 14.83 |
| Vss_obs | mL/kg | 67.46 | | 65.53 | | | 58.53 | | 43.48 |

| FGF21 PEG Isomer PK properties-SC | | | | | | | | | |
|---|---|---|---|---|---|---|---|---|---|
| PEG 30K | | Subcutaneous 0.25 mg/kg | | | | | | | |
| Isomer | | R72 | R77 | H87 | E91 | Y104 | E110 | R126 | P146 |
| Lambda_z | 1/hr | 0.049 | | 0.043 | 0.035 | | | | 0.0317 |
| Lambda_z_lower | hr | 24 | | 24 | 24 | | | | 24 |
| Lambda_z_upper | hr | 96 | | 90 | 96 | | | | 96 |
| HL_Lambda_z | hr | 14.72 | | 16.14 | 19.93 | | | | 22.01 |
| Tmax | hr | 24 | | 24 | 22 | | | | 24 |
| Cmax | ng/mL | 254.5 | | 174.3 | 229.7 | | | | 321.3 |

| | -continued | | | | | |
|---|---|---|---|---|---|---|
| AUCINF_obs | hr * ng/mL | 11824.7 | 8206.7 | 12177.2 | | 15908.4 |
| Vz_obs | mL/kg | 458.9 | 731.1 | 606.2 | | 503.4 |
| Cl_obs | mL/hr/kg | 21.92 | 31.67 | 20.91 | | 15.86 |
| MRTINF_obs | hr | 36.52 | 36.31 | 40.35 | | 40.07 |

Increased Tmax of PEGylated compounds
Increased T1/2 of PEGylated compounds
Increased AUC of PEGylated compounds
PEGylation site-dependent PK attributes

Example 29

In Vivo Studies of PEGylated FGF-21

PEG-FGF-21, unmodified FGF-21 and buffer solution are administered to mice or rats. The results will show superior activity and prolonged half life of the PEGylated FGF-21 of the present invention compared to unmodified FGF-21. Similarly, modified FGF-21, unmodified FGF-21, and buffer solution are administered to mice or rats.

Pharmacokinetic Analysis

WO 2005/091944 describes pharmacokinetic studies that can be performed with the FGF-21 compounds of the present invention. A FGF-21 polypeptide of the invention is administered by intravenous or subcutaneous routes to mice. The animals are bled prior to and at time points after dosing. Plasma is collected from each sample and analyzed by radio-immunoassay. Elimination half-life can be calculated and compared between FGF-21 polypeptides comprising a non-naturally encoded amino acid and wild-type FGF-21 or various forms of FGF-21 polypeptides of the invention. Similarly, FGF-21 polypeptides of the invention may be administered to cynomolgus monkeys. The animals are bled prior to and at time points after dosing. Plasma is collected from each sample and analyzed by radioimmunoassay.

Polypeptides of the invention may be administered to ZDF male rats (diabetic, fat rats; 8 weeks of age at beginning of study, Charles River-GMI). Rats are fed Purina 5008 feed ad libitum. The following test groups are set up: Saline; Insulin 4 U/day; FGF-21, 500 ug/day Acute (Acute dosing group is dosed once and bled at T=0, 2, 4, 8, and 24 hours post dose); FGF-21, 100 ug/day; FGF-21, 250 ug/day; FGF-21, 500 ug/day; FGF-21(once/day) 500 ug/ml; Lean Saline; Lean Insulin 4 U/day; Lean FGF-21 500 ug/day. Lean groups represent non-diabetic, lean, ZDF rats.

Compounds are injected s.c. (b.i.d.), except for the second 500 ug/day group which receives one injection per day for the duration of the study (7 days). Control rats are injected with vehicle (PBS; 0.1 ml). Following 7 days of dosing, the animals are subjected to an oral glucose tolerance test. Blood for glucose and triglycerides are collected by tail clip bleeding without anesthetic. FGF-21 polypeptides may reduce plasma glucose levels in a dose-dependent manner. Also lean ZDF rats may not become hypoglycemic after exposure to FGF-21 polypeptides of the invention when compared to rats dosed with insulin.

ob/ob Obesity Model

The ob/ob mouse model is an animal model for hyperglycemia, insulin resistance, and obesity. Plasma glucose levels after treatment with FGF-21 polypeptide compared to vehicle and insulin control groups may be measured in ob/ob mice. In this obesity model, the test groups of male ob/ob mice (7 weeks old) are injected with vehicle alone (PBS), insulin (4 U/day), or FGF-21 polypeptide (5 µg/day and 25 µg/day), subcutaneously (0.1 ml, b.i.d) for seven days. Blood is collected by tail clip bleeding on days 1, 3, and 7, one hour after the first compound injection, and plasma glucose levels are measured using a standard protocol. FGF-21 polypeptides of the invention stimulate glucose uptake if they reduce plasma glucose levels when compared to the vehicle control group. Triglyceride levels may be compared after treatment with FGF-21 polypeptides of the invention compared to other molecules. The polypeptide may be administered the mice via multiple doses, continuous infusion, or a single dose, etc.

Example 30

Pharmacokinetic evaluation of FGF21 analogs: The pharmacokinetic properties of 30 KPEG-pAF(N6-His)FGF21 analogs with varying sites of PEG conjugation were evaluated in rat. Other parameters studied were PEG MW, as well as dose of compound administered. The percent bioavailability for a few 30 KPEG-pAF(N-6-His)FGF21 variants was determined.

Animals. All animal experimentation was conducted under protocols approved by the Institutional Animal Care and Use Committee. Male (175-300 g) Sprague-Dawley rats were obtained from Charles River Laboratories. Rats were housed individually in cages in rooms with a 12-h light/dark cycle and acclimated to the Ambrx vivarium for at least 3 days prior to experimentation. Animals were provided access to certified Purina rodent chow 5001 and water ad libitum.

Dosing and Serum Collection. Catheters were surgically installed into the jugular vein for blood collection by CRL prior to shipment. Following successful catheter patency, animals were assigned to treatment groups prior to dosing. A single-dose of compound was administered intravenously or subcutaneously in a dose volume of 1 mL/kg. Compound dose concentrations were derived by dilution in PBS using the stock concentration as assigned in the Certificate of Release. Blood samples were collected at various time points via the indwelling catheter and placed into SST microfuge tubes. Serum was collected after centrifugation, and stored at −80° C. until analysis.

Pharmacokinetics Analysis: The assay for the quantification of PEG-FGF-21 in Sprague-Dawley rat serum was developed at Ambrx Inc., La Jolla, Calif. Microplate wells are coated with goat anti-human FGF-21 IgG polyclonal antibody (PAb; RnD Systems, clone AF2539) that is used as the capture reagent. Standard (STD) and quality control (QC) samples, both made by spiking PEG-FGF-21 analog into 100% Sprague Dawley rat serum, and study samples are loaded into the wells after pre-treating 1:100 with I-Block buffer. The FGF-21 in the STDs, QCs and study samples is captured by the immobilized PAb. Unbound materials are removed by washing the wells. Biotin goat anti-human FGF-21 IgG PAb (RnD Systems, clone BAF2539) is added to the wells followed by a wash step and the addition of streptavidin horseradish peroxidase (SA-HRP; RnD Systems, Catalog #DY998) for detection of the captured PEG-FGF-21. After another washing step, tetramethylbenzidine (TMB, Kirkegaard Perry Laboratories) substrate solution is added to the wells. TMB reacts with the peroxide in the presence of HRP and produces a colorimetric signal proportional to the amount of PEG-FGF-21 analog bound by the capture reagent in the initial step. The color development is stopped by the addition of 2N sulphuric acid and the intensity of the color (optical density, OD) is measured at 450 nm. The conversion of OD units for the study samples and the QCs to concentration is achieved through a computer software mediated comparison to a standard curve on the same plate, which is regressed according to a 5-parameter logistic regression model using SOFTmax Pro v5 data reduction package. Results are reported in ng/mL concentration units.

Concentrations may also be measured by a double antibody sandwich assay or other methods known to those skilled in the art. Concentrations were calculated using a standard curve generated from the corresponding dosed compound. Pharmacokinetic parameters were estimated using the modeling program WinNonlin (Pharsight, version 4.1). Noncompartmental analysis for individual animal data with linear-up/log-down trapezoidal integration was used, and concentration data was uniformly weighted.

Conclusions. The pharmacokinetic properties of WT N6-His FGF21 was in line with that reported by Kharitonenkov et al, 2005 and was comparable to the non-tagged WT FGF21 protein.

The pharmacokinetic profiles of the 30 KPEG-pAF(N6-His)FGF21 isomers were significantly increased in by the addition of a 30 kDa PEG molecule as compared to results obtained from WT (un-PEGylated) FGF21.

The PEGylated compounds exhibited markedly different PK profiles when dosed at the 0.25 mg/kg level subcutaneously. H87 and L86 tended to have inferior PK attribute as compared to the other isomers. Further, R131 and Q108 PEG30 compounds differentially generated superior PK properties. More specifically, these compound had improved AUC, Cmax and terminal half-life. An in-depth structure-activity analysis may reveal structural explanations for the various PK properties of each isomer.

Comparison of PEG molecular weight showed 30 KPEG-pAF91(N6-His)FGF21 to have a slightly greater persistence in the circulation than 20 KPEG-pAF91(N6-His)FGF21. However, as the 20 kDa isomer had a higher Cmax value, the total AUCinf for the two compounds was comparable. Bioavailability for the 20 kDa isoform was slightly better than the 30 kDa variant at 30% versus 20%, respectively.

Serum concentration versus time curves were evaluated by noncompartmental analysis (Pharsight, version 4.1). N=3-4 rats per compound. ND: not done; NE: not evaluated. Tmax: time to reach Cmax; Cmax: maximum concentration; terminal $t_{1/2}$: terminal half-life; $AUC_{last}$: area under the concentration-time curve to the last plasma sample/timepoint; $AUC_{inf}$: area under the concentration-time curve extrapolated to infinity; MRT: mean residence time; Cl/f: apparent total plasma clearance; Vz/f: apparent volume of distribution during terminal phase.

TABLE 4

Pharmacokinetic parameter values for 20KPEG-pAF91(N6-hHis)FGF21 dosed 0.25 mg/kg subcutaneously in rat.

|  |  | Rat #1 | Rat #2 | Rat #3 | Rat #4 |
| --- | --- | --- | --- | --- | --- |
| Terminal $t_{1/2}$ | hr | 22.6 | 24.4 | 17.3 | 16.9 |
| Tmax | hr | 8 | 8 | 8 | 24 |
| Cmax | ng/mL | 163.0 | 182.1 | 155.7 | 88.8 |
| $AUC_{all}$ | hr * ng/mL | 7629.1 | 7659.1 | 6461.4 | 4375.4 |
| $AUC_{INF}$ | hr * ng/mL | 8232.0 | 8333.8 | 6661.2 | 4521.7 |
| Vz/f | mL/kg | 989.8 | 1054.2 | 937.3 | 1347.7 |
| Cl/f | mL/hr/kg | 30.4 | 30.0 | 37.5 | 55.3 |
| $MRT_{INF}$ | hr | 39.9 | 41.0 | 32.5 | 34.3 |

Concentration versus time curves were evaluated by noncompartmental analysis (Pharsight, version 4.1). ND: not done; NE: could not be evaluated. Tmax: time to reach Cmax; Cmax: maximum concentration; terminal $t_{1/2}$: terminal half-life; $AUC_{last}$: area under the concentration-time curve to the last plasma sample/timepoint; $AUC_{inf}$: area under the concentration-time curve extrapolated to infinity; MRT: mean residence time; Cl/f: apparent total plasma clearance; Vz/f: apparent volume of distribution during terminal phase.

Example 31

Human Clinical Trial of the Safety and/or Efficacy of PEGylated FGF-21 Comprising a Non-Naturally Encoded Amino Acid.

Objective To observe the safety and pharmacokinetics of subcutaneously administered PEGylated recombinant human FGF-21 comprising a non-naturally encoded amino acid.

Patients Eighteen healthy volunteers ranging between 20-40 years of age and weighing between 60-90 kg are

TABLE 3

Pharmacokinetic parameter values for compounds dosed 0.25 mg/kg subcutaneously in rat.

| 0.25 mg/kg SC | Terminal $t_{1/2}$ hr | Tmax hr | Cmax ng/mL | $AUC_{all}$ hr * ng/mL | $AUC_{INF}$ hr * ng/mL | Vz/f mL/kg | Cl/f mL/hr/kg | $MRT_{INF}$ hr |
| --- | --- | --- | --- | --- | --- | --- | --- | --- |
| N6His WT | 1.26 | 0.9 | 92.1 | 261.6 | 297.3 | 1768.9 | 971.2 | 2.52 |
| PP WT | 1.19 | 1.5 | 96.6 | 259.8 | 294.7 | 1576.2 | 910.4 | 2.53 |
| R72 | 14.72 | 24 | 254.5 | NE | 11824.7 | 458.9 | 21.9 | 36.52 |
| R77 | 32.30 | 22 | 237.0 | 14571.9 | 17687.8 | 655.8 | 14.4 | 59.18 |
| L86 | 33.90 | 27 | 52.2 | 3215.7 | 3928.8 | 3153.3 | 66.0 | 59.27 |
| H87 | 16.14 | 24 | 174.3 | NE | 8206.7 | 731.1 | 31.7 | 36.31 |
| E91 | 19.93 | 22 | 229.7 | NE | 12177.2 | 606.2 | 20.9 | 40.35 |
| Y104 | 12.37 | 24 | 321.9 | 19085.8 | 21188.1 | 416.3 | 11.9 | 47.63 |
| Q108 | 27.31 | 24 | 590.3 | 31837.4 | 36387.1 | 272.4 | 7.0 | 51.71 |
| R126 | 16.48 | 20 | 248.1 | 13238.3 | 15033.4 | 643.0 | 16.8 | 49.57 |
| R131 | 26.13 | 24 | 545.4 | 27373.4 | 30786.0 | 315.0 | 8.3 | 50.41 |
| P146 | 22.01 | 24 | 321.3 | NE | 15908.4 | 503.4 | 15.9 | 40.07 | enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to FGF-21 within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This will be a Phase I, single-center, open-label, randomized, two-period crossover study in healthy male volunteers. Eighteen subjects are randomly assigned to one of two treatment sequence groups (nine subjects/group). FGF-21 is administered over two separate dosing periods as a bolus s.c. injection in the upper thigh using equivalent doses of the PEGylated FGF-21 comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated FGF-21 as well. The experimental formulation of FGF-21 is the PEGylated FGF-21 comprising a non-naturally encoded amino acid.

Blood Sampling Serial blood is drawn by direct vein puncture before and after administration of FGF-21. Venous blood samples (5 mL) for determination of serum FGF-21 concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods An ELISA kit is used for the determination of serum FGF-21 concentrations.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline FGF-21 concentrations by subtracting from each of the post-dose values the mean baseline FGF-21 concentration determined from averaging the FGF-21 levels from the three samples collected at 30, 20, and 10 minutes before dosing. Pre-dose serum FGF-21 concentrations are not included in the calculation of the mean value if they are below the quantification level of the assay. Pharmacokinetic parameters are determined from serum concentration data corrected for baseline FGF-21 concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results Mean serum FGF-21 concentration-time profiles (uncorrected for baseline FGF-21 levels) in all 18 subjects after receiving PEGylated FGF-21 comprising a non-naturally encoded amino acid at each time point measured. All subjects should have pre-dose baseline FGF-21 concentrations within the normal physiologic range. Pharmacokinetic parameters are determined from serum data corrected for pre-dose mean baseline FGF-21 concentrations and the $C_{max}$ and $t_{max}$ are determined. The mean $t_{max}$ for the any clinical comparator(s) chosen is significantly shorter than the $t_{max}$ for the PEGylated FGF-21 comprising the non-naturally encoded amino acid. Terminal half-life values are significantly shorter for the preclinical comparator(s) tested compared with the terminal half-life for the PEGylated FGF-21 comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated FGF-21 comprising non-naturally encoded amino acid will be safe and well tolerated by healthy male subjects. Based on a comparative incidence of adverse events, clinical laboratory values, vital signs, and physical examination results, the safety profiles of the commercially available forms of FGF-21 and PEGylated FGF-21 comprising non-naturally encoded amino acid will be equivalent. The PEGylated FGF-21 comprising non-naturally encoded amino acid potentially provides large clinical utility to patients and health care providers.

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 5

Sequences Cited.

| SEQ ID # | Sequence Name |
|---|---|
| 1 | Amino acid sequence of FGF-21 without leader (P form) |
| | HPIPDSSPLLQFGGQVRQRYLYTDDAQQTEAHLEIREDGTVGGAADQSPE<br>SLLQLKALKPGVIQILGVKTSRFLCQRPDGALYGSLHFDPEACSFRELLLE<br>DGYNVYQSEAHGLPLHLPGNKSPHRDPAPRGPARFLPLPGLPPAPPEPPGI<br>LAPQPPDVGSSDPLSMVGPSQGRSPSYAS |
| 2 | Amino acid sequence of FGF-21 without leader (P form) - His tagged |
| | MHHHHHHSGGHPIPDSSPLLQFGGQVRQRYLYTDDAQQTEAHLEIREDG<br>TVGGAADQSPESLLQLKALKPGVIQILGVKTSRFLCQRPDGALYGSLHFD<br>PEACSFRELLLEDGYNVYQSEAHGLPLHLPGNKSPHRDPAPRGPARFLPLP<br>GLPPAPPEPPGILAPQPPDVGSSDPLSMVGPSQGRSPSYAS |
| 3 | Amino acid sequence of FGF-21 with leader (P form) - leader with 3 leucines (209 amino acid P-form) |
| | MDSDETGFEHSGLWVSVLAGLLLGACQAHPIPDSSPLLQFGGQVRQRYL<br>YTDDAQQTEAHLEIREDGTVGGAADQSPESLLQLKALKPGVIQILGVKTS<br>RFLCQRPDGALYGSLHFDPEACSFRELLLEDGYNVYQSEAHGLPLHLPGN<br>KSPHRDPAPRGPARFLPLPGLPPAPPEPPGILAPQPPDVGSSDPLSMVGPSQ<br>GRSPSYAS |
| 4 | Amino acid sequence of FGF-21 with leader (P form) - leader with two leucines |
| | MDSDETGFEHSGLWVSVLAGLLGACQAHPIPDSSPLLQFGGQVRQRYLY<br>TDDAQQTEAHLEIREDGTVGGAADQSPESLLQLKALKPGVIQILGVKTSR<br>FLCQRPDGALYGSLHFDPEACSFRELLLEDGYNVYQSEAHGLPLHLPGNK<br>SPHRDPAPRGPARFLPLPGLPPAPPEPPGILAPQPPDVGSSDPLSMVGPSQG<br>RSPSYAS |
| 5 | Amino acid sequence of FGF-21 without leader (L form) |
| | His Pro Ile Pro Asp Ser Ser Pro Leu Leu Gln Phe Gly Gly Gln Val Arg Gln Arg<br>Tyr Leu Tyr Thr Asp Asp Ala Gln Gln Thr Glu Ala His Leu Glu Ile Arg Glu Asp<br>Gly Thr Val Gly Gly Ala Ala Asp Gln Ser Pro Glu Ser Leu Leu Gln Leu Lys Ala<br>Leu Lys Pro Gly Val Ile Gln Ile Leu Gly Val Lys Thr Ser Arg Phe Leu Cys Gln<br>Arg Pro Asp Gly Ala Leu Tyr Gly Ser Leu His Phe Asp Pro Glu Ala Cys Ser Phe<br>Arg Glu Leu Leu Leu Glu Asp Gly Tyr Asn Val Tyr Gln Ser Glu Ala His Gly<br>Leu Pro Leu His Leu Pro Gly Asn Lys Ser Pro His Arg Asp Pro Ala Pro Arg Gly<br>Pro Ala Arg Phe Leu Pro Leu Pro Gly Leu Pro Pro Ala Leu Pro Glu Pro Pro Gly<br>Ile Leu Ala Pro Gln Pro Pro Asp Val Gly Ser Ser Asp Pro Leu Ser Met Val Gly<br>Pro Ser Gln Gly Arg Ser Pro Ser Tyr Ala Ser |
| 6 | Amino acid sequence of FGF-21 with leader (L form) - leader with 3 leucines (209 amino acid L-form) |
| | Met Asp Ser Asp Glu Thr Gly Phe Glu His Ser Gly Leu Trp Val Ser Val Leu Ala<br>Gly Leu Leu Leu Gly Ala Cys Gln Ala His Pro Ile Pro Asp Ser Ser Pro Leu Leu<br>Gln Phe Gly Gly Gln Val Arg Gln Arg Tyr Leu Tyr Thr Asp Asp Ala Gln Gln<br>Thr Glu Ala His Leu Glu Ile Arg Glu Asp Gly Thr Val Gly Gly Ala Ala Asp Gln<br>Ser Pro Glu Ser Leu Leu Gln Leu Lys Ala Leu Lys Pro Gly Val Ile Gln Ile Leu<br>Gly Val Lys Thr Ser Arg Phe Leu Cys Gln Arg Pro Asp Gly Ala Leu Tyr Gly Ser<br>Leu His Phe Asp Pro Glu Ala Cys Ser Phe Arg Glu Leu Leu Leu Glu Asp Gly<br>Tyr Asn Val Tyr Gln Ser Glu Ala His Gly Leu Pro Leu His Leu Pro Gly Asn Lys<br>Ser Pro His Arg Asp Pro Ala Pro Arg Gly Pro Ala Arg Phe Leu Pro Leu Pro Gly<br>Leu Pro Pro Ala Leu Pro Glu Pro Pro Gly Ile Leu Ala Pro Gln Pro Pro Asp Val<br>Gly Ser Ser Asp Pro Leu Ser Met Val Gly Pro Ser Gln Gly Arg Ser Pro Ser Tyr<br>Ala Ser |
| 7 | Amino acid sequence of FGF-21 with leader (L form) - leader with 2 leucines (208 amino acid L-form) |
| | Met Asp Ser Asp Glu Thr Gly Phe Glu His Ser Gly Leu Trp Val Ser Val Leu Ala<br>Gly Leu Leu Gly Ala Cys Gln Ala His Pro Ile Pro Asp Ser Ser Pro Leu Leu Gln<br>Phe Gly Gly Gln Val Arg Gln Arg Tyr Leu Tyr Thr Asp Asp Ala Gln Gln Thr<br>Glu Ala His Leu Glu Ile Arg Glu Asp Gly Thr Val Gly Gly Ala Ala Asp Gln Ser<br>Pro Glu Ser Leu Leu Gln Leu Lys Ala Leu Lys Pro Gly Val Ile Gln Ile Leu Gly |

TABLE 5-continued

Sequences Cited.

| SEQ ID # | Sequence Name |
|---|---|

Val Lys Thr Ser Arg Phe Leu Cys Gln Arg Pro Asp Gly Ala Leu Tyr Gly Ser Leu
His Phe Asp Pro Glu Ala Cys Ser Phe Arg Glu Leu Leu Leu Glu Asp Gly Tyr
Asn Val Tyr Gln Ser Glu Ala His Gly Leu Pro Leu His Leu Pro Gly Asn Lys Ser
Pro His Arg Asp Pro Ala Pro Arg Gly Pro Ala Arg Phe Leu Pro Leu Pro Gly Leu
Pro Pro Ala Leu Pro Glu Pro Pro Gly Ile Leu Ala Pro Gln Pro Pro Asp Val Gly
Ser Ser Asp Pro Leu Ser Met Val Gly Pro Ser Gln Gly Arg Ser Pro Ser Tyr Ala
Ser

8     Nucleotide Sequence for FGF-21 without leader (P form)

```
CACCCCATCCCTGACTCCAGTCCTCTCCTGCAATTCGGGGGCCAAGTC
CGGCAGCGGTACCTCTACACAGATGATGCCCAGCAGACAGAAGCCCA
CCTGGAGATCAGGGAGGATGGGACGGTGGGGGGCGCTGCTGACCAGA
GCCCCGAAAGTCTCCTGCAGCTGAAAGCCTTGAAGCCGGGAGTTATTC
AAATCTTGGGAGTCAAGACATCCAGGTTCCTGTGCCAGCGGCCAGATG
GGGCCCTGTATGGATCGCTCCACTTTGACCCTGAGGCCTGCAGCTTCC
GGGAGCTGCTTCTTGAGGACGGATACAATGTTTACCAGTCCGAAGCCC
ACGGCCTCCCGCTGCACCTGCCAGGGAACAAGTCCCCACACCGGGAC
CCTGCACCCCGAGGACCAGCTCGCTTCCTGCCACTACCAGGCCTGCCC
CCCGCACCCCCGGAGCCACCCGGAATCCTGGCCCCCCAGCCCCCGAT
GTGGGCTCCTCGGACCCTCTGAGCATGGTGGGACCTTCCCAGGGCCGA
AGCCCCAGCTACGCTTCCTGA
```

9     Nucleotide Sequence for FGF-21 without leader (P form) - His tagged

```
ATGCATCATCATCATCATCATAGCGGCGGCCACCCCATCCCTGACTCC
AGTCCTCTCCTGCAATTCGGGGGCCAAGTCCGGCAGCGGTACCTCTAC
ACAGATGATGCCCAGCAGACAGAAGCCCACCTGGAGATCAGGGAGGA
TGGGACGGTGGGGGGCGCTGCTGACCAGAGCCCCGAAAGTCTCCTGC
AGCTGAAAGCCTTGAAGCCGGGAGTTATTCAAATCTTGGGAGTCAAG
ACATCCAGGTTCCTGTGCCAGCGGCCAGATGGGGCCCTGTATGGATCG
CTCCACTTTGACCCTGAGGCCTGCAGCTTCCGGGAGCTGCTTCTTGAG
GACGGATACAATGTTTACCAGTCCGAAGCCCACGGCCTCCCGCTGCAC
CTGCCAGGGAACAAGTCCCCACACCGGGACCCTGCACCCCGAGGACC
AGCTCGCTTCCTGCCACTACCAGGCCTGCCCCCCGCACCCCCGGAGCC
ACCCGGAATCCTGGCCCCCCAGCCCCCGATGTGGGCTCCTCGGACCC
TCTGAGCATGGTGGGACCTTCCCAGGGCCGAAGCCCCAGCTACGCTTC
CTGA
```

10     Nucleotide Sequence for FGF-21 with leader (P form) - leader with 3 leucines

```
ATGGACTCGGACGAGACCGGGTTCGAGCACTCAGGACTGTGGGTTTCT
GTGCTGGCTGGTCTTCTGCTGGGAGCCTGCCAGGCACACCCCATCCCT
GACTCCAGTCCTCTCCTGCAATTCGGGGGCCAAGTCCGGCAGCGGTAC
CTCTACACAGATGATGCCCAGCAGACAGAAGCCCACCTGGAGATCAG
GGAGGATGGGACGGTGGGGGGCGCTGCTGACCAGAGCCCCGAAAGTC
TCCTGCAGCTGAAAGCCTTGAAGCCGGGAGTTATTCAAATCTTGGGAG
TCAAGACATCCAGGTTCCTGTGCCAGCGGCCAGATGGGGCCCTGTATG
GATCGCTCCACTTTGACCCTGAGGCCTGCAGCTTCCGGGAGCTGCTTC
TTGAGGACGGATACAATGTTTACCAGTCCGAAGCCCACGGCCTCCCGC
TGCACCTGCCAGGGAACAAGTCCCCACACCGGGACCCTGCACCCCGA
GGACCAGCTCGCTTCCTGCCACTACCAGGCCTGCCCCCCGCACCCCCG
GAGCCACCCGGAATCCTGGCCCCCCAGCCCCCGATGTGGGCTCCTCG
GACCCTCTGAGCATGGTGGGACCTTCCCAGGGCCGAAGCCCCAGCTAC
GCTTCCTGA
```

11     Nucleotide Sequence for FGF-21 with leader (P form) - leader with 2 leucines

```
ATGGACTCGGACGAGACCGGGTTCGAGCACTCAGGACTGTGGGTTTCT
GTGCTGGCTGGTCTTCTGGGAGCCTGCCAGGCACACCCCATCCCTGAC
TCCAGTCCTCTCCTGCAATTCGGGGGCCAAGTCCGGCAGCGGTACCTC
TACACAGATGATGCCCAGCAGACAGAAGCCCACCTGGAGATCAGGGA
GGATGGGACGGTGGGGGGCGCTGCTGACCAGAGCCCCGAAAGTCTCC
TGCAGCTGAAAGCCTTGAAGCCGGGAGTTATTCAAATCTTGGGAGTCA
AGACATCCAGGTTCCTGTGCCAGCGGCCAGATGGGGCCCTGTATGGAT
CGCTCCACTTTGACCCTGAGGCCTGCAGCTTCCGGGAGCTGCTTCTTG
AGGACGGATACAATGTTTACCAGTCCGAAGCCCACGGCCTCCCGCTGC
ACCTGCCAGGGAACAAGTCCCCACACCGGGACCCTGCACCCCGAGGA
CCAGCTCGCTTCCTGCCACTACCAGGCCTGCCCCCCGCACCCCGGAG
CCACCCGGAATCCTGGCCCCCCAGCCCCCGATGTGGGCTCCTCGGAC
CCTCTGAGCATGGTGGGACCTTCCCAGGGCCGAAGCCCCAGCTACGCT
TCCTGA
```

TABLE 5-continued

Sequences Cited.

| SEQ ID # | Sequence Name |
|---|---|

12  Nucleotide Sequence for FGF-21 without leader (L form)

```
CACCCCATCCCTGACTCCAGTCCTCTCCTGCAATTCGGGGCCAAGTCC
GGCAGCGGTACCTCTACACAGATGATGCCCAGCAGACAGAAGCCCAC
CTGGAGATCAGGGAGGATGGGACGGTGGGGGGCGCTGCTGACCAGAG
CCCCGAAAGTCTCCTGCAGCTGAAAGCCTTGAAGCCGGGAGTTATTCA
AATCTTGGGAGTCAAGACATCCAGGTTCCTGTGCCAGCGGCCAGATGG
GGCCCTGTATGGATCGCTCCACTTTGACCCTGAGGCCTGCAGCTTCCG
GGAGCTGCTTCTTGAGGACGGATACAATGTTTACCAGTCCGAAGCCCA
CGGCCTCCCGCTGCACCTGCCAGGGAACAAGTCCCCACACCGGGACCC
TGCACCCCGAGGACCAGCTCGCTTCCTGCCACTACCAGGCCTGCCCCC
CGCACTCCCGGAGCCACCCGGAATCCTGGCCCCCCAGCCCCCCGATGT
GGGCTCCTCGGACCCTCTGAGCATGGTGGGACCTTCCCAGGGCCGAAG
CCCAGCTACGCTTCCTGA
```

13  Nucleotide Sequence for FGF-21 with leader (L form) - leader with 3 leucines

```
ATG GAC TCG GAC GAG ACC GGG TTC GAG CAC TCA GGA CTG TGG
GTT TCT GTG CTG GCT GGT CTT CTG CTG GGA GCC TGC CAG GCA
CAC CCC ATC CCT GAC TCC AGT CCT CTC CTG CAA TTC GGG GGC
CAA GTC CGG CAG CGG TAC CTC TAC ACA GAT GAT GCC CAG CAG
ACA GAA GCC CAC CTG GAG ATC AGG GAG GAT GGG ACG GTG GGG
GGC GCT GCT GAC CAG AGC CCC GAA AGT CTC CTG CAG CTG AAA
GCC TTG AAG CCG GGA GTT ATT CAA ATC TTG GGA GTC AAG ACA
TCC AGG TTC CTG TGC CAG CGG CCA GAT GGG GCC CTG TAT GGA
TCG CTC CAC TTT GAC CCT GAG GCC TGC AGC TTC CGG GAG CTG
CTT CTT GAG GAC GGA TAC AAT GTT TAC CAG TCC GAA GCC CAC
GGC CTC CCG CTG CAC CTG CCA GGG AAC AAG TCC CCA CAC CGG
GAC CCT GCA CCC CGA GGA CCA GCT CGC TTC CTG CCA CTA CCA
GGC CTG CCC CCG CA CTC CCG GAG CCA CCC GGA ATC CTG GCC
CCC CAG CCC CCC GAT GTG GGC TCC TCG GAC CCT CTG AGC ATG
GTG GGA CCT TCC CAG GGC CGA AGC CCC AGC TAC GCT TCC TGA
```

14  Nucleotide Sequence for FGF-21 with leader (L form) - leader with 2 leucines

```
ATG GAC TCG GAC GAG ACC GGG TTC GAG CAC TCA GGA CTG TGG
GTT TCT GTG CTG GCT GGT CTT CTG GGA GCC TGC CAG GCA CAC
CCC ATC CCT GAC TCC AGT CCT CTC CTG CAA TTC GGG GGC CAA
GTC CGG CAG CGG TAC CTC TAC ACA GAT GAT GCC CAG CAG ACA
GAA GCC CAC CTG GAG ATC AGG GAG GAT GGG ACG GTG GGG GGC
GCT GCT GAC CAG AGC CCC GAA AGT CTC CTG CAG CTG AAA GCC
TTG AAG CCG GGA GTT ATT CAA ATC TTG GGA GTC AAG ACA TCC
AGG TTC CTG TGC CAG CGG CCA GAT GGG GCC CTG TAT GGA TCG
CTC CAC TTT GAC CCT GAG GCC TGC AGC TTC CGG GAG CTG CTT
CTT GAG GAC GGA TAC AAT GTT TAC CAG TCC GAA GCC CAC GGC
CTC CCG CTG CAC CTG CCA GGG AAC AAG TCC CCA CAC CGG GAC
CCT GCA CCC CGA GGA CCA GCT CGC TTC CTG CCA CTA CCA GGC
CTG CCC CCG CA CTC CCG GAG CCA CCC GGA ATC CTG GCC CCC
CAG CCC CCC GAT GTG GGC TCC TCG GAC CCT CTG AGC ATG GTG
GGA CCT TCC CAG GGC CGA AGC CCC AGC TAC GCT TCC TGA
```

34  Amino acid sequence of FGF-21 (*Rattus norvegicus* - ref|NP_570108.1|[18543365])

```
Met Asp Trp Met Lys Ser Arg Val Gly Ala Pro Gly Leu Trp Val Cys Leu Leu
Leu Pro Val Phe Leu Leu Gly Val Cys Glu Ala Tyr Pro Ile Ser Asp Ser Ser Pro
Leu Leu Gln Phe Gly Gly Gln Val Arg Gln Arg Tyr Leu Tyr Thr Asp Asp Asp
Gln Asp Thr Glu Ala His Leu Glu Ile Arg Glu Asp Gly Thr Val Val Gly Ala
His Arg Ser Pro Glu Ser Leu Leu Glu Leu Lys Ala Leu Lys Pro Gly Val Ile Gln
Ile Leu Gly Val Lys Ala Ser Arg Phe Leu Cys Gln Gln Pro Asp Gly Thr Leu Tyr
Gly Ser Pro His Phe Asp Pro Glu Ala Cys Ser Phe Arg Glu Leu Leu Leu Lys Asp
Gly Tyr Asn Val Tyr Gln Ser Glu Ala His Gly Leu Pro Leu Arg Leu Pro Gln Leu
Asp Ser Gln Asp Pro Ala Thr Arg Gly Pro Val Arg Phe Leu Pro Met Pro Gly Leu
Pro His Glu Pro Gln Glu Gln Pro Gly Val Leu Pro Pro Glu Pro Pro Asp Val Gly
Ser Ser Asp Pro Leu Ser Met Val Glu Pro Leu Gln Gly Arg Ser Pro Ser Tyr Ala
Ser
```

35  Amino acid sequence of FGF-21 (*Mus musculus* - ref|NP_064397.1|[9910218])

```
Met Glu Trp Met Arg Ser Arg Val Gly Thr Leu Gly Leu Trp Val Arg Leu Leu
Leu Ala Val Phe Leu Leu Gly Val Tyr Gln Ala Tyr Pro Ile Pro Asp Ser Ser Pro
Leu Leu Gln Phe Gly Gly Gln Val Arg Gln Arg Tyr Leu Tyr Thr Asp Asp Asp
Gln Asp Thr Glu Ala His Leu Glu Ile Arg Glu Asp Gly Thr Val Val Gly Ala Ala
His Arg Ser Pro Glu Ser Leu Leu Glu Leu Lys Ala Leu Lys Pro Gly Val Ile Gln
```

TABLE 5-continued

Sequences Cited.

| SEQ ID # | Sequence Name |
|---|---|
| | Ile Leu Gly Val Lys Ala Ser Arg Phe Leu Cys Gln Gln Pro Asp Gly Ala Leu Tyr<br>Gly Ser Pro His Phe Asp Pro Glu Ala Cys Ser Phe Arg Glu Leu Leu Leu Glu Asp<br>Gly Tyr Asn Val Tyr Gln Ser Glu Ala His Gly Leu Pro Leu Arg Leu Pro Gln Lys<br>Asp Ser Pro Asn Gln Asp Ala Thr Ser Trp Gly Pro Val Arg Phe Leu Pro Met Pro<br>Gly Leu Leu His Glu Pro Gln Asp Gln Ala Gly Phe Leu Pro Pro Glu Pro Pro Asp<br>Val Gly Ser Ser Asp Pro Leu Ser Met Val Glu Pro Leu Gln Gly Arg Ser Pro Ser<br>Tyr Ala Ser |
| 36 | Amino acid sequence of FGF-21 (*Danio rerio* -<br>ref\|NP_001038789.1\|[113671792]) |
| | Met Leu Phe Ala Cys Phe Phe Ile Phe Phe Ala Leu Phe Pro His Leu Arg Trp Cys<br>Met Tyr Val Pro Ala Gln Asn Val Leu Leu Gln Phe Gly Thr Gln Val Arg Glu<br>Arg Leu Leu Tyr Thr Asp Gly Leu Phe Leu Glu Met Asn Pro Asp Gly Ser Val<br>Lys Gly Ser Pro Glu Lys Asn Leu Asn Cys Val Leu Glu Leu Arg Ser Val Lys Ala<br>Gly Glu Thr Val Ile Gln Ser Ala Ala Thr Ser Leu Tyr Leu Cys Val Asp Asp Gln<br>Asp Lys Leu Lys Gly Gln His His Tyr Ser Ala Leu Cys Thr Phe Gln Glu Leu<br>Leu Leu Asp Gly Tyr Ser Phe Phe Leu Ser Pro His Thr Asn Leu Pro Val Ser Leu<br>Leu Ser Lys Arg Gln Lys His Gly Asn Pro Leu Ser Arg Phe Leu Pro Val Ser Arg<br>Ala Glu Asp Ser Arg Thr Gln Glu Val Lys Gln Tyr Ile Gln Asp Ile Asn Leu Asp<br>Ser Asp Asp Pro Leu Gly Met Gly His Arg Ser His Leu Gln Thr Val Phe Ser Pro<br>Ser Leu His Thr Lys Lys |
| 37 | Amino acid sequence of Klotho beta (*Homo sapiens* -<br>ref\|NP_783864.1\|[28376633]) |
| | MKPGCAAGSPGNEWIFFSTDEITTRYRNTMSNGGLQRSVILSALILLRAVT<br>GFSGDGRAIWSKNPNFTPVNESQLFLYDTFPKNFFWGIGTGALQVEGSWK<br>KDGKGPSIWDHFIHTHLKNVSSTNGSSDSYIFLEKDLSALDFIGVSFYQFSI<br>SWPRLFPDGIVTVANAKGLQYYSTLLDALVLRNIEIVTLYHWDLPLALQE<br>KYGGWKNDTIIDIFNDYATYCFQMFGDRVKYWITIHNPYLVAWHGYGTG<br>MHAPGEKGNLAAVYTVGHNLIKAHSKVWHNYNTHFRPHQKGWLSITLG<br>SHWIEPNRSENTMDIFKCQQSMVSVLGWFANPIHGDGDYPEGMRKKLFS<br>VLPIFSEAEKHEMRGTADFFAFSFGPNNFKPLNTMAKMGQNVSLNLREAL<br>NWIKLEYNNPRILIAENGWFTDSRVKTEDTTAIYMMKNFLSQVLQAIRLD<br>EIRVFGYTAWSLLDGFEWQDAYTIRRGLFYVDFNSKQKERKPKSSAHYY<br>KQIIRENGFSLKESTPDVQGQFPCDFSWGVTESVLKPESVASSPQFSDPHL<br>YVWNATGNRLLHRVEGVRLKTRPAQCTDFVNIKKQLEMLARMKVTHYR<br>FALDWASVLPTGNLSAVNRQALRYYRCVVSEGLKLGISAMVTLYYPTHA<br>HLGLPEPLLHADGWLNPSTAEAFQAYAGLCFQELGDLVKLWITINEPNRL<br>SDIYNRSGNDTYGAAHNLLVAHALAWRLYDRQFRPSQRGAVSLSLHAD<br>WAEPANPYADSHWRAAERFLQFEIAWFAEPLFKTGDYPAAMREYIASKH<br>RRGLSSSALPRLTEAERRLLKGTVDFCALNHFTTRFVMHEQLAGSRYDSD<br>RDIQFLQDITRLSSPTRLAVIPWGVRKLLRWVRRNYGDMDIYITASGIDDQ<br>ALEDDRLRKYYLGKYLQEVLKAYLIDKVRIKGYYAFKLAEEKSKPRFGFF<br>TSDFKAKSSIQFYNKVISSRGFPFENSSSRCSQTQENTECTVCLFLVQKKPL<br>IFLGCCFFSTLVLLLSIAIFQRQKRRKFWKAKNLQHIPLKKGKRVVS |
| 38 | Amino acid sequence of Klotho beta (*Mus musculus* -<br>refNP_112457.1 GI: 13626032) |
| | MKTGCAAGSPGNEWIFFSSDERNTRSRKTMSNRALQRSAVLSAFVLLRA<br>VTGFSGDGKAIWDKKQYVSPVNPSQLFLYDTFPKNFSWGVGTGAFQVEG<br>SWKTDGRGPSIWDRYVYSHLRGVNGTDRSTDSYIFLEKDLLALDFLGVSF<br>YQFSISWPRLFPNGTVAAVNAQGLRYYRALLDSLVLRNIEPIVTLYHWDL<br>PLTLQEEYGGWKNATMIDLFNDYATYCFQTFGDRVKYWITIHNPYLVAW<br>HGFGTGMHAPGEKGNLTAVYTVGHNLIKAHSKVWHNYDKNFRPHQKG<br>WLSITLGSHWIEPNRTDNMEDVINCQHSMSSVLGWFANPIHGDGDYPEF<br>MKTGAMIPEFSEAEKEEVRGTADFFAFSFGPNNFRPSNTVVKMGQNVSLN<br>LRQVLNWIKLEYDDPQILISENGWFTDSYIKTEDTTAIYMMKNFLNQVLQ<br>AIKFDEIRVFGYTAWTLLDGFEWQDAYTTRRGLFYVDFNSEQKERKPKSS<br>AHYYKQIIQDNGFPLKESTPDMKGRFPCDFSWGVTESVLKPEFTVSSPQFT<br>DPHLYVWNVTGNRLLYRVEGVRLKTRPSQCTDYVSIKKRVEMLAKMKV<br>THYQFALDWTSILPTGNLSKVNRQVLRYYRCVVSEGLKLGVFPMVTLYH<br>PTHSHLGLPLPLLSSGGWLNMNTAKAFQDYAELCFRELGDLVKLWITINE<br>PNRLSDMYNRTSNDTYRAAHNLMIAHAQVWHLYDRQYRPVQHGAVSLS<br>LHCDWAEPANPFVDSHWKAAERFLQFEIAWFADPLFKTGDYPSVMKEYI<br>ASKNQRGLSSSVLPRFTAKESRLVKGTVDFYALNHFTTRFVIHKQLNTNR<br>SVADRDVQFLQDITRLSSPSRLAVTPWGVRKLLAWIRRNYRDRDIYITAN<br>GIDDLALEDDQIRKYYLEKYVQEALKAYLIDKVKIGYYAFKLTEEKSKP<br>RFGFFTSDFRAKSSVQFYSKLISSSGLPAENRSPACGQPAEDTDCTICSFLV<br>EKKPLIFFGCCFISTLAVLLSITVFHHQKRRFQKARNLQ<br>NIPLKKGHSRVFS |

TABLE 5-continued

Sequences Cited.

| SEQ ID # | Sequence Name |
|---|---|
| 39 | OmpA nucleotide leader sequence |
| | atgaaaaaaactgctatcgcgatcgctgtagctctggctggtttcgcgaccgtagctaacgct |
| 40 | OmpA amino acid leader sequence |
| | M K K T A I A I A V A L A G F A T V A N A |
| 41 | MalE nucleotide leader sequence |
| | atgaaaataaaaacaggtgcacgcatcctcgcattatccgcattaacgacgatgatgttttccgcctcggctctcgcc |
| 42 | MalE amino acid leader sequence |
| | M K I K T G A R I L A L S A L T T M M F S A S A L A |
| 43 | StII nucleotide leader sequence |
| | atgaaaaagaatatcgcatttcttcttgcatctatgttcgtttttttctattgctacaaatgcctatgca |
| 44 | StII amino acid leader sequence |
| | M K K N I A F L L A S M F V F S I A T N A Y A |

What is claimed is:

1. A biologically active variant of FGF-21 comprising the amino acid sequence of SEQ ID NO:1 and comprising one or more non-naturally encoded amino acids wherein at least one of the one or more non-naturally encoded amino acids occurs at position 108 in the FGF-21 variant, and wherein the non-naturally encoded amino acid has the structure:

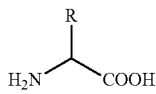

and wherein the R group is any substituent other than one used in the twenty natural amino acids.

2. The FGF-21 variant of claim 1, wherein the FGF-21 variant comprises one or more post-translational modifications.

3. The FGF-21 variant of claim 1, wherein the non-naturally occurring amino acid is linked to a linker, polymer, or biologically active molecule.

4. The FGF-21 variant of claim 3, wherein the variant is linked to a water soluble polymer.

5. The FGF-21 variant of claim 1, wherein the variant is linked to a bifunctional polymer, bifunctional linker, or at least one additional FGF-21 polypeptide.

6. The FGF-21 variant of claim 5, wherein the bifunctional linker or polymer is linked to a second polypeptide.

7. The FGF-21 variant of claim 6, wherein the second polypeptide is a FGF-21 polypeptide.

8. The FGF-21 variant of claim 4, wherein the water soluble polymer comprises a poly(ethylene glycol) moiety.

9. The FGF-21 variant of claim 4, wherein said water soluble polymer is linked to a non-naturally encoded amino acid present in said FGF-21 variant.

10. The FGF-21 variant of claim 3, wherein the non-naturally encoded amino acid is a phenylalanine derivative.

11. The FGF-21 variant of claim 1, wherein the FGF-21 variant comprises one or more amino acid substitution, addition or deletion that modulates affinity of the FGF-21 variant for a FGF-21 receptor.

12. The FGF-21 variant of claim 1, wherein the FGF-21 variant comprises one or more amino acid substitution, addition or deletion that increases the stability or solubility of the FGF-21 variant.

13. The FGF-21 variant of claim 1, wherein the FGF-21 variant comprises one or more amino acid substitution, addition or deletion that increases the expression of the FGF-21 variant in a recombinant host cell or synthesized in vitro.

14. The FGF-21 variant of claim 1, wherein the FGF-21 variant comprises one or more amino acid substitution, addition or deletion that increases protease resistance of the FGF-21 variant.

15. The FGF-21 variant of claim 1, wherein the one or more non-naturally encoded amino acid(s) is reactive toward a linker, polymer, or biologically active molecule that is otherwise unreactive toward any of the 20 common amino acids in the polypeptide.

16. The FGF-21 variant of claim 1, wherein the one or more non-naturally encoded amino acid(s) comprises a carbonyl group, an aminooxy group, a hydrazine group, a hydrazide group, a semicarbazide group, an azide group, or an alkyne group.

17. The FGF-21 variant of claim 16, wherein the one or more non-naturally encoded amino acid(s) comprises a carbonyl group.

18. The FGF-21 variant of claim 4, wherein the water soluble polymer has a molecular weight of between about 0.1 kDa and about 100 kDa.

19. The FGF-21 variant of claim 18, wherein the water soluble polymer has a molecular weight of between about 0.1 kDa and about 50 kDa.

20. The FGF-21 variant of claim 4, which is made by reacting a FGF-21 polypeptide comprising a carbonyl-containing amino acid with a water soluble polymer comprising an aminooxy, hydrazine, hydrazide or semicarbazide group.

21. The FGF-21 variant of claim 20, wherein the aminooxy, hydrazine, hydrazide or semicarbazide group is linked to the water soluble polymer through an amide linkage.

22. The FGF-21 variant of claim 4, which is made by reacting a water soluble polymer comprising a carbonyl group with a polypeptide comprising a non-naturally encoded amino acid that comprises an aminooxy, a hydrazine, a hydrazide or a semicarbazide group.

23. The FGF-21 variant of claim 4, wherein the water soluble polymer is a branched or multiarmed polymer.

24. The FGF-21 variant of claim 23, wherein each branch of the water soluble polymer has a molecular weight of between about 1 kDa and about 100 kDa.

25. The FGF-21 variant of claim 1, wherein the variant is a FGF-21 antagonist.

26. The FGF-21 variant of claim 25, wherein the variant comprises one or more post-translational modification, linker, polymer, or biologically active molecule.

27. The FGF-21 variant of claim 26, wherein the polymer comprises a moiety selected from a group consisting of a water soluble polymer and poly(ethylene glycol).

28. The FGF-21 variant according to claim 25, wherein the polypeptide prevents activation of the FGF-21 receptor.

29. The FGF-21 variant of claim 1, wherein the one or more non-naturally encoded amino acid(s) comprises a saccharide moiety.

30. The FGF-21 variant of claim 3, wherein the linker, polymer, or biologically active molecule is linked to the polypeptide via a saccharide moiety.

31. A composition comprising the FGF-21 variant of claim 1 and a pharmaceutically acceptable carrier.

32. The composition of claim 31, wherein the one or more non-naturally encoded amino acid(s) is linked to a water soluble polymer.

33. An FGF-21 variant encoded by a polynucleotide having a sequence shown in SEQ ID NO: 8, 9, 10, 11, 12, 13, or 14, wherein said polynucleotide comprises a selector codon, and wherein said variant comprises at least one non-naturally encoded amino acid substituted at a corresponding residue position 108 in SEQ ID NO: 1 or the corresponding amino acids of SEQ ID NOs: 2-7, wherein the non-naturally occurring amino acid has the structure:

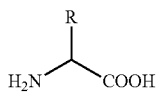

and wherein the R group is any substituent other than one used in the twenty natural amino acids.

34. The FGF-21 variant of claim 33, wherein the non-naturally encoded amino acid is linked to a linker, polymer, water soluble polymer, or biologically active molecule.

35. The FGF-21 variant of claim 34, wherein the water soluble polymer comprises a polyethylene glycol) moiety.

36. The FGF-21 variant of claim 33, wherein the non-naturally encoded amino acid is a phenylalanine derivative.

37. The FGF-21 variant of claim 33, wherein the non-naturally encoded amino acid comprises a carbonyl group, an aminooxy group, a hydrazide group, a hydrazine group, a semicarbazide group, an azide group, or an alkyne group.

38. The FGF-21 variant of claim 35, wherein the poly (ethylene glycol) moiety has a molecular weight of between about 0.1 kDa and about 100 kDa.

39. The FGF-21 variant of claim 35, wherein the poly (ethylene glycol) moiety is a branched or multiarmed polymer.

40. The FGF-21 variant of claim 39, wherein the poly (ethylene glycol) moiety has a molecular weight of between about 1 kDa and about 100 kDa.

41. A composition comprising the FGF-21 variant of claim 33 and a pharmaceutically acceptable carrier.

42. A FGF-21 variant comprising one or more amino acid substitution, addition or deletion wherein at least one of the one or more amino acid substitution, addition, or deletions occurs at amino acid position 108 of SEQ ID NO.: 1 that increases the expression of the FGF-21 variant in a recombinant host cell.

43. The FGF-21 variant of claim 35, wherein the water soluble polymer comprises a poly(ethylene glycol) moiety.

44. The FGF-21 variant of claim 35, wherein the amino acid covalently linked to the water soluble polymer is a non-naturally encoded amino acid.

45. The FGF-21 variant of claim 10 wherein said non-naturally encoded amino acid is linked to a poly(ethylene glycol) molecule.

46. The FGF-21 polypeptide of claim 45, wherein said FGF-21 polypeptide is monoPEGylated.

47. A biologically functional FGF-21 variant comprising a non-naturally encoded amino acid at position 108 of SEQ ID NO.: 1, and a linker, polymer or biologically active molecule that is attached to the non-naturally encoded amino acid wherein said non-naturally encoded amino acid is ribosomally incorporated into the polypeptide.

48. The FGF-21 variant of claim 47, wherein the FGF-21 variant comprises one said linker, polymer, or biologically active molecule.

49. The FGF-21 variant of claim 1, wherein the FGF-21 variant comprises one or more amino acid substitution, addition, or deletion that modulates immunogenicity of the FGF-21 polypeptide.

50. The FGF-21 variant of claim 1, wherein the FGF-21 variant comprises one or more amino acid substitution, addition, or deletion that modulates serum half-life or circulation time of the FGF-21 variant.

51. The FGF-21 variant of claim 1, wherein the one or more non-naturally encoded amino acid(s) comprises a ketone group.

52. The FGF-21 variant of claim 1, wherein the polypeptide also comprises a naturally encoded amino acid substitution.

* * * * *

UNITED STATES PATENT AND TRADEMARK OFFICE
CERTIFICATE OF CORRECTION

PATENT NO. : 8,012,931 B2  Page 1 of 1
APPLICATION NO. : 12/051830
DATED : September 6, 2011
INVENTOR(S) : Thomas P. Cujec et al.

It is certified that error appears in the above-identified patent and that said Letters Patent is hereby corrected as shown below:

Col. 271, claim 35, line 33, "polyethylene glycol)" should be changed to --poly(ethylene glycol)--.

Col. 272, claim 46, line 20, "polypeptide" should be changed to --variant--; line 21, "polypeptide" should be changed to --variant--.

Signed and Sealed this
Nineteenth Day of June, 2012

David J. Kappos
*Director of the United States Patent and Trademark Office*

SEQUENCE LISTING

<160> NUMBER OF SEQ ID NOS: 44

<210> SEQ ID NO 1
<211> LENGTH: 181
<212> TYPE: PRT
<213> ORGANISM: Homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser

-continued

```
                180

<210> SEQ ID NO 2
<211> LENGTH: 191
<212> TYPE: PRT
<213> ORGANISM: Homo sapiens

<400> SEQUENCE: 2

Met His His His His His His Ser Gly Gly His Pro Ile Pro Asp Ser
1               5                   10                  15

Ser Pro Leu Leu Gln Phe Gly Gly Gln Val Arg Gln Arg Tyr Leu Tyr
            20                  25                  30

Thr Asp Asp Ala Gln Gln Thr Glu Ala His Leu Glu Ile Arg Glu Asp
        35                  40                  45

Gly Thr Val Gly Gly Ala Ala Asp Gln Ser Pro Glu Ser Leu Leu Gln
    50                  55                  60

Leu Lys Ala Leu Lys Pro Gly Val Ile Gln Ile Leu Gly Val Lys Thr
65                  70                  75                  80

Ser Arg Phe Leu Cys Gln Arg Pro Asp Gly Ala Leu Tyr Gly Ser Leu
                85                  90                  95

His Phe Asp Pro Glu Ala Cys Ser Phe Arg Glu Leu Leu Leu Glu Asp
            100                 105                 110

Gly Tyr Asn Val Tyr Gln Ser Glu Ala His Gly Leu Pro Leu His Leu
        115                 120                 125

Pro Gly Asn Lys Ser Pro His Arg Asp Pro Ala Pro Arg Gly Pro Ala
    130                 135                 140

Arg Phe Leu Pro Leu Pro Gly Leu Pro Pro Ala Pro Pro Glu Pro Pro
145                 150                 155                 160

Gly Ile Leu Ala Pro Gln Pro Pro Asp Val Gly Ser Ser Asp Pro Leu
                165                 170                 175

Ser Met Val Gly Pro Ser Gln Gly Arg Ser Pro Ser Tyr Ala Ser
            180                 185                 190

<210> SEQ ID NO 3
<211> LENGTH: 209
<212> TYPE: PRT
<213> ORGANISM: Homo sapiens

<400> SEQUENCE: 3

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140
```

```
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
            165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
        195                 200                 205

Ser

<210> SEQ ID NO 4
<211> LENGTH: 208
<212> TYPE: PRT
<213> ORGANISM: Homo sapiens

<400> SEQUENCE: 4

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Gln Thr Glu Ala His Leu Glu Ile Arg Glu
    50                  55                  60

Asp Gly Thr Val Gly Gly Ala Ala Asp Gln Ser Pro Glu Ser Leu Leu
65                  70                  75                  80

Gln Leu Lys Ala Leu Lys Pro Gly Val Ile Gln Ile Leu Gly Val Lys
            85                  90                  95

Thr Ser Arg Phe Leu Cys Gln Arg Pro Asp Gly Ala Leu Tyr Gly Ser
        100                 105                 110

Leu His Phe Asp Pro Glu Ala Cys Ser Phe Arg Glu Leu Leu Leu Glu
    115                 120                 125

Asp Gly Tyr Asn Val Tyr Gln Ser Glu Ala His Gly Leu Pro Leu His
130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Pro Pro Glu Pro
            165                 170                 175

Pro Gly Ile Leu Ala Pro Gln Pro Pro Asp Val Gly Ser Ser Asp Pro
        180                 185                 190

Leu Ser Met Val Gly Pro Ser Gln Gly Arg Ser Pro Ser Tyr Ala Ser
    195                 200                 205

<210> SEQ ID NO 5
<211> LENGTH: 181
<212> TYPE: PRT
<213> ORGANISM: Homo sapiens

<400> SEQUENCE: 5

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
```

```
                    50                  55                  60
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 6
<211> LENGTH: 209
<212> TYPE: PRT
<213> ORGANISM: Homo sapiens

<400> SEQUENCE: 6

Met Asp Ser Asp Glu Thr Gly Phe Glu His Ser Gly Leu Trp Val Ser
 1               5                  10                  15

Val Leu Ala Gly Leu Leu Gly Ala Cys Gln Ala His Pro Ile Pro
                 20                  25                  30

Asp Ser Ser Pro Leu Leu Gln Phe Gly Gly Gln Val Arg Gln Arg Tyr
             35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 7
<211> LENGTH: 208
<212> TYPE: PRT
<213> ORGANISM: Homo sapiens
```

<400> SEQUENCE: 7

| | | | | | | | | | | | | | | | |
|---|---|---|---|---|---|---|---|---|---|---|---|---|---|---|---|
| Met | Asp | Ser | Asp | Glu | Thr | Gly | Phe | Glu | His | Ser | Gly | Leu | Trp | Val | Ser |
| 1 | | | | 5 | | | | | 10 | | | | | 15 | |
| Val | Leu | Ala | Gly | Leu | Leu | Gly | Ala | Cys | Gln | Ala | His | Pro | Ile | Pro | Asp |
| | | | 20 | | | | | 25 | | | | | 30 | | |
| Ser | Ser | Pro | Leu | Leu | Gln | Phe | Gly | Gly | Gln | Val | Arg | Gln | Arg | Tyr | Leu |
| | | 35 | | | | | 40 | | | | | 45 | | | |
| Tyr | Thr | Asp | Asp | Ala | Gln | Gln | Thr | Glu | Ala | His | Leu | Glu | Ile | Arg | Glu |
| | 50 | | | | | 55 | | | | | 60 | | | | |
| Asp | Gly | Thr | Val | Gly | Gly | Ala | Ala | Asp | Gln | Ser | Pro | Glu | Ser | Leu | Leu |
| 65 | | | | | 70 | | | | | 75 | | | | | 80 |
| Gln | Leu | Lys | Ala | Leu | Lys | Pro | Gly | Val | Ile | Gln | Ile | Leu | Gly | Val | Lys |
| | | | | 85 | | | | | 90 | | | | | 95 | |
| Thr | Ser | Arg | Phe | Leu | Cys | Gln | Arg | Pro | Asp | Gly | Ala | Leu | Tyr | Gly | Ser |
| | | | 100 | | | | | 105 | | | | | 110 | | |
| Leu | His | Phe | Asp | Pro | Glu | Ala | Cys | Ser | Phe | Arg | Glu | Leu | Leu | Leu | Glu |
| | | 115 | | | | | 120 | | | | | 125 | | | |
| Asp | Gly | Tyr | Asn | Val | Tyr | Gln | Ser | Glu | Ala | His | Gly | Leu | Pro | Leu | His |
| | 130 | | | | | 135 | | | | | 140 | | | | |
| Leu | Pro | Gly | Asn | Lys | Ser | Pro | His | Arg | Asp | Pro | Ala | Pro | Arg | Gly | Pro |
| 145 | | | | | 150 | | | | | 155 | | | | | 160 |
| Ala | Arg | Phe | Leu | Pro | Leu | Pro | Gly | Leu | Pro | Pro | Ala | Leu | Pro | Glu | Pro |
| | | | | 165 | | | | | 170 | | | | | 175 | |
| Pro | Gly | Ile | Leu | Ala | Pro | Gln | Pro | Pro | Asp | Val | Gly | Ser | Ser | Asp | Pro |
| | | | 180 | | | | | 185 | | | | | 190 | | |
| Leu | Ser | Met | Val | Gly | Pro | Ser | Gln | Gly | Arg | Ser | Pro | Ser | Tyr | Ala | Ser |
| | | 195 | | | | | 200 | | | | | 205 | | | |

<210> SEQ ID NO 8
<211> LENGTH: 546
<212> TYPE: DNA
<213> ORGANISM: Homo sapiens

<400> SEQUENCE: 8

```
caccccatcc ctgactccag tcctctcctg caattcgggg gccaagtccg gcagcggtac     60
ctctacacag atgatgccca gcagacagaa gcccacctgg agatcaggga ggatgggacg    120
gtggggggcg ctgctgacca gagccccgaa agtctcctgc agctgaaagc cttgaagccg    180
ggagttattc aaatcttggg agtcaagaca tccaggttcc tgtgccagcg gccagatggg    240
gccctgtatg gatcgctcca ctttgaccct gaggcctgca gcttccggga gctgcttctt    300
gaggacggat acaatgttta ccagtccgaa gcccacggcc tccgctgca cctgccaggg    360
aacaagtccc acaccgggga ccctgcaccc cgaggaccag ctcgcttcct gccactacca    420
ggcctgcccc ccgcaccccc ggagccaccc ggaatcctgg cccccagcc cccgatgtg     480
ggctcctcgg accctctgag catggtggga ccttcccagg gccgaagccc cagctacgct    540
tcctga                                                              546
```

<210> SEQ ID NO 9
<211> LENGTH: 576
<212> TYPE: DNA
<213> ORGANISM: Homo sapiens

<400> SEQUENCE: 9

```
atgcatcatc atcatcatca tagcggcggc caccccatcc ctgactccag tcctctcctg     60
```

-continued

```
caattcgggg gccaagtccg gcagcggtac ctctacacag atgatgccca gcagacagaa      120
gcccacctgg agatcaggga ggatgggacg gtggggggcg ctgctgacca gagcccgaa       180 agtctcctgc agctgaaagc cttgaagccg ggagttattc aaatcttggg agtcaagaca     240
tccaggttcc tgtgccagcg gccagatggg gccctgtatg gatcgctcca ctttgaccct     300
gaggcctgca gcttccggga gctgcttctt gaggacggat acaatgttta ccagtccgaa     360
gcccacggcc tccgctgca cctgccaggg aacaagtccc cacaccggga ccctgcaccc       420
cgaggaccag ctcgcttcct gccactacca ggcctgcccc ccgcaccccc ggagccaccc     480
ggaatcctgg ccccccagcc ccccgatgtg ggctcctcgg accctctgag catggtggga     540
ccttcccagg gccgaagccc cagctacgct tcctga                                576
```

<210> SEQ ID NO 10
<211> LENGTH: 630
<212> TYPE: DNA
<213> ORGANISM: Homo sapiens

<400> SEQUENCE: 10

```
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg ggcgctgctg accagagccc cgaaagtctc     240
ctgcagctga aagccttgaa gccgggagtt attcaaatct gggagtcaa gacatccagg     300 ttcctgtgcc agcggccaga tggggccctg tatggatcgc tccactttga ccctgaggcc     360
tgcagcttcc gggagctgct tcttgaggac ggatacaatg tttaccagtc cgaagcccac     420
ggcctcccgc tgcacctgcc agggaacaag tccccacacc gggaccctgc accccgagga     480
ccagctcgct tcctgccact accaggcctg cccccgcac ccccggagcc acccggaatc     540
ctggcccccc agccccccga tgtgggctcc tcggaccctc tgagcatggt gggaccttcc     600
cagggccgaa gccccagcta cgcttcctga                                      630
```

<210> SEQ ID NO 11
<211> LENGTH: 627
<212> TYPE: DNA
<213> ORGANISM: Homo sapiens

<400> SEQUENCE: 11

```
atggactcgg acgagaccgg gttcgagcac tcaggactgt gggtttctgt gctggctggt      60
cttctgggag cctgccaggc acaccccatc ctgactcca gtcctctcct gcaattcggg      120
ggccaagtcc ggcagcggta cctctacaca gatgatgccc agcagacaga agcccacctg     180 agatcaggg aggatgggac ggtgggggc gctgctgacc agagcccga aagtctcctg       240 cagctgaaag ccttgaagcc gggagttatt caaatcttgg gagtcaagac atccaggttc    300
ctgtgccagc ggccagatgg ggccctgtat ggatcgctcc actttgaccc tgaggcctgc     360
agcttccggg agctgcttct tgaggacgga tacaatgttt accagtccga agcccacggc    420
ctcccgctgc acctgccagg gaacaagtcc ccacaccggg accctgcacc ccgaggacca    480
gctcgcttcc tgccactacc aggcctgccc ccgcaccccc ggagccaccc ggaatcctg     540 gccccccagc ccccgatgt gggctcctcg accctctga gcatggtggg accttcccag      600
ggccgaagcc ccagctacgc ttcctga                                         627
```

<210> SEQ ID NO 12

<211> LENGTH: 545
<212> TYPE: DNA
<213> ORGANISM: homo sapiens

<400> SEQUENCE: 12

```
cacccatcc ctgactccag tcctctcctg caattcgggg gccaagtccg gcagcggtac      60
ctctacacag atgatgccca gcagacagaa gcccacctgg agatcaggga ggatgggacg     120
gtggggggcg ctgctgacca gagccccgaa agtctcctgc agctgaaagc cttgaagccg     180
ggagttattc aaatcttggg agtcaagaca tccaggttcc tgtgccagcg gccagatggg     240
gccctgtatg gatcgctcca ctttgaccct gaggcctgca gcttccggga gctgcttctt     300
gaggacggat acaatgttta ccagtccgaa gcccacggcc tcccgctgca cctgccaggg     360
aacaagtccc cacaccggga ccctgcaccc cgaggaccag ctcgcttcct gccactacca     420
ggcctgcccc ccgcactccc ggagccaccc ggaatcctgg ccccccagcc cccgatgtg      480
ggctcctcgg accctctgag catggtggga ccttcccagg ccgaagccc agctacgctt     540
cctga                                                                 545
```

<210> SEQ ID NO 13
<211> LENGTH: 630
<212> TYPE: DNA
<213> ORGANISM: Homo sapiens

<400> SEQUENCE: 13

```
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca ggaggatgg gacggtgggg ggcgctgctg accagagccc cgaaagtctc     240
ctgcagctga aagccttgaa gccgggagtt attcaaatct tgggagtcaa gacatccagg     300
ttcctgtgcc agcggccaga tggggccctg tatggatcgc tccactttga ccctgaggcc     360
tgcagcttcc gggagctgct tcttgaggac ggatacaatg tttaccagtc cgaagcccac     420
ggcctcccgc tgcacctgcc agggaacaag tccccacacc gggaccctgc accccgagga     480
ccagctcgct tcctgccact accaggcctg cccccgcac tcccggagcc acccggaatc     540
ctggccccc agcccccga tgtgggctcc tcggaccctc tgagcatggt gggaccttcc     600
cagggccgaa gccccagcta cgcttcctga                                     630
```

<210> SEQ ID NO 14
<211> LENGTH: 627
<212> TYPE: DNA
<213> ORGANISM: Homo sapiens

<400> SEQUENCE: 14

```
atggactcgg acgagaccgg gttcgagcac tcaggactgt gggtttctgt gctggctggt      60
cttctgggag cctgccaggc acccccatc cctgactcca gtcctctcct gcaattcggg     120
ggccaagtcc ggcagcggta cctctacaca gatgatgccc agcagacaga agcccacctg     180
gagatcaggg aggatgggac ggtgggggc gctgctgacc agagccccga aagtctcctg     240
cagctgaaag ccttgaagcc gggagttatt caaatcttgg gagtcaagac atccaggttc     300
ctgtgccagc ggccagatgg ggccctgtat ggatcgctcc actttgaccc tgaggcctgc     360
agcttccggg agctgcttct tgaggacgga tacaatgttt accagtccga agcccacggc     420
ctcccgctgc acctgccagg gaacaagtcc ccacaccggg accctgcacc ccgaggacca     480
```

```
gctcgcttcc tgccactacc aggcctgccc ccgcactcc cggagccacc cggaatcctg      540 gcccccage  ccccgatgt  gggctcctcg  daccctctga  gcatggtggg  accttcccag  600
ggccgaagcc  ccagctacgc  ttcctga                                        627
```

<210> SEQ ID NO 15
<211> LENGTH: 77
<212> TYPE: DNA
<213> ORGANISM: Artificial
<220> FEATURE:
<223> OTHER INFORMATION: Mutant tRNA derived from Methanococcus
      jannaschii tRNA

<400> SEQUENCE: 15

```
ccggcggtag ttcagcaggg cagaacggcg gactctaaat ccgcatggcg ctggttcaaa      60
tccagcccgc cggacca                                                     77
```

<210> SEQ ID NO 16
<211> LENGTH: 306
<212> TYPE: PRT
<213> ORGANISM: Artificial
<220> FEATURE:
<223> OTHER INFORMATION: Mutant synthetase derived from Methanococcus
      jannaschii synthetase

<400> SEQUENCE: 16

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Val
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Tyr Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu His Gly Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

```
Arg Pro Glu Lys Phe Gly Gly Asp Leu Thr Val Asn Ser Tyr Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 17
<211> LENGTH: 77
<212> TYPE: DNA
<213> ORGANISM: Methanococcus jannaschii

<400> SEQUENCE: 17
ccggcggtag ttcagcaggg cagaacggcg gactctaaat ccgcatggcg ctggttcaaa    60
tccggcccgc cggacca                                                   77

<210> SEQ ID NO 18
<211> LENGTH: 88
<212> TYPE: DNA
<213> ORGANISM: Artificial
<220> FEATURE:
<223> OTHER INFORMATION: An optimized amber supressor tRNA

<400> SEQUENCE: 18
cccagggtag ccaagctcgg ccaacggcga cggactctaa atccgttctc gtaggagttc    60
gagggttcga atcccttccc tgggacca                                       88

<210> SEQ ID NO 19
<211> LENGTH: 89
<212> TYPE: DNA
<213> ORGANISM: Artificial
<220> FEATURE:
<223> OTHER INFORMATION: An optimized AGGA frameshift supressor tRNA

<400> SEQUENCE: 19
gcgagggtag ccaagctcgg ccaacggcga cggacttcct aatccgttct cgtaggagtt    60
cgagggttcg aatccctccc ctcgcacca                                      89

<210> SEQ ID NO 20
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-L-phenylalanine

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95
```

```
Gly Leu Lys Ala Lys Tyr Val Tyr Gly Ser Thr Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 21
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-benzoyl-L-phenylalanine

<400> SEQUENCE: 21

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140
```

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
    290                 295                 300

Arg Leu
305

<210> SEQ ID NO 22
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 22

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
            195                 200                 205

Gly Asn Phe Ile Ala Val Asp Asp Ser Pro Glu Glu Ile Arg Ala Lys
            210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
            245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
            290                 295                 300

Leu
305

<210> SEQ ID NO 23
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 23

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
            165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
            195                 200                 205

Gly Asn Phe Ile Ala Val Asp Asp Ser Pro Glu Glu Ile Arg Ala Lys
            210                 215                 220

Ile Lys Lys Ala Tyr Cys Pro Ala Gly Val Val Glu Gly Asn Pro Ile
225                 230                 235                 240

```
Met Glu Ile Ala Lys Tyr Phe Leu Glu Tyr Pro Leu Thr Ile Lys Arg
            245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
    290                 295                 300

Leu
305

<210> SEQ ID NO 24
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 24

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285
```

```
Ala Val Ala Glu Glu Leu Ile Lys Ile Leu Glu Pro Ile Arg Lys Arg
    290                 295                 300
Leu
305

<210> SEQ ID NO 25
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 25

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 26
```

<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 26

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 27
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 27

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305
```

<210> SEQ ID NO 28
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 28

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45
```

```
Ile Lys Lys Met Ile Asp Leu Gln Asn Ala Gly Phe Asp Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95

Gly Leu Lys Ala Lys Tyr Val Tyr Gly Ser Ser Phe Gln Leu Asp Lys
                100                 105                 110

Asp Tyr Thr Leu Asn Val Tyr Arg Leu Ala Leu Lys Thr Thr Leu Lys
             115                 120                 125

Arg Ala Arg Arg Ser Met Glu Leu Ile Ala Arg Glu Asp Glu Asn Pro
         130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
             180                 185                 190

Asn Pro Val Leu Thr Gly Leu Asp Gly Glu Gly Lys Met Ser Ser Ser
         195                 200                 205

Lys Gly Asn Phe Ile Ala Val Asp Asp Ser Pro Glu Glu Ile Arg Ala
 210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
             260                 265                 270

Leu Glu Ser Leu Phe Lys Asn Lys Glu Leu His Pro Met Asp Leu Lys
         275                 280                 285

Asn Ala Val Ala Glu Glu Leu Ile Lys Ile Leu Glu Pro Ile Arg Lys
 290                 295                 300

Arg Leu
305

<210> SEQ ID NO 29
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-acetyl-phenylalanine

<400> SEQUENCE: 29

Met Asp Glu Phe Glu Met Ile Lys Arg Asn Thr Ser Glu Ile Ile Ser
1               5                  10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
             35                  40                  45

Ile Lys Lys Met Ile Asp Leu Gln Asn Ala Gly Phe Asp Ile Ile
 50                  55                  60

Leu Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
                 85                  90                  95
```

-continued

```
Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 30
<211> LENGTH: 306
<212> TYPE: PRT
<213> ORGANISM: Artificial
<220> FEATURE:
<223> OTHER INFORMATION: Aminoacyl tRNA synthetase  for the
      incorporation of p-acetyl-phenylalanine

<400> SEQUENCE: 30

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140
```

-continued

```
Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 31
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-acetyl-phenylalanine

<400> SEQUENCE: 31

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 32
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 32

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
Asn Ala Val Ala Glu Glu Leu Ile Lys Ile Leu Glu Pro Ile Arg Lys
        290                 295                 300
Arg Leu
305

<210> SEQ ID NO 33
<211> LENGTH: 306
<212> TYPE: PRT
<213> ORGANISM: Artificial
<220> FEATURE:
<223> OTHER INFORMATION: Aminoacyl tRNA synthetase for the
      incorporation of p-azido-phenylalanine

<400> SEQUENCE: 33

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Gly
                20                  25                  30
Ile Gly Phe Glu Pro Ser Gly Lys Ile His Leu Gly His Tyr Leu Gln
            35                  40                  45
Ile Lys Lys Met Ile Asp Leu Gln Asn Ala Gly Phe Asp Ile Ile Ile
        50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Thr Phe Gln Leu Asp Lys
                100                 105                 110
Asp Tyr Thr Leu Asn Val Tyr Arg Leu Ala Leu Lys Thr Thr Leu Lys
            115                 120                 125
Arg Ala Arg Arg Ser Met Glu Leu Ile Ala Arg Glu Asp Glu Asn Pro
        130                 135                 140
Lys Val Ala Glu Val Ile Tyr Pro Ile Met Gln Val Asn Thr Tyr Tyr
145                 150                 155                 160
Tyr Leu Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
                180                 185                 190
Asn Pro Val Leu Thr Gly Leu Asp Gly Glu Gly Lys Met Ser Ser Ser
            195                 200                 205
Lys Gly Asn Phe Ile Ala Val Asp Asp Ser Pro Glu Glu Ile Arg Ala
        210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
            275                 280                 285
```

```
Asn Ala Val Ala Glu Glu Leu Ile Lys Ile Leu Glu Pro Ile Arg Lys
            290                 295                 300

Arg Leu
305

<210> SEQ ID NO 34
<211> LENGTH: 208
<212> TYPE: PRT
<213> ORGANISM: Rattus norvegicus

<400> SEQUENCE: 34

Met Asp Trp Met Lys Ser Arg Val Gly Ala Gly Leu Trp Val Cys
1               5                   10                  15

Leu Leu Leu Pro Val Phe Leu Leu Gly Val Cys Glu Ala Tyr Pro Ile
            20                  25                  30

Ser Asp Ser Ser Pro Leu Leu Gln Phe Gly Gly Gln Val Arg Gln Arg
        35                  40                  45

Tyr Leu Tyr Thr Asp Asp Gln Asp Thr Glu Ala His Leu Glu Ile
50                  55                  60

Arg Glu Asp Gly Thr Val Val Gly Thr Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Thr Leu Tyr
            100                 105                 110

Gly Ser Pro His Phe Asp Pro Glu Ala Cys Ser Phe Arg Glu Leu Leu
        115                 120                 125

Leu Lys Asp Gly Tyr Asn Val Tyr Gln Ser Glu Ala His Gly Leu Pro
130                 135                 140

Leu Arg Leu Pro Gln Lys Asp Ser Gln Asp Pro Ala Thr Arg Gly Pro
145                 150                 155                 160

Val Arg Phe Leu Pro Met Pro Gly Leu Pro His Glu Pro Gln Glu Gln
                165                 170                 175

Pro Gly Val Leu Pro Glu Pro Pro Asp Val Gly Ser Ser Asp Pro
            180                 185                 190

Leu Ser Met Val Glu Pro Leu Gln Gly Arg Ser Pro Ser Tyr Ala Ser
        195                 200                 205

<210> SEQ ID NO 35
<211> LENGTH: 210
<212> TYPE: PRT
<213> ORGANISM: Mus musculus

<400> SEQUENCE: 35

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
        35                  40                  45

Tyr Leu Tyr Thr Asp Asp Asp Gln Asp Thr Glu Ala His Leu Glu Ile
50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
```

-continued

```
                    100                 105                 110
Gly Ser Pro His Phe Asp Pro Glu Ala Cys Ser Phe Arg Glu Leu Leu
                115                 120                 125

Leu Glu Asp Gly Tyr Asn Val Tyr Gln Ser Glu Ala His Gly Leu Pro
            130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210

<210> SEQ ID NO 36
<211> LENGTH: 194
<212> TYPE: PRT
<213> ORGANISM: Danio rerio

<400> SEQUENCE: 36

Met Leu Phe Ala Cys Phe Phe Ile Phe Phe Ala Leu Phe Pro His Leu
1               5                   10                  15

Arg Trp Cys Met Tyr Val Pro Ala Gln Asn Val Leu Leu Gln Phe Gly
                20                  25                  30

Thr Gln Val Arg Glu Arg Leu Leu Tyr Thr Asp Gly Leu Phe Leu Glu
            35                  40                  45

Met Asn Pro Asp Gly Ser Val Lys Gly Ser Pro Glu Lys Asn Leu Asn
        50                  55                  60

Cys Val Leu Glu Leu Arg Ser Val Lys Ala Gly Glu Thr Val Ile Gln
65                  70                  75                  80

Ser Ala Ala Thr Ser Leu Tyr Leu Cys Val Asp Asp Gln Asp Lys Leu
                85                  90                  95

Lys Gly Gln His His Tyr Ser Ala Leu Asp Cys Thr Phe Gln Glu Leu
                100                 105                 110

Leu Leu Asp Gly Tyr Ser Phe Phe Leu Ser Pro His Thr Asn Leu Pro
            115                 120                 125

Val Ser Leu Leu Ser Lys Arg Gln Lys His Gly Asn Pro Leu Ser Arg
        130                 135                 140

Phe Leu Pro Val Ser Arg Ala Glu Asp Ser Arg Thr Gln Glu Val Lys
145                 150                 155                 160

Gln Tyr Ile Gln Asp Ile Asn Leu Asp Ser Asp Pro Leu Gly Met
                165                 170                 175

Gly His Arg Ser His Leu Gln Thr Val Phe Ser Pro Ser Leu His Thr
            180                 185                 190

Lys Lys

<210> SEQ ID NO 37
<211> LENGTH: 1043
<212> TYPE: PRT
<213> ORGANISM: Homo sapiens

<400> SEQUENCE: 37

Met Lys Pro Gly Cys Ala Ala Gly Ser Pro Gly Asn Glu Trp Ile Phe
1               5                   10                  15
```

-continued

```
Phe Ser Thr Asp Glu Ile Thr Thr Arg Tyr Arg Asn Thr Met Ser Asn
             20                  25                  30
Gly Gly Leu Gln Arg Ser Val Ile Leu Ser Ala Leu Ile Leu Leu Arg
         35                  40                  45
Ala Val Thr Gly Phe Ser Gly Asp Gly Arg Ala Ile Trp Ser Lys Asn
 50                  55                  60
Pro Asn Phe Thr Pro Val Asn Glu Ser Gln Leu Phe Leu Tyr Asp Thr
 65                  70                  75                  80
Phe Pro Lys Asn Phe Phe Trp Gly Ile Gly Thr Gly Ala Leu Gln Val
                 85                  90                  95
Glu Gly Ser Trp Lys Lys Asp Gly Lys Gly Pro Ser Ile Trp Asp His
             100                 105                 110
Phe Ile His Thr His Leu Lys Asn Val Ser Ser Thr Asn Gly Ser Ser
         115                 120                 125
Asp Ser Tyr Ile Phe Leu Glu Lys Asp Leu Ser Ala Leu Asp Phe Ile
130                 135                 140
Gly Val Ser Phe Tyr Gln Phe Ser Ile Ser Trp Pro Arg Leu Phe Pro
145                 150                 155                 160
Asp Gly Ile Val Thr Val Ala Asn Ala Lys Gly Leu Gln Tyr Tyr Ser
                 165                 170                 175
Thr Leu Leu Asp Ala Leu Val Leu Arg Asn Ile Glu Ile Val Thr Leu
             180                 185                 190
Tyr His Trp Asp Leu Pro Leu Ala Leu Gln Glu Lys Tyr Gly Gly Trp
         195                 200                 205
Lys Asn Asp Thr Ile Ile Asp Ile Phe Asn Asp Tyr Ala Thr Tyr Cys
210                 215                 220
Phe Gln Met Phe Gly Asp Arg Val Lys Tyr Trp Ile Thr Ile His Asn
225                 230                 235                 240
Pro Tyr Leu Val Ala Trp His Gly Tyr Gly Thr Gly Met His Ala Pro
                 245                 250                 255
Gly Glu Lys Gly Asn Leu Ala Ala Val Tyr Thr Val Gly His Asn Leu
             260                 265                 270
Ile Lys Ala His Ser Lys Val Trp His Asn Tyr Asn Thr His Phe Arg
         275                 280                 285
Pro His Gln Lys Gly Trp Leu Ser Ile Thr Leu Gly Ser His Trp Ile
290                 295                 300
Glu Pro Asn Arg Ser Glu Asn Thr Met Asp Ile Phe Lys Cys Gln Gln
305                 310                 315                 320
Ser Met Val Ser Val Leu Gly Trp Phe Ala Asn Pro Ile His Gly Asp
                 325                 330                 335
Gly Asp Tyr Pro Glu Gly Met Arg Lys Lys Leu Phe Ser Val Leu Pro
             340                 345                 350
Ile Phe Ser Glu Ala Glu Lys His Glu Met Arg Gly Thr Ala Asp Phe
         355                 360                 365
Phe Ala Phe Ser Phe Gly Pro Asn Asn Phe Lys Pro Leu Asn Thr Met
370                 375                 380
Ala Lys Met Gly Gln Asn Val Ser Leu Asn Leu Arg Glu Ala Leu Asn
385                 390                 395                 400
Trp Ile Lys Leu Glu Tyr Asn Asn Pro Arg Ile Leu Ile Ala Glu Asn
                 405                 410                 415
Gly Trp Phe Thr Asp Ser Arg Val Lys Thr Glu Asp Thr Thr Ala Ile
             420                 425                 430
Tyr Met Met Lys Asn Phe Leu Ser Gln Val Leu Gln Ala Ile Arg Leu
         435                 440                 445
```

```
Asp Glu Ile Arg Val Phe Gly Tyr Thr Ala Trp Ser Leu Leu Asp Gly
    450                 455                 460

Phe Glu Trp Gln Asp Ala Tyr Thr Ile Arg Arg Gly Leu Phe Tyr Val
465                 470                 475                 480

Asp Phe Asn Ser Lys Gln Lys Glu Arg Lys Pro Lys Ser Ser Ala His
                485                 490                 495

Tyr Tyr Lys Gln Ile Ile Arg Glu Asn Gly Phe Ser Leu Lys Glu Ser
                500                 505                 510

Thr Pro Asp Val Gln Gly Gln Phe Pro Cys Asp Phe Ser Trp Gly Val
                515                 520                 525

Thr Glu Ser Val Leu Lys Pro Glu Ser Val Ala Ser Ser Pro Gln Phe
                530                 535                 540

Ser Asp Pro His Leu Tyr Val Trp Asn Ala Thr Gly Asn Arg Leu Leu
545                 550                 555                 560

His Arg Val Glu Gly Val Arg Leu Lys Thr Arg Pro Ala Gln Cys Thr
                565                 570                 575

Asp Phe Val Asn Ile Lys Lys Gln Leu Glu Met Leu Ala Arg Met Lys
                580                 585                 590

Val Thr His Tyr Arg Phe Ala Leu Asp Trp Ala Ser Val Leu Pro Thr
                595                 600                 605

Gly Asn Leu Ser Ala Val Asn Arg Gln Ala Leu Arg Tyr Tyr Arg Cys
610                 615                 620

Val Val Ser Glu Gly Leu Lys Leu Gly Ile Ser Ala Met Val Thr Leu
625                 630                 635                 640

Tyr Tyr Pro Thr His Ala His Leu Gly Leu Pro Glu Pro Leu Leu His
                645                 650                 655

Ala Asp Gly Trp Leu Asn Pro Ser Thr Ala Glu Ala Phe Gln Ala Tyr
                660                 665                 670

Ala Gly Leu Cys Phe Gln Glu Leu Gly Asp Leu Val Lys Leu Trp Ile
                675                 680                 685

Thr Ile Asn Glu Pro Asn Arg Leu Ser Asp Ile Tyr Asn Arg Ser Gly
690                 695                 700

Asn Asp Thr Tyr Gly Ala Ala His Asn Leu Leu Val Ala His Ala Leu
705                 710                 715                 720

Ala Trp Arg Leu Tyr Asp Arg Gln Phe Arg Pro Ser Gln Arg Gly Ala
                725                 730                 735

Val Ser Leu Ser Leu His Ala Asp Trp Ala Glu Pro Ala Asn Pro Tyr
                740                 745                 750

Ala Asp Ser His Trp Arg Ala Ala Glu Arg Phe Leu Gln Phe Glu Ile
                755                 760                 765

Ala Trp Phe Ala Glu Pro Leu Phe Lys Thr Gly Asp Tyr Pro Ala Ala
                770                 775                 780

Met Arg Glu Tyr Ile Ala Ser Lys His Arg Arg Gly Leu Ser Ser Ser
785                 790                 795                 800

Ala Leu Pro Arg Leu Thr Glu Ala Glu Arg Arg Leu Leu Lys Gly Thr
                805                 810                 815

Val Asp Phe Cys Ala Leu Asn His Phe Thr Thr Arg Phe Val Met His
                820                 825                 830

Glu Gln Leu Ala Gly Ser Arg Tyr Asp Ser Asp Arg Asp Ile Gln Phe
                835                 840                 845

Leu Gln Asp Ile Thr Arg Leu Ser Ser Pro Thr Arg Leu Ala Val Ile
850                 855                 860

Pro Trp Gly Val Arg Lys Leu Leu Arg Trp Val Arg Arg Asn Tyr Gly
```

```
865                 870                 875                 880
Asp Met Asp Ile Tyr Ile Thr Ala Ser Gly Ile Asp Asp Gln Ala Leu
                    885                 890                 895

Glu Asp Asp Arg Leu Arg Lys Tyr Tyr Leu Gly Lys Tyr Leu Gln Glu
            900                 905                 910

Val Leu Lys Ala Tyr Leu Ile Asp Lys Val Arg Ile Lys Gly Tyr Tyr
        915                 920                 925

Ala Phe Lys Leu Ala Glu Glu Lys Ser Lys Pro Arg Phe Gly Phe Phe
    930                 935                 940

Thr Ser Asp Phe Lys Ala Lys Ser Ser Ile Gln Phe Tyr Asn Lys Val
945                 950                 955                 960

Ile Ser Ser Arg Gly Phe Pro Phe Glu Asn Ser Ser Arg Cys Ser
                965                 970                 975

Gln Thr Gln Glu Asn Thr Glu Cys Thr Val Cys Leu Phe Leu Val Gln
            980                 985                 990

Lys Lys Pro Leu Ile Phe Leu Gly Cys Cys Phe Phe Ser  Thr Leu Val
        995                 1000                1005

Leu Leu  Leu Ser Ile Ala Ile  Phe Gln Arg Gln Lys  Arg Arg Lys
    1010                1015                1020

Phe Trp  Lys Ala Lys Asn Leu  Gln His Ile Pro Leu  Lys Lys Gly
    1025                1030                1035

Lys Arg  Val Val Ser
    1040

<210> SEQ ID NO 38
<211> LENGTH: 1043
<212> TYPE: PRT
<213> ORGANISM: Mus musculus

<400> SEQUENCE: 38

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
```

-continued

```
            195                 200                 205
Trp Lys Asn Ala Thr Met Ile Asp Leu Phe Asn Asp Tyr Ala Thr Tyr
210                 215                 220
Cys Phe Gln Thr Phe Gly Asp Arg Val Lys Tyr Trp Ile Thr Ile His
225                 230                 235                 240
Asn Pro Tyr Leu Val Ala Trp His Gly Phe Gly Thr Gly Met His Ala
                245                 250                 255
Pro Gly Glu Lys Gly Asn Leu Thr Ala Val Tyr Thr Val Gly His Asn
                260                 265                 270
Leu Ile Lys Ala His Ser Lys Val Trp His Asn Tyr Asp Lys Asn Phe
                275                 280                 285
Arg Pro His Gln Lys Gly Trp Leu Ser Ile Thr Leu Gly Ser His Trp
                290                 295                 300
Ile Glu Pro Asn Arg Thr Asp Asn Met Glu Asp Val Ile Asn Cys Gln
305                 310                 315                 320
His Ser Met Ser Ser Val Leu Gly Trp Phe Ala Asn Pro Ile His Gly
                325                 330                 335
Asp Gly Asp Tyr Pro Glu Phe Met Lys Thr Gly Ala Met Ile Pro Glu
                340                 345                 350
Phe Ser Glu Ala Glu Lys Glu Val Arg Gly Thr Ala Asp Phe Phe
                355                 360                 365
Ala Phe Ser Phe Gly Pro Asn Asn Phe Arg Pro Ser Asn Thr Val Val
                370                 375                 380
Lys Met Gly Gln Asn Val Ser Leu Asn Leu Arg Gln Val Leu Asn Trp
385                 390                 395                 400
Ile Lys Leu Glu Tyr Asp Asp Pro Gln Ile Leu Ile Ser Glu Asn Gly
                405                 410                 415
Trp Phe Thr Asp Ser Tyr Ile Lys Thr Glu Asp Thr Thr Ala Ile Tyr
                420                 425                 430
Met Met Lys Asn Phe Leu Asn Gln Val Leu Gln Ala Ile Lys Phe Asp
                435                 440                 445
Glu Ile Arg Val Phe Gly Tyr Thr Ala Trp Thr Leu Leu Asp Gly Phe
450                 455                 460
Glu Trp Gln Asp Ala Tyr Thr Thr Arg Arg Gly Leu Phe Tyr Val Asp
465                 470                 475                 480
Phe Asn Ser Glu Gln Lys Glu Arg Lys Pro Lys Ser Ser Ala His Tyr
                485                 490                 495
Tyr Lys Gln Ile Ile Gln Asp Asn Gly Phe Pro Leu Lys Glu Ser Thr
                500                 505                 510
Pro Asp Met Lys Gly Arg Phe Pro Cys Asp Phe Ser Trp Gly Val Thr
                515                 520                 525
Glu Ser Val Leu Lys Pro Glu Phe Thr Val Ser Ser Pro Gln Phe Thr
530                 535                 540
Asp Pro His Leu Tyr Val Trp Asn Val Thr Gly Asn Arg Leu Leu Tyr
545                 550                 555                 560
Arg Val Glu Gly Val Arg Leu Lys Thr Arg Pro Ser Gln Cys Thr Asp
                565                 570                 575
Tyr Val Ser Ile Lys Lys Arg Val Glu Met Leu Ala Lys Met Lys Val
                580                 585                 590
Thr His Tyr Gln Phe Ala Leu Asp Trp Thr Ser Ile Leu Pro Thr Gly
                595                 600                 605
Asn Leu Ser Lys Val Asn Arg Gln Val Leu Arg Tyr Tyr Arg Cys Val
                610                 615                 620
```

-continued

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
            645                 650                 655

Gly Gly Trp Leu Asn Met Asn Thr Ala Lys Ala Phe Gln Asp Tyr Ala
            660                 665                 670

Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
            740                 745                 750

Asp Ser His Trp Lys Ala Ala Glu Arg Phe Leu Gln Phe Glu Ile Ala
            755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
                805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
            835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
                885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
            915                 920                 925

Phe Lys Leu Thr Glu Glu Lys Ser Lys Pro Arg Phe Gly Phe Phe Thr
            930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
                965                 970                 975

Pro Ala Glu Asp Thr Asp Cys Thr Ile Cys Ser Phe Leu Val Glu Lys
            980                 985                 990

Lys Pro Leu Ile Phe Phe Gly Cys Cys Phe Ile Ser Thr Leu Ala Val
            995                 1000                1005

Leu Leu Ser Ile Thr Val Phe His His Gln Lys Arg Arg Lys Phe
    1010                1015                1020

Gln Lys Ala Arg Asn Leu Gln Asn Ile Pro Leu Lys Lys Gly His
    1025                1030                1035

Ser Arg Val Phe Ser
    1040

<210> SEQ ID NO 39
<211> LENGTH: 63
<212> TYPE: DNA
<213> ORGANISM: Artificial
<220> FEATURE:
<223> OTHER INFORMATION: FGF21 secretion constructs, cloned into pVK7ara
      (Nde/Eco)

<400> SEQUENCE: 39
atgaaaaaaa ctgctatcgc gatcgctgta gctctggctg gtttcgcgac cgtagctaac      60
gct                                                                   63

<210> SEQ ID NO 40
<211> LENGTH: 21
<212> TYPE: PRT
<213> ORGANISM: Artificial
<220> FEATURE:
<223> OTHER INFORMATION: FGF21 secretion constructs, cloned into pVK7ara
      (Nde/Eco)

<400> SEQUENCE: 40

Met Lys Lys Thr Ala Ile Ala Ile Ala Val Ala Leu Ala Gly Phe Ala
1               5                   10                  15

Thr Val Ala Asn Ala
            20

<210> SEQ ID NO 41
<211> LENGTH: 78
<212> TYPE: DNA
<213> ORGANISM: Artificial
<220> FEATURE:
<223> OTHER INFORMATION: FGF21 secretion constructs, cloned into pVK7ara
      (Nde/Eco)

<400> SEQUENCE: 41
atgaaaataa aaacaggtgc acgcatcctc gcattatccg cattaacgac gatgatgttt      60
tccgcctcgg ctctcgcc                                                   78

<210> SEQ ID NO 42
<211> LENGTH: 26
<212> TYPE: PRT
<213> ORGANISM: Artificial
<220> FEATURE:
<223> OTHER INFORMATION: FGF21 secretion constructs, cloned into pVK7ara
      (Nde/Eco)

<400> SEQUENCE: 42

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 43
<211> LENGTH: 69
<212> TYPE: DNA
<213> ORGANISM: Artificial
<220> FEATURE:
<223> OTHER INFORMATION: FGF21 secretion constructs, cloned into pVK7ara
      (Nde/Eco)

<400> SEQUENCE: 43
atgaaaaaga atatcgcatt tcttcttgca tctatgttcg ttttttctat tgctacaaat      60
gcctatgca                                                             69

```
<210> SEQ ID NO 44
<211> LENGTH: 23
<212> TYPE: PRT
<213> ORGANISM: Artificial
<220> FEATURE:
<223> OTHER INFORMATION: FGF21 secretion constructs, cloned into pVK7ara
      (Nde/Eco)

<400> SEQUENCE: 44

Met Lys Lys Asn Ile Ala Phe Leu Leu Ala Ser Met Phe Val Phe Ser
1               5                   10                  15

Ile Ala Thr Asn Ala Tyr Ala
            20
```